United States Patent
Mueller et al.

(10) Patent No.: US 7,897,603 B2
(45) Date of Patent: Mar. 1, 2011

(54) SELECTED CGRP-ANTAGONISTS, PROCESSES FOR PREPARING THEM AND THEIR USE AS PHARMACEUTICAL COMPOSITIONS

(75) Inventors: Stephan Georg Mueller, Warthausen (DE); Klaus Rudolf, Warthausen (DE); Philipp Lustenberger, Basel (CH); Dirk Stenkamp, Biberach (DE); Marco Santagostino, Mittelbiberach (DE); Fabio Paleari, Monza (IT); Henri Doods, Warthausen (DE); Kirsten Arndt, Biberach (DE); Gerhard Schaenzle, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/485,434

(22) Filed: Jun. 16, 2009

(65) Prior Publication Data

US 2009/0253680 A1 Oct. 8, 2009

Related U.S. Application Data

(62) Division of application No. 11/533,096, filed on Sep. 19, 2006, now Pat. No. 7,582,625.

(30) Foreign Application Priority Data

Sep. 29, 2005 (EP) .................... 05021236

(51) Int. Cl.
| | |
|---|---|
| C07D 401/14 | (2006.01) |
| A61K 31/45 | (2006.01) |
| A61P 25/06 | (2006.01) |
| A61P 5/50 | (2006.01) |

(52) U.S. Cl. ............... 514/236.2; 514/253.09; 514/318; 544/129; 544/364; 546/189

(58) Field of Classification Search ............... 514/236.2, 514/253.09, 318; 544/129, 364; 546/189
See application file for complete search history.

(56) References Cited

U.S. PATENT DOCUMENTS 6,344,449 B1 2/2002 Rudolf et al.

| | | |
|---|---|---|
| 2004/0132716 A1 | 7/2004 | Rudolf et al. |
| 2004/0192729 A1 | 9/2004 | Rudolf et al. |
| 2005/0234067 A1 | 10/2005 | Mueller et al. |
| 2005/0250763 A1 | 11/2005 | Mueller et al. |
| 2005/0282857 A1 | 12/2005 | Rudolf et al. |
| 2006/0079504 A1 | 4/2006 | Rudolf et al. |
| 2006/0252750 A1 | 11/2006 | Mueller et al. |
| 2006/0252931 A1 | 11/2006 | Mueller et al. |
| 2007/0049581 A1 | 3/2007 | Mueller et al. |
| 2007/0238715 A1 | 10/2007 | Rudolf et al. |
| 2007/0244099 A1 | 10/2007 | Rudolf et al. |

FOREIGN PATENT DOCUMENTS

| | | |
|---|---|---|
| WO | 9811128 A1 | 3/1998 |
| WO | 2004063171 A1 | 7/2004 |
| WO | 2005092880 A1 | 10/2005 |

OTHER PUBLICATIONS

International Search Report, Form PCT/ISA/210, for corresponding PCT/EP2006/066783.

*Primary Examiner*—Bruck Kifle
(74) *Attorney, Agent, or Firm*—Michael P. Morris; Alan R. Stempel

(57) ABSTRACT

The present invention relates to the CGRP-antagonists of general formula I

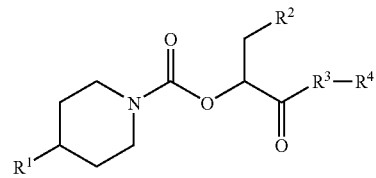

wherein $R^1$, $R^2$, $R^3$ and $R^4$ are defined as in claim 1, the tautomers, the isomers, the diastereomers, the enantiomers, the hydrates thereof, the mixtures thereof and the salts thereof and the hydrates of the salts thereof, particularly the physiologically acceptable salts thereof with inorganic or organic acids or bases, as well as those compounds of general formula I wherein one or more hydrogen atoms are replaced by deuterium, pharmaceutical compositions containing these compounds, their use and processes for preparing them.

10 Claims, No Drawings

SELECTED CGRP-ANTAGONISTS, PROCESSES FOR PREPARING THEM AND THEIR USE AS PHARMACEUTICAL COMPOSITIONS

RELATED APPLICATIONS

This application is a divisional of U.S. application Ser. No. 11/533,096, filed on Sep. 19, 2006.

The present invention relates to CGRP antagonists of general formula I

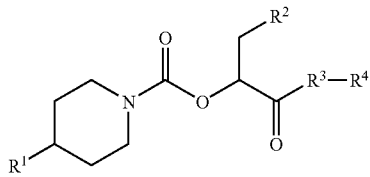

wherein $R^1$, $R^2$, $R^3$ and $R^4$ are as herein defined, the tautomers, the isomers, the diastereomers, the enantiomers, the hydrates thereof, the mixtures thereof and the salts thereof and the hydrates of the salts thereof, particularly the physiologically acceptable salts thereof with inorganic or organic acids or bases, as well as those compounds of general formula I wherein one or more hydrogen atoms are replaced by deuterium, pharmaceutical compositions containing these compounds, their use and processes for preparing them.

PRIOR ART

CGRP antagonists for the treatment of migraine have already been described in International Patent Applications PCT/EP97/04862 and PCT/EP04/000087.

DETAILED DESCRIPTION OF THE INVENTION

In the above general formula I in a first embodiment $R^1$ denotes a group selected from

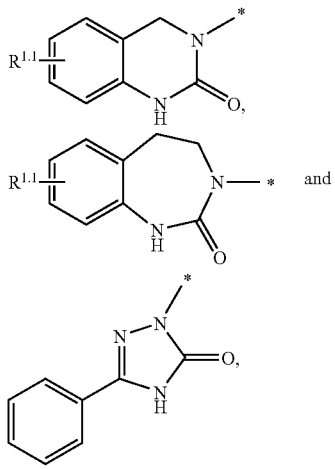

wherein
$R^{1.1}$ denotes H or $H_3C$—O—,
$R^2$ denotes a group of general formula II

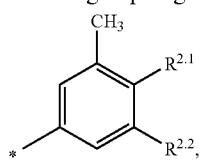

wherein
$R^{2.1}$ denotes HO, $H_3CO$, H—C(O)—O or $H_3C$—C(O)—O— and
$R^{2.2}$ denotes $C_{1-2}$-alkyl or $H_3CO$—,
$R^3$ denotes $R^4$—$C_{2-8}$-alkylene-NH— and
$R^4$ denotes H, $H_2N$, $C_{1-3}$-alkyl-NH, $(C_{1-3}$-alkyl$)_2$-N or $C_{1-6}$-alkyl-O—C(O)—NH—, or
$R^3$ denotes a group of general formulae III

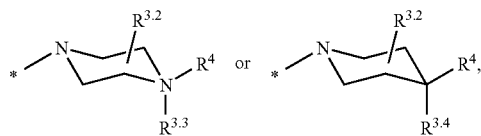

wherein
$R^{3.2}$ denotes H or $C_{1-3}$-alkyl,
$R^{3.3}$ denotes a free electron pair or an oxygen atom,
$R^{3.4}$ denotes H or $C_{1-3}$-alkyl-, and
$R^4$ denotes H, $C_{1-6}$-alkyl, $H_2N$—$C_{2-6}$-alkylene, $C_{1-3}$-alkyl-NH—$C_{2-6}$-alkylene, $(C_{1-3}$-alkyl$)_2$-N—$C_{1-6}$-alkylene, $C_{3-6}$-cycloalkyl-$C_{1-3}$-alkylene, $NH_2$, $C_{1-3}$-alkyl-NH or $(C_{1-3}$-alkyl$)_2$-N, or
$R^4$ denotes a group selected from

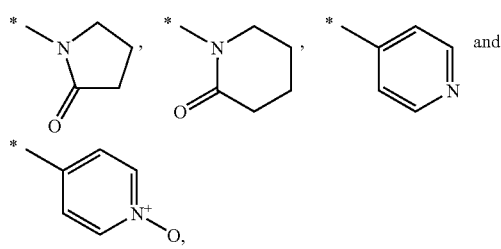

or
$R^4$ denotes a group of general formulae IV

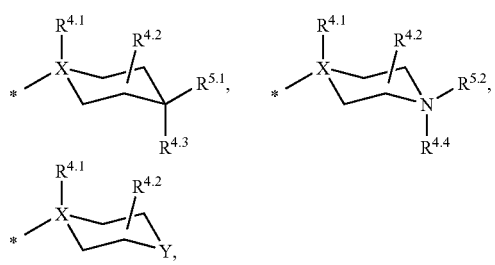

wherein
X denotes C and
$R^{4.1}$ denotes H, OH or $C_{1-3}$-alkyl, or
X denotes N and
$R^{4.1}$ denotes a free electron pair or an oxygen atom,
Y denotes O, S, S(O), $S(O)_2$, if X=N, or
Y denotes S, S(O), $S(O)_2$, if X=C,
$R^{4.2}$ denotes H or $C_{1-3}$-alkyl,
$R^{4.3}$ denotes H or $C_{1-3}$-alkyl,
$R^{4.4}$ denotes a free electron pair or, if $R^{5.2}$ is not H or $C_{1-3}$-alkyl-C(O)—, an oxygen atom, $R^{5.1}$ denotes H, CN, OH, $C_{1-3}$-alkyl, $C_{1-3}$-alkyl-C(O)—O, $C_{1-3}$-alkyl-O, $R^{5.1,1}$—O—C(O), $R^{5.1,1}$—O—C(O)—$C_{2-4}$-alkylene or $R^{5.1,1}$—O—C(O)—$C_{1-3}$-alkylene-O, $R^{5.1.1}$ denotes H, $C_{1-6}$-alkyl, $H_2N$—C(O)—$C_{1-3}$-alkylene, $C_{1-3}$-alkyl-NH—C(O)—$C_{1-3}$-alkylene, $(C_{1-3}$-alkyl$)_2$-N—C(O)—$C_{1-3}$-alkylene or $C_{1-3}$-alkyl-O—C(O)—O—$C_{1-3}$-alkylene, or $R^{5.2}$ denotes H, $C_{1-3}$-alkyl, $C_{3-6}$-cycloalkyl, $C_{3-6}$-cycloalkyl-$C_{1-3}$-alkylene, $C_{1-3}$-alkyl-C(O), $R^{5.2.1}$—O—C(O)—$C_{1-3}$-alkylene or $R^{5.2.2}$—$C_{2-4}$-alkylene-O—C(O)—$C_{1-3}$-alkylene, $R^{5.2.1}$ denotes H, $C_{1-6}$-alkyl, $C_{1-6}$-alkyl-C(O)—O—$C_{1-3}$-alkylene, $C_{1-3}$-alkyl-O—C(O)—O—$C_{1-3}$-alkylene, $C_{3-7}$-cycloalkyl-O—C(O)—O—$C_{1-3}$-alkylene, $H_2N$—C(O)—$C_{1-3}$-alkylene, $C_{1-3}$-alkyl-NH—C(O)—$C_{1-3}$-alkylene, $(C_{1-3}$-alkyl$)_2$-N—C(O)—$C_{1-3}$-alkylene or $R^{5.2.1,1}$—C(O)—$C_{1-3}$-alkylene and $R^{5.2.1.1}$ denotes a group selected from

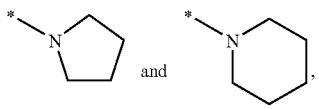

or $R^{5.2.1}$ denotes a group selected from

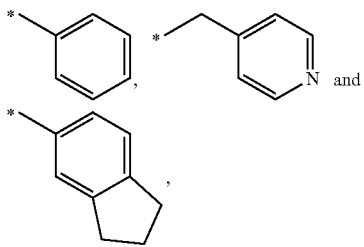

$R^{5.2.2}$ denotes $H_2N$, $C_{1-3}$-alkyl-NH, $(C_{1-3}$-alkyl$)_2$-N, $C_{1-3}$-alkyl-O or $C_{1-3}$-alkyl-O—$C_{2-4}$-alkylene-O, or $R^{5.2.2}$ denotes a group selected from

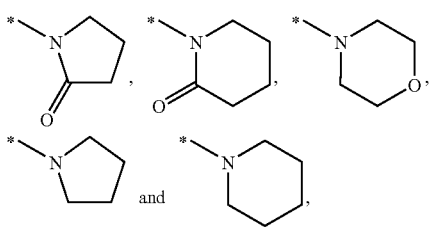

with the proviso that $R^3$ and $R^4$ are not bound to one another simultaneously via an N atom, the tautomers, the diastereomers, the enantiomers, the hydrates, the mixtures thereof and the salts thereof and the hydrates of the salts thereof, particularly the physiologically acceptable salts thereof with inorganic or organic acids or bases.

A preferred first embodiment of the present invention comprises the compounds of the above general formula I, wherein $R^1$, $R^2$, $R^3$ and $R^4$ are as hereinbefore defined in the first embodiment, with the proviso that the compounds (a) (R)-1-(4-hydroxy-3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate, (b) (R)-1-(4-hydroxy-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidin-1-carboxylate, (c) (R)-1-(4-hydroxy-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate, (d) (R)-1-(4-hydroxy-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate, (e) (R)-1-(4-hydroxy-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate, (f) (R)-2-4,4'-bipiperidinyl-1-yl-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (g) (R)-2-1,4'-bipiperidinyl-1'-yl-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (h) (R)-2-(4-dimethylamino-piperidin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (i) (R)-1-(4-methoxy-3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate, (j) (R)-1-(4-methoxy-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (k) (R)-1-(4-methoxy-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate, (l) (R)-1-(4-methoxy-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate, (m) (R)-1-(4-methoxy-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate, (n) (R)-2-4,4'-bipiperidinyl-1-yl-1-(4-methoxy-3,5-dimethyl-benzyl)-2-oxo-ethyl 4-(2-oxo-1,2,4,5-tetrahydro-1,3-benzodiazepin-3-yl)-piperidine-1-carboxylate, (o) (R)-2-1,4'-bipiperidinyl-1'-yl-1-(4-methoxy-3,5-dimethyl-benzyl)-2-oxo-ethyl 4-(2-oxo-1,2,4,5-tetrahydro-1,3-benzodiazepin-3-yl)-piperidine-1-carboxylate, (p) (R)-2-(4-dimethylamino-piperidin-1-yl)-1-(4-methoxy-3,5-dimethyl-benzyl)-2-oxo-ethyl 4-(2-oxo-1,2,4,5-tetrahydro-1,3-benzodiazepin-3-yl)-piperidine-1-carboxylate, (q) (R)-1-(4-hydroxy-3,5-dimethyl-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate, (r) (R)-2-(4-cyclohexyl-piperazin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (s) (R)-2-(4,4-dimethyl-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (t) (R)-2-(4-hydroxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (u) (R)-1-(4-hydroxy-3,5-dimethyl-benzyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate, (v) (R)-2-(4-ethyl-4-hydroxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (w) (R)-2-[4-(1,1-dioxo-1$\lambda^6$-thiomorpholin-4-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (x) (R)-2-(1'-ethoxycarbonylmethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (y) (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (z) (R)-2-[4-(4-ethoxycarbonylmethyl-piperazin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (aa) (R)-2-[4-(4-carboxymethyl-piperazin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ab) (R)-2-[4-(1-ethoxycarbonylmethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ac) (R)-2-[4-(1-carboxymethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ad) (R)-2-[1'-(2-ethoxycarbonyl-ethyl)-4,4'-bipiperidinyl-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ae) (R)-2-[1'-(2-carboxy-ethyl)-4,4'-bipiperidinyl-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (af) (R)-2-{4-[1-(2-ethoxycarbonyl-ethyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ag) (R)-2-{4-[1-(2-carboxy-ethyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ah) (R)-2-{4-[4-(2-ethoxycarbonyl-ethyl)-piperazin-1-yl]-piperidin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ai) (R)-2-{4-[4-(2-carboxy-ethyl)-piperazin-1-yl]-piperidin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, are excluded from the scope of protection, the tautomers, the diastereomers, the enantiomers, the hydrates, the mixtures thereof and the salts thereof and the hydrates of the salts thereof, particularly the physiologically acceptable salts thereof with inorganic or organic acids or bases.

In the above general formula I in a second embodiment $R^1$ denotes a group selected from

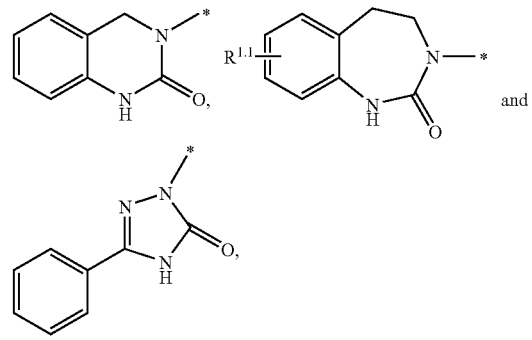

wherein
$R^{1.1}$ denotes H or $H_3C$—O—,
$R^2$ denotes a group of general formula II

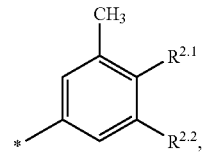

wherein
$R^{2.1}$ denotes HO, $H_3CO$, H—C(O)—O or $H_3C$—C(O)—O— and
$R^{2.2}$ denotes $C_{1-2}$-alkyl or $H_3CO$—,
$R^3$ denotes $R^4$—$C_{2-8}$-alkylene-NH— and
$R^4$ denotes $H_2N$, $C_{1-3}$-alkyl-NH or $(C_{1-3}$-alkyl$)_2$-N, $C_{1-6}$-alkyl-O—C(O)—NH—, or
$R^3$ denotes a group of general formulae III

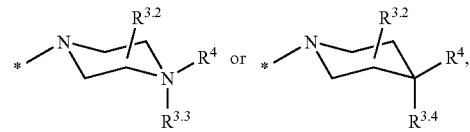

wherein
$R^{3.2}$ denotes H,
$R^{3.3}$ denotes a free electron pair or an oxygen atom,
$R^{3.4}$ denotes H or $C_{1-3}$-alkyl, and
$R^4$ denotes H, $C_{1-6}$-alkyl, $H_2N$—$C_{2-6}$-alkylene, $C_{1-3}$-alkyl-NH—$C_{2-6}$-alkylene, $(C_{1-3}$-alkyl$)_2$-N—$C_{1-6}$-alkylene, $C_{3-6}$-cycloalkyl-$C_{1-3}$-alkylene, $H_2N$, $C_{1-3}$-alkyl-NH or $(C_{1-3}$-alkyl$)_2$-N, or $R^4$ denotes a group selected from

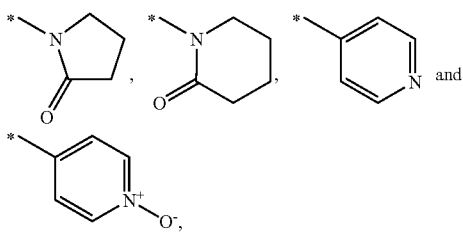

or
$R^4$ denotes a group of general formulae IV

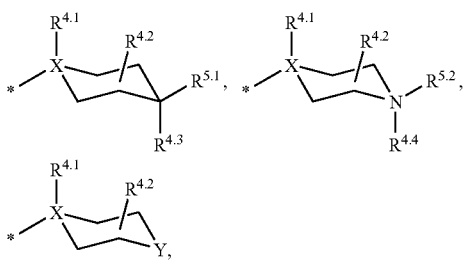

wherein
X denotes C and
$R^{4.1}$ denotes H, OH, $C_{1-3}$-alkyl or
X denotes N and
$R^{4.1}$ denotes a free electron pair or an oxygen atom,
Y denotes O, S, S(O), S(O)$_2$, if X=N, or
Y denotes S, S(O), S(O)$_2$, if X=C,
$R^{4.2}$ denotes H,
$R^{4.3}$ denotes H or $C_{1-3}$-alkyl,
$R^{4.4}$ denotes a free electron pair or, if $R^{5.2}$ is not H or $C_{1-3}$-alkyl-C(O)—, an oxygen atom,
$R^{5.1}$ denotes H, CN, OH, $C_{1-3}$-alkyl, $C_{1-3}$-alkyl-C(O)—O, $C_{1-3}$-alkyl-O, $R^{5.1.1}$—O—C(O), $R^{5.1.1}$—O—C(O)—$C_{2-4}$-alkylene or $R^{5.1.1}$—O—C(O)—$C_{1-3}$-alkylene-O,
$R^{5.1.1}$ denotes H, $C_{1-6}$-alkyl, $H_2N$—C(O)—$C_{1-3}$-alkylene, $C_{1-3}$-alkyl-NH—C(O)—$C_{1-3}$-alkylene, $(C_{1-3}$-alkyl)$_2$-N—C(O)—$C_{1-3}$-alkylene or $C_{1-3}$-alkyl-O—C(O)—O—$C_{1-3}$-alkylene,
$R^{5.2}$ denotes H, $C_{1-3}$-alkyl, $C_{3-6}$-cycloalkyl, $C_{3-6}$-cycloalkyl-$C_{1-3}$-alkylene, $C_{1-3}$-alkyl-C(O), $R^{5.2.1}$—O—C(O)—$C_{1-3}$-alkylene or $R^{5.2.2}$—$C_{2-4}$-alkylene-O—C(O)—$C_{1-3}$-alkylene,
$R^{5.2.1}$ denotes H, $C_{1-6}$-alkyl, $C_{1-6}$-alkyl-C(O)—O—$C_{1-3}$-alkylene, $C_{1-3}$-alkyl-O—C(O)—O—$C_{1-3}$-alkylene, $C_{3-7}$-cycloalkyl-O—C(O)—O—$C_{1-3}$-alkylene, $H_2N$—C(O)—$C_{1-3}$-alkylene, $C_{1-3}$-alkyl-NH—C(O)—$C_{1-3}$-alkylene, $(C_{1-3}$-alkyl)$_2$-N—C(O)—$C_{1-3}$-alkylene or $R^{5.2.1.1}$—C(O)—$C_{1-3}$-alkylene and
$R^{5.2.1.1}$ denotes a group selected from

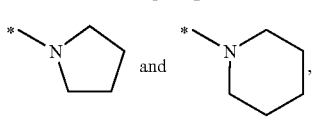

or
$R^{5.2.1}$ denotes a group selected from

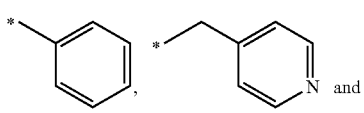

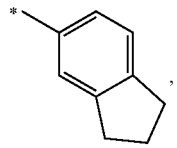

$R^{5.2.2}$ denotes $H_2N$, $C_{1-3}$-alkyl-NH, $(C_{1-3}$-alkyl)$_2$-N, $C_{1-3}$-alkyl-O or $C_{1-3}$-alkyl-O—$C_{2-4}$-alkylene-O, or
$R^{5.2.2}$ denotes a group selected from

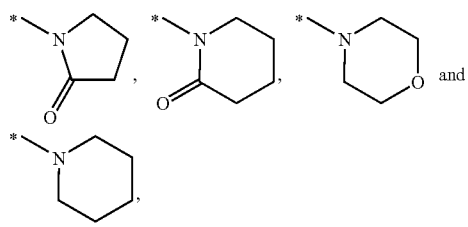

with the proviso that $R^3$ and $R^4$ are not bound to one another simultaneously via an N atom, the tautomers, the diastereomers, the enantiomers, the hydrates, the mixtures thereof and the salts thereof and the hydrates of the salts thereof, particularly the physiologically acceptable salts thereof with inorganic or organic acids or bases.

A third embodiment of the present invention comprises the compounds of the above general formula I, wherein
$R^1$ denotes a group selected from

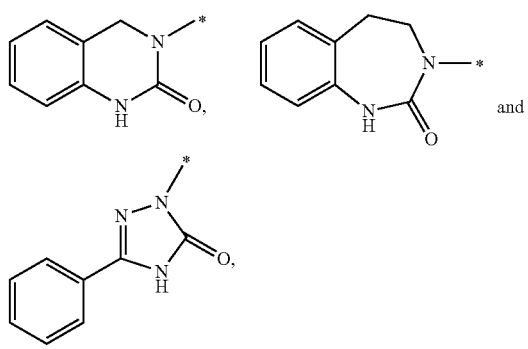

$R^2$ denotes a group selected from

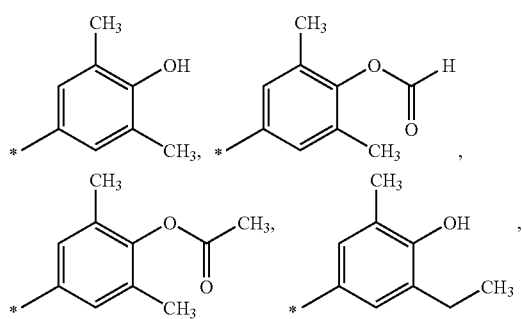

-continued

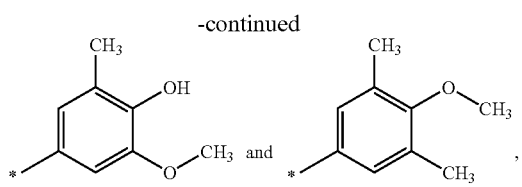

$R^3$ denotes $R^4$—$C_{2-8}$-alkylene-NH— and
  $R^4$ denotes H, $H_2N$, $(C_{1-3}\text{-alkyl})_2$-N or $C_{1-4}$-alkyl-O—C(O)—NH—, or
$R^3$ denotes a group selected from

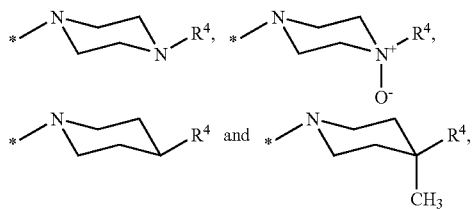

and
$R^4$ denotes H, $C_{1-6}$-alkyl, $(C_{1-3}\text{-alkyl})_2$-N—$C_{1-6}$-alkylene, $C_{3-6}$-cycloalkyl-$C_{1-3}$-alkylene or $(C_{1-3}\text{-alkyl})_2$-N, or
$R^4$ denotes a group selected from

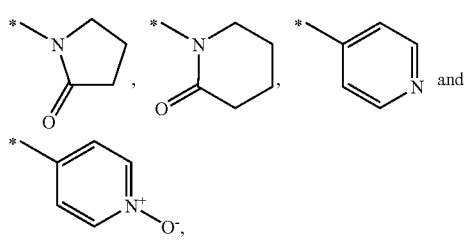

or
$R^4$ denotes a group selected from

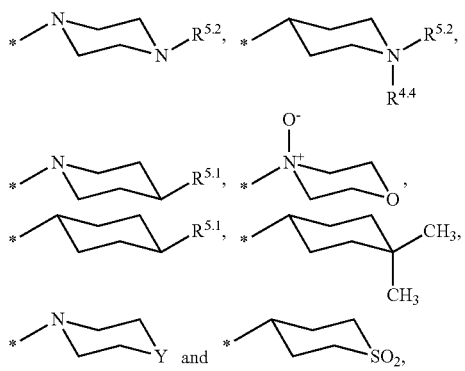

wherein
  Y denotes O, S, S(O), $S(O)_2$,
  $R^{4.4}$ denotes a free electron pair or, if $R^{5.2}$ is not H or $C_{1-3}$-alkyl-C(O)—, an oxygen atom, $R^{5.1}$ denotes H, CN, OH, $C_{1-3}$-alkyl, $C_{1-3}$-alkyl-C(O)—O, $C_{1-3}$-alkyl-O, $R^{5.1.1}$—O—C(O), $R^{5.1.1}$—O—C(O)—$C_{2-4}$-alkylene or $R^{5.1.1}$—O—C(O)—$C_{1-3}$-alkylene-O, $R^{5.1.1}$ denotes H, $C_{1-6}$-alkyl, $H_2N$—C(O)—$C_{1-3}$-alkylene, $C_{1-3}$-alkyl-NH—C(O)—$C_{1-3}$-alkylene, $(C_{1-3}\text{-alkyl})_2$-N—C(O)—$C_{1-3}$-alkylene or $C_{1-3}$-alkyl-O—C(O)—O—$C_{1-3}$-alkylene, $R^{5.2}$ denotes H, $C_{1-3}$-alkyl, cyclopropyl, cyclopropyl-methylene, $C_{1-3}$-alkyl-C(O), $R^{5.2.1}$—O—C(O)—$C_{1-3}$-alkylene or $R^{5.2.2}$—$C_{2-4}$-alkylene-O—C(O)—$C_{1-3}$-alkylene, $R^{5.2.1}$ denotes H, $C_{1-6}$-alkyl, $C_{1-6}$-alkyl-C(O)—O—$C_{1-3}$-alkylene, $C_{1-3}$-alkyl-O—C(O)—O—$C_{1-3}$-alkylene, $(C_{1-3}\text{-alkyl})_2$-N—C(O)—$C_{1-3}$-alkylene or $R^{5.2.1.1}$—C(O)—$C_{1-3}$-alkylene and $R^{5.2.1.1}$ denotes a group selected from

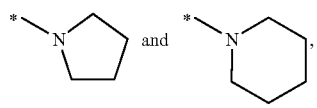

or
$R^{5.2.1}$ denotes a group selected from

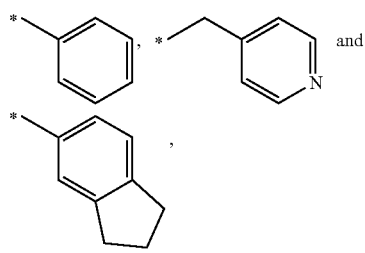

$R^{5.2.2}$ denotes $(C_{1-3}\text{-alkyl})_2$-N, $C_{1-3}$-alkyl-O or $C_{1-3}$-alkyl-O—$C_{2-4}$-alkylene-O, or
$R^{5.2.2}$ denotes a group selected from

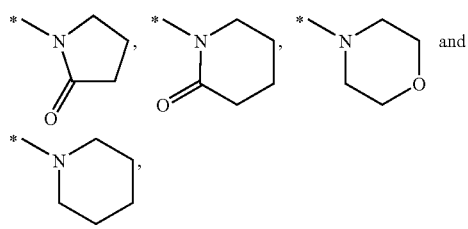

with the proviso that $R^3$ and $R^4$ are not bound to one another simultaneously via an N atom, the tautomers, the diastereomers, the enantiomers, the hydrates, the mixtures thereof and the salts thereof and the hydrates of the salts thereof, particularly the physiologically acceptable salts thereof with inorganic or organic acids or bases.

A fourth embodiment of the present invention comprises the compounds of the above general formula I, wherein R[1] denotes a group selected from
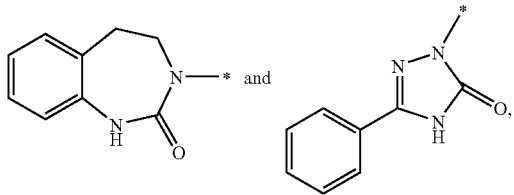
R[2] denotes a group selected from
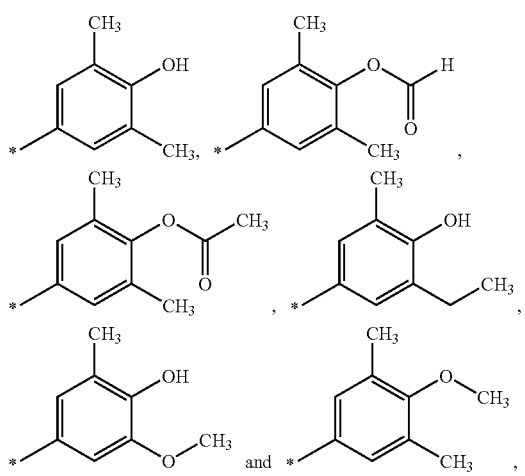
R[3]-R[4] together denote a group selected from
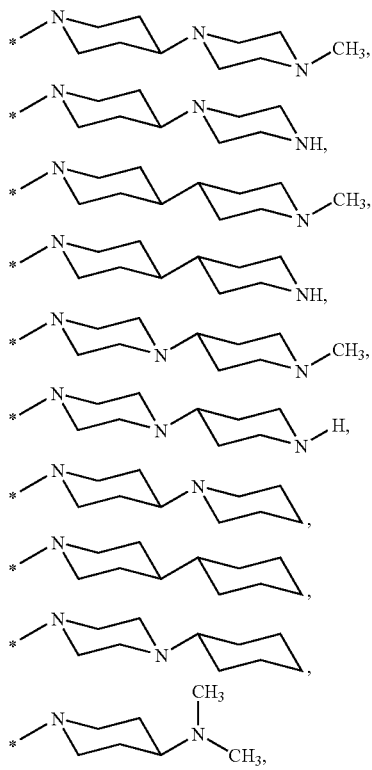
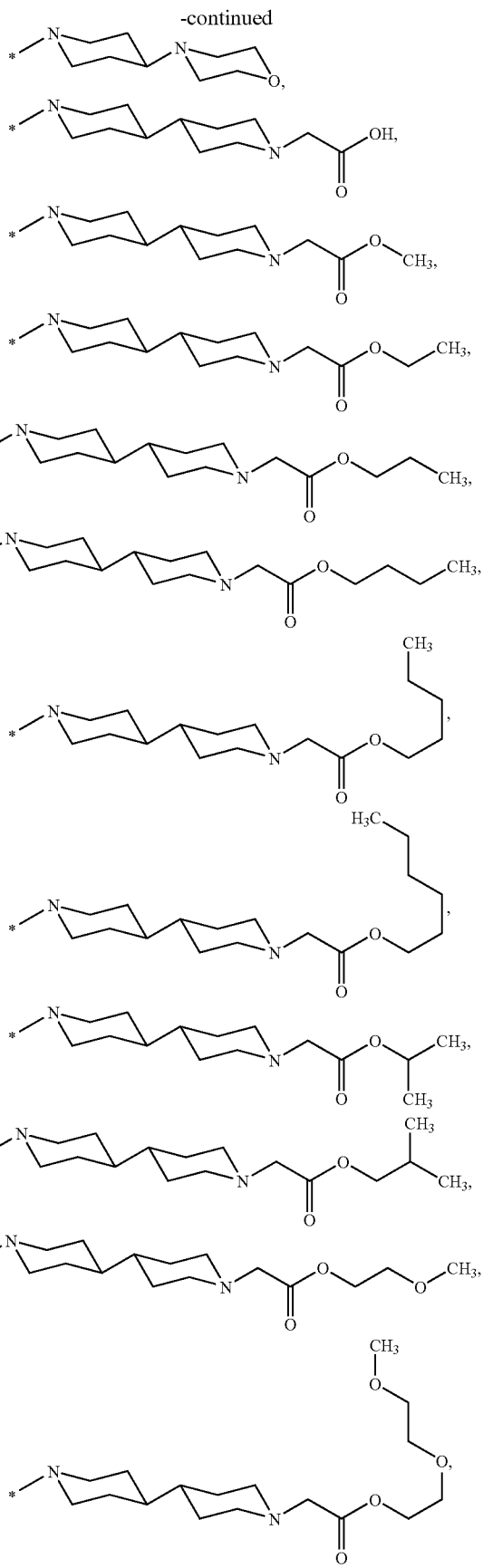

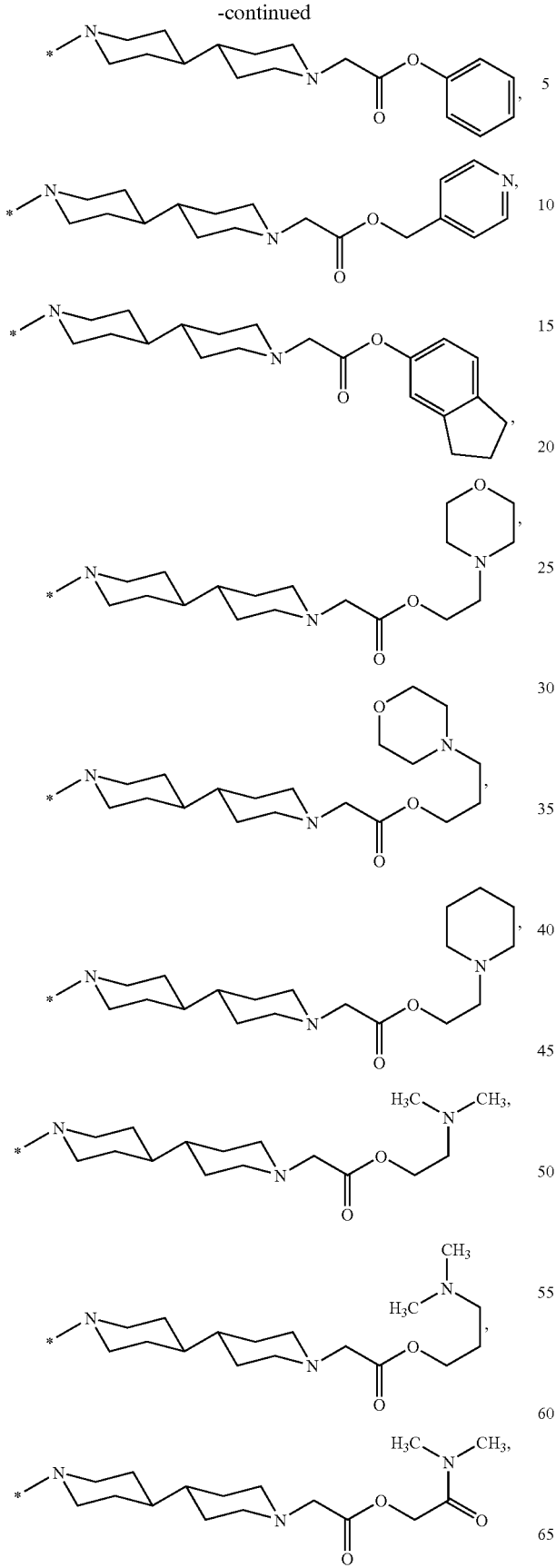
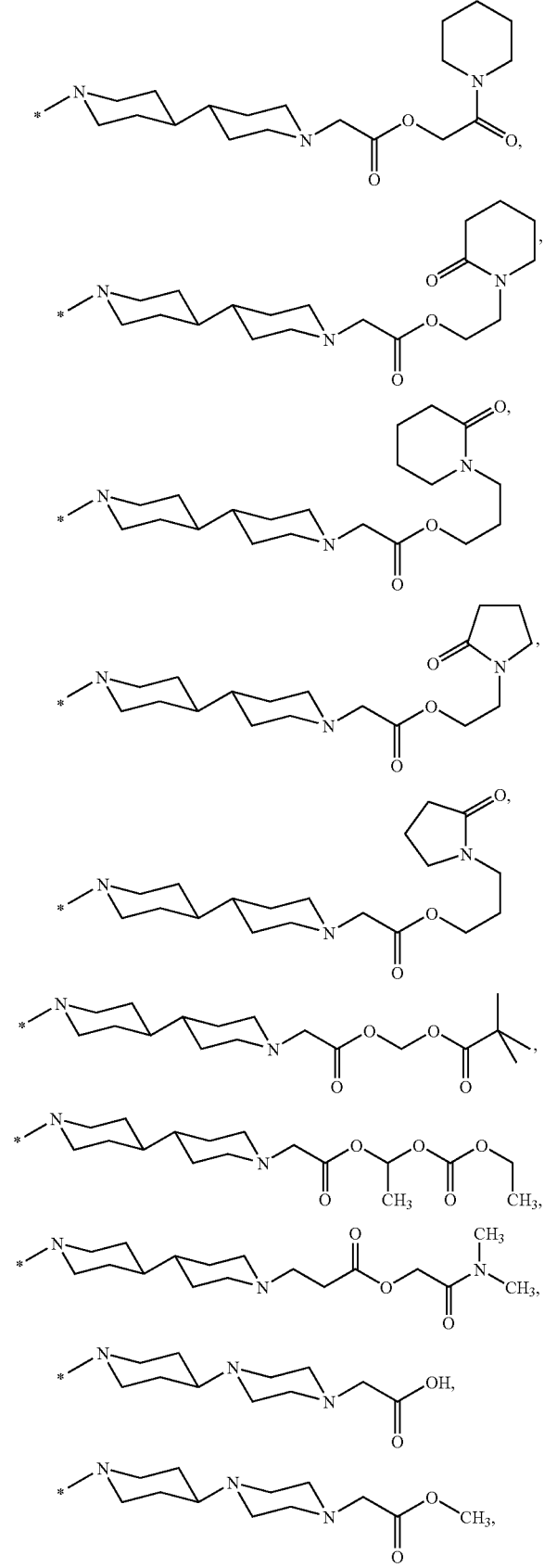

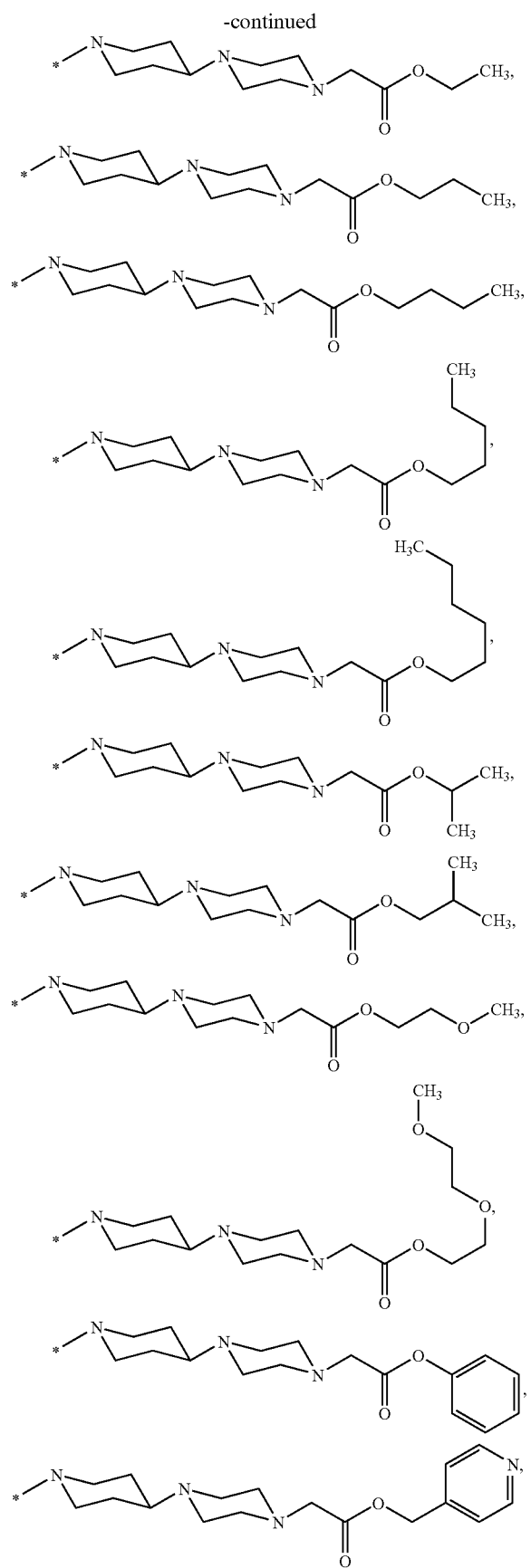
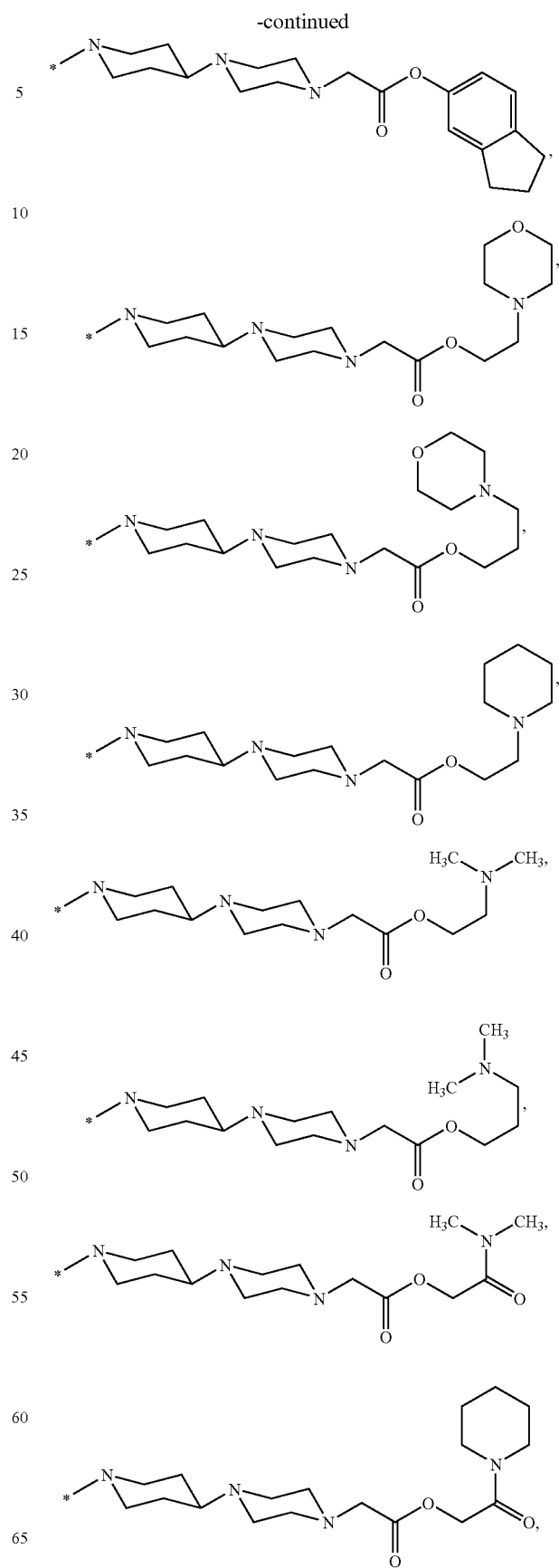

-continued
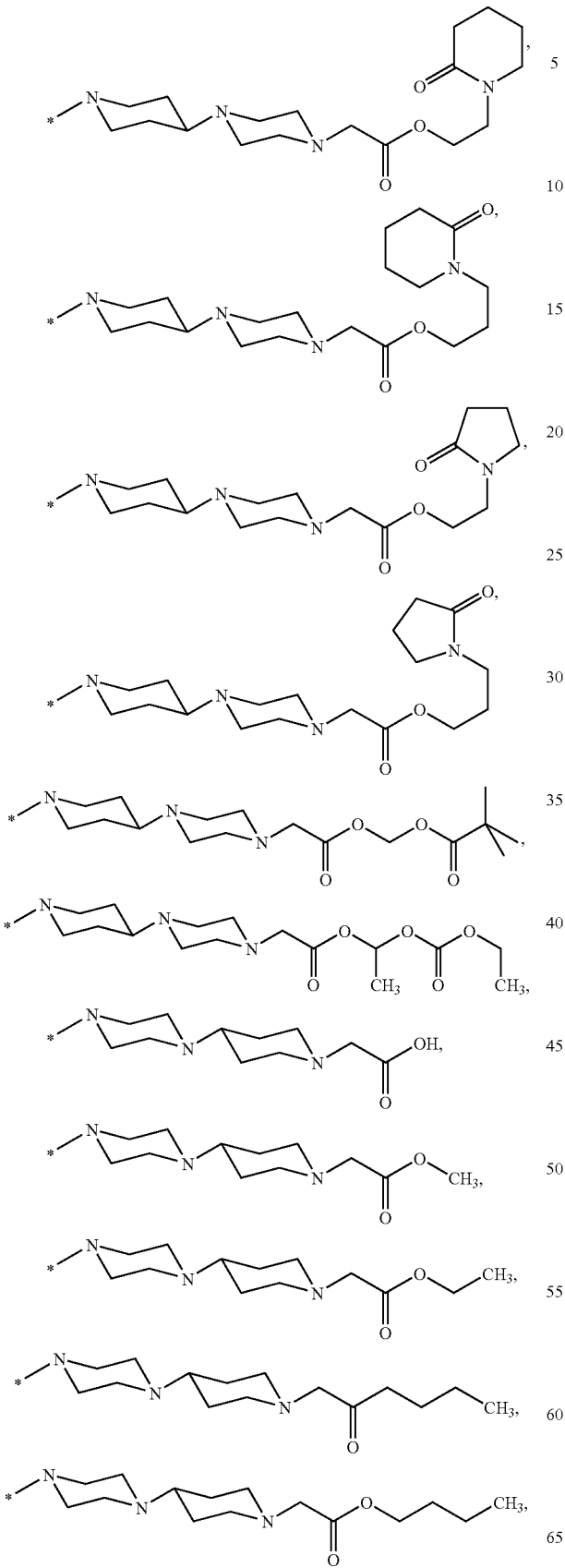
-continued
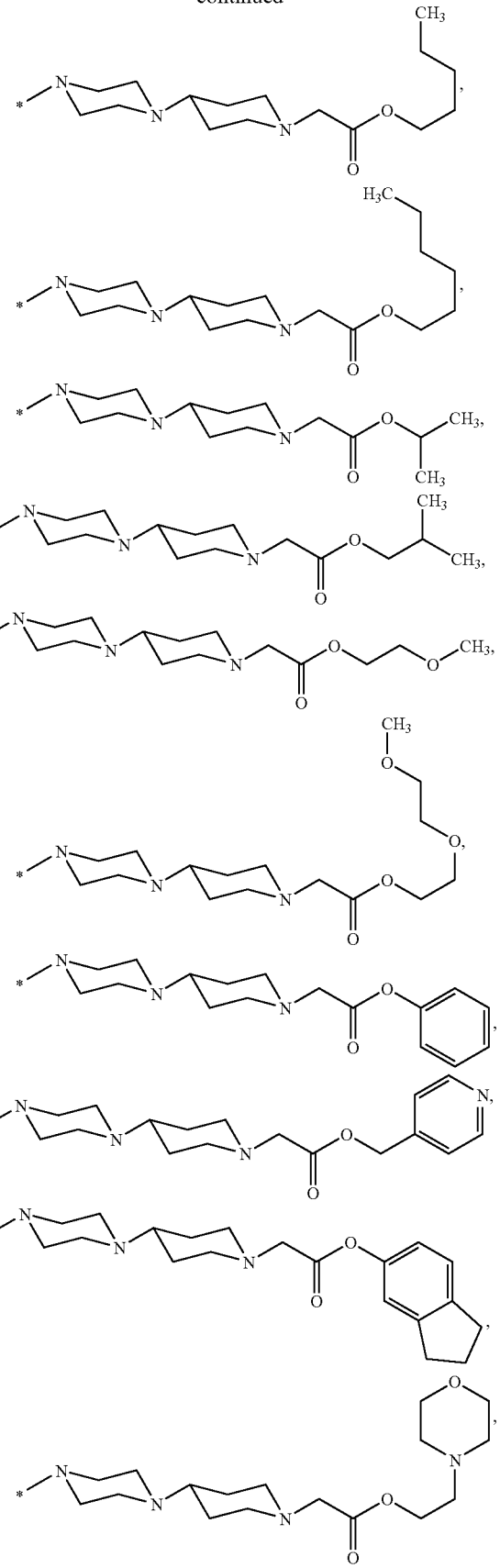

-continued
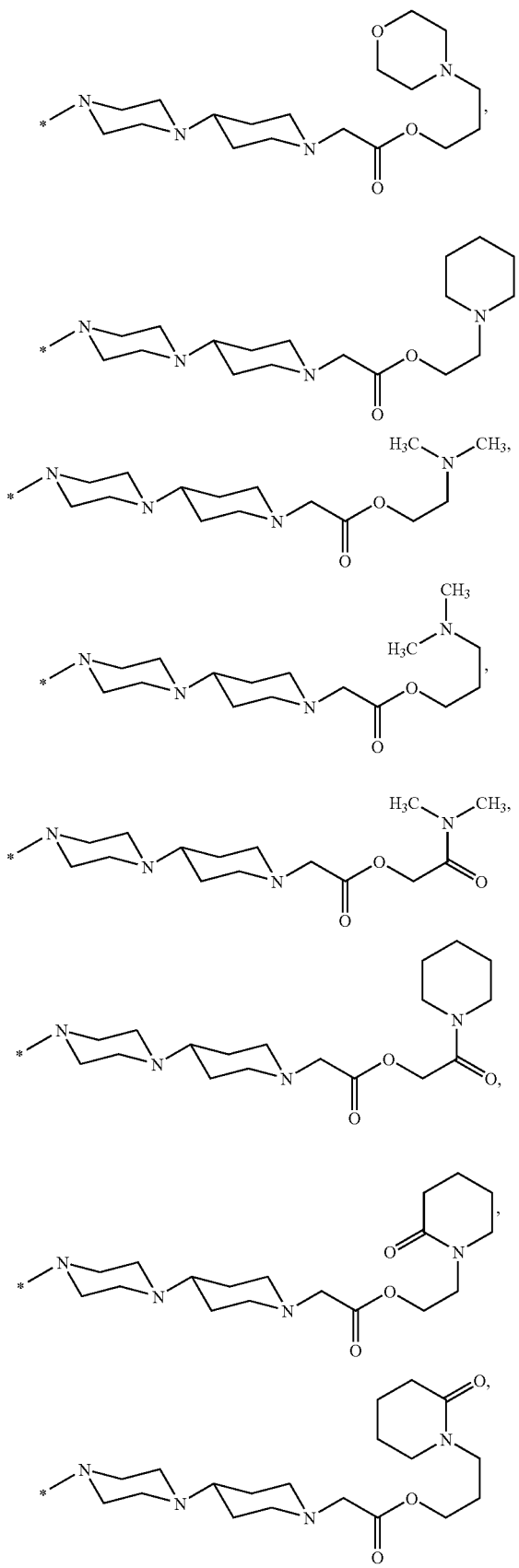
-continued
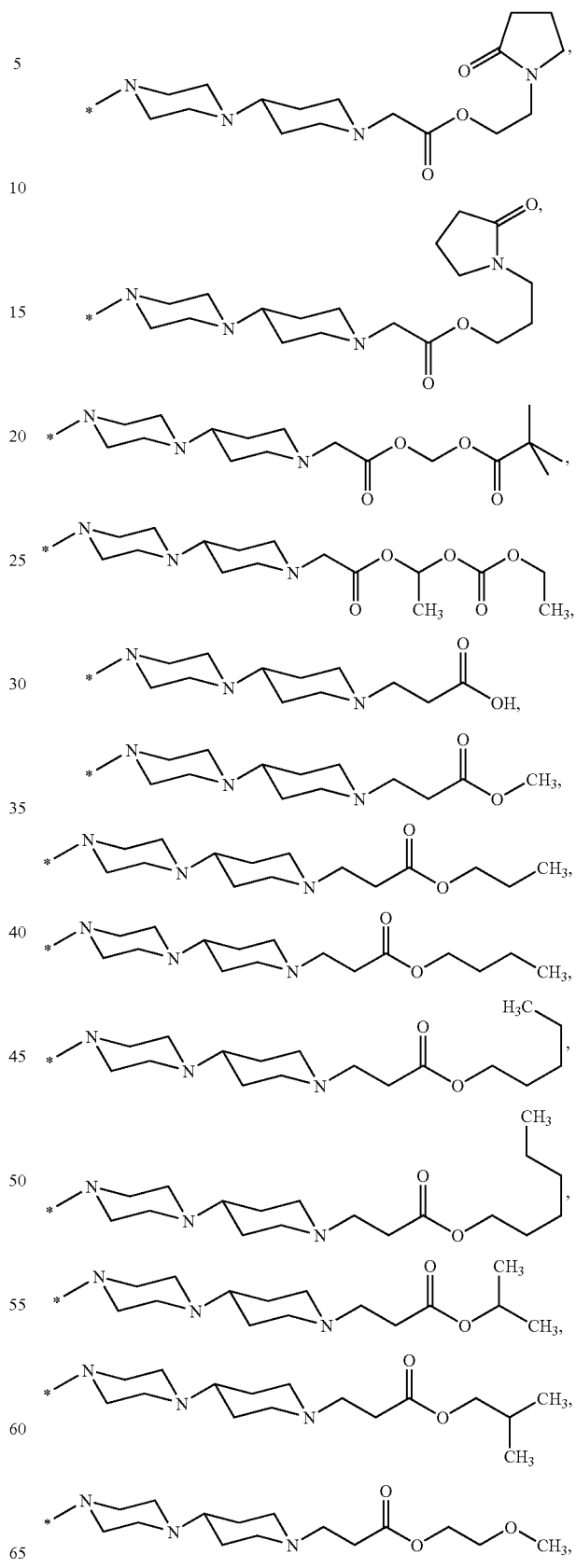

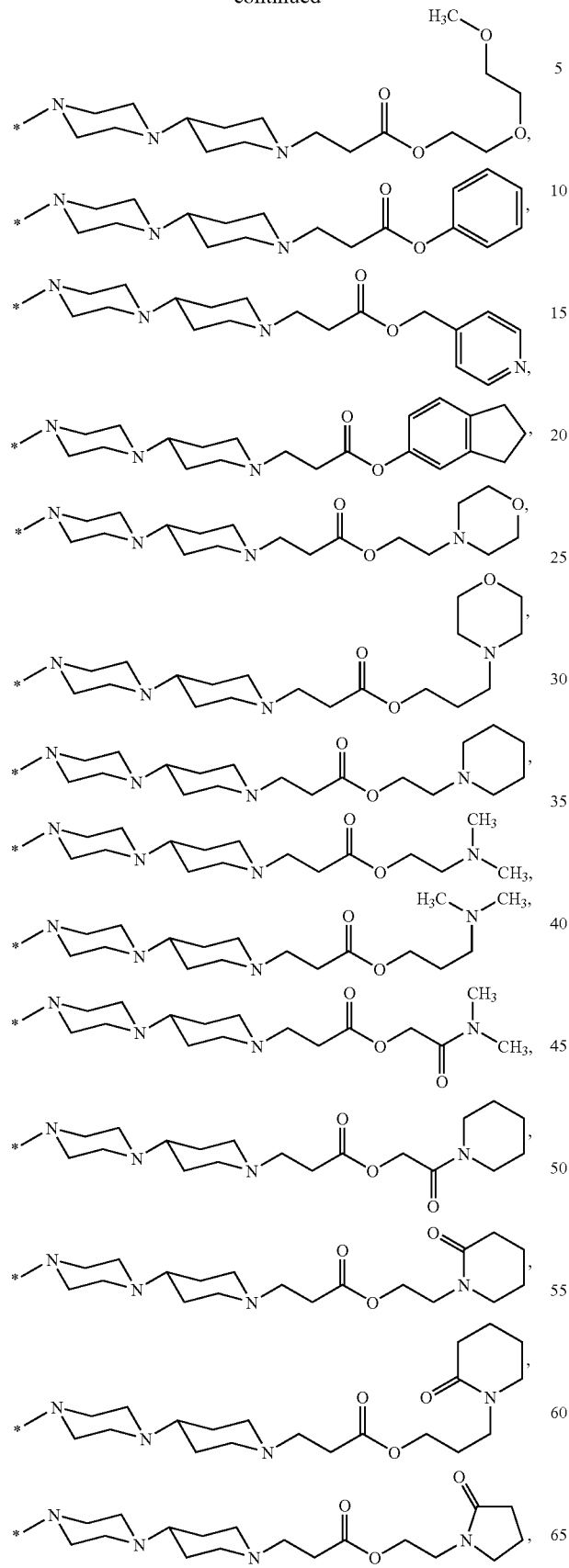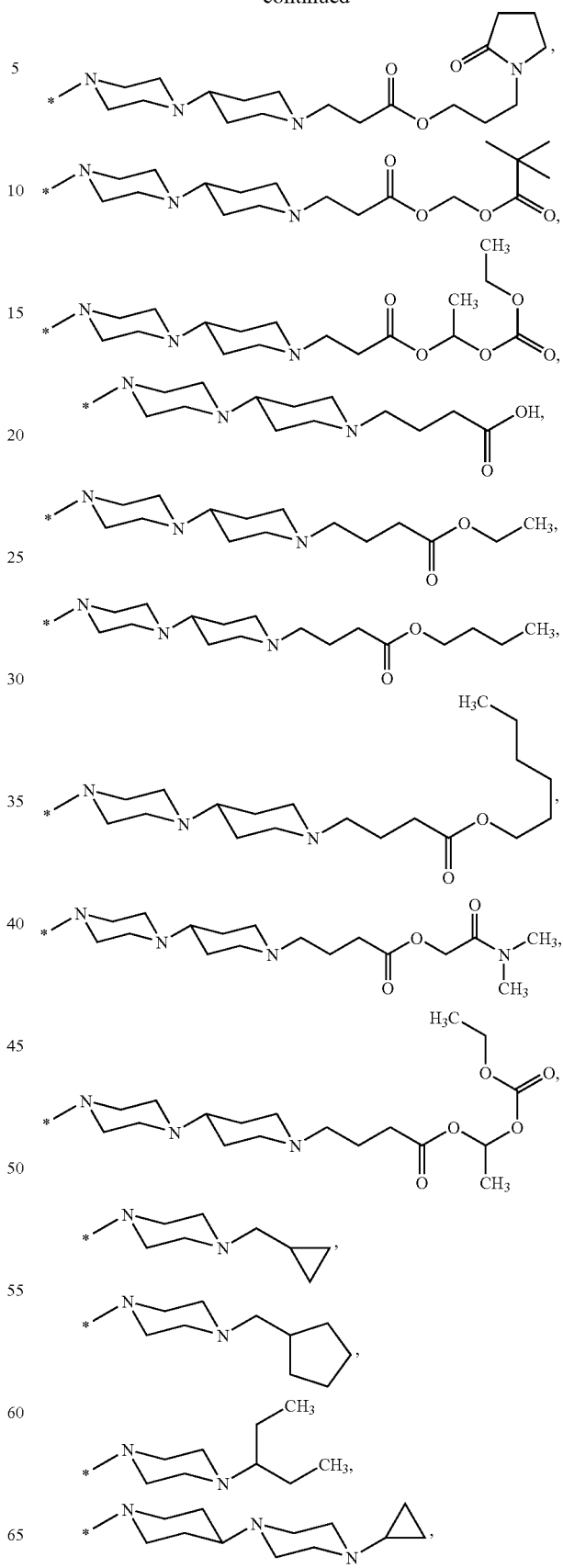

-continued
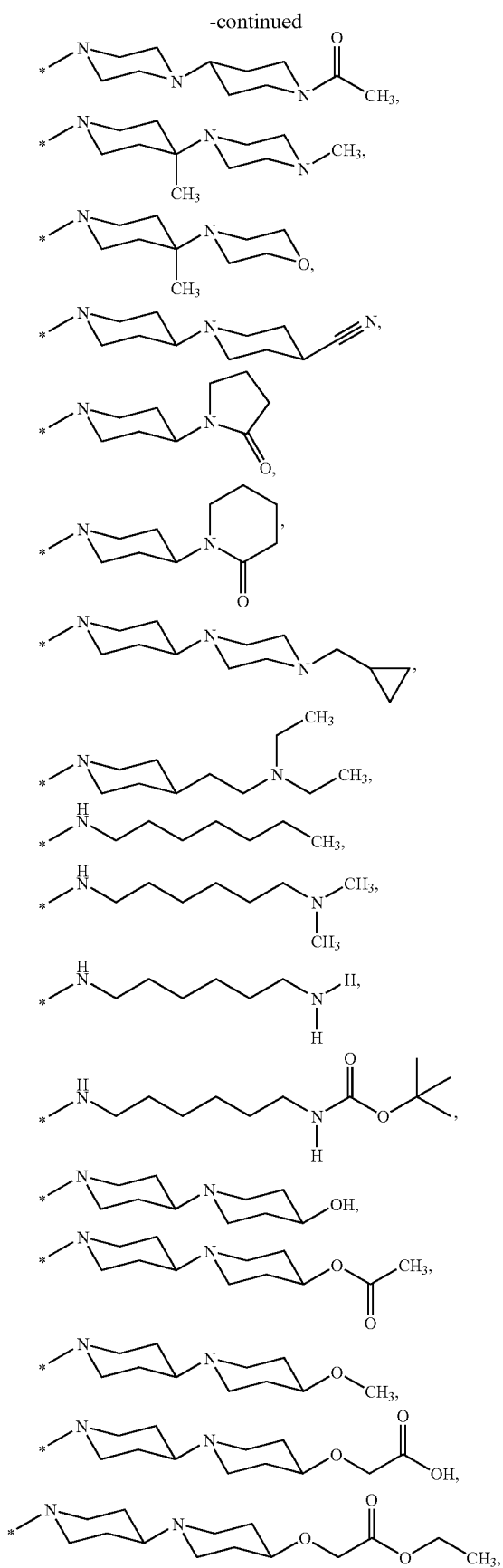
-continued
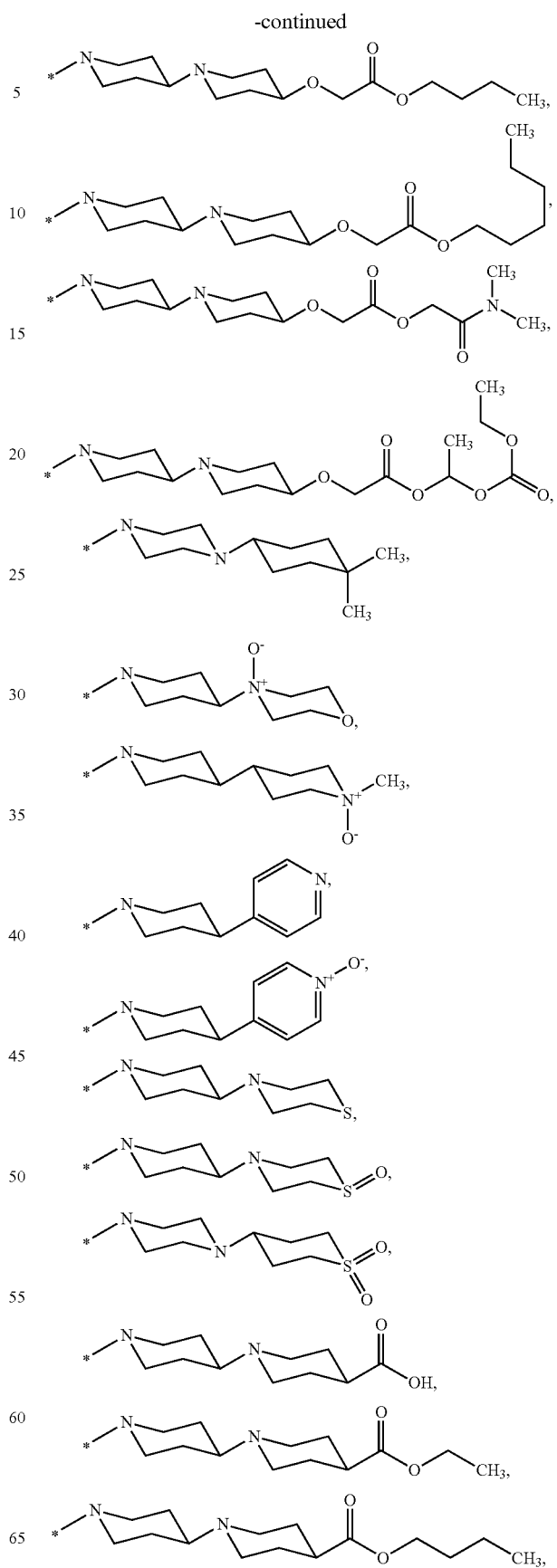

-continued

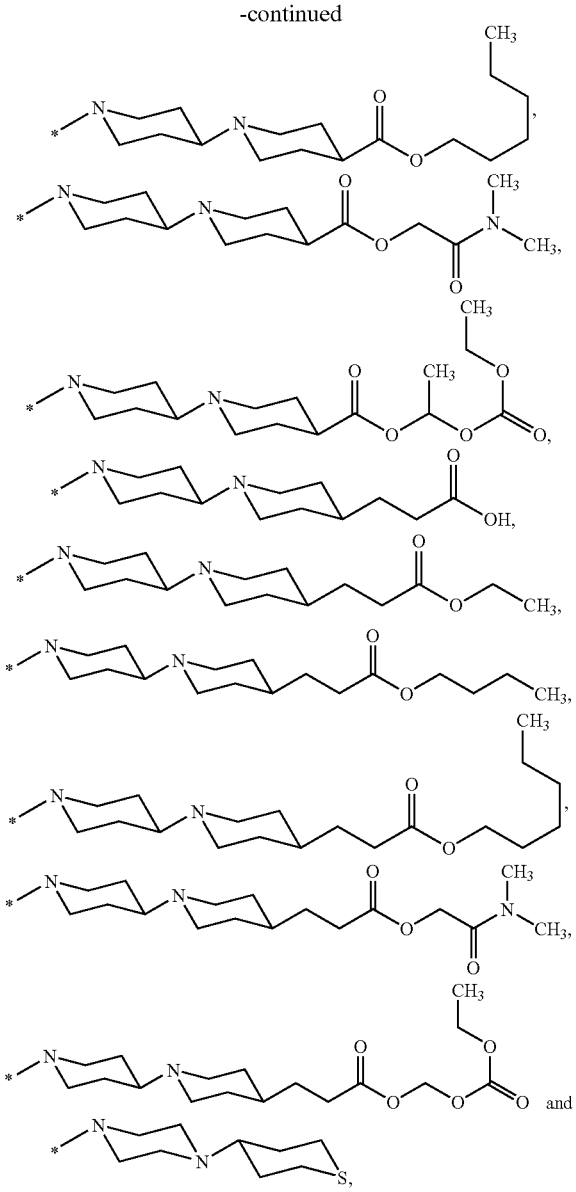

the tautomers, the diastereomers, the enantiomers, the hydrates, the mixtures thereof and the salts thereof and the hydrates of the salts thereof, particularly the physiologically acceptable salts thereof with inorganic or organic acids or bases.

A fifth embodiment of the present invention comprises the compounds of the above general formula I, wherein $R^1$ denotes a group selected from

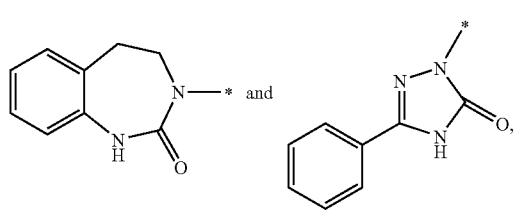

$R^2$ denotes a group selected from

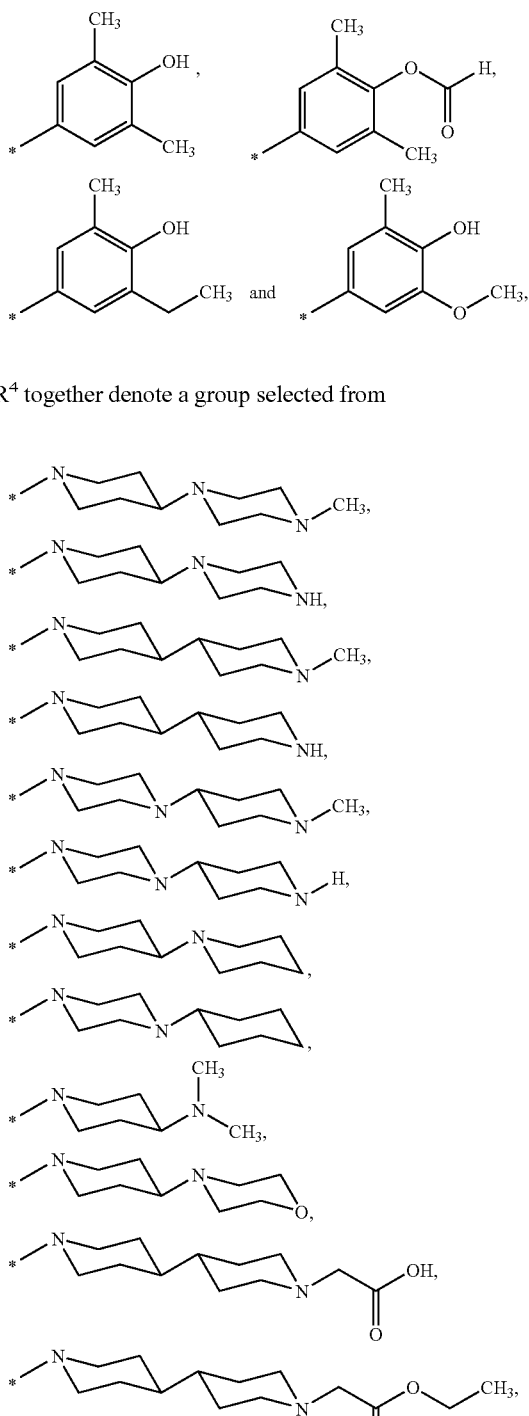

$R^3$-$R^4$ together denote a group selected from

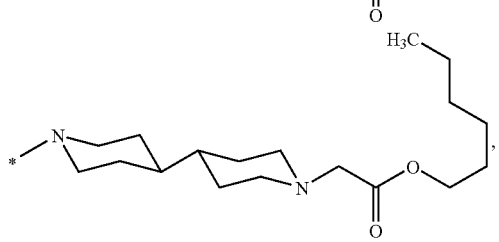

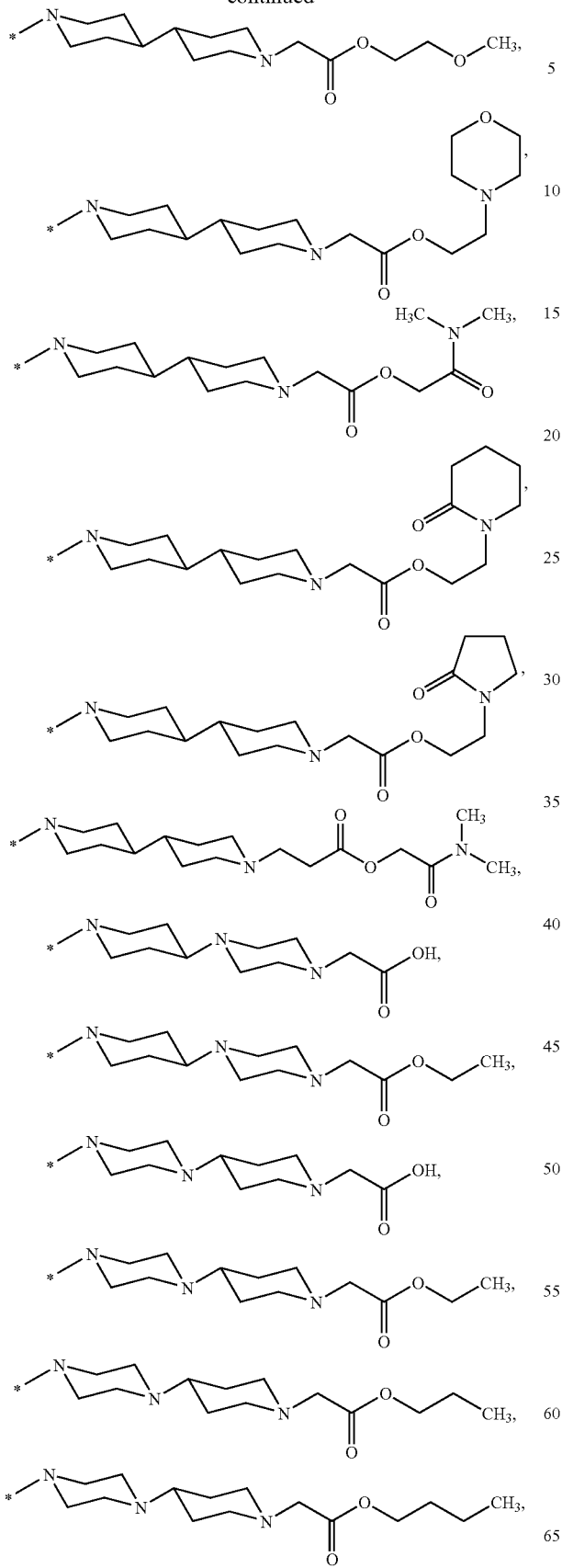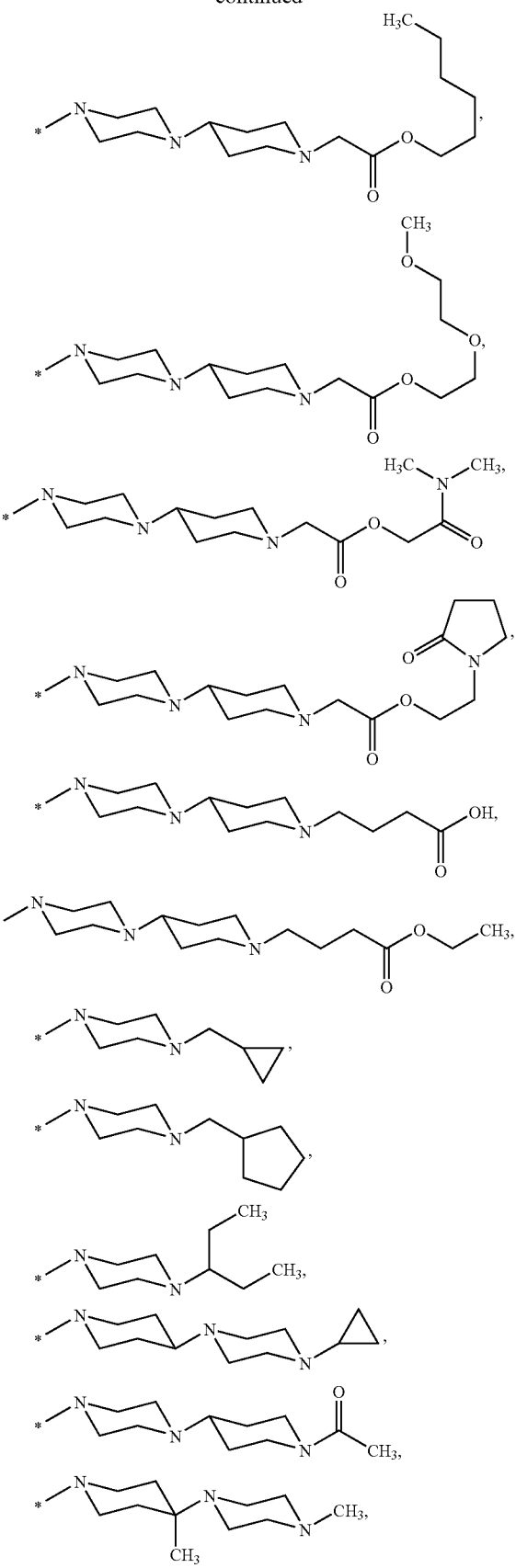

-continued

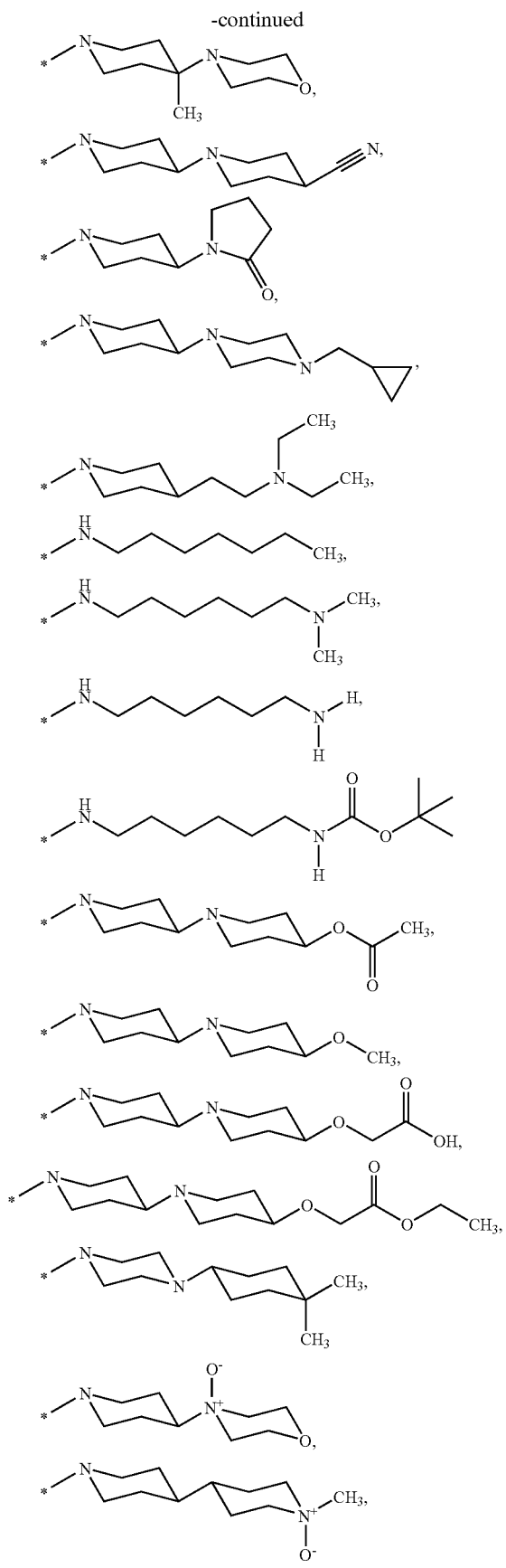

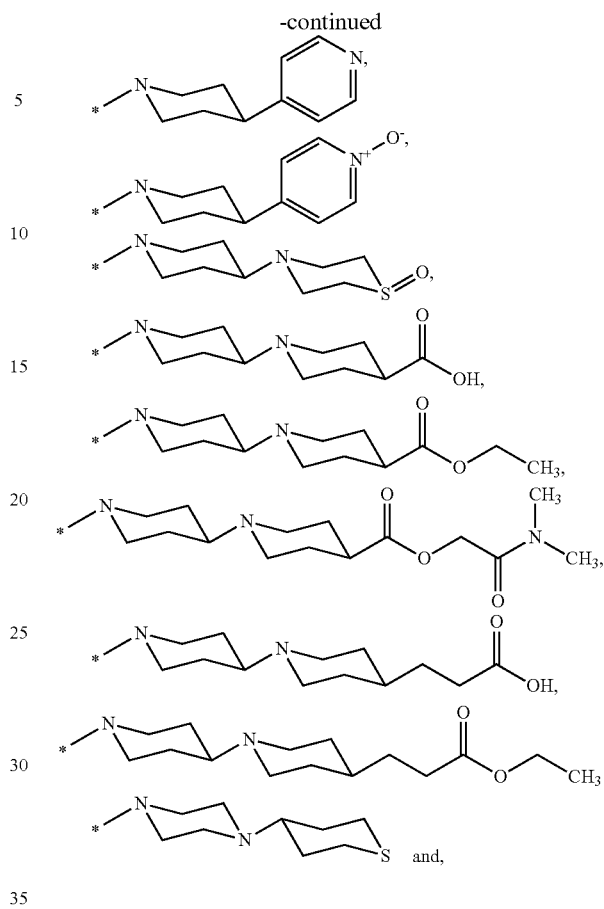

the tautomers, the diastereomers, the enantiomers, the hydrates, the mixtures thereof and the salts thereof and the hydrates of the salts thereof, particularly the physiologically acceptable salts thereof with inorganic or organic acids or bases.

A sixth embodiment of the present invention comprises the compounds of the above general formula I, wherein $R^1$ denotes a group

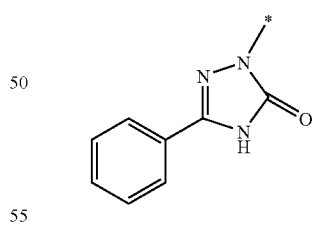

and $R^2$, $R^3$ and $R^4$ are as hereinbefore defined in the first embodiment, the tautomers, the diastereomers, the enantiomers, the hydrates, the mixtures thereof and the salts thereof and the hydrates of the salts thereof, particularly the physiologically acceptable salts thereof with inorganic or organic acids or bases.

A seventh embodiment of the present invention comprises the compounds of the above general formula I, wherein $R^1$ denotes a group

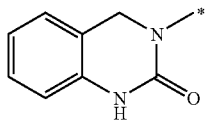

and $R^2$, $R^3$ and $R^4$ are as defined in the first embodiment hereinbefore, the tautomers, the diastereomers, the enantiomers, the hydrates, the mixtures thereof and the salts thereof and the hydrates of the salts thereof, particularly the physiologically acceptable salts thereof with inorganic or organic acids or bases.

An eighth embodiment of the present invention comprises the compounds of the above general formula I, wherein $R^1$ denotes a group

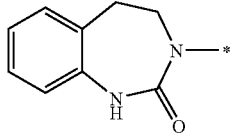

and $R^2$, $R^3$ and $R^4$ are as defined in the first embodiment hereinbefore, with the proviso that the compounds (a) (R)-1-(4-hydroxy-3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate, (b) (R)-1-(4-hydroxy-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (c) (R)-1-(4-hydroxy-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate, (d) (R)-1-(4-hydroxy-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate, (e) (R)-1-(4-hydroxy-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate, (f) (R)-2-4,4'-bipiperidinyl-1-yl-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (g) (R)-2-1,4'-bipiperidinyl-1'-yl-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (h) (R)-2-(4-dimethylamino-piperidin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (i) (R)-1-(4-methoxy-3,5-dimethyl-benzyl)-2-[4-(1-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate, (j) (R)-1-(4-methoxy-3,5-dimethyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate, (k) (R)-1-(4-methoxy-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate, (l) (R)-1-(4-methoxy-3,5-dimethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate, (m) (R)-1-(4-methoxy-3,5-dimethyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate, (n) (R)-2-4,4'-bipiperidinyl-1-yl-1-(4-methoxy-3,5-dimethyl-benzyl)-2-oxo-ethyl 4-(2-oxo-1,2,4,5-tetrahydro-1,3-benzodiazepin-3-yl)-piperidine-1-carboxylate, (o) (R)-2-1,4'-bipiperidinyl-1'-yl-1-(4-methoxy-3,5-dimethyl-benzyl)-2-oxo-ethyl 4-(2-oxo-1,2,4,5-tetrahydro-1,3-benzodiazepin-3-yl)-piperidine-1-carboxylate, (p) (R)-2-(4-dimethylamino-piperidin-1-yl)-1-(4-methoxy-3,5-dimethyl-benzyl)-2-oxo-ethyl 4-(2-oxo-1,2,4,5-tetrahydro-1,3-benzodiazepin-3-yl)-piperidine-1-carboxylate, (q) (R)-1-(4-hydroxy-3,5-dimethyl-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate, (r) (R)-2-(4-cyclohexyl-piperazin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (s) (R)-2-(4,4-dimethyl-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (t) (R)-2-(4-hydroxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (u) (R)-1-(4-hydroxy-3,5-dimethyl-benzyl)-2-(4-hydroxy-4-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate, (v) (R)-2-(4-ethyl-4-hydroxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (w) (R)-2-[4-(1,1-dioxo-1$\lambda^6$-thiomorpholin-4-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (x) (R)-2-(1'-ethoxycarbonylmethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (y) (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (z) (R)-2-[4-(4-ethoxycarbonylmethyl-piperazin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (aa) (R)-2-[4-(4-carboxymethyl-piperazin-1-yl)-piperidin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ab) (R)-2-[4-(1-ethoxycarbonylmethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ac) (R)-2-[4-(1-carboxymethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ad) (R)-2-[1'-(2-ethoxycarbonyl-ethyl)-4,4'-bipiperidinyl-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ae) (R)-2-[1'-(2-carboxy-ethyl)-4,4'-bipiperidinyl-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (af) (R)-2-{4-[1-(2-ethoxycarbonyl-ethyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ag) (R)-2-{4-[1-(2-carboxy-ethyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ah) (R)-2-{4-[4-(2-ethoxycarbonyl-ethyl)-piperazin-1-yl]-piperidin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, (ai) (R)-2-{4-[4-(2-carboxy-ethyl)-piperazin-1-yl]-piperidin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, are excluded from the scope of protection, the tautomers, the diastereomers, the enantiomers, the hydrates, the mixtures thereof and the salts thereof and the hydrates of the salts thereof, particularly the physiologically acceptable salts thereof with inorganic or organic acids or bases.

The following compounds are mentioned as examples of most particularly preferred compounds of the above general formula I:

| No. | Structure |
|---|---|
| (1) | 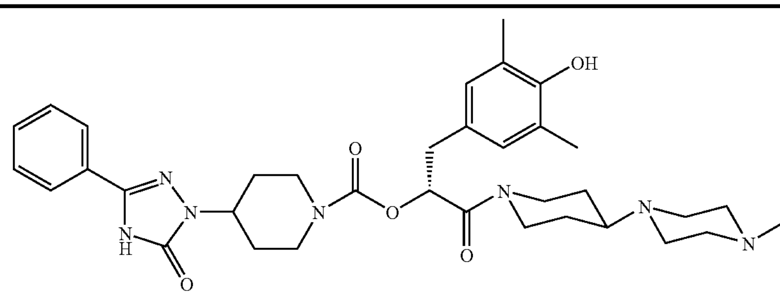 |
| (2) | 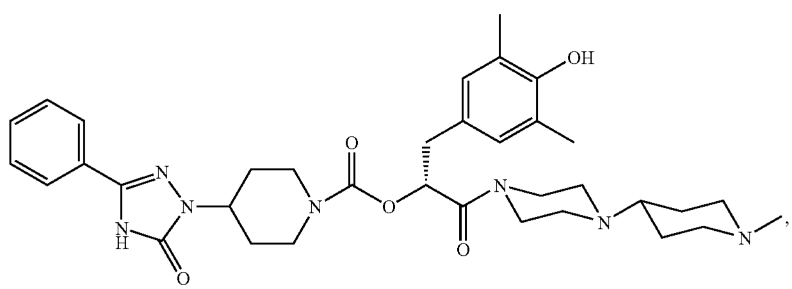 |
| (3) | 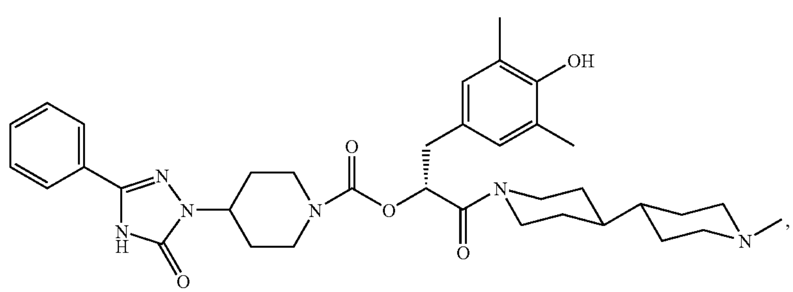 |

-continued

| No. | Structure |
|---|---|
| (4) | 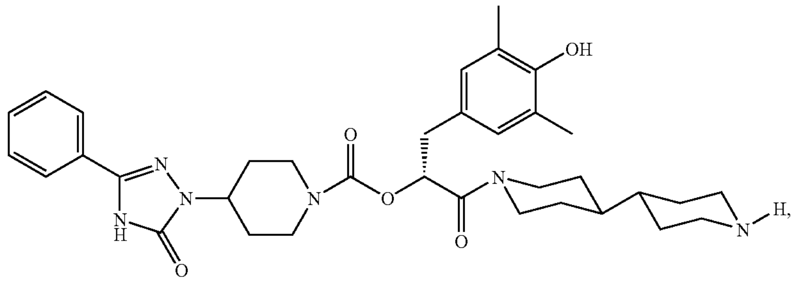 |
| (5) | 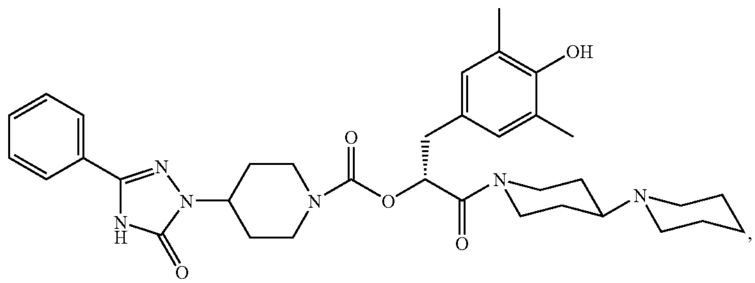 |
| (6) | 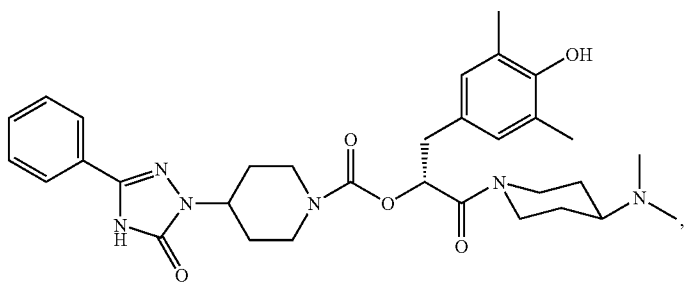 |
| (7) | 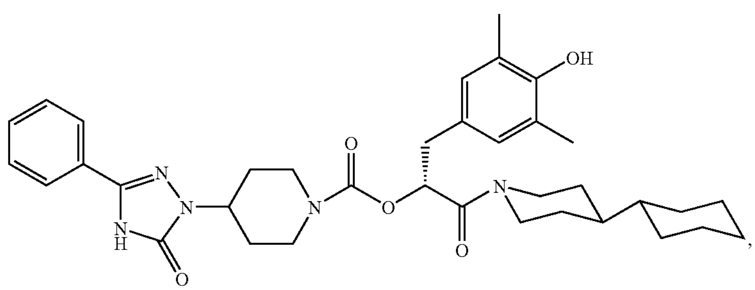 |
| (8) | 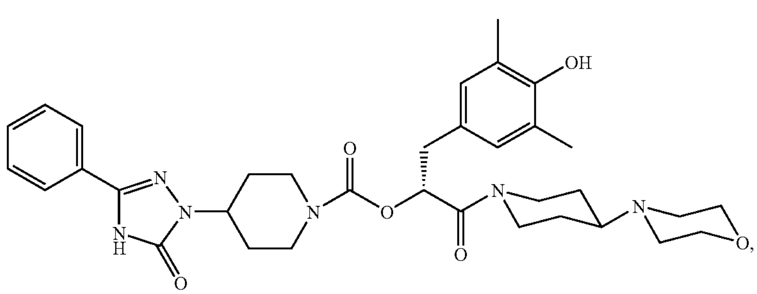 |

-continued
| No. | Structure |
|---|---|
| (9) | 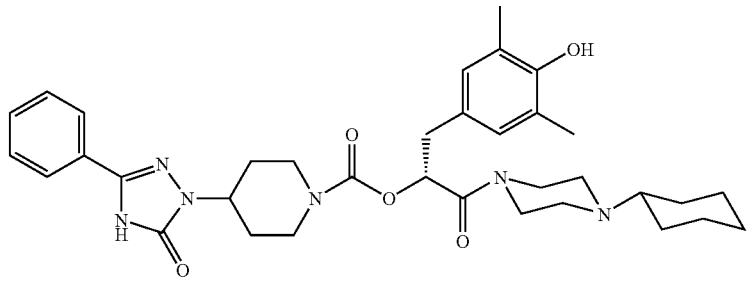 |
| (10) | 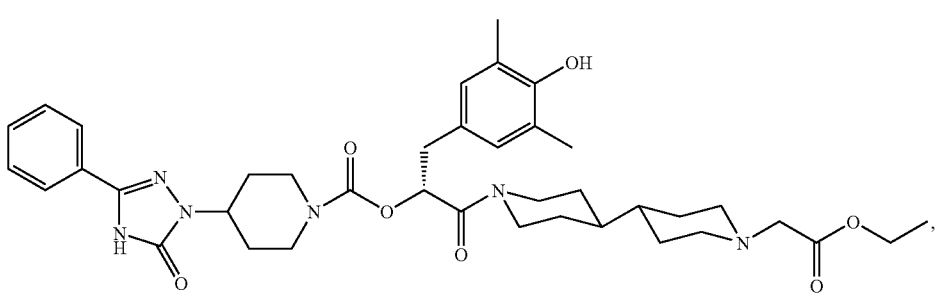 |
| (11) | 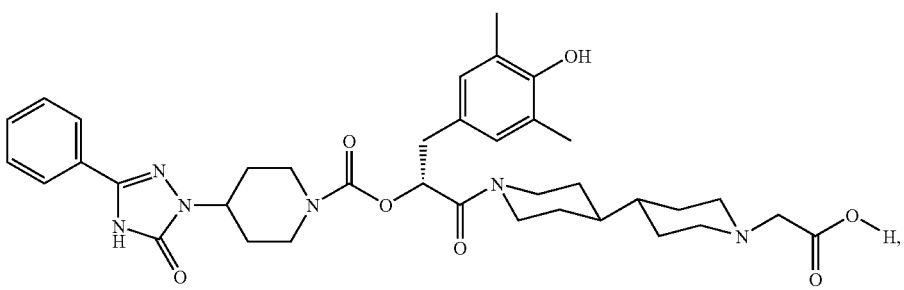 |
| (12) | 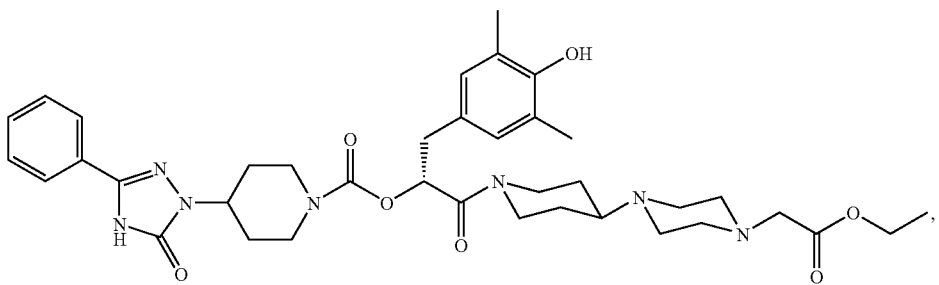 |
| (13) | 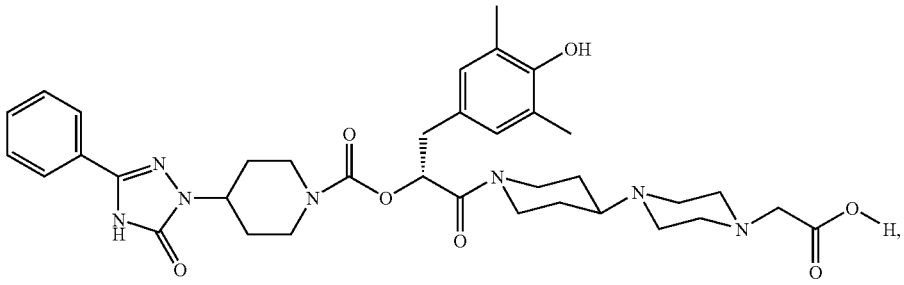 |

-continued

| No. | Structure |
|-----|-----------|
| (14) | 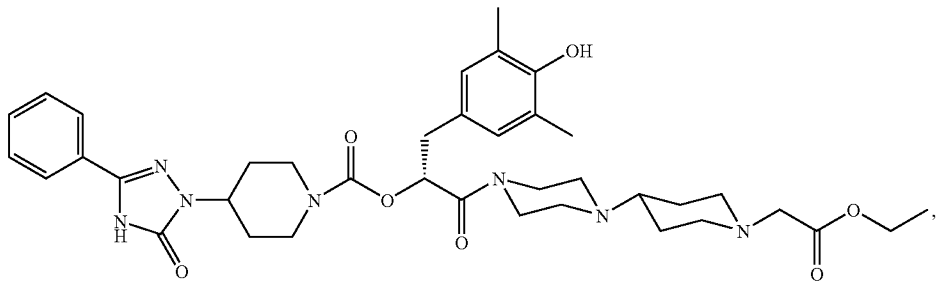 |
| (15) | 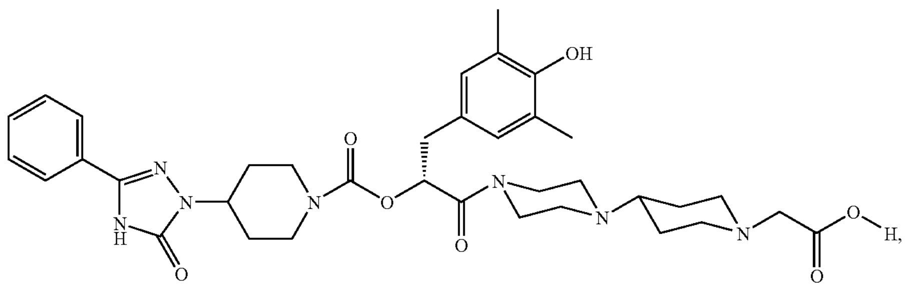 |
| (16) | 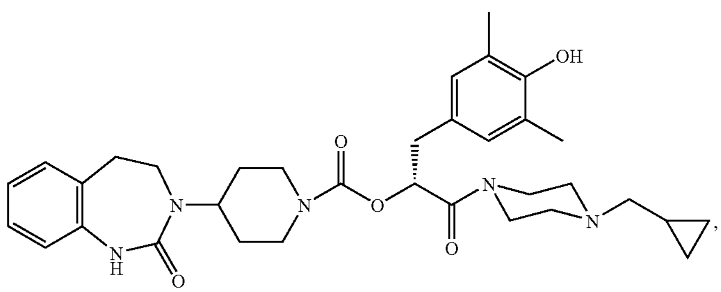 |
| (17) | 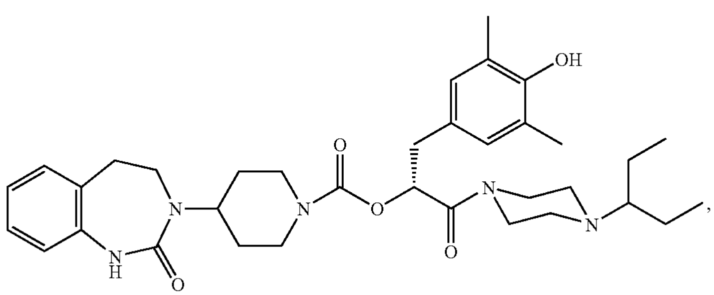 |
| (18) | 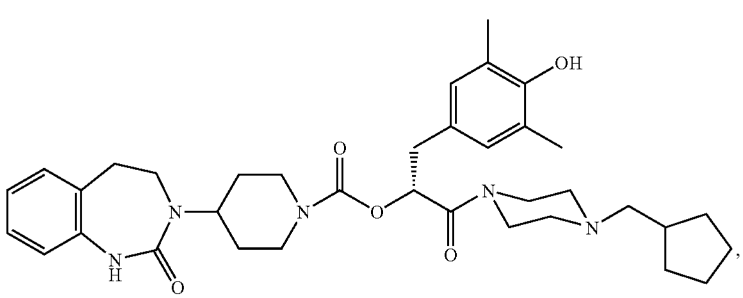 |

-continued
| No. | Structure |
|---|---|
| (19) | 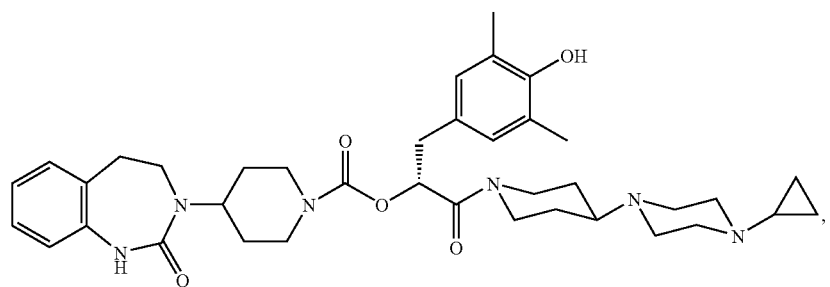 |
| (20) | 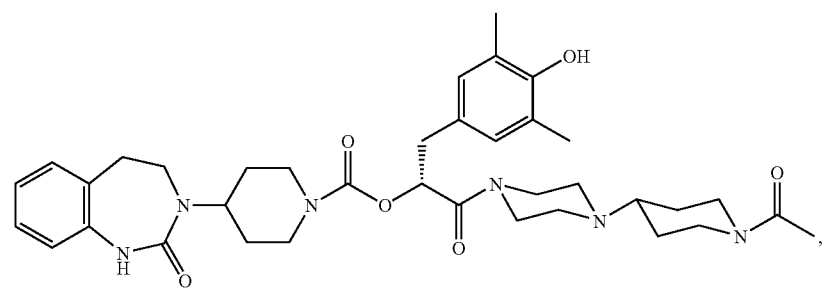 |
| (21) | 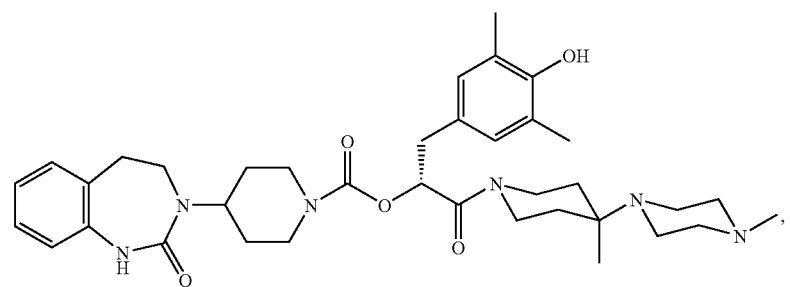 |
| (22) | 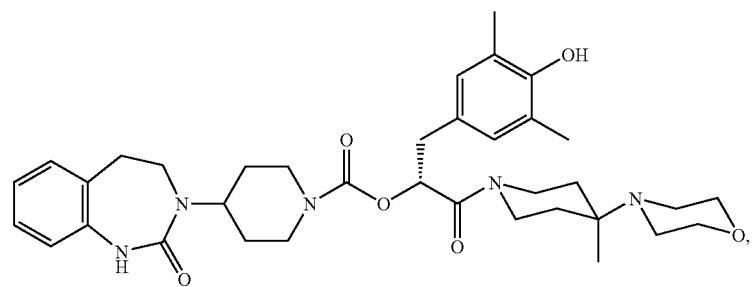 |
| (23) | 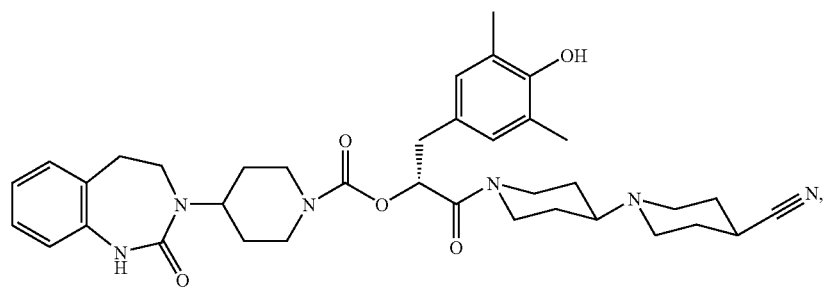 |

-continued
| No. | Structure |
|---|---|
| (24) | 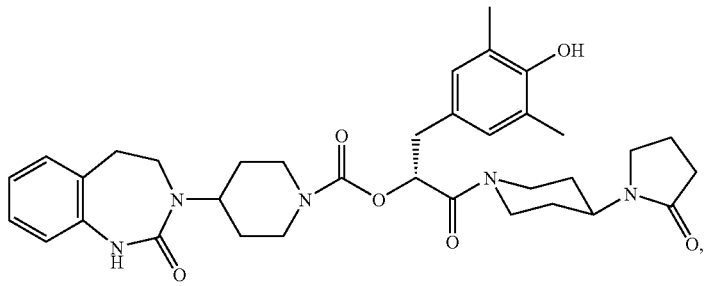 |
| (25) | 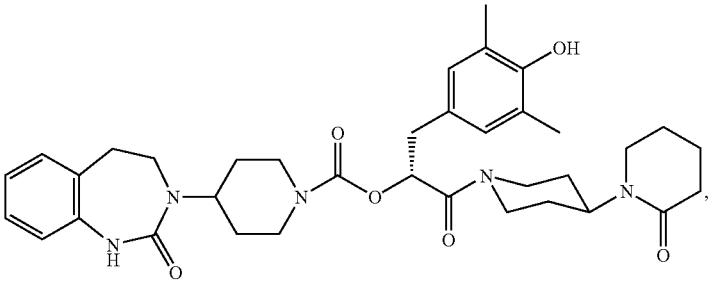 |
| (26) | 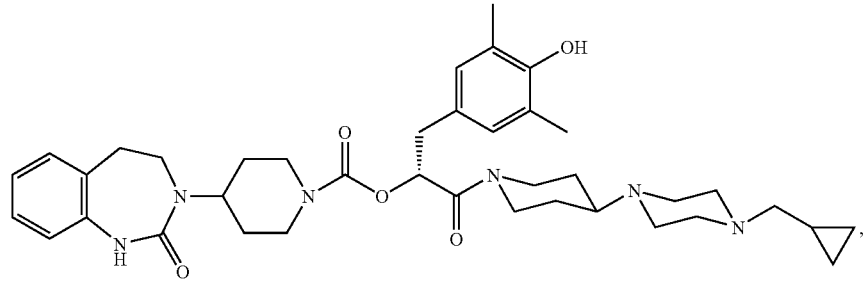 |
| (27) | 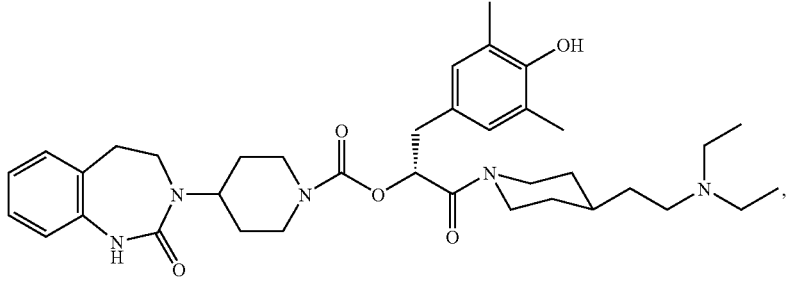 |
| (28) | 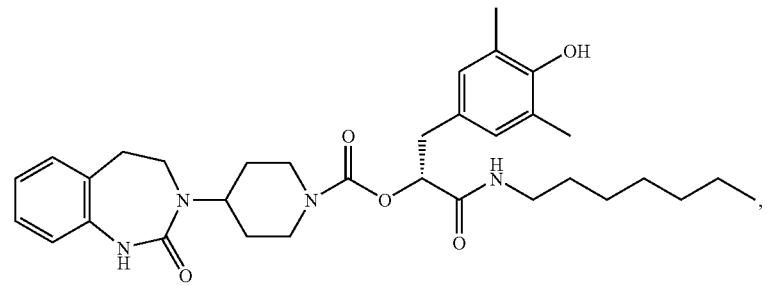 |

-continued
| No. | Structure |
|---|---|
| (29) | 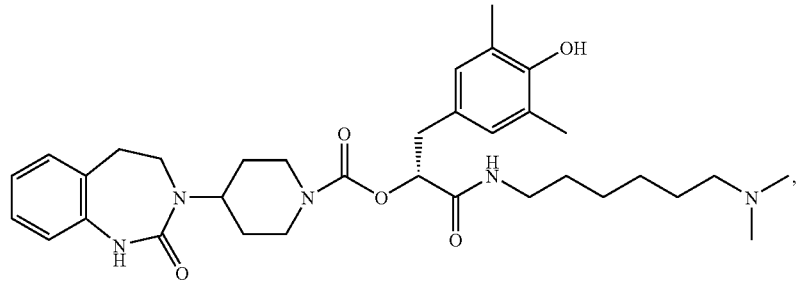 |
| (30) | 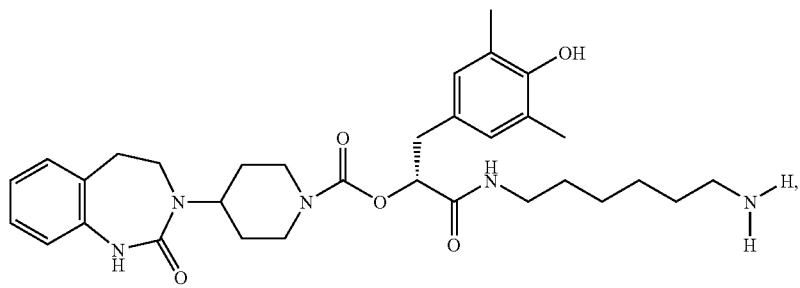 |
| (31) | 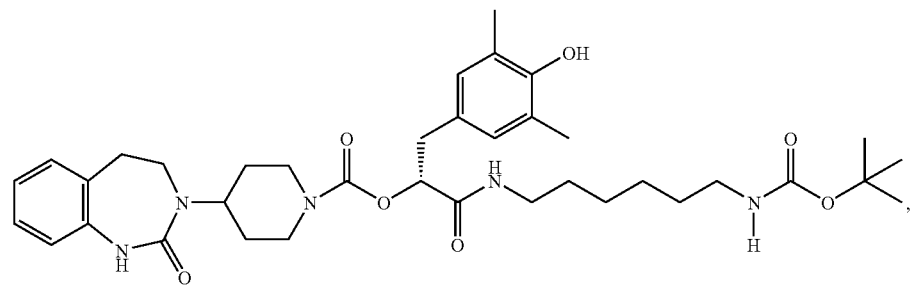 |
| (32) | 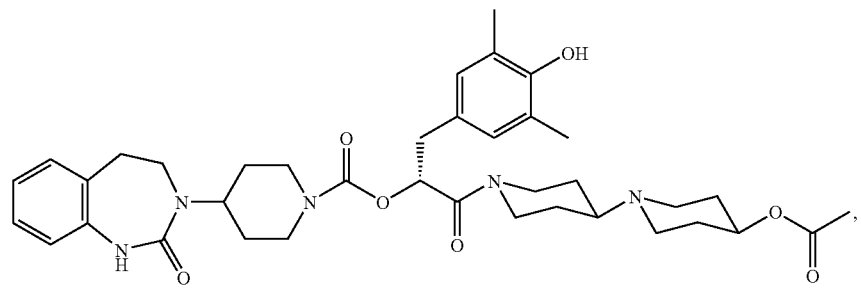 |
| (33) | 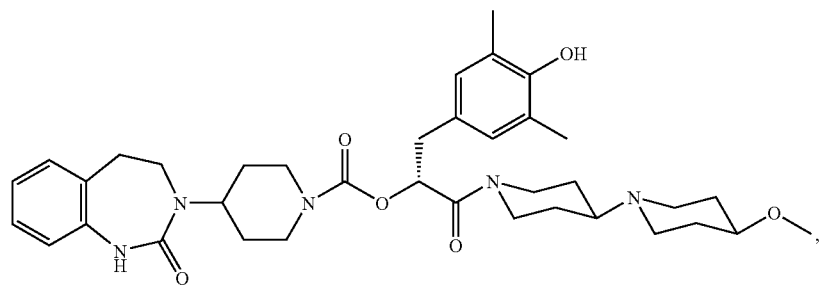 |

| No. | Structure |
|---|---|
| (34) | 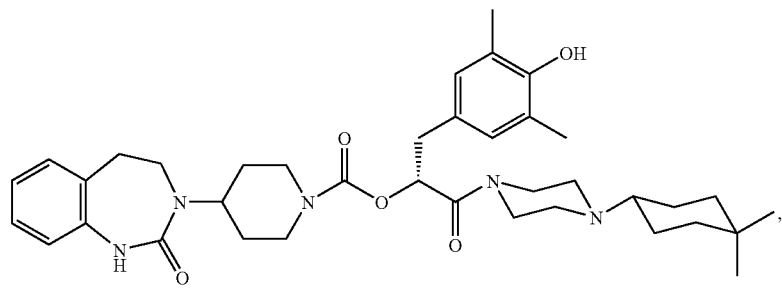 |
| (35) | 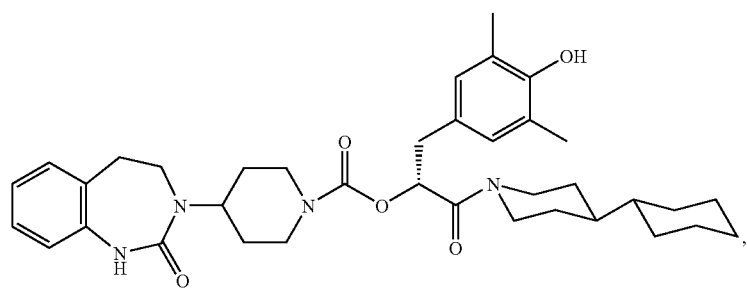 |
| (36) | 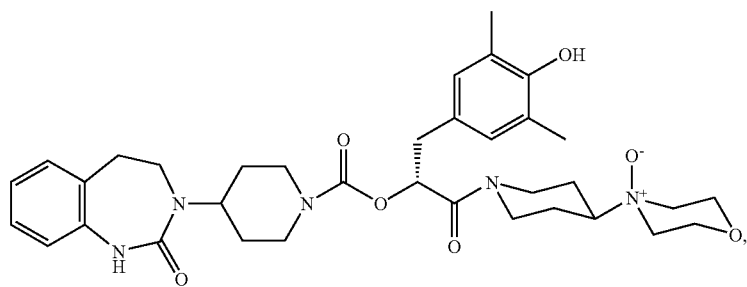 |
| (37) | 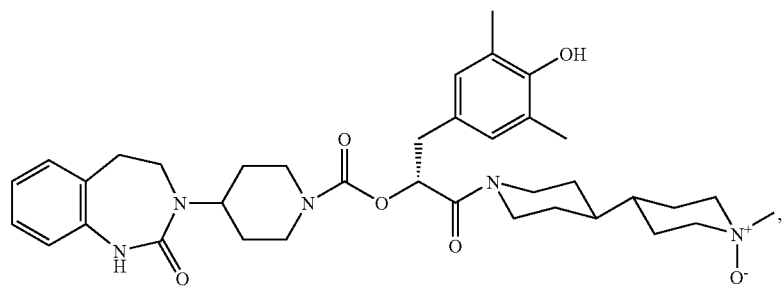 |
| (38) | 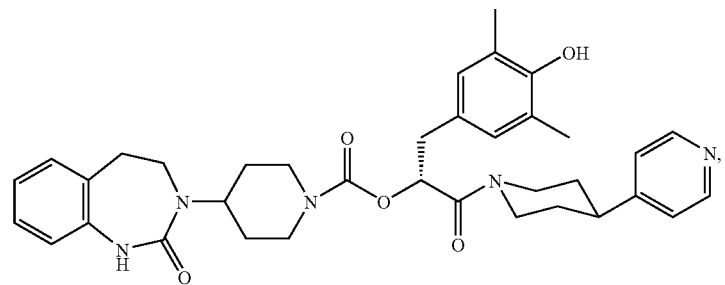 |

| No. | Structure |
|---|---|
| (39) | 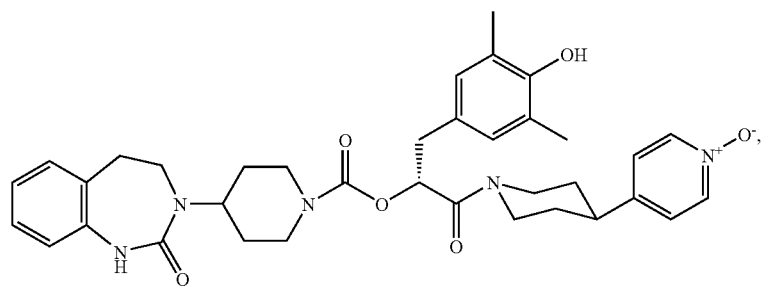 |
| (40) | 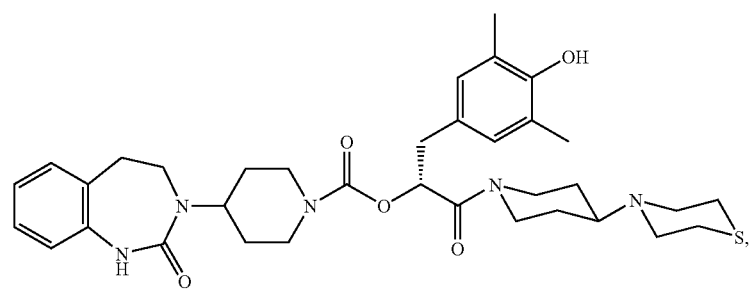 |
| (41) | 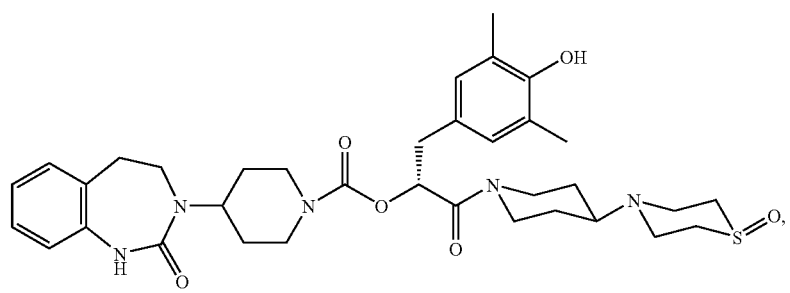 |
| (42) | 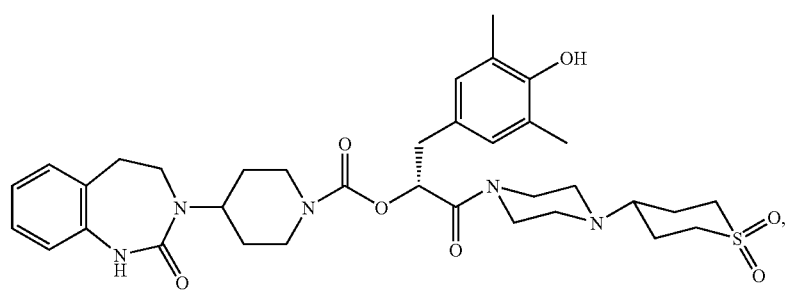 |
| (43) | 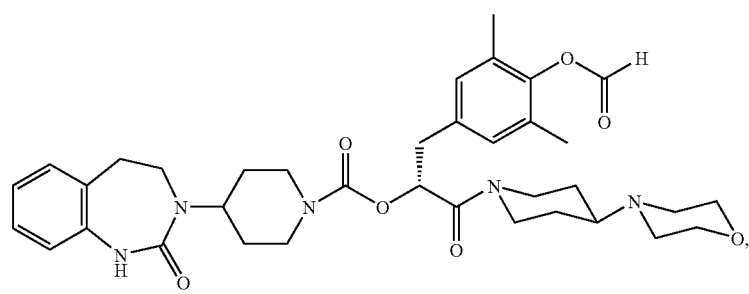 |

-continued
| No. | Structure |
|---|---|
| (44) | 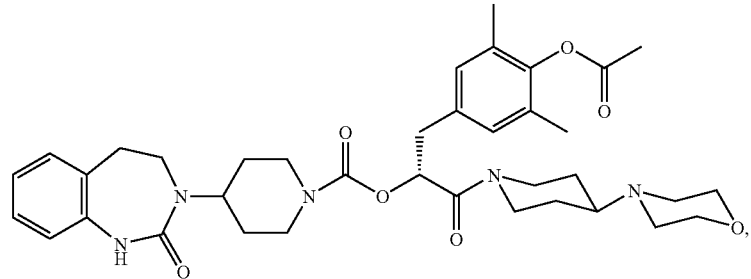 |
| (45) | 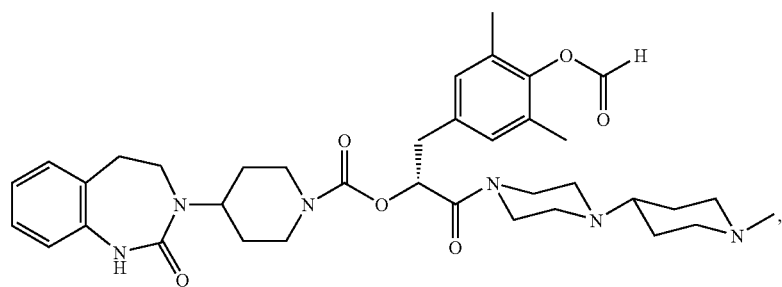 |
| (46) | 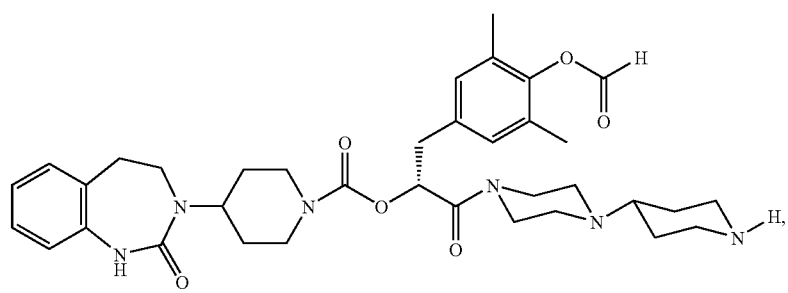 |
| (47) | 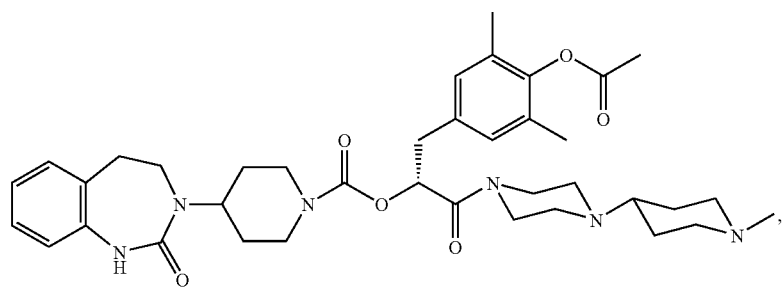 |
| (48) | 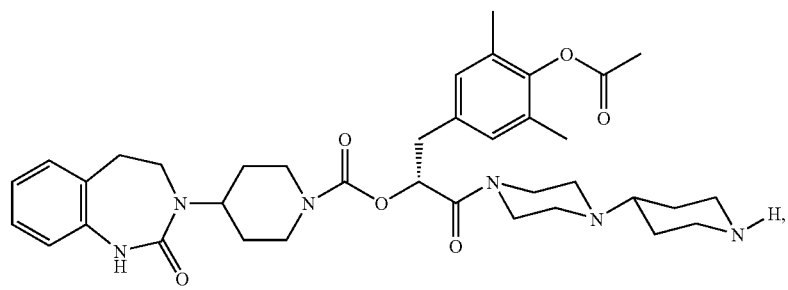 |

| No. | Structure |
|---|---|
| (49) | 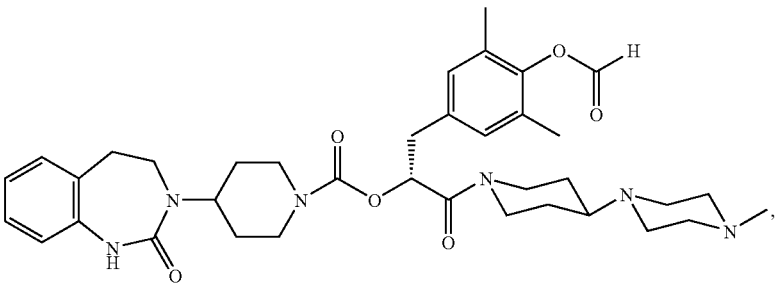 |
| (50) | 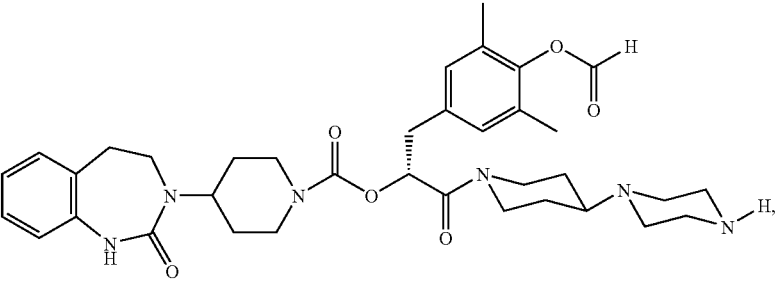 |
| (51) | 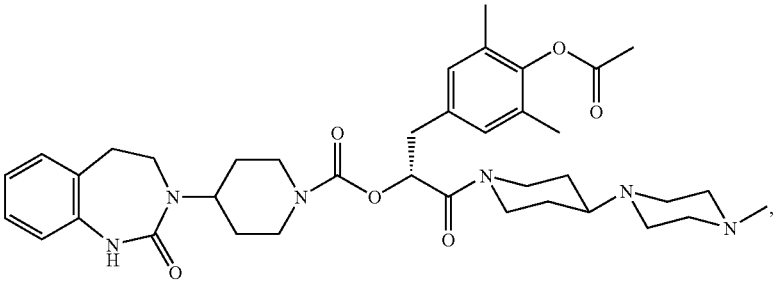 |
| (52) | 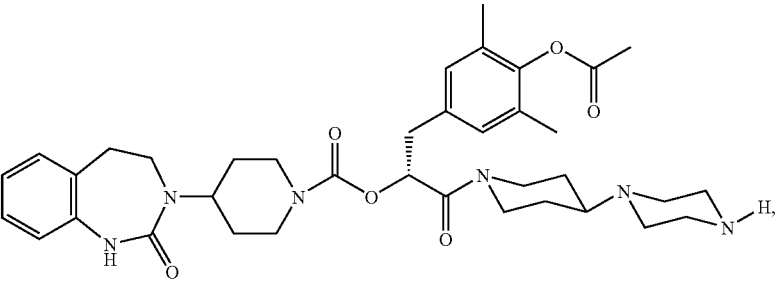 |
| (53) | 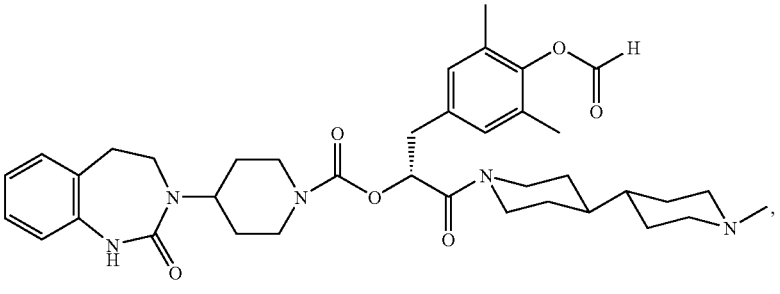 |

-continued
| No. | Structure |
|---|---|
| (54) | 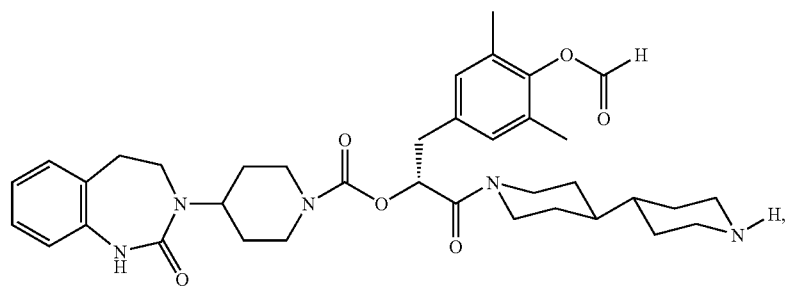 |
| (55) | 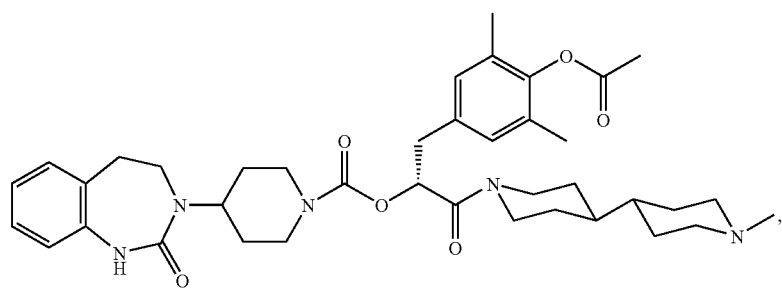 |
| (56) | 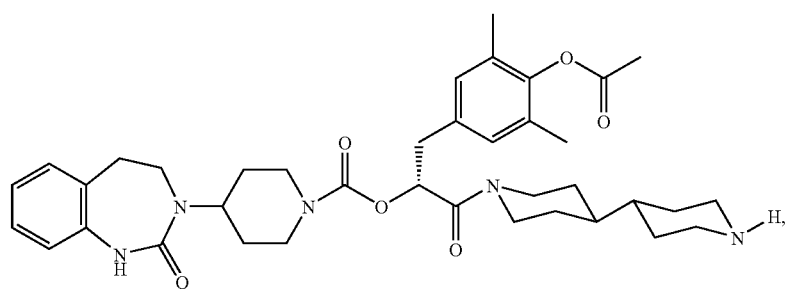 |
| (57) | 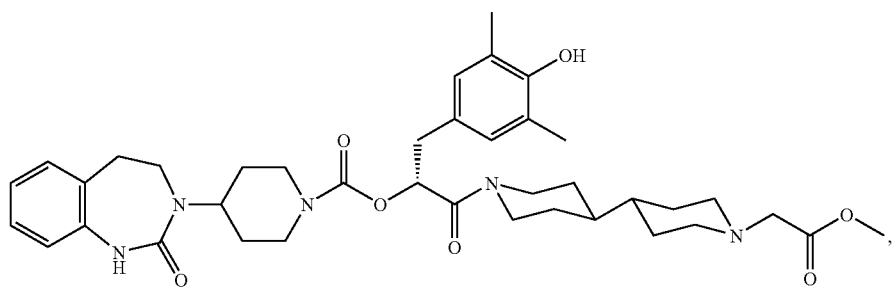 |
| (58) | 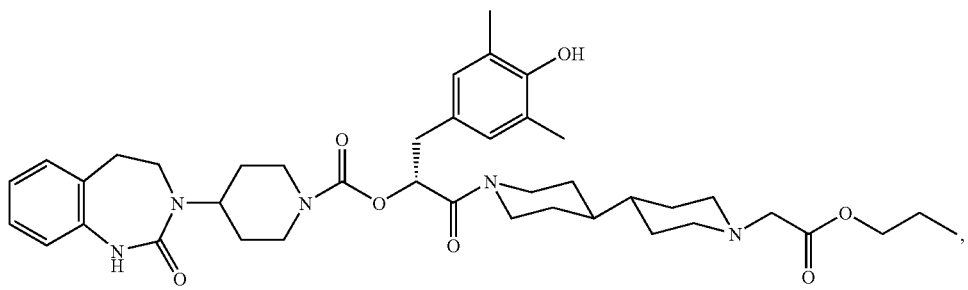 |

| No. | Structure |
|---|---|
| (59) | 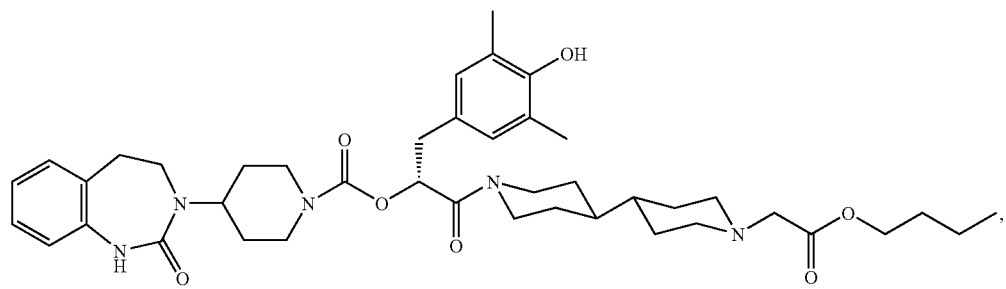 |
| (60) | 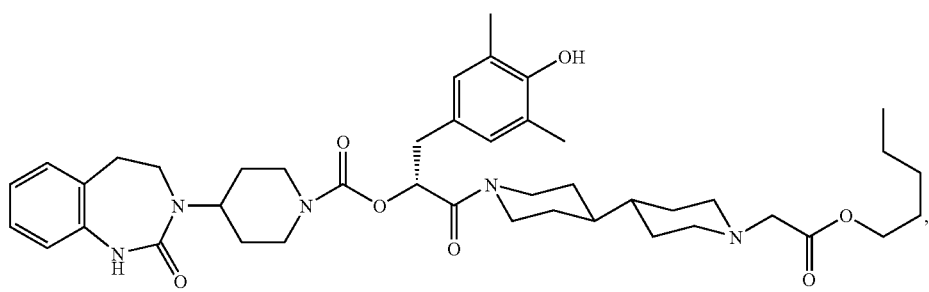 |
| (61) | 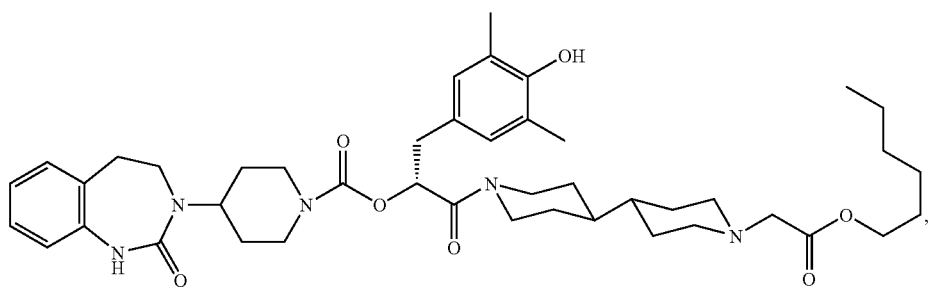 |
| (62) | 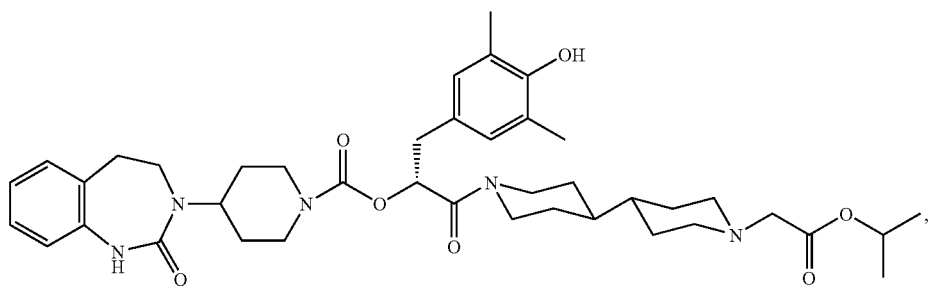 |
| (63) | 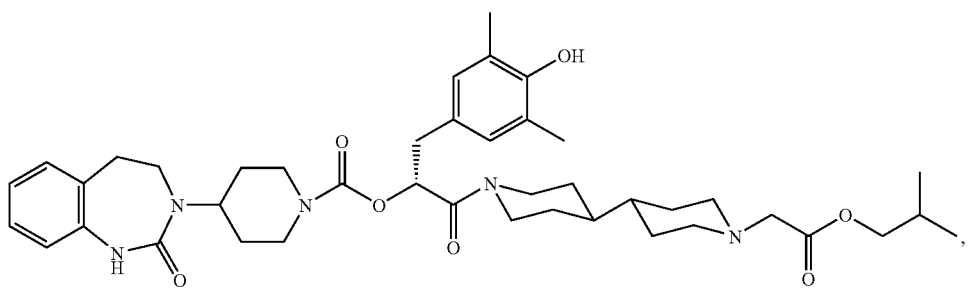 |

| No. | Structure |
|---|---|
| (64) | 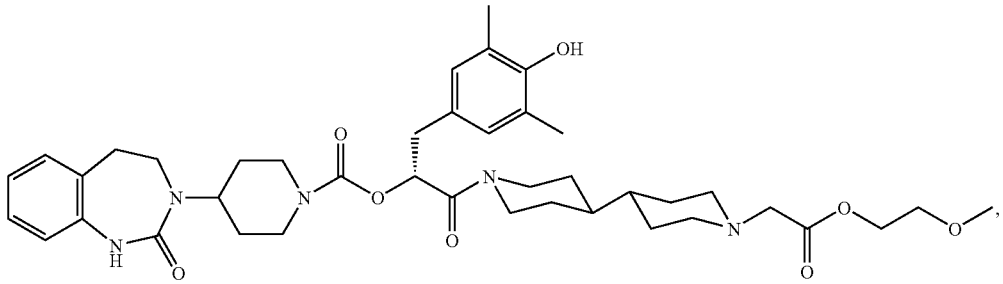 |
| (65) | 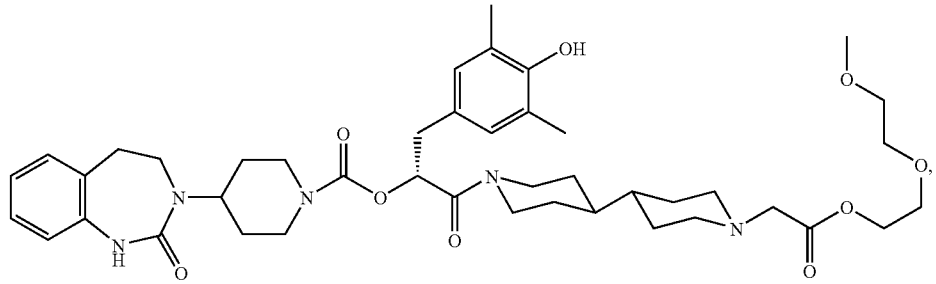 |
| (66) | 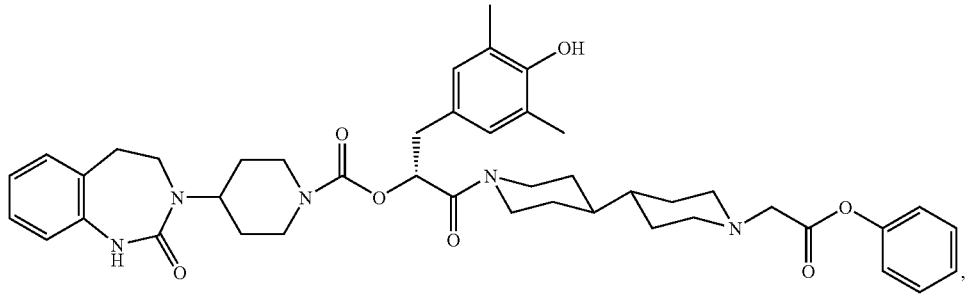 |
| (67) | 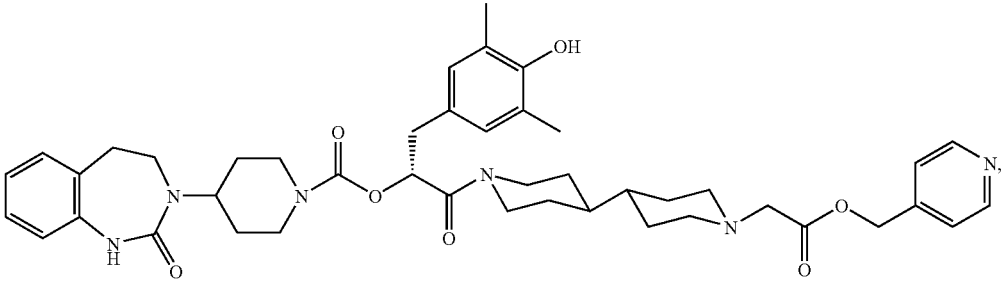 |
| (68) | 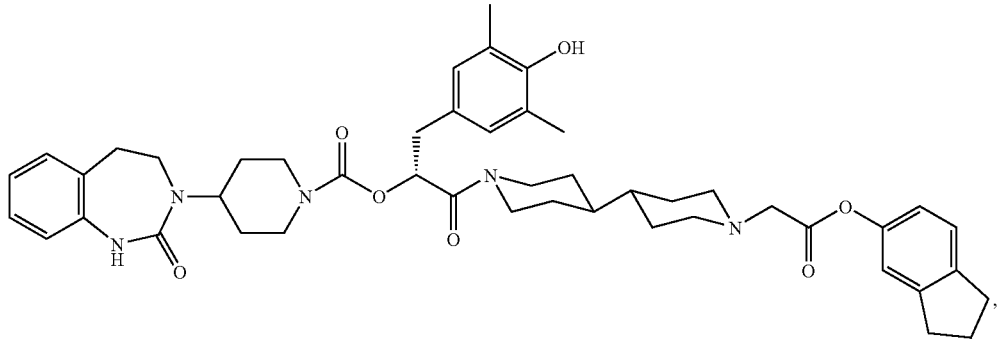 |

-continued
| No. | Structure |
|---|---|
| (69) | 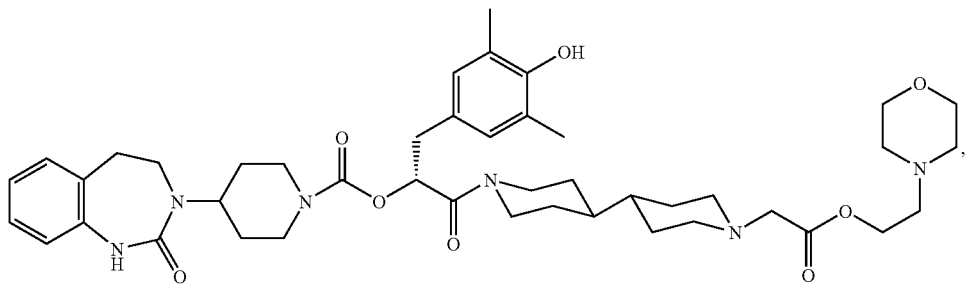 |
| (70) | 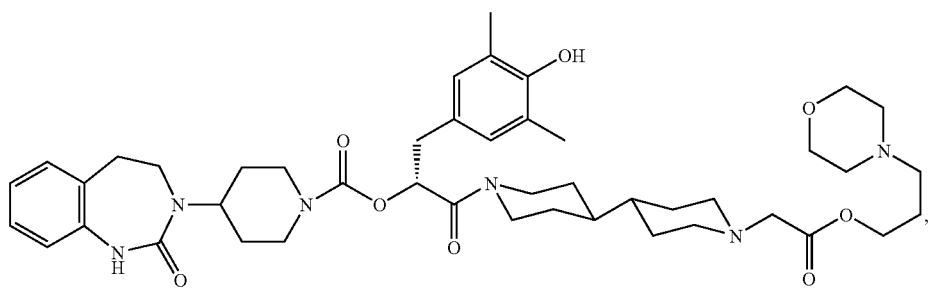 |
| (71) | 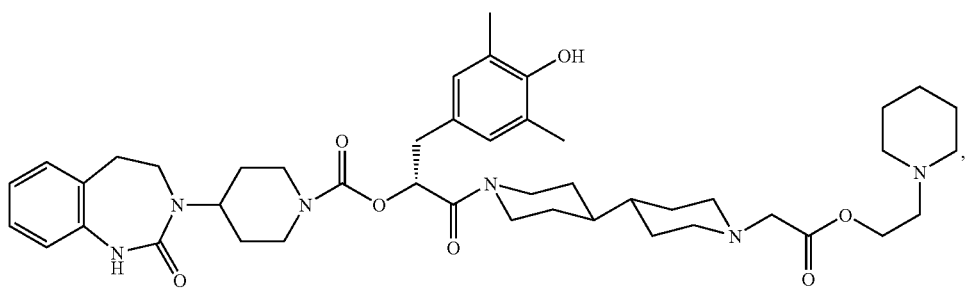 |
| (72) | 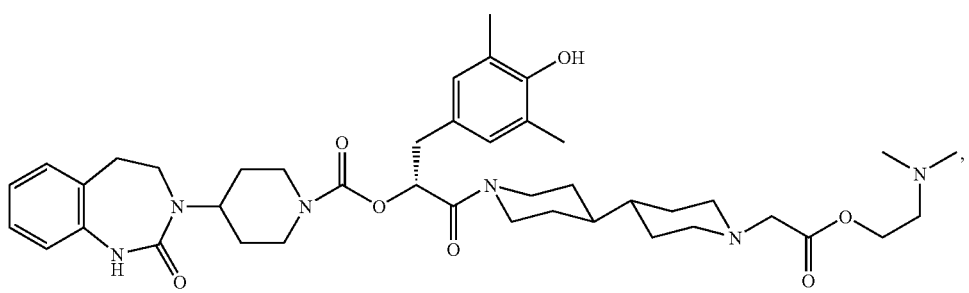 |
| (73) | 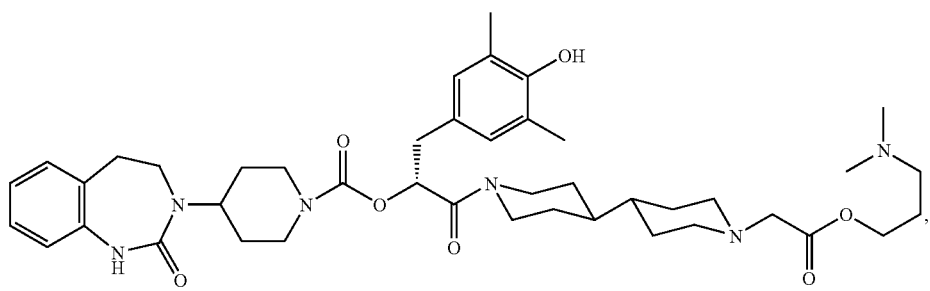 |

| No. | Structure |
|---|---|
| (74) | 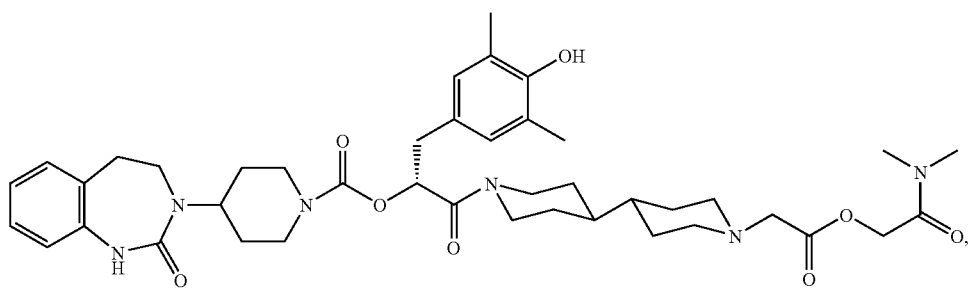 |
| (75) | 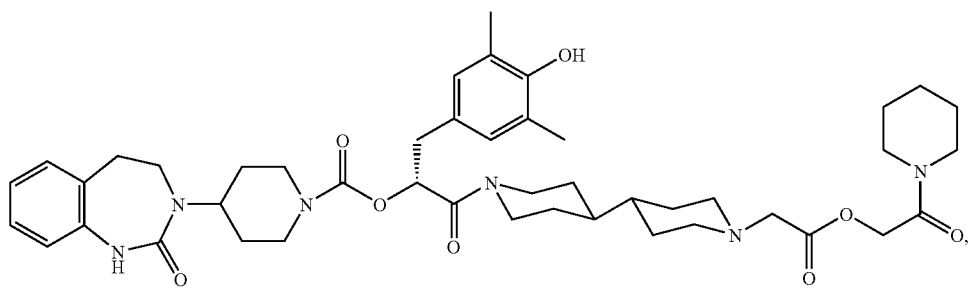 |
| (76) | 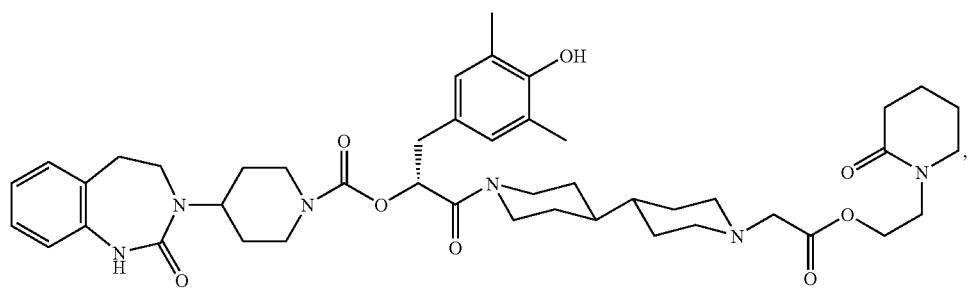 |
| (77) | 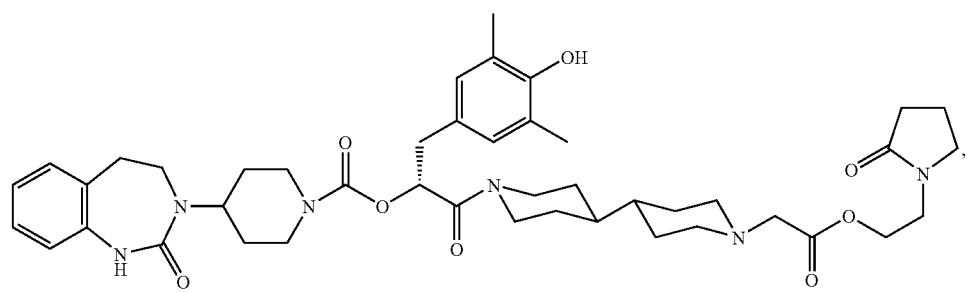 |
| (78) | 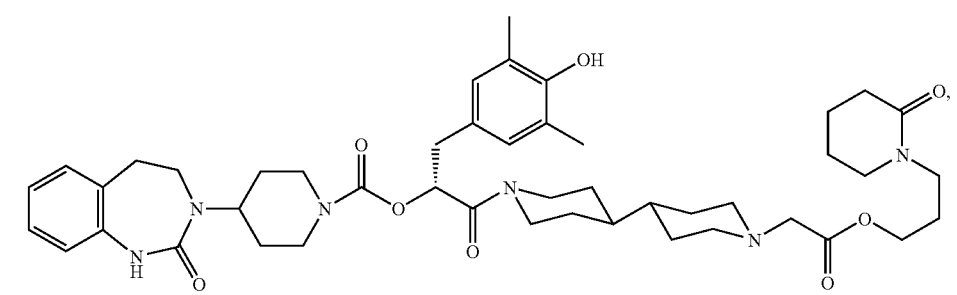 |

| No. | Structure |
|---|---|
| (79) | 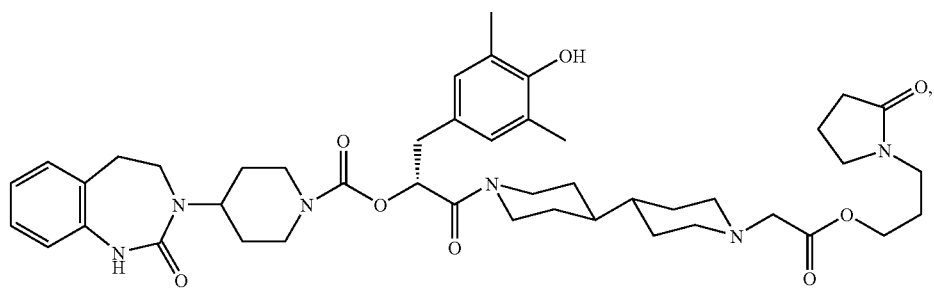 |
| (80) | 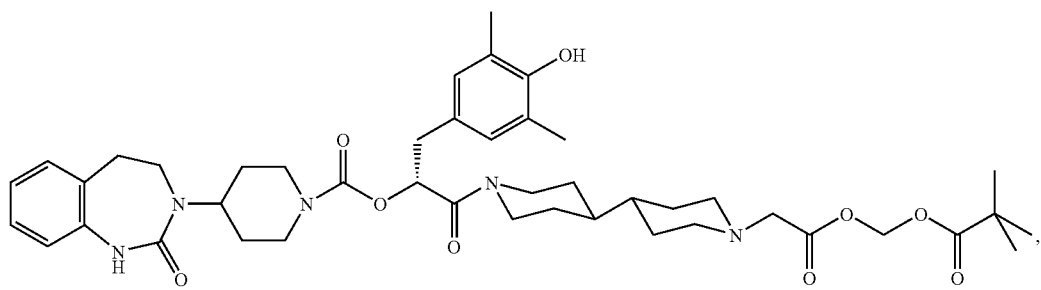 |
| (81) | 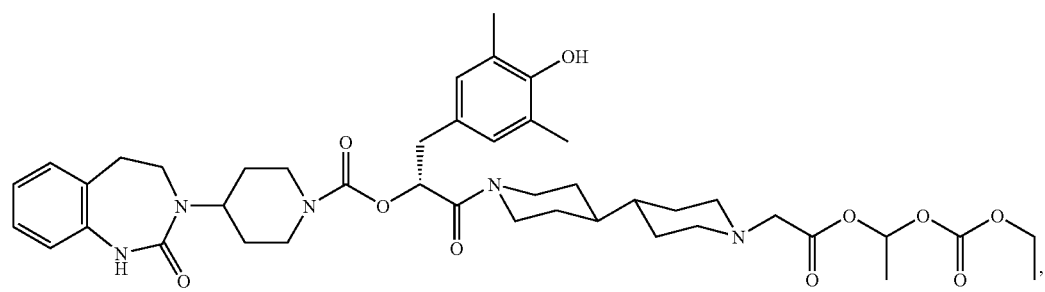 |
| (82) | 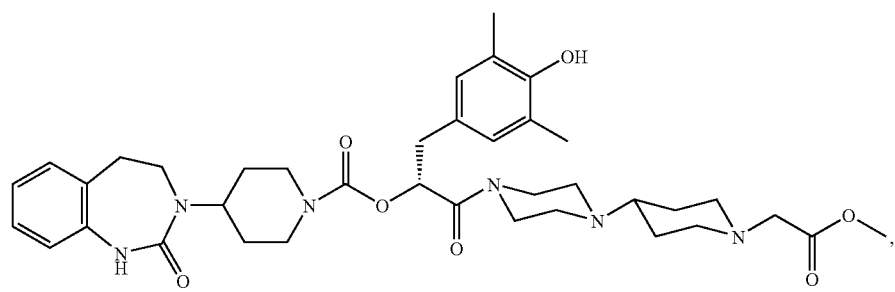 |
| (83) | 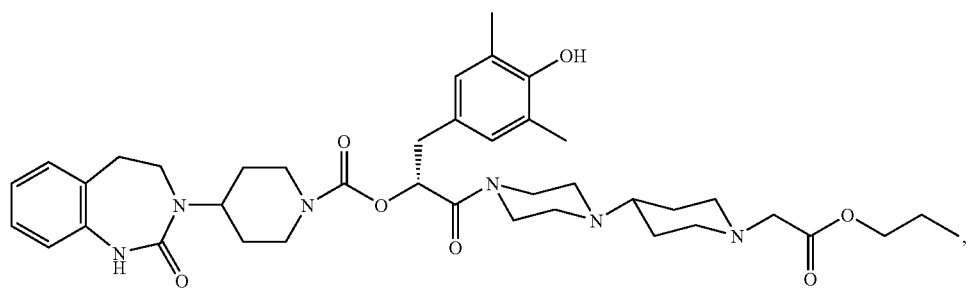 |

-continued
| No. | Structure |
|---|---|
| (84) | 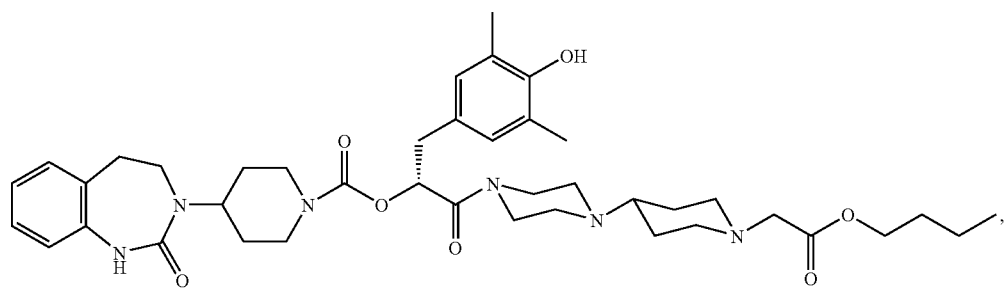 |
| (85) | 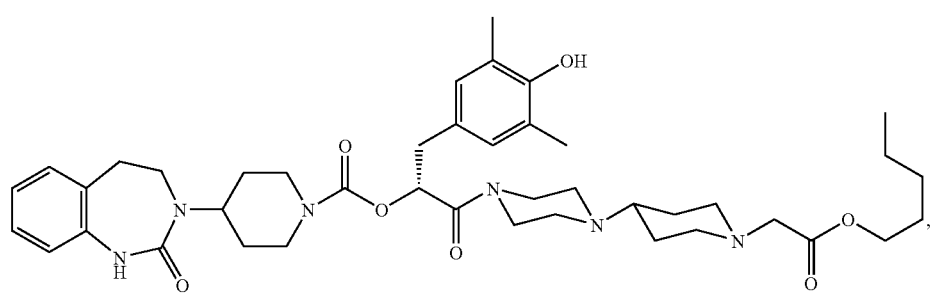 |
| (86) | 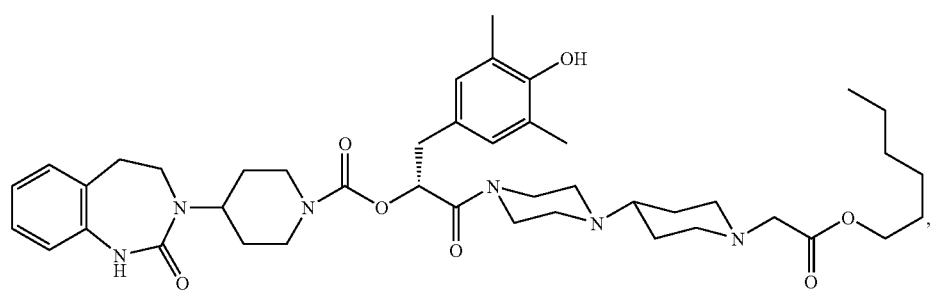 |
| (87) | 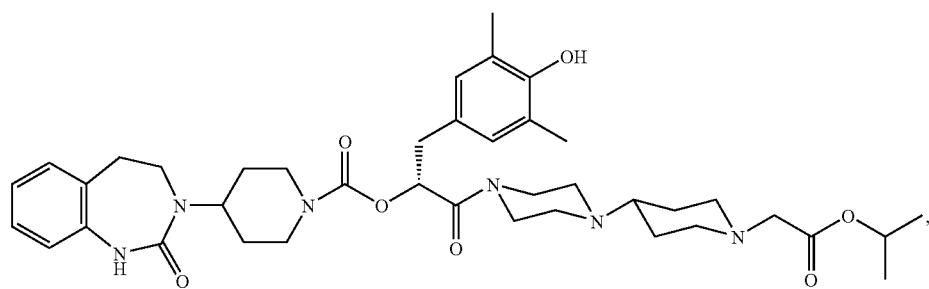 |
| (88) | 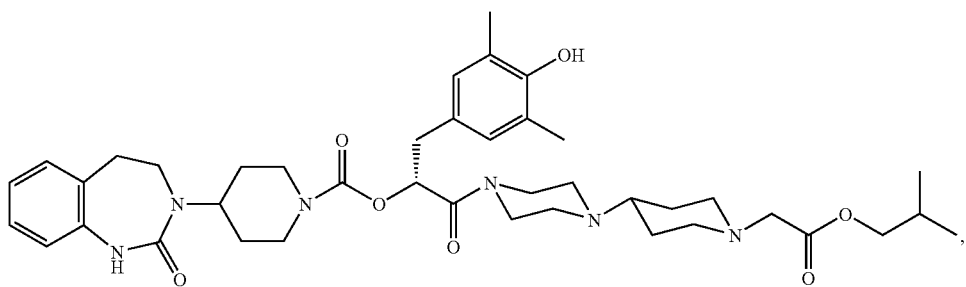 |

| No. | Structure |
|---|---|
| (89) | 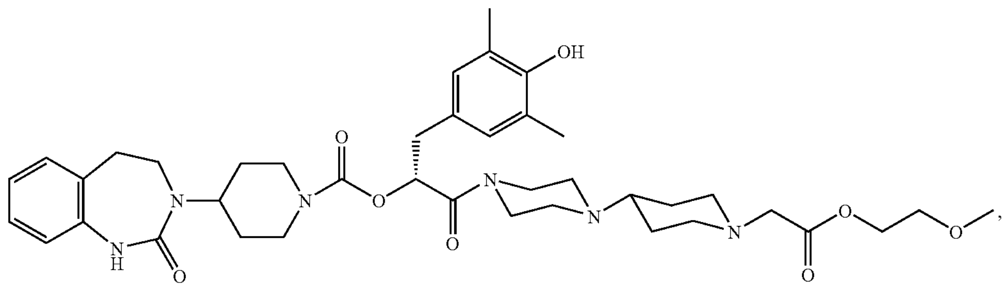 |
| (90) | 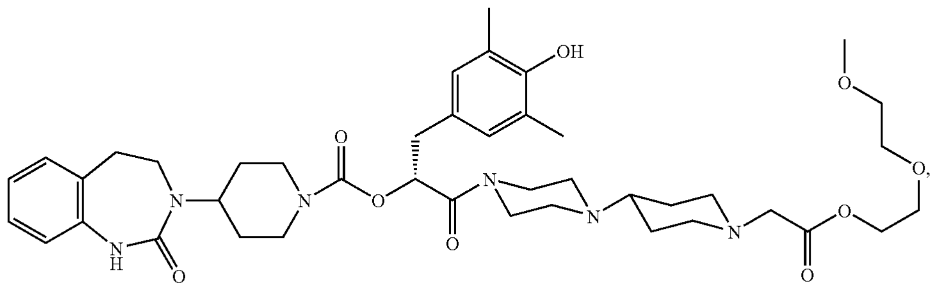 |
| (91) | 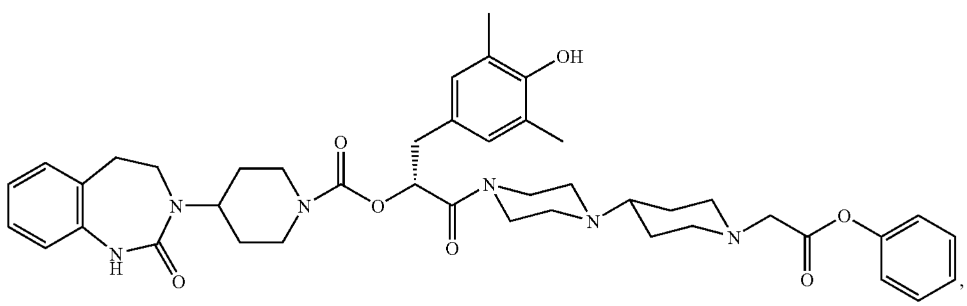 |
| (92) | 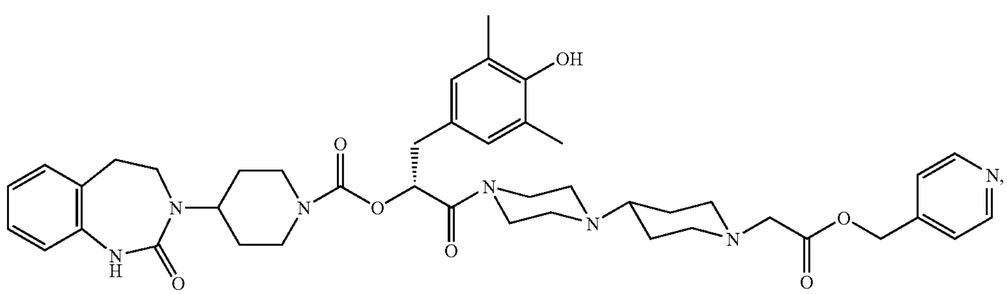 |
| (93) | 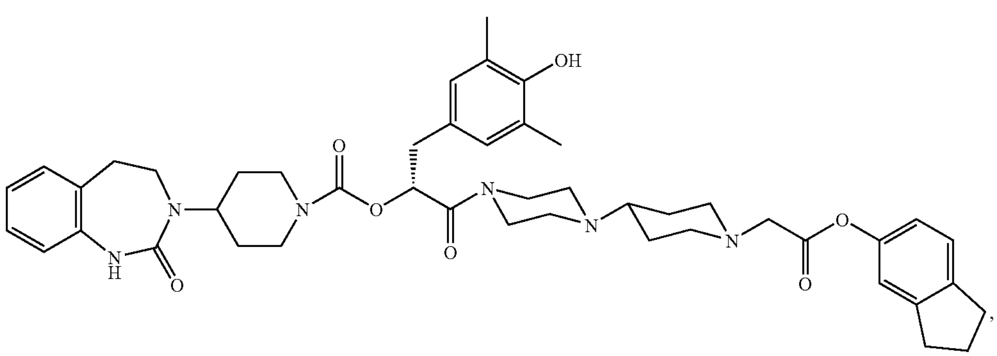 |

-continued
| No. | Structure |
|---|---|
| (94) | 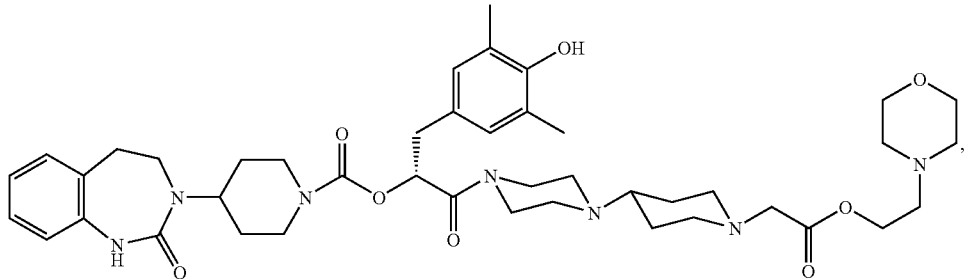 |
| (95) | 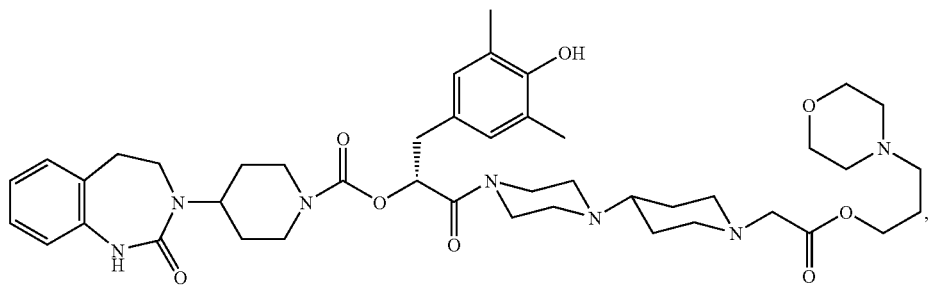 |
| (96) | 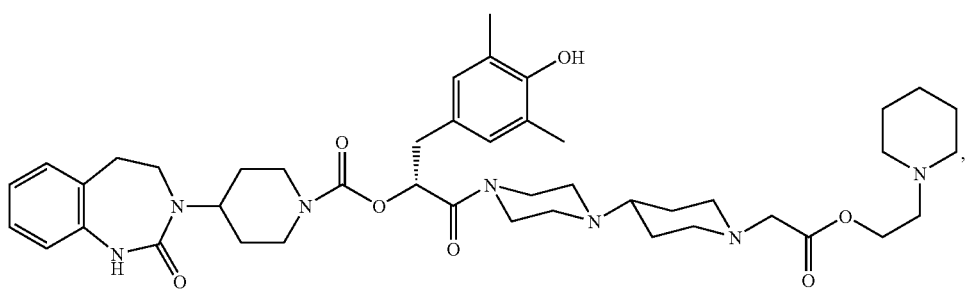 |
| (97) | 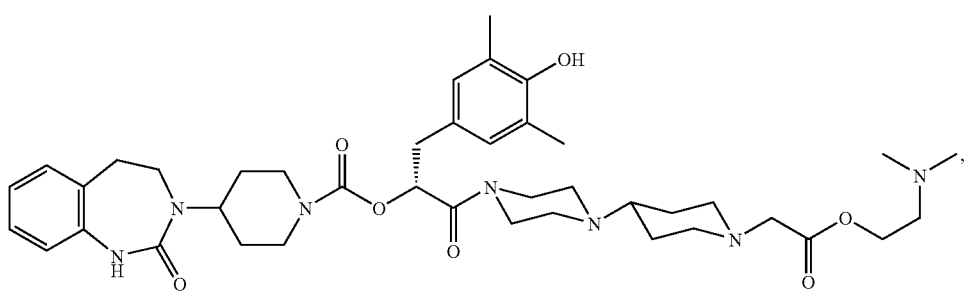 |
| (98) | 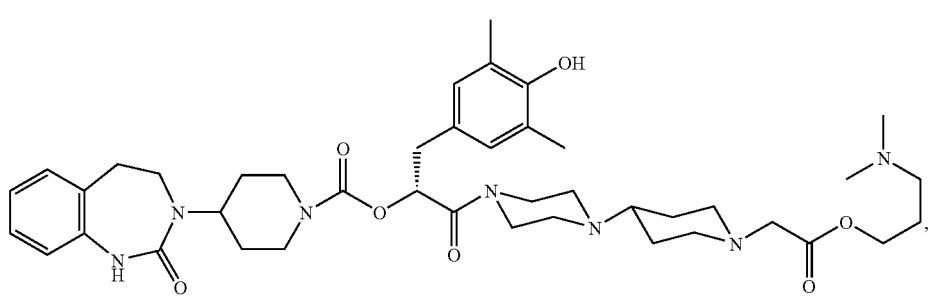 |

| No. | Structure |
|---|---|
| (99) | 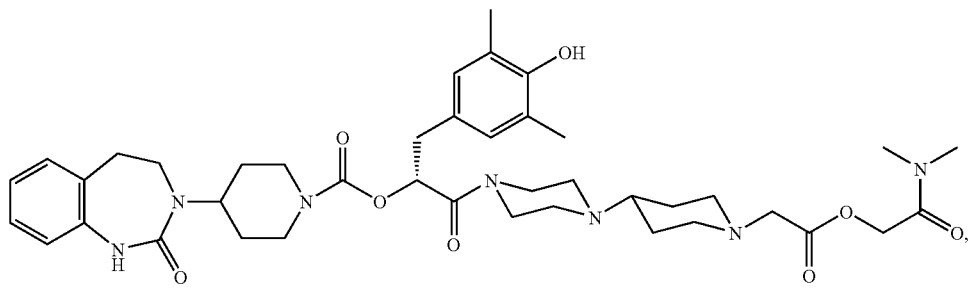 |
| (100) | 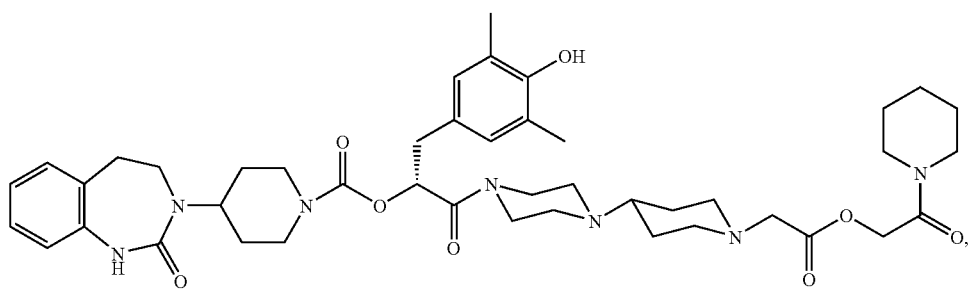 |
| (101) | 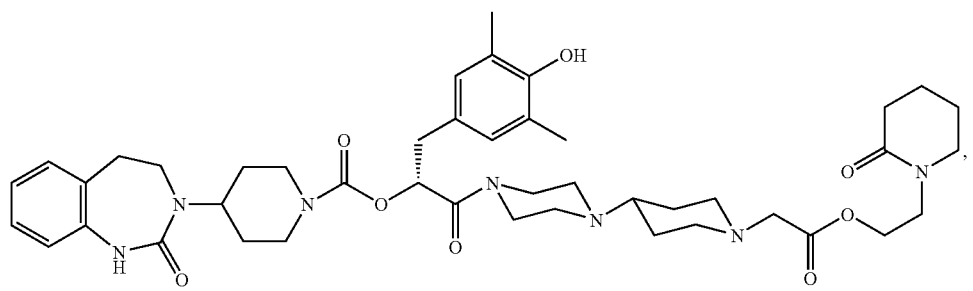 |
| (102) | 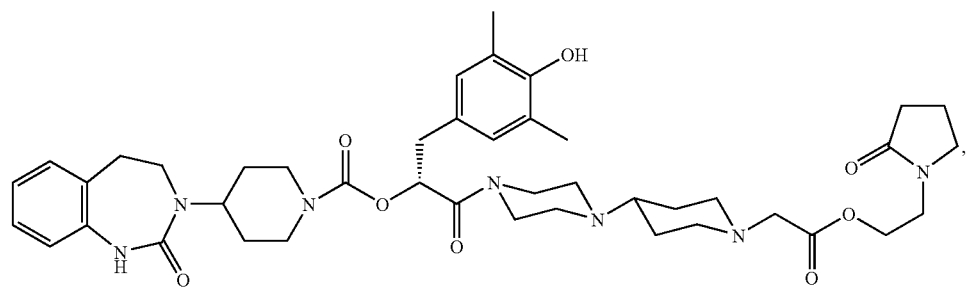 |
| (103) | 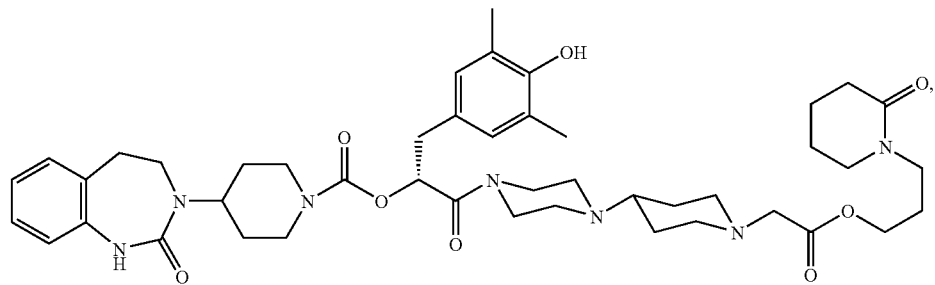 |

-continued
| No. | Structure |
|---|---|
| (104) | 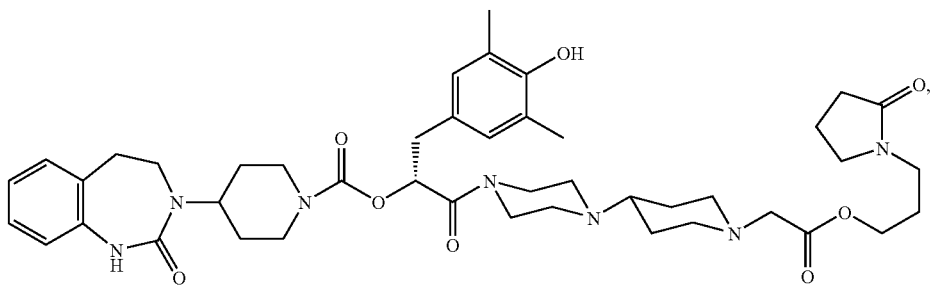 |
| (105) | 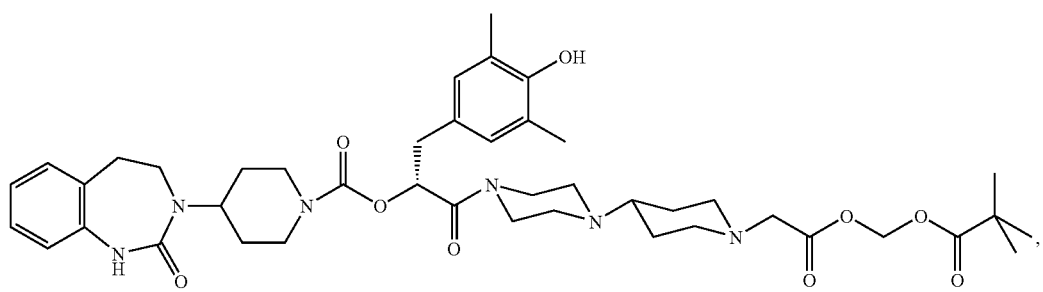 |
| (106) | 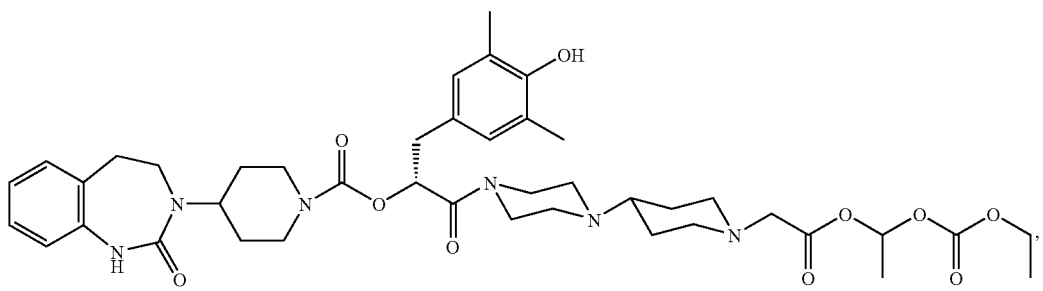 |
| (107) | 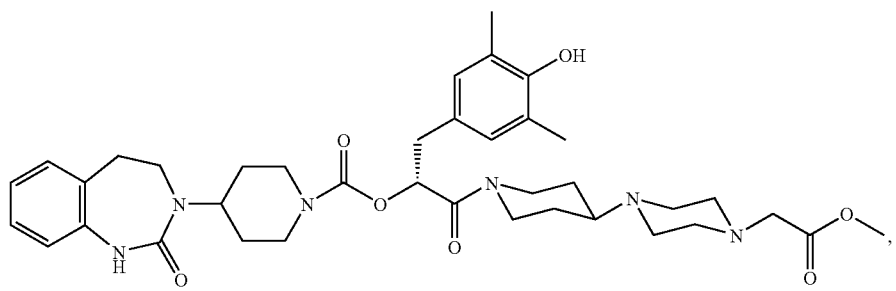 |
| (108) | 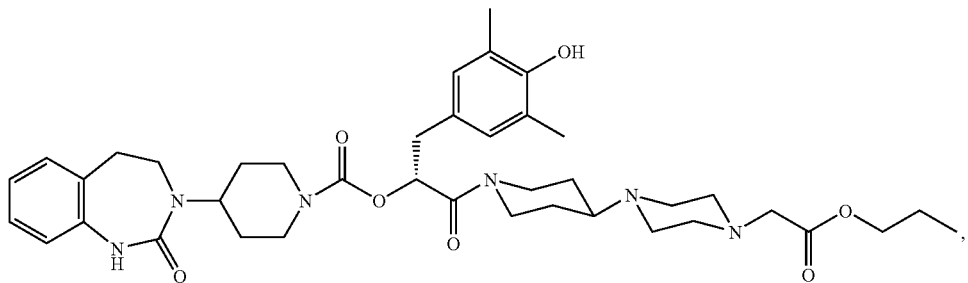 |

| No. | Structure |
|---|---|
| (109) | 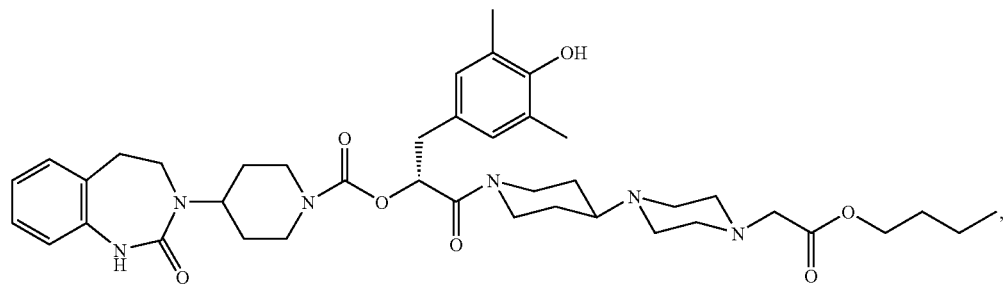 |
| (110) | 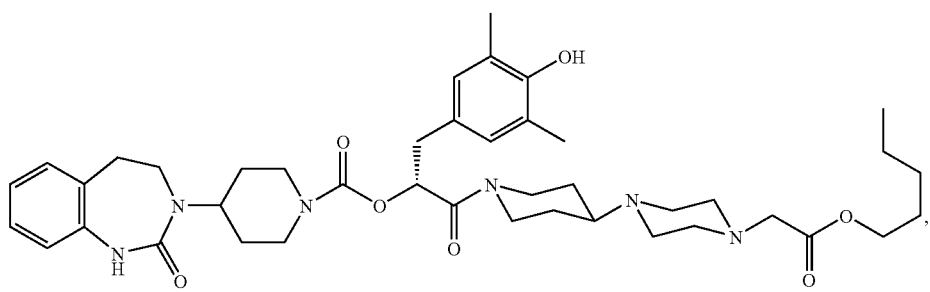 |
| (111) | 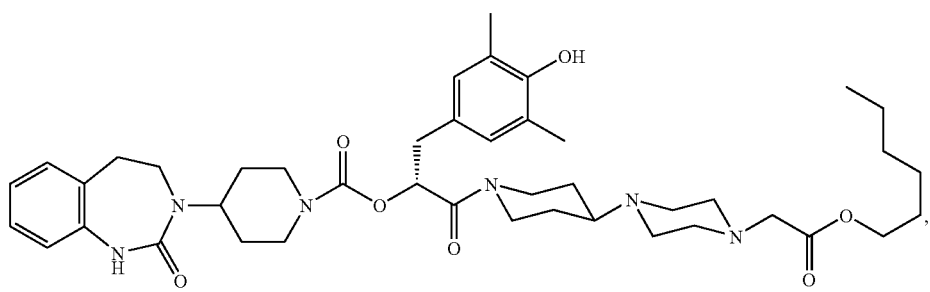 |
| (112) | 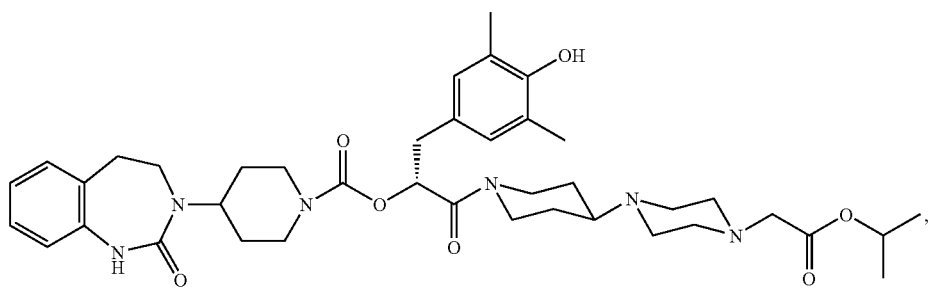 |
| (113) | 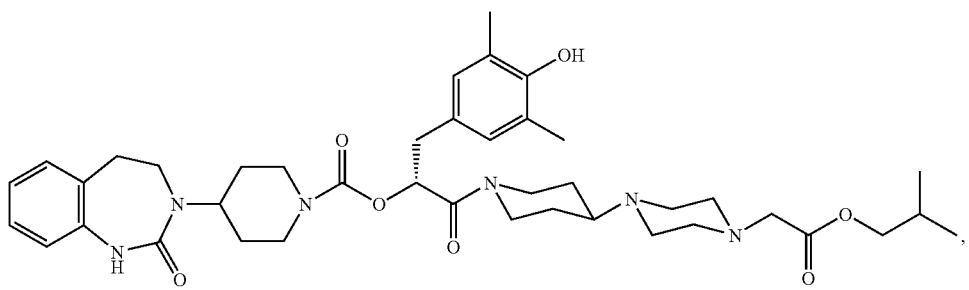 |

-continued
| No. | Structure |
|---|---|
| (114) | 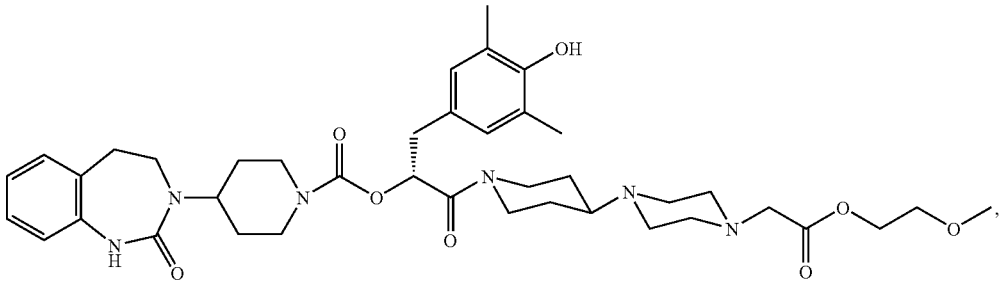 |
| (115) | 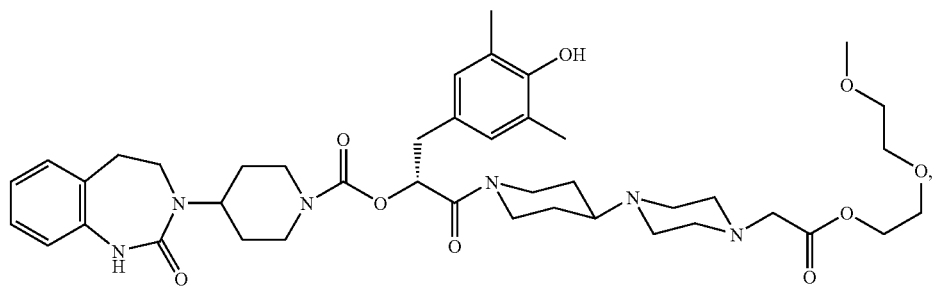 |
| (116) | 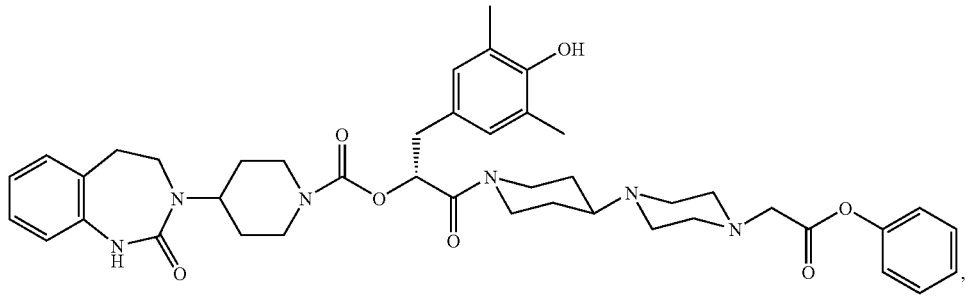 |
| (117) | 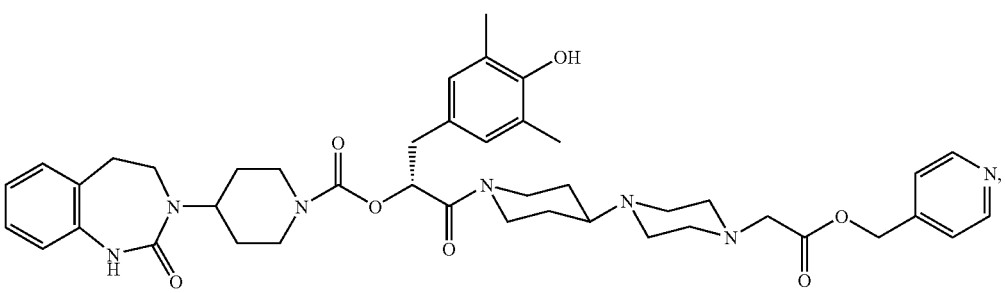 |
| (118) | 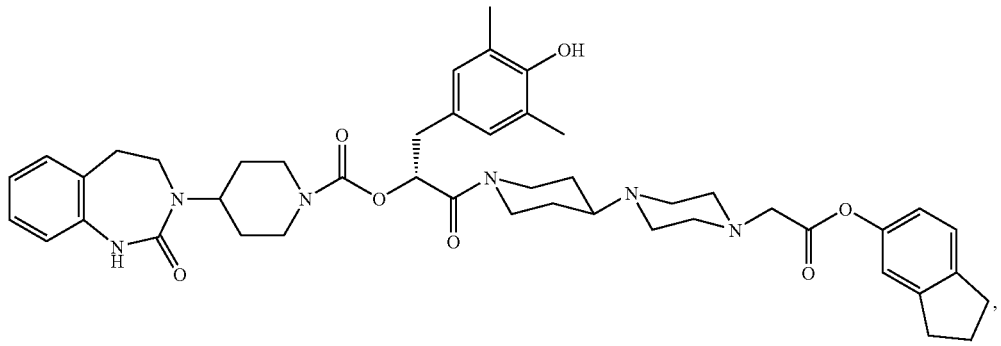 |

-continued
| No. | Structure |
|---|---|
| (119) | 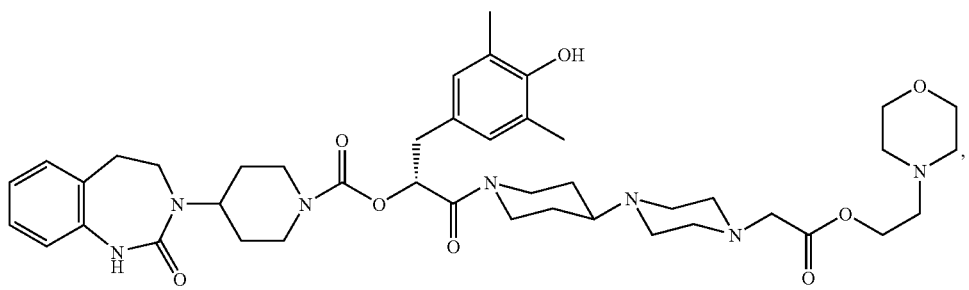 |
| (120) | 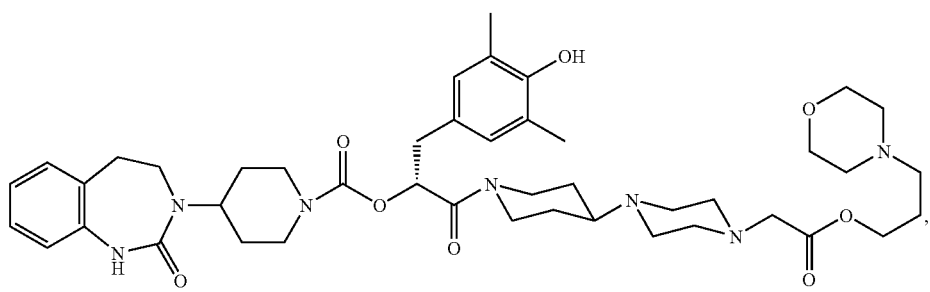 |
| (121) | 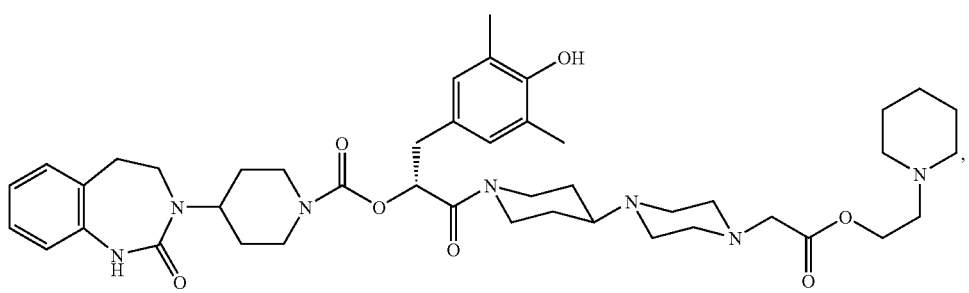 |
| (122) | 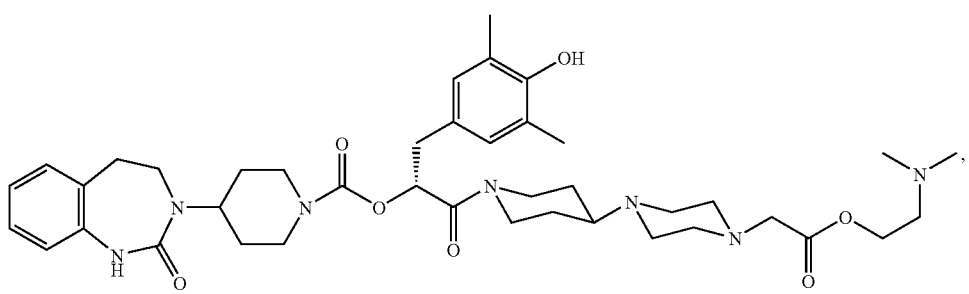 |
| (123) | 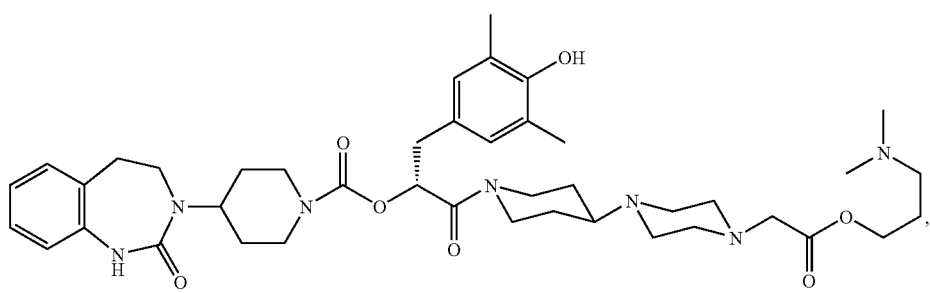 |

-continued
| No. | Structure |
|---|---|
| (124) | 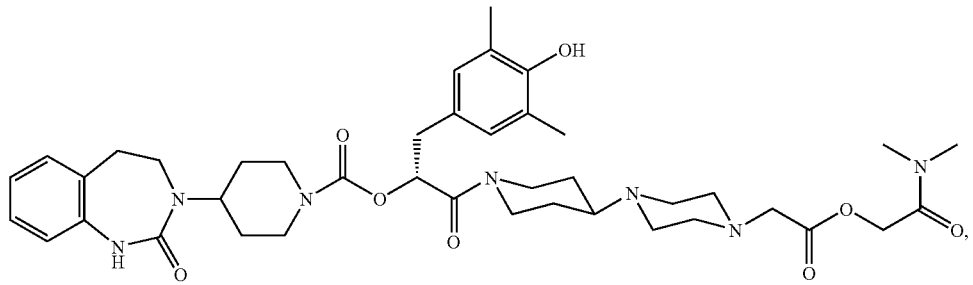 |
| (125) | 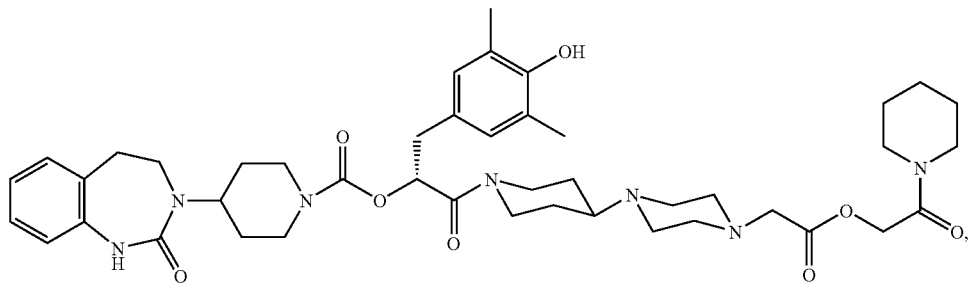 |
| (126) | 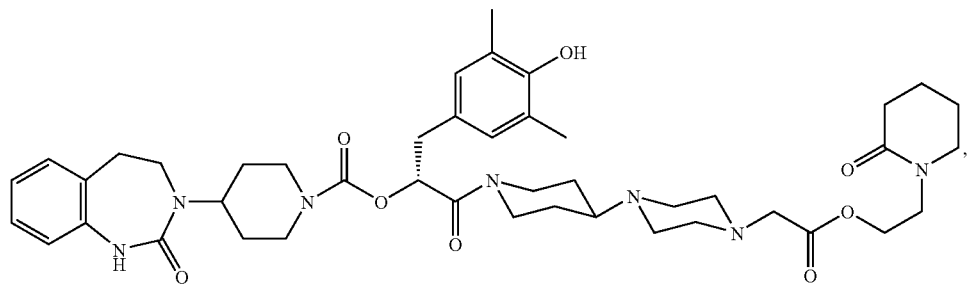 |
| (127) | 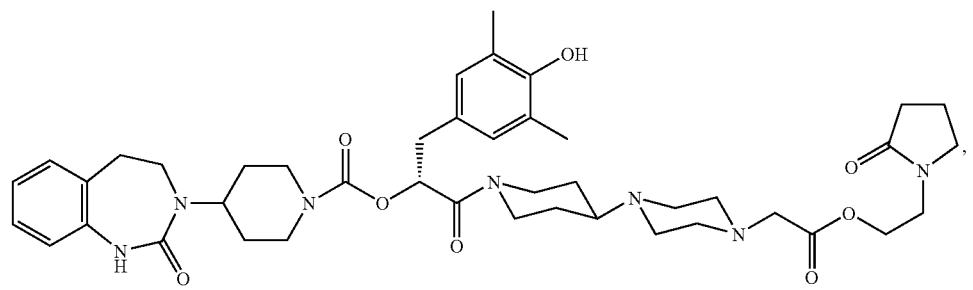 |
| (128) | 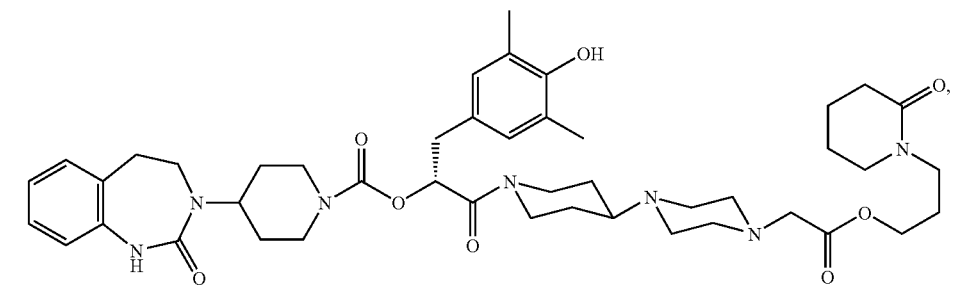 |

|No.|Structure|
|---|---|
|(129)|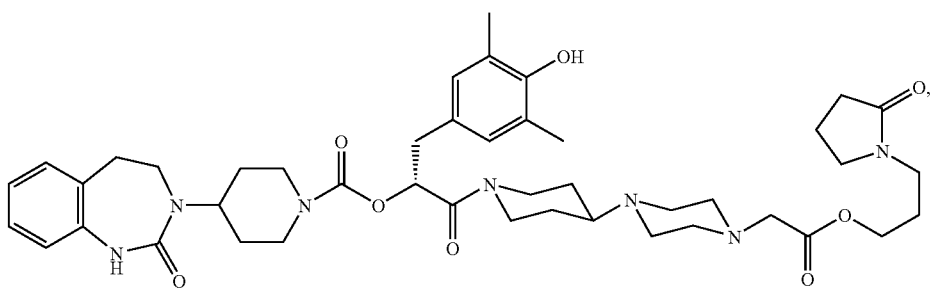|
|(130)|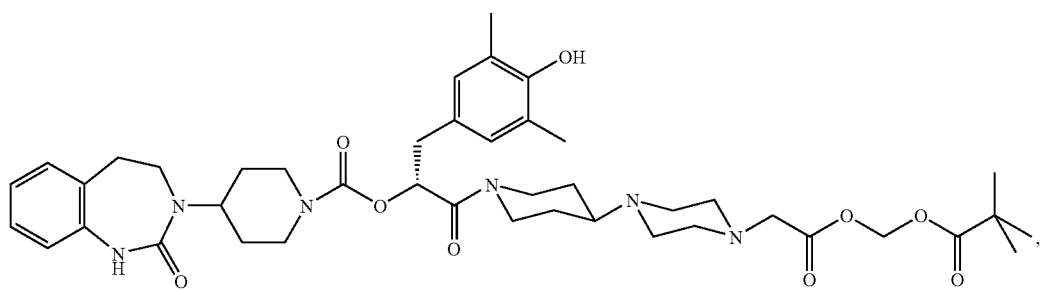|
|(131)|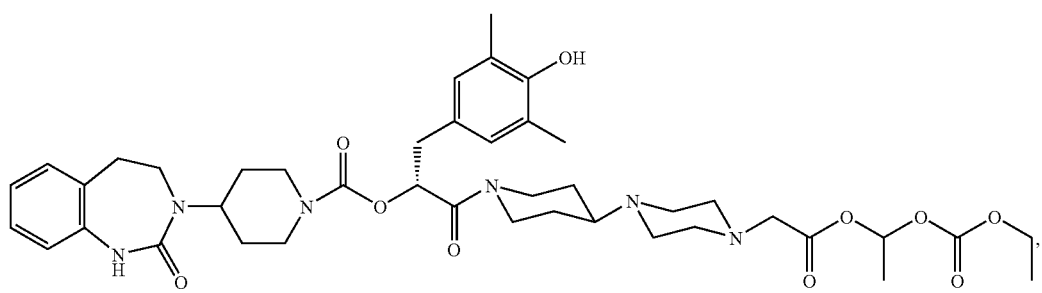|
|(132)|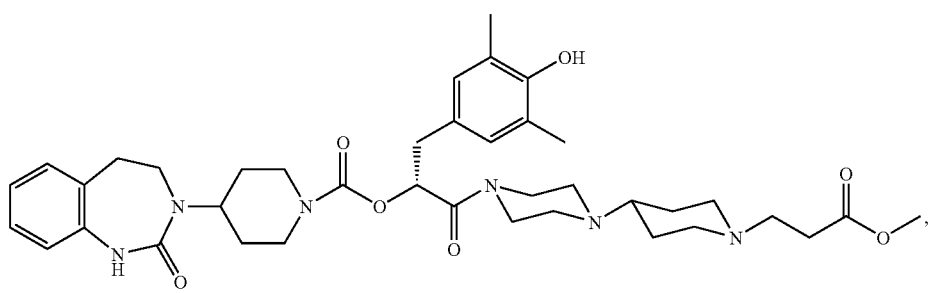|
|(133)|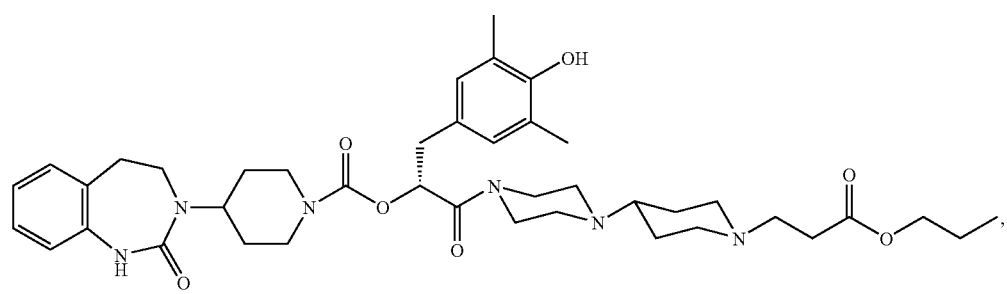|

| No. | Structure |
|---|---|
| (134) | 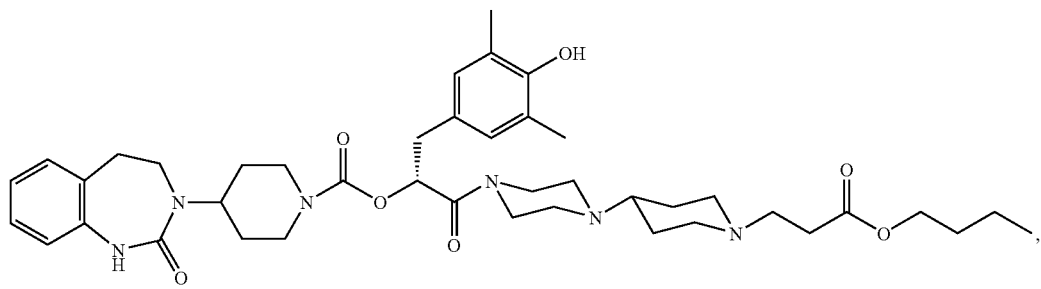 |
| (135) | 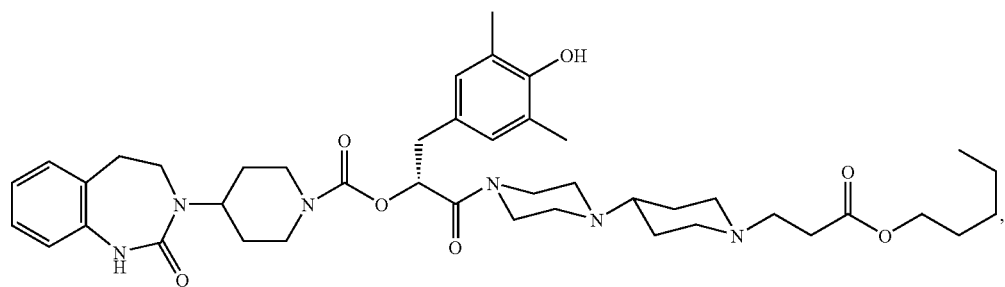 |
| (136) | 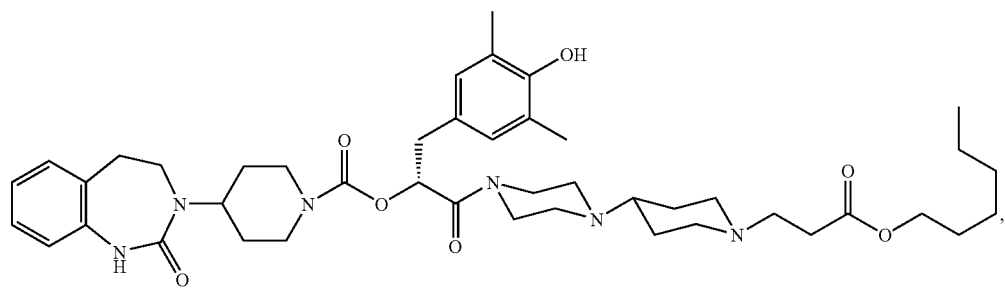 |
| (137) | 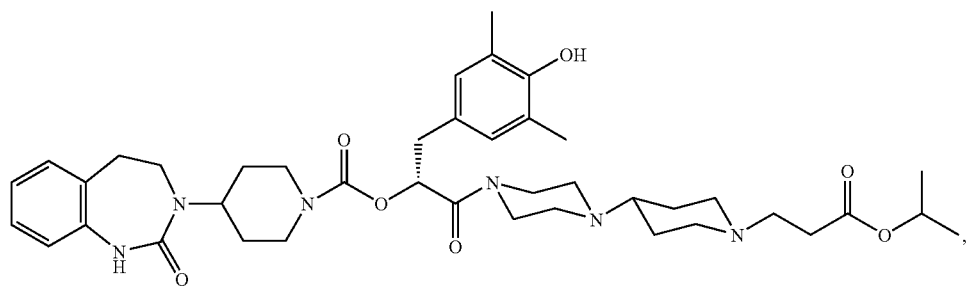 |
| (138) | 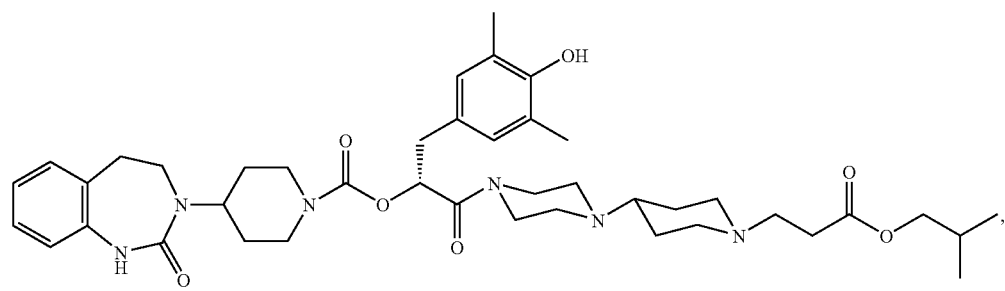 |

-continued
| No. | Structure |
|---|---|
| (139) | 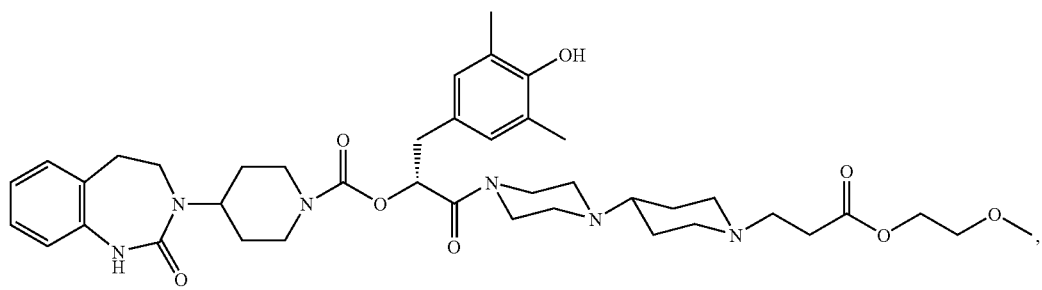 |
| (140) | 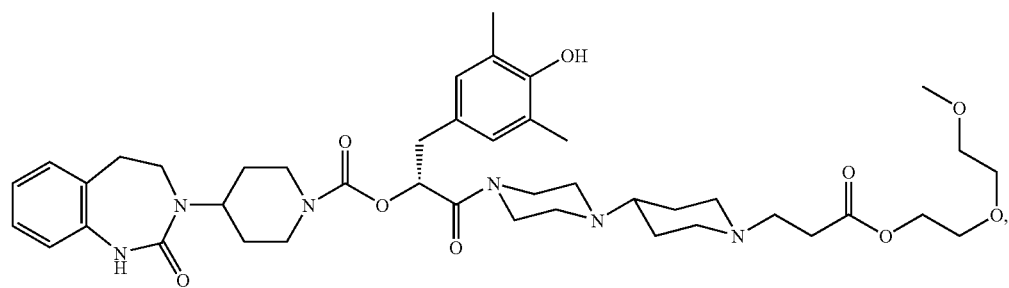 |
| (141) | 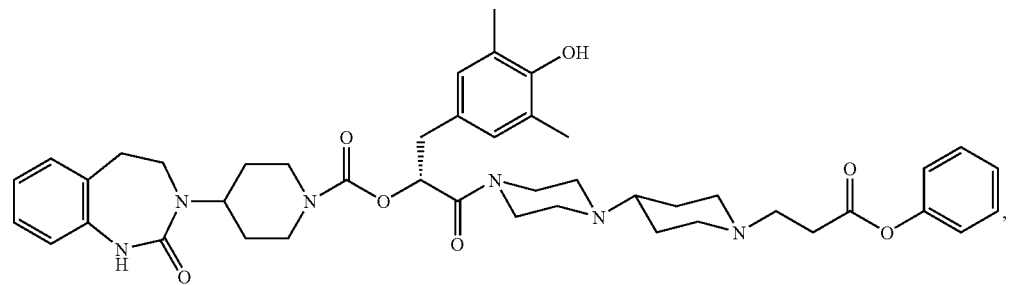 |
| (142) | 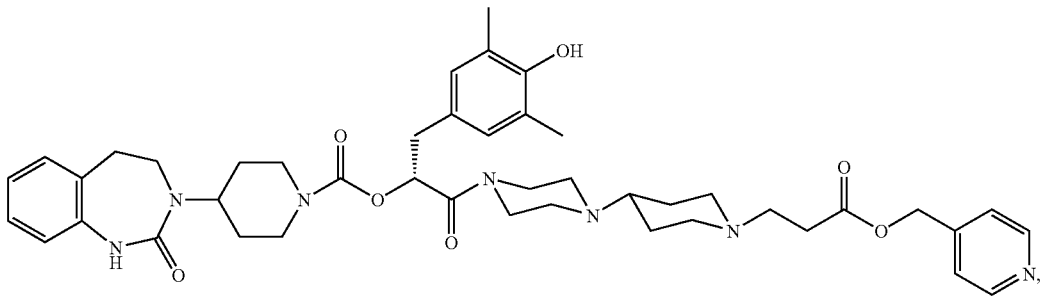 |
| (143) | 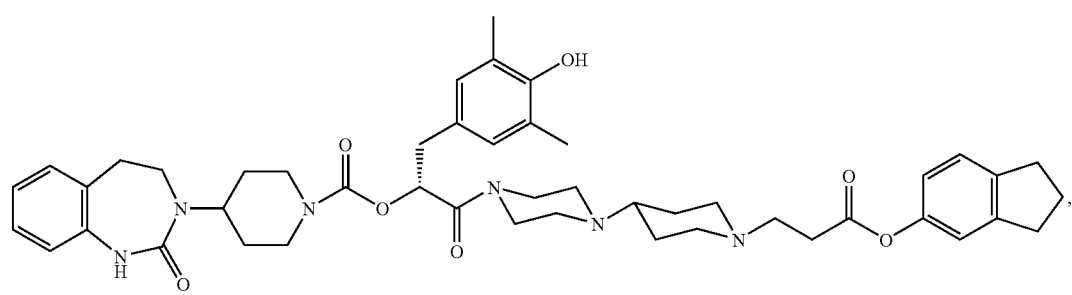 |

-continued
| No. | Structure |
|---|---|
| (144) | 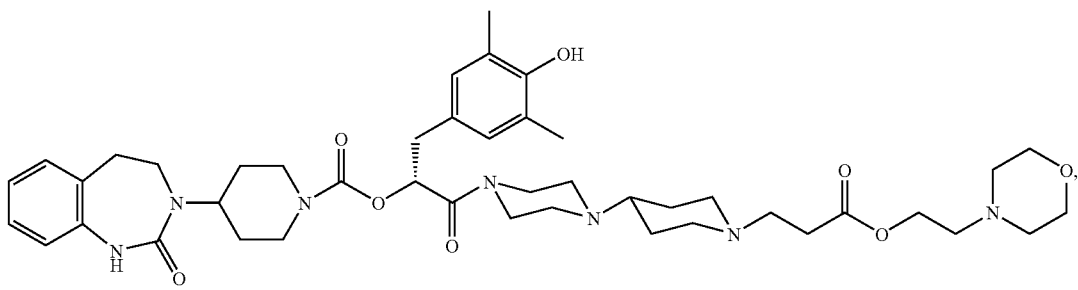 |
| (145) | 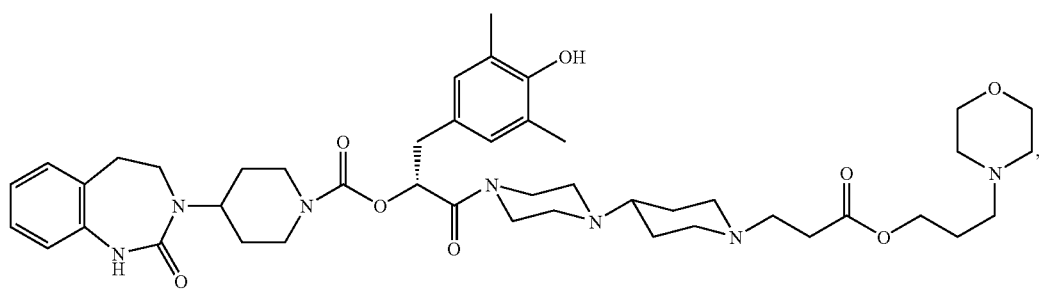 |
| (146) | 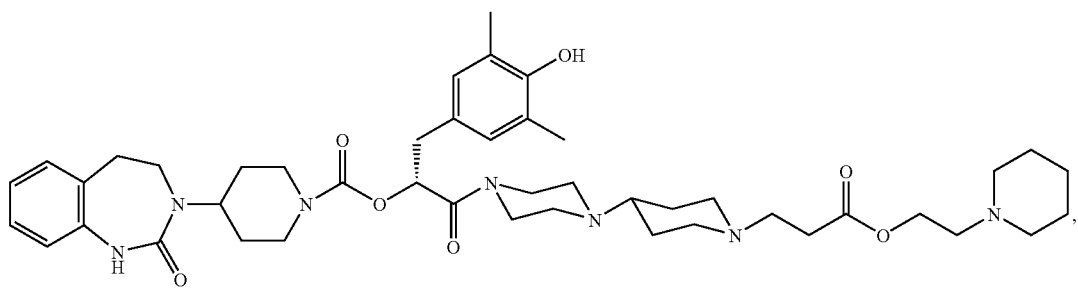 |
| (147) | 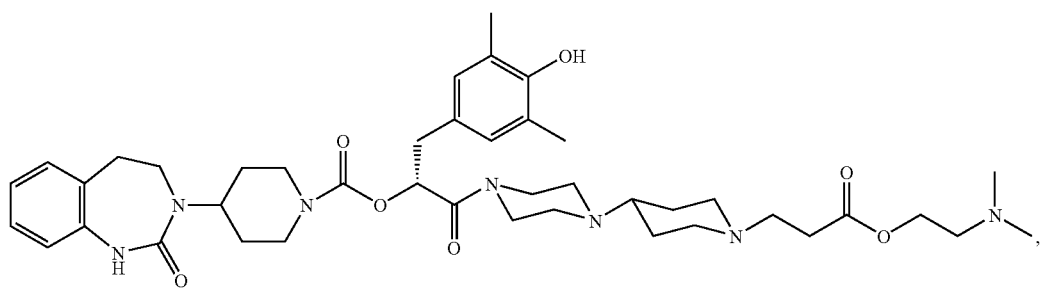 |
| (148) | 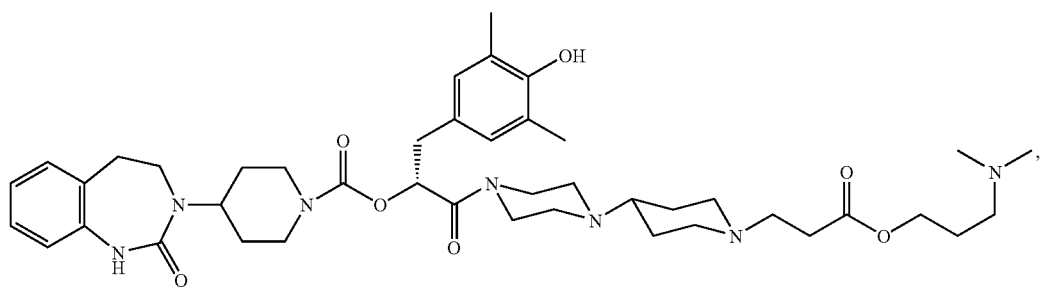 |

| No. | Structure |
|---|---|
| (149) | 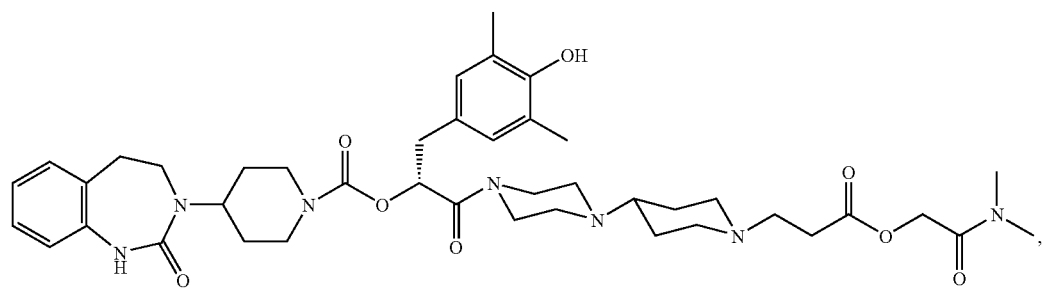 |
| (150) | 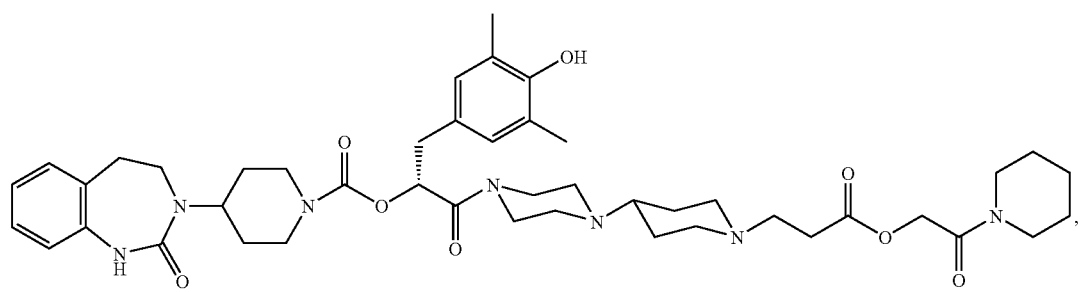 |
| (151) | 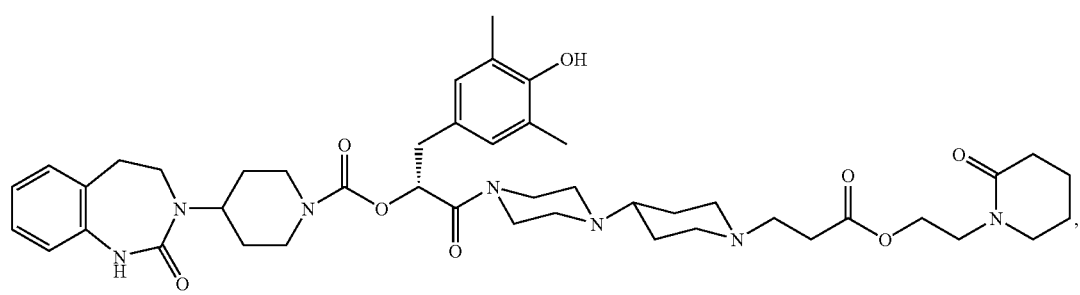 |
| (152) | 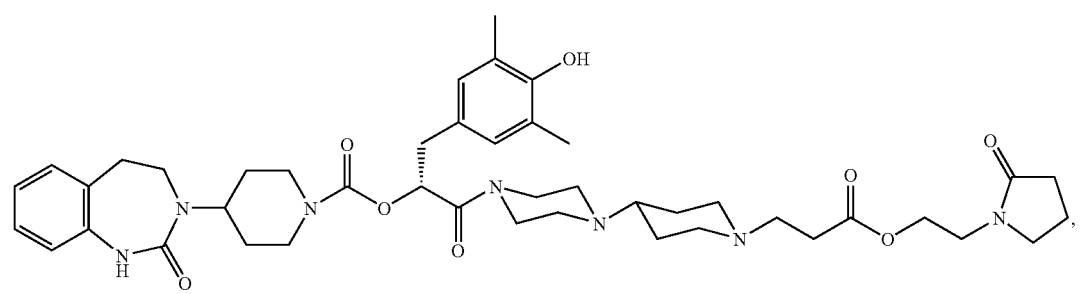 |
| (153) | 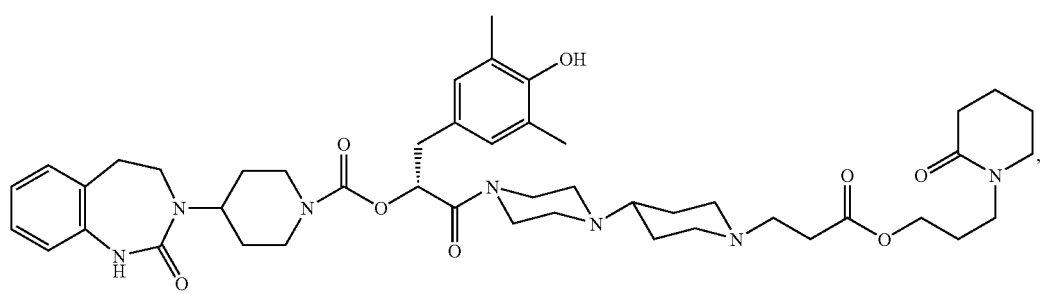 |

| No. | Structure |
|---|---|
| (154) | 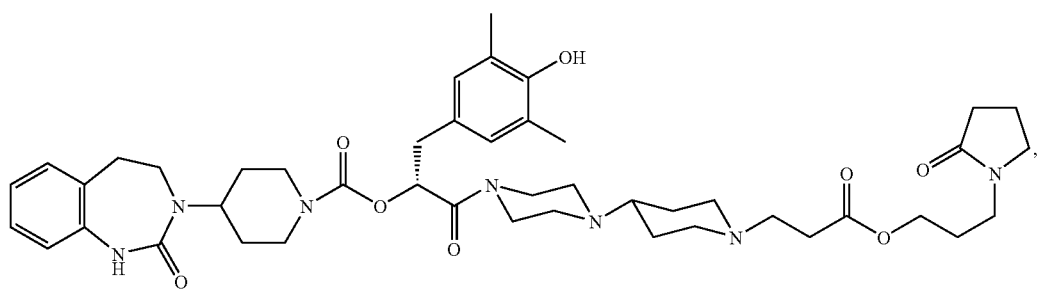 |
| (155) | 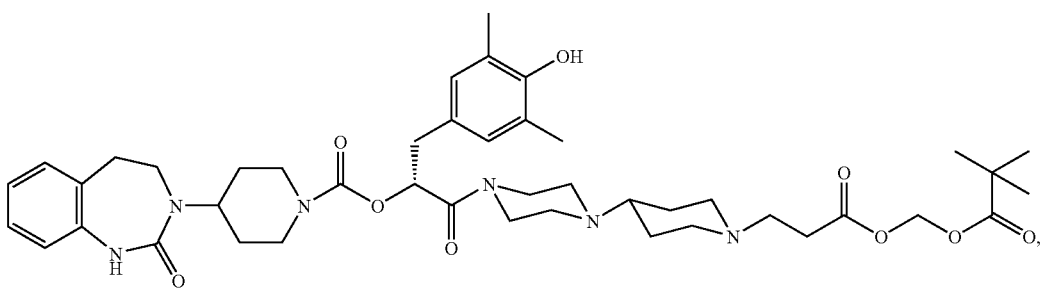 |
| (156) | 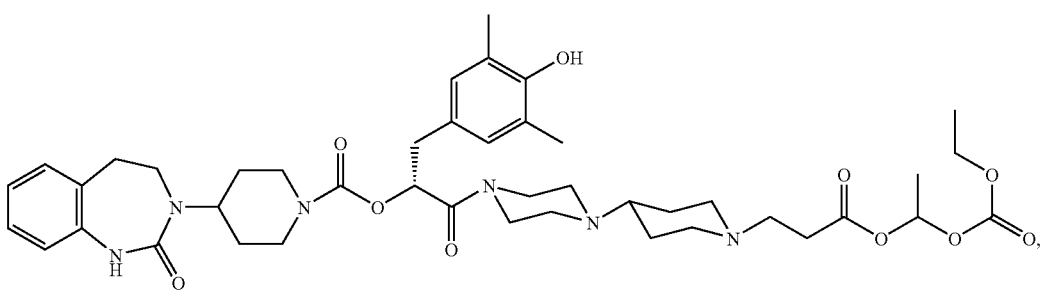 |
| (157) | 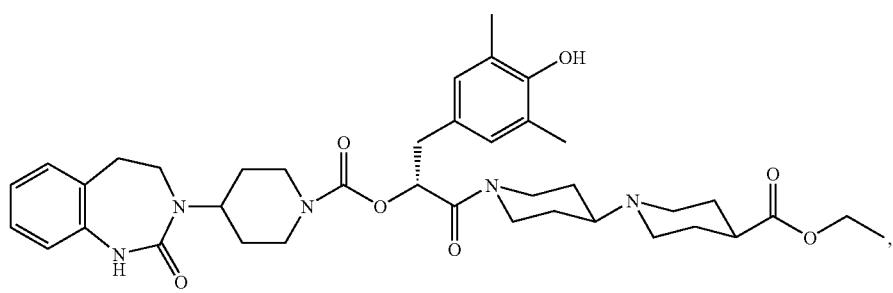 |
| (158) | 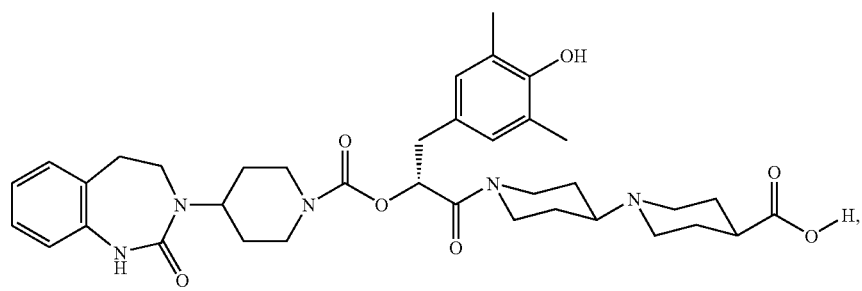 |

| No. | Structure |
|---|---|
| (159) | 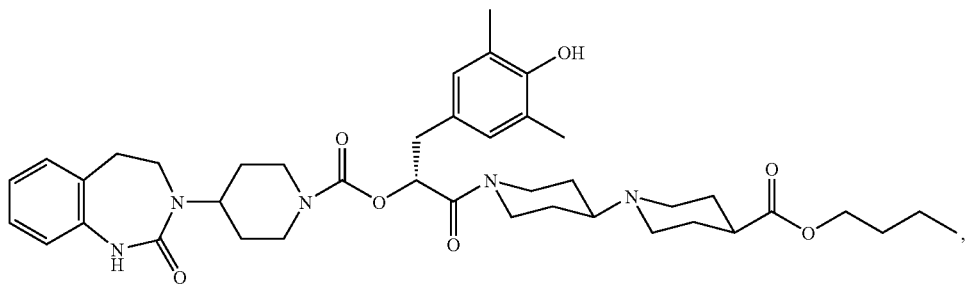 |
| (160) | 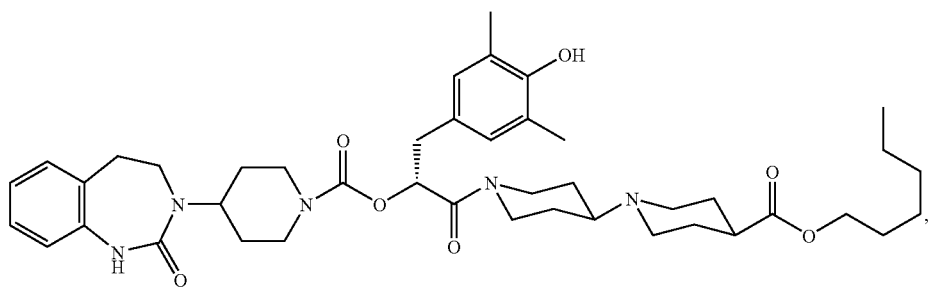 |
| (161) | 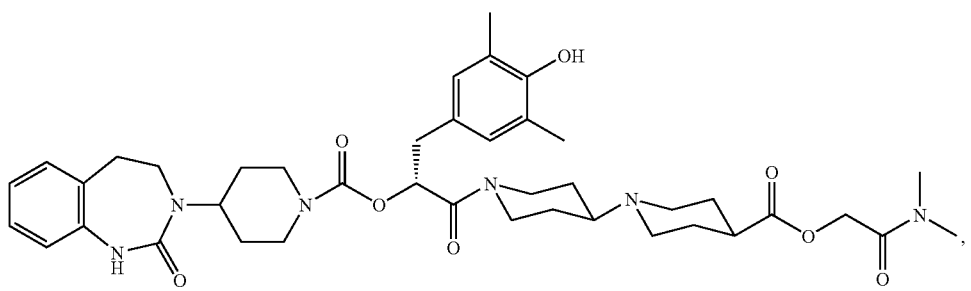 |
| (162) | 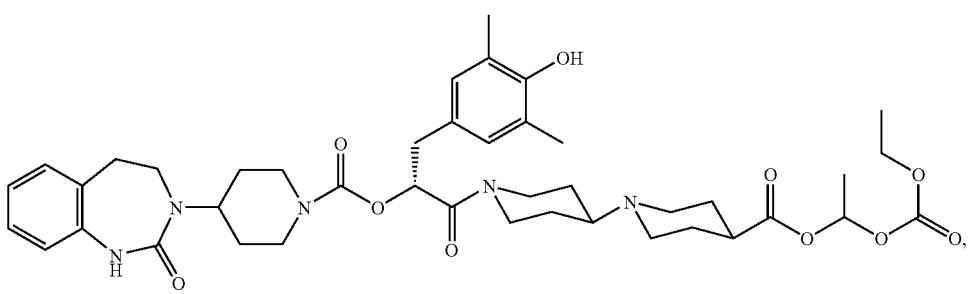 |
| (163) | 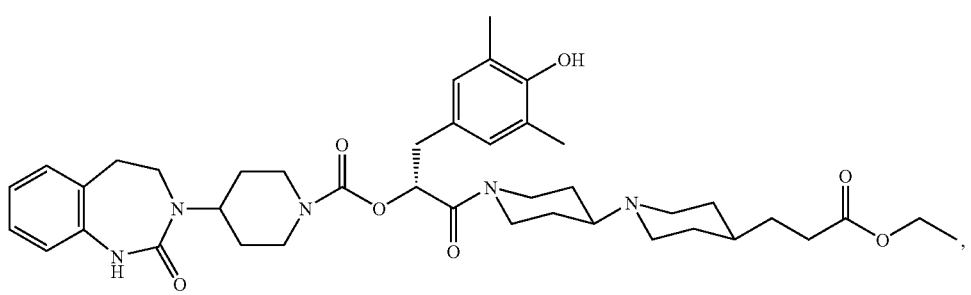 |

-continued
| No. | Structure |
|---|---|
| (164) | 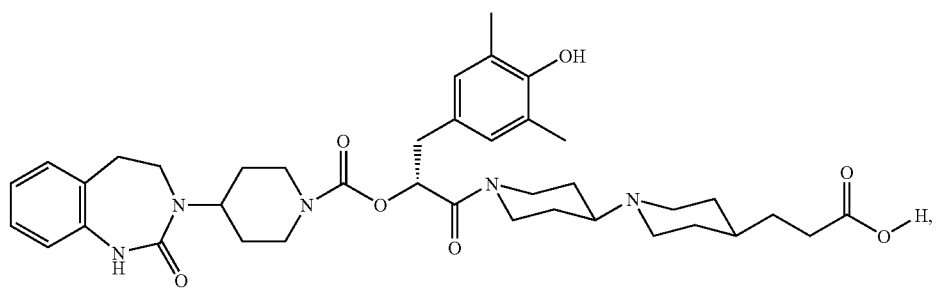 |
| (165) | 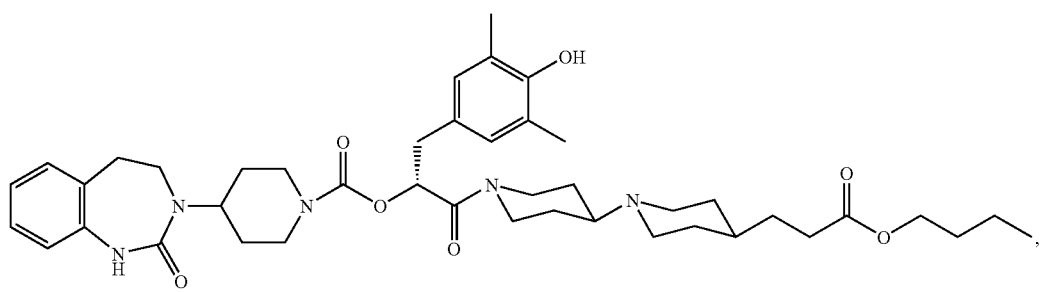 |
| (166) | 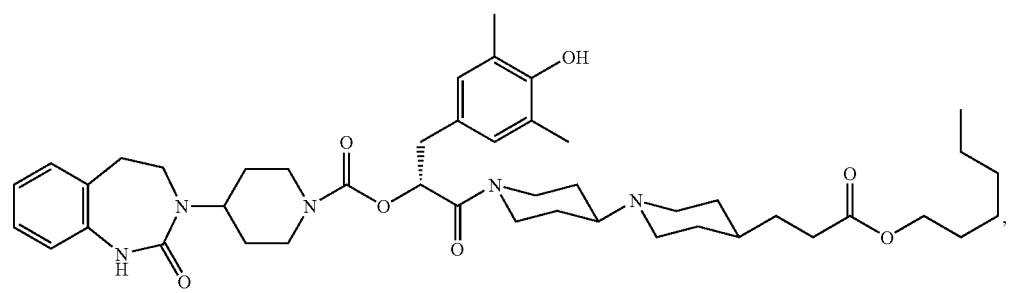 |
| (167) | 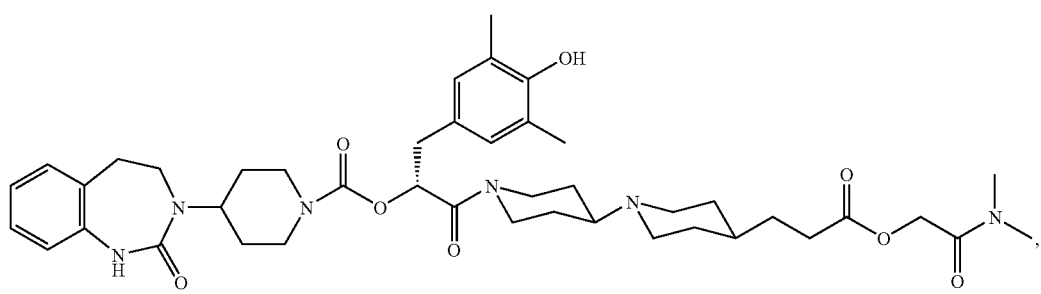 |
| (168) | 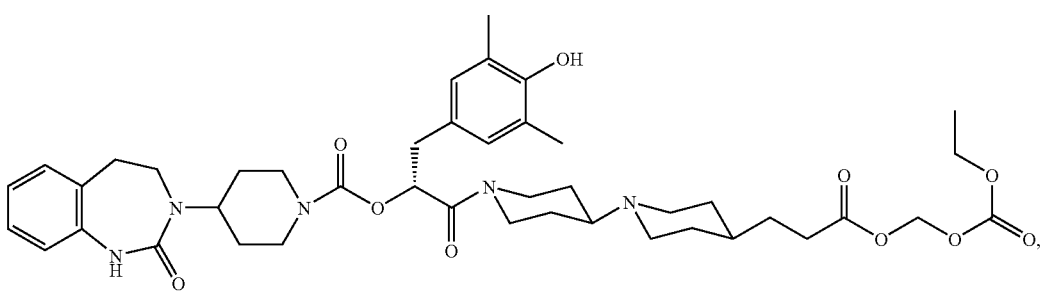 |

-continued
| No. | Structure |
|---|---|
| (169) | 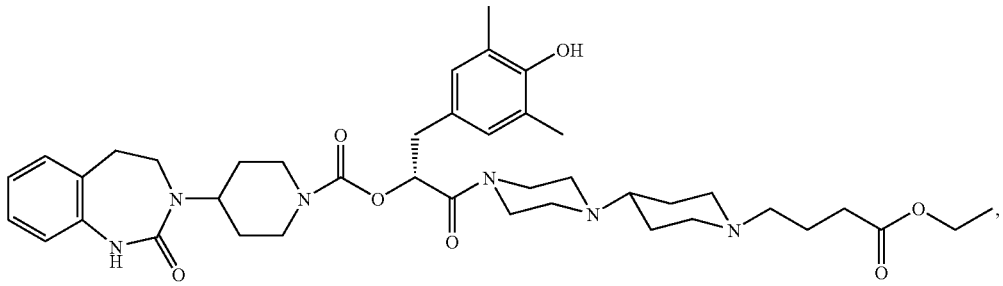 |
| (170) | 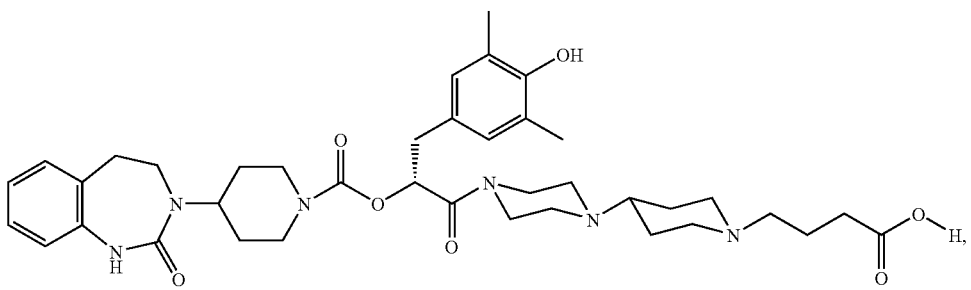 |
| (171) | 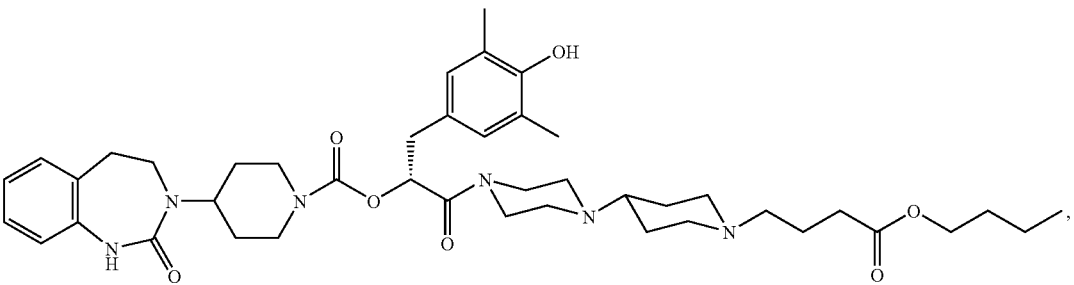 |
| (172) | 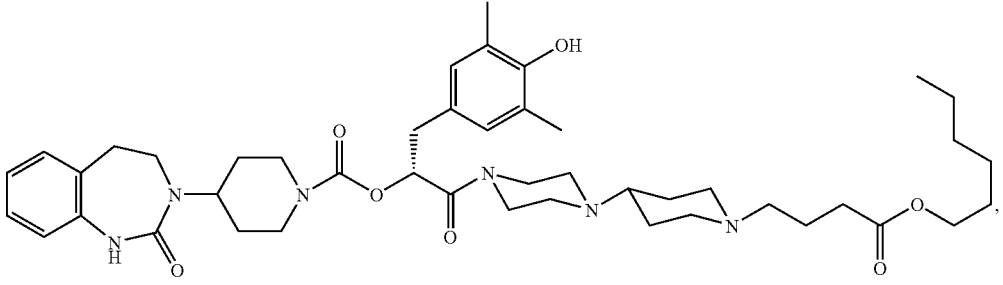 |
| (173) | 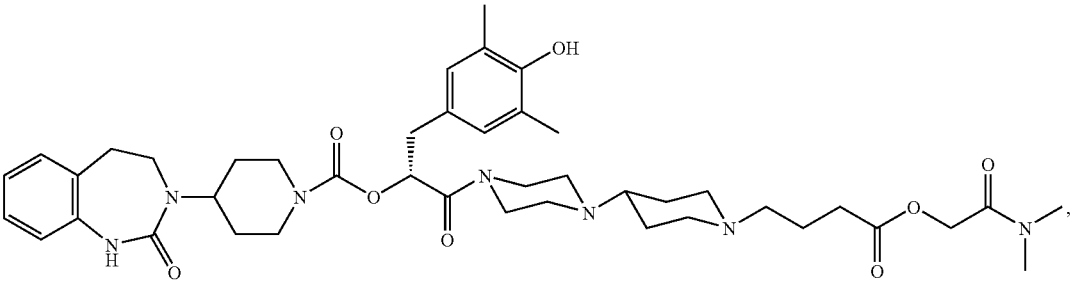 |

-continued
| No. | Structure |
|---|---|
| (174) | 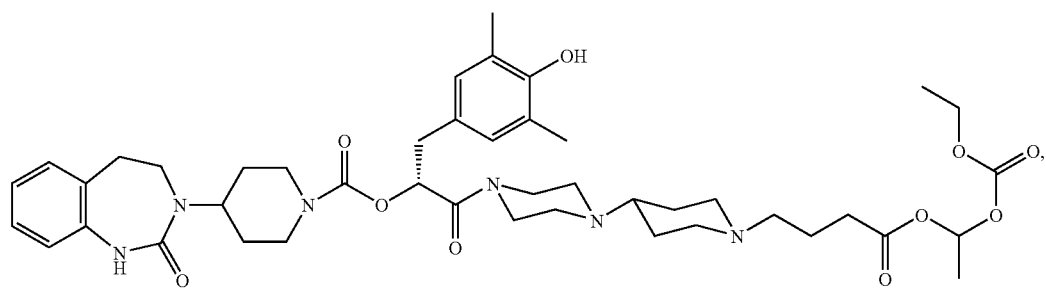 |
| (175) | 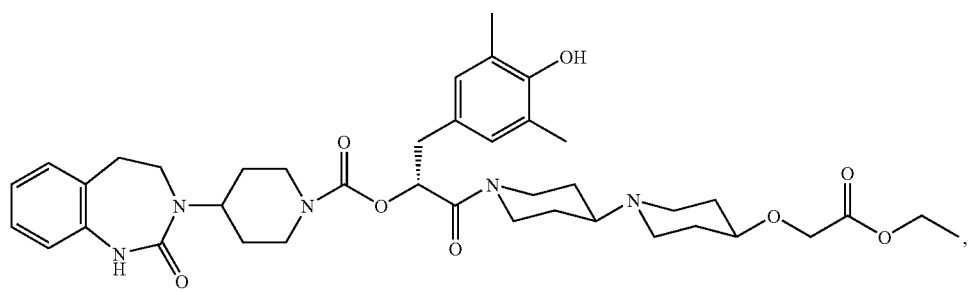 |
| (176) | 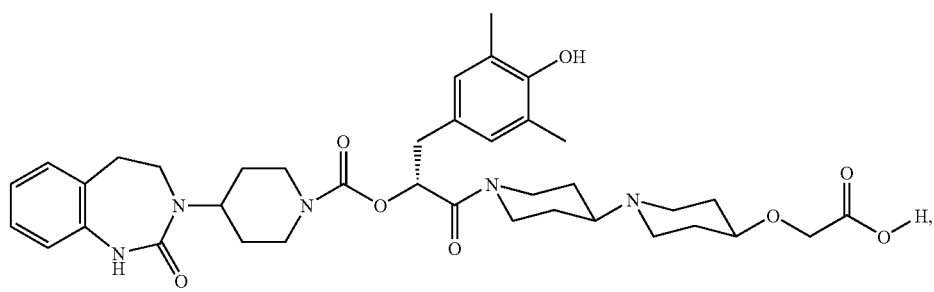 |
| (177) | 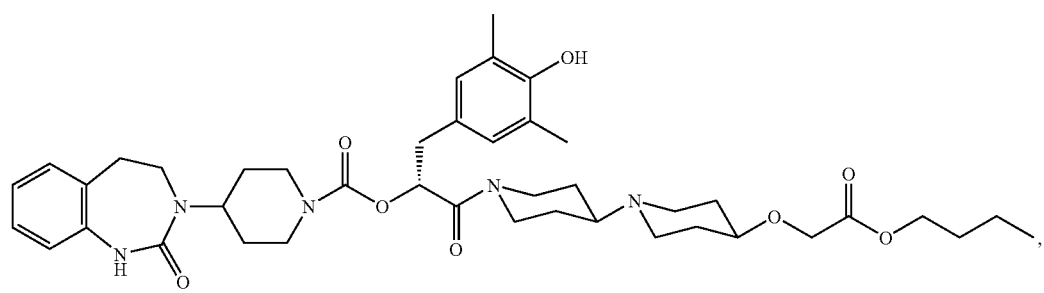 |
| (178) | 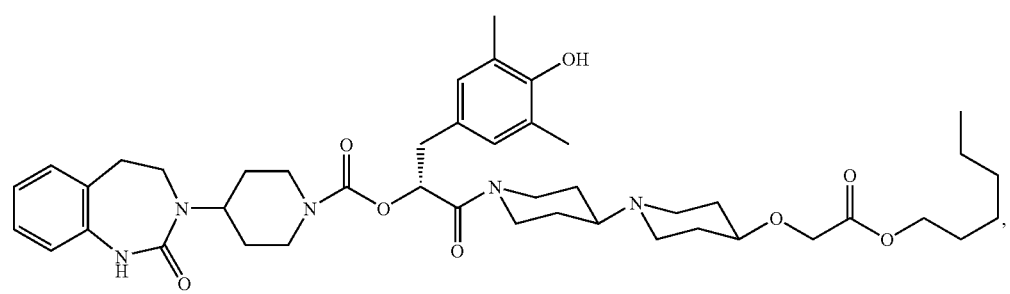 |

| No. | Structure |
|---|---|
| (179) | 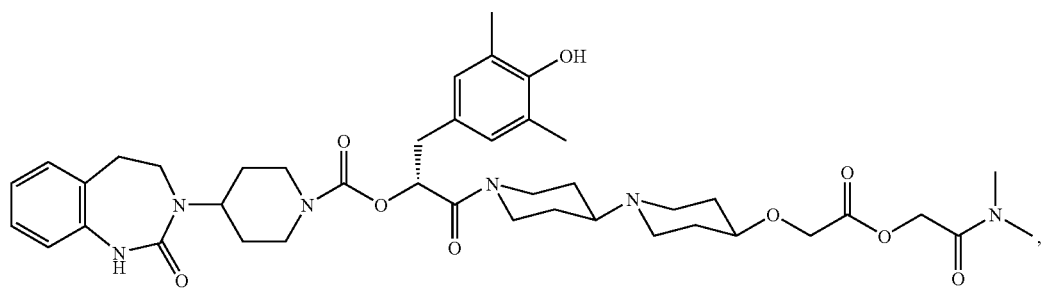 |
| (180) | 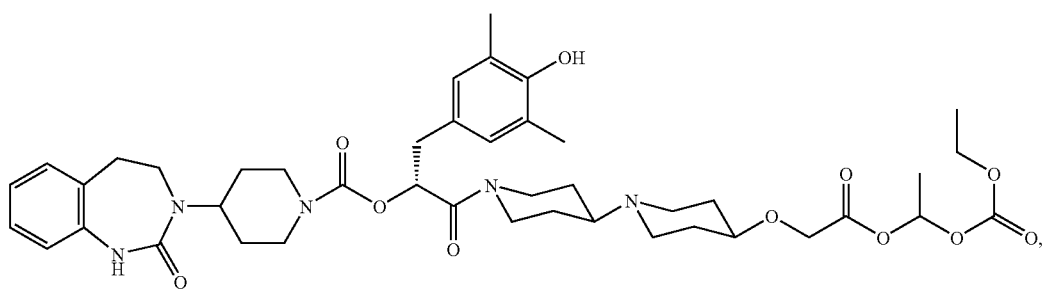 |
| (181) | 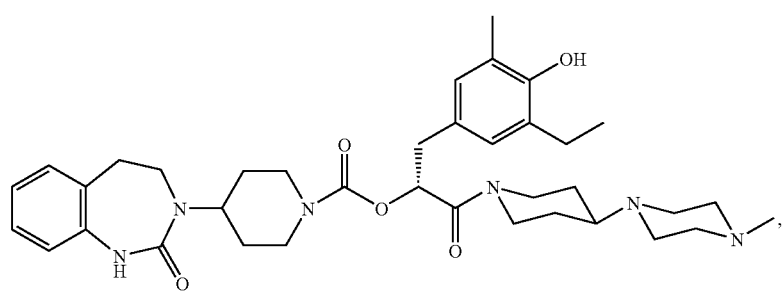 |
| (182) | 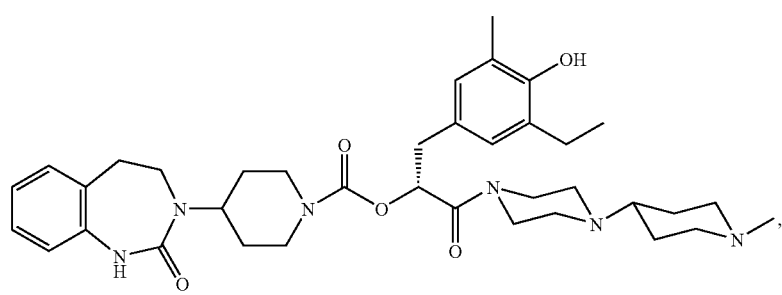 |
| (183) | 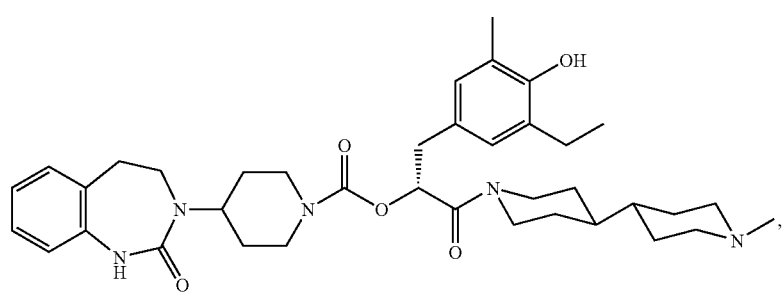 |

-continued
| No. | Structure |
|---|---|
| (184) | 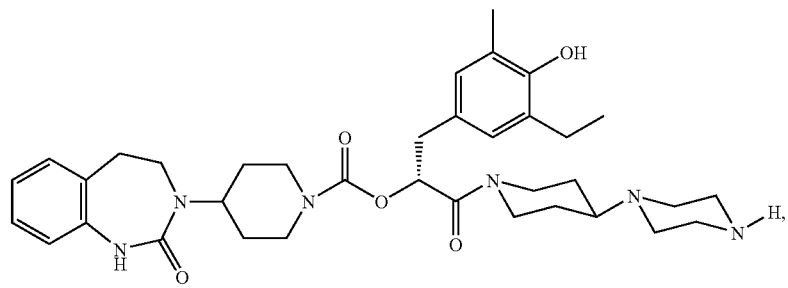 |
| (185) | 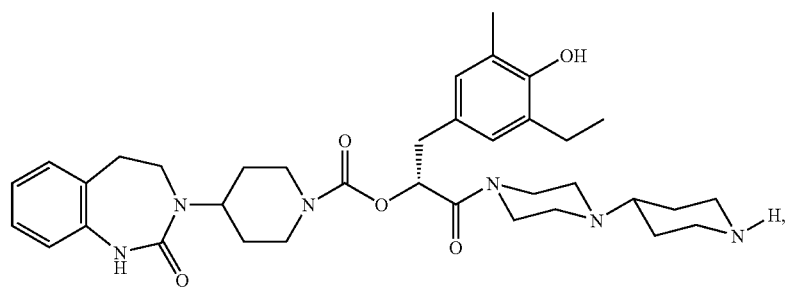 |
| (186) | 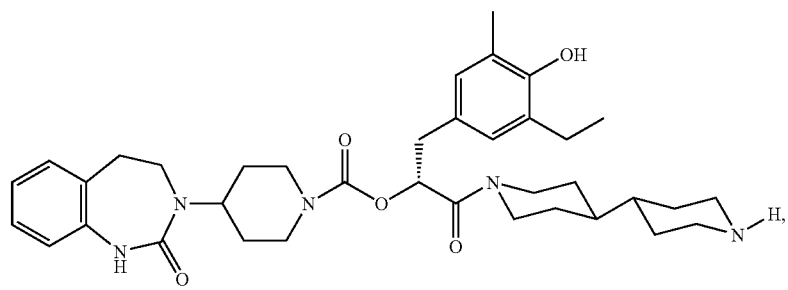 |
| (187) | 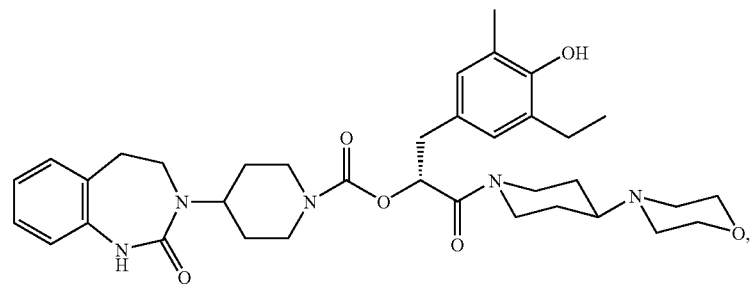 |
| (188) | 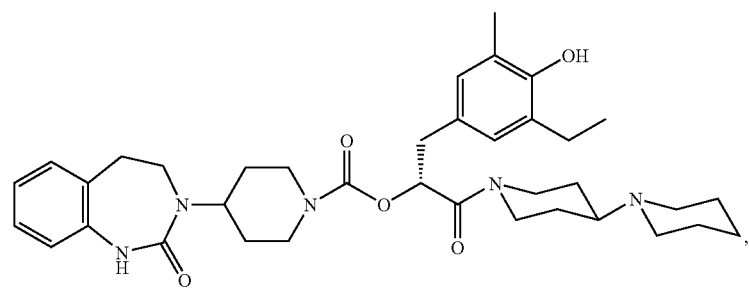 |

-continued
| No. | Structure |
|---|---|
| (189) | 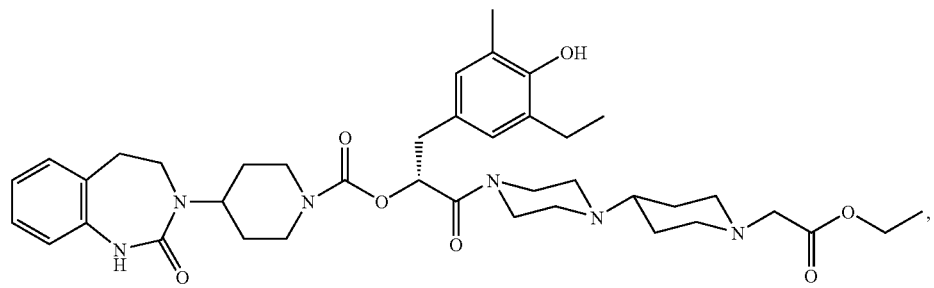 |
| (190) | 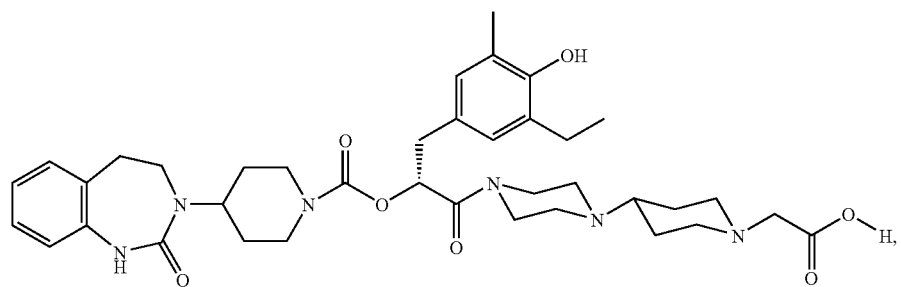 |
| (191) | 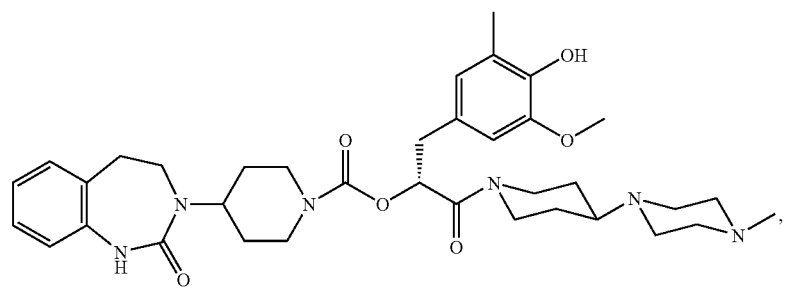 |
| (192) | 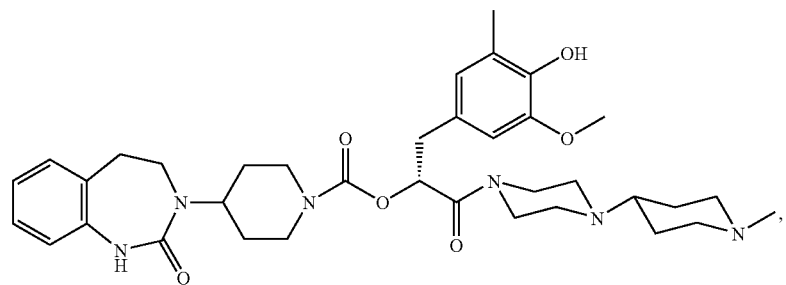 |
| (193) | 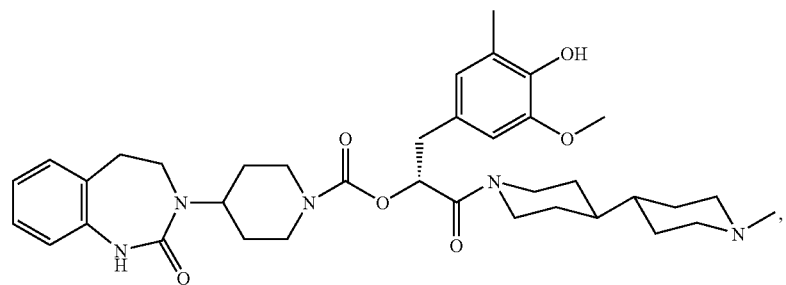 |

| No. | Structure |
|---|---|
| (194) | 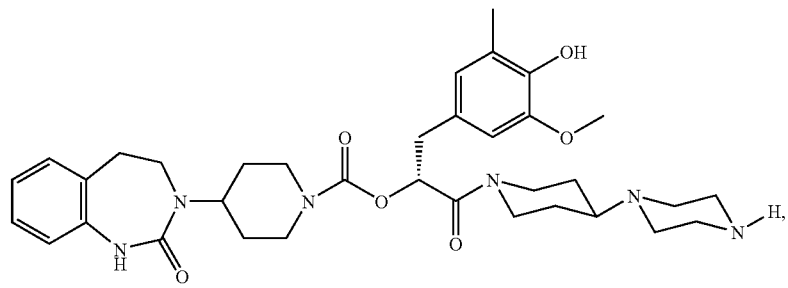 |
| (195) | 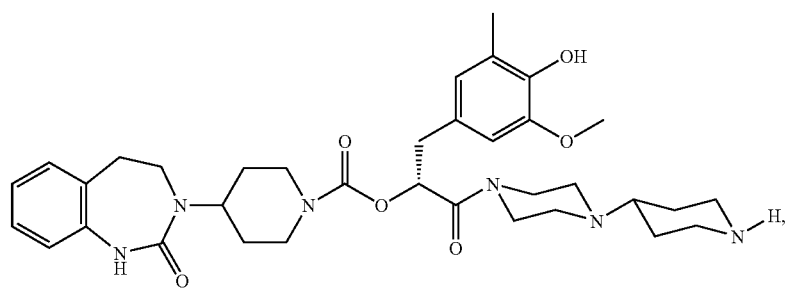 |
| (196) | 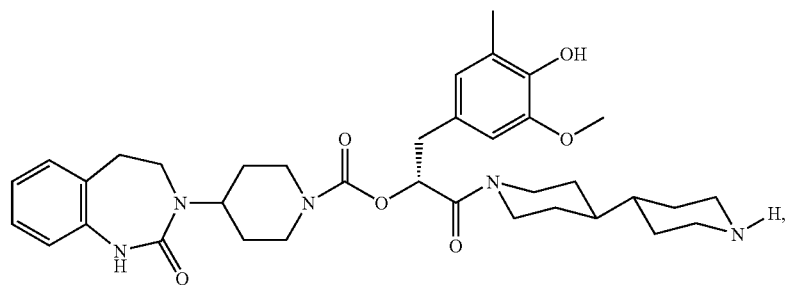 |
| (197) | 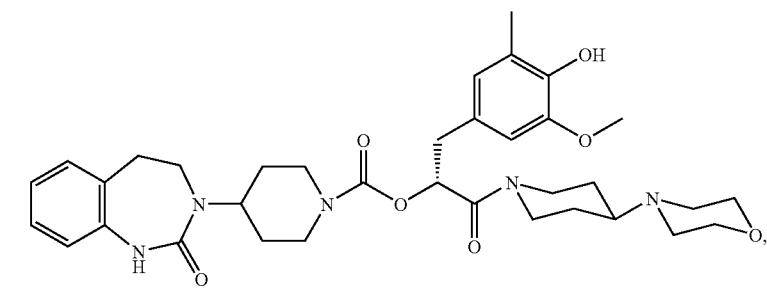 |
| (198) | 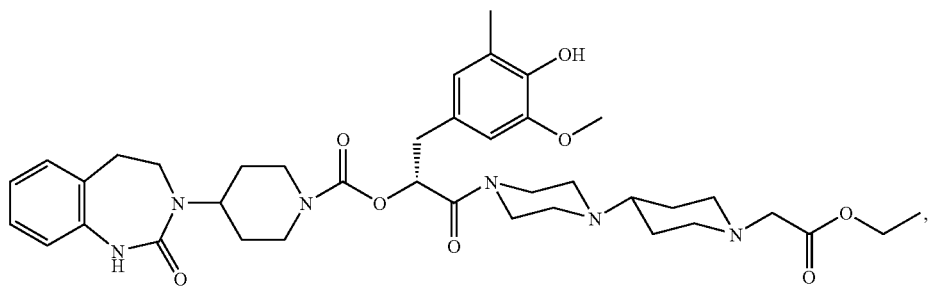 |

| No. | Structure |
|---|---|
| (199) | 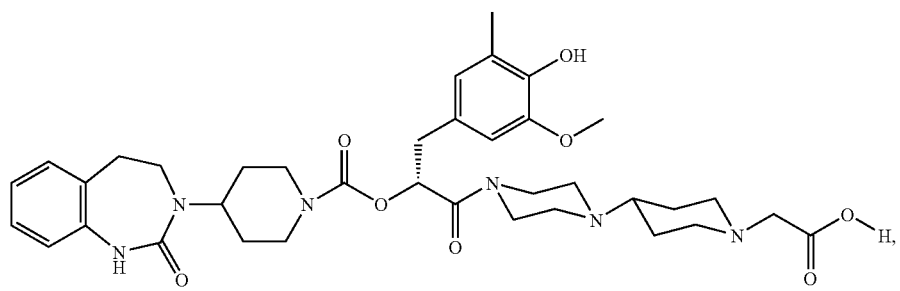 |
| (200) | 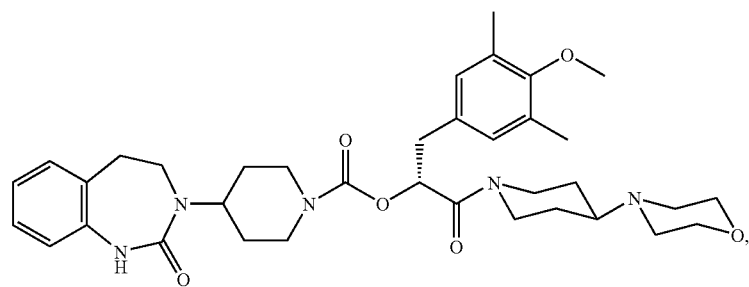 |
| (201) | 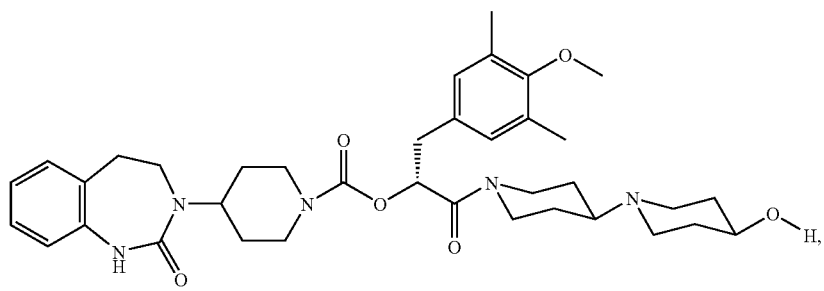 |
| (202) | 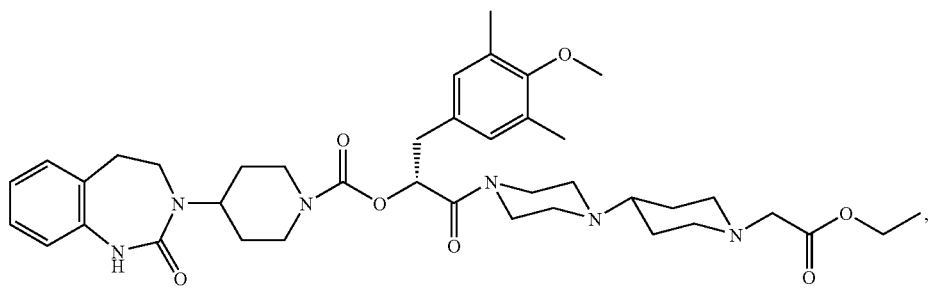 |
| (203) | 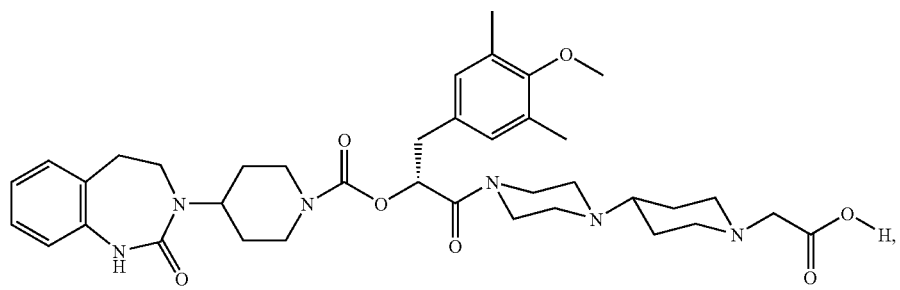 |

-continued
| No. | Structure |
|---|---|
| (204) | 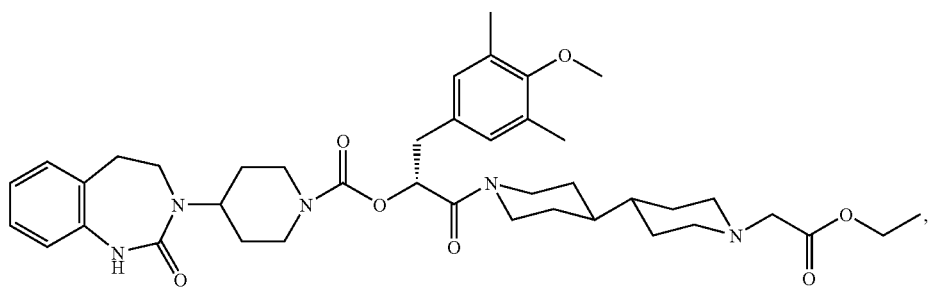 |
| (205) | 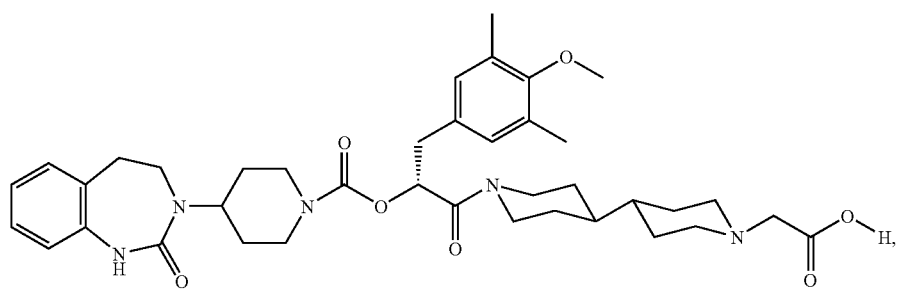 |
| (206) | 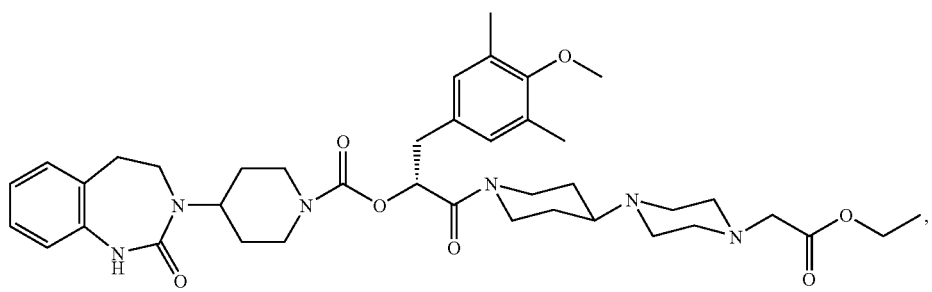 |
| (207) | 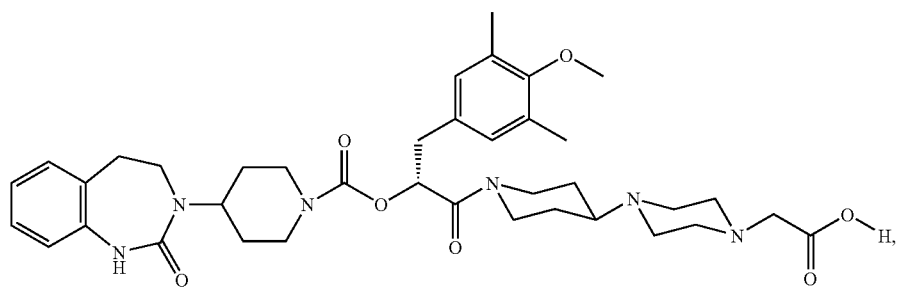 |
| (208) | 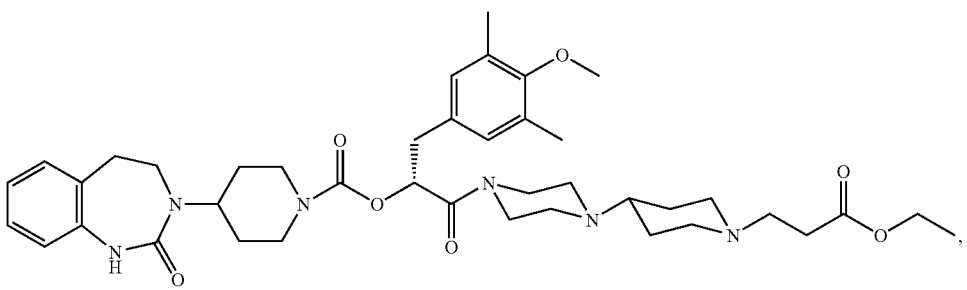 |

| No. | Structure |
|---|---|
| (209) | 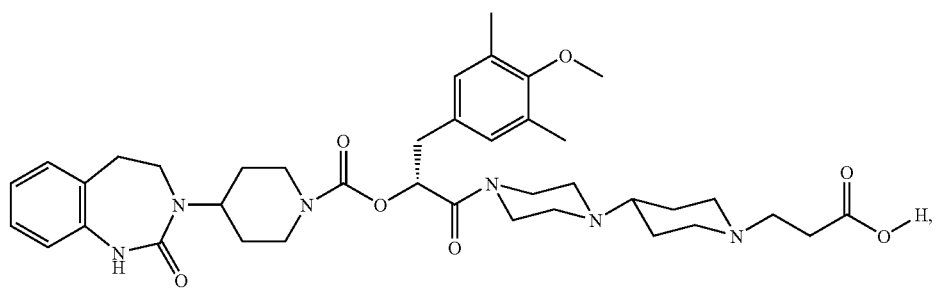 |
| (210) | 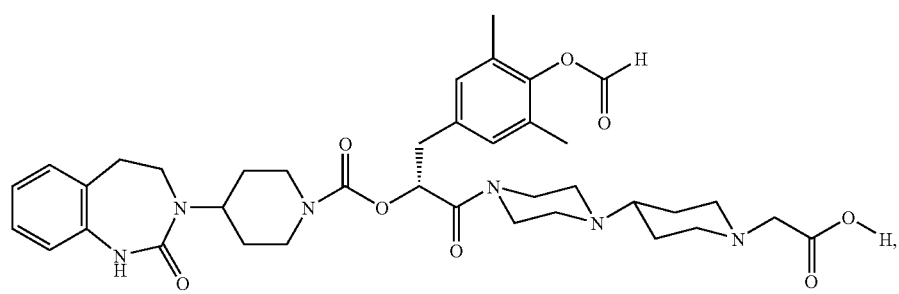 |
| (211) | 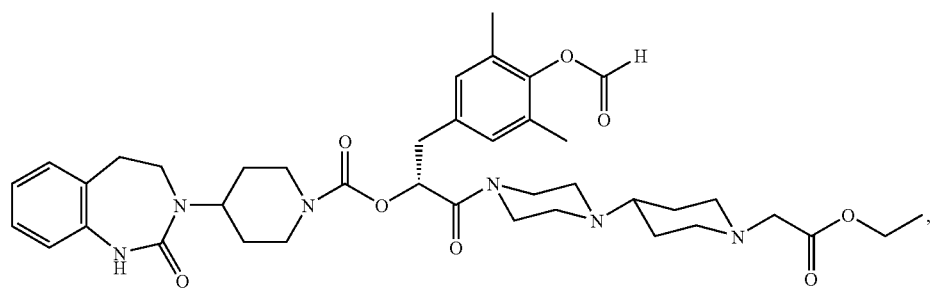 |
| (212) | 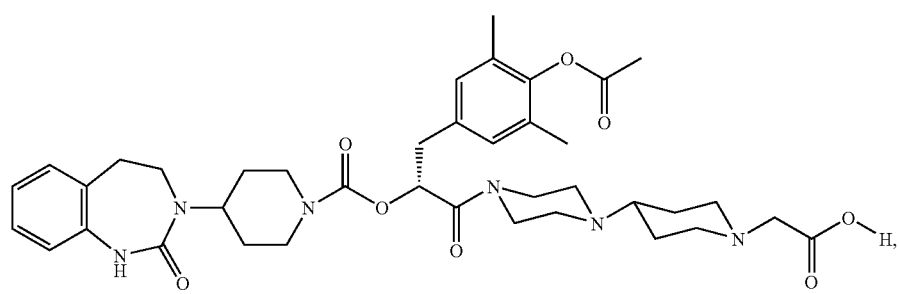 |
| (213) | 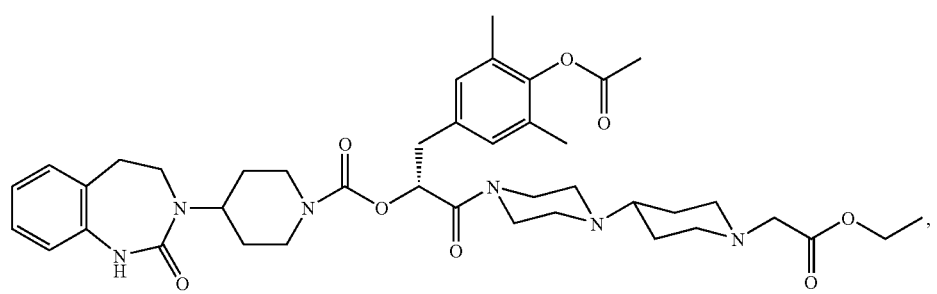 |

-continued
| No. | Structure |
|---|---|
| (214) | 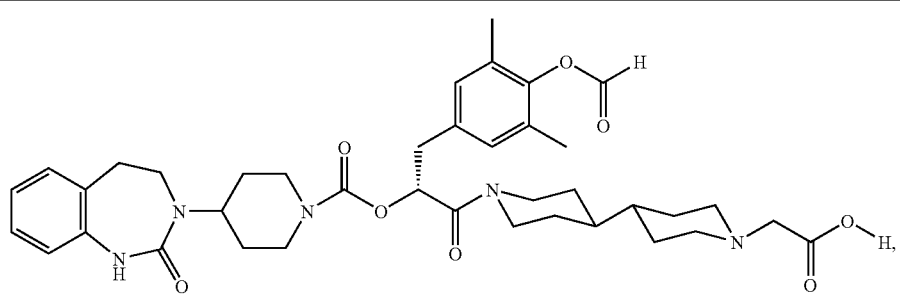 |
| (215) | 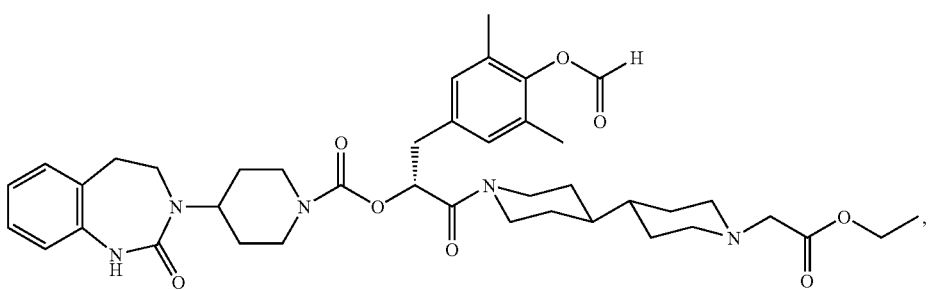 |
| (216) | 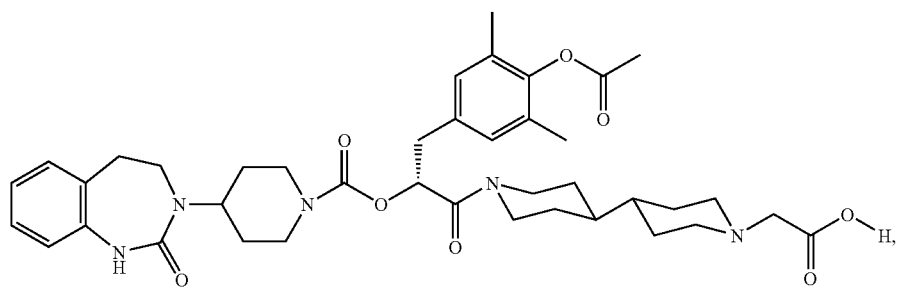 |
| (217) | 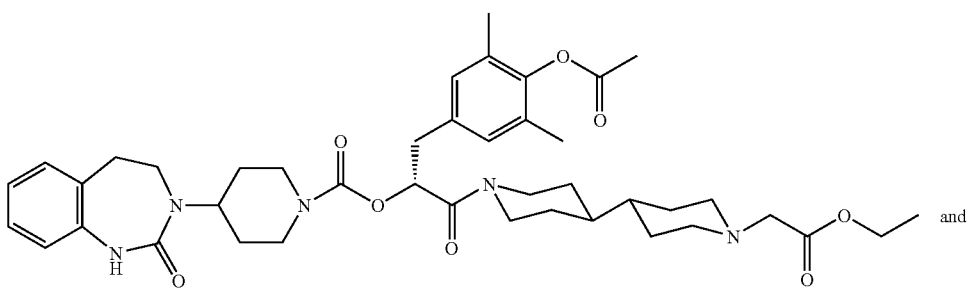 and |
| (218) | 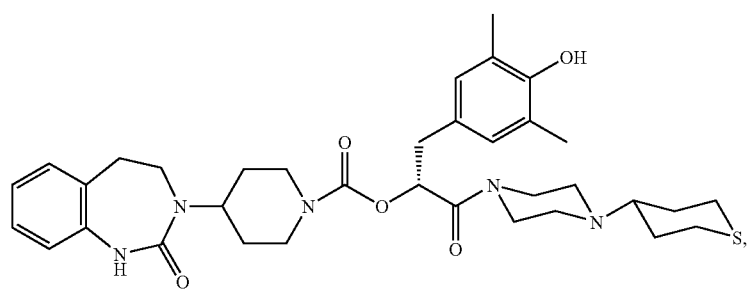 | the tautomers, the diastereomers, the enantiomers, the hydrates, the mixtures thereof and the salts thereof and the hydrates of the salts thereof, particularly the physiologically acceptable salts thereof with inorganic or organic acids or bases.

TERMS AND DEFINITIONS USED

Unless otherwise stated, all the substituents are independent of one another. If for example there are a plurality of $C_{1-6}$-alkyl groups as substituents in one group, in the case of three $C_{1-6}$-alkyl substituents, independently of one another, one may represent methyl, one n-propyl and one tert-butyl.

Within the scope of this application, in the definition of possible substituents, these may also be represented in the form of a structural formula. If present, an asterisk (*) in the structural formula of the substituent is to be understood as being the linking point to the rest of the molecule.

The subject-matter of this invention also includes the compounds according to the invention, including the salts thereof, wherein one or more hydrogen atoms, for example one, two, three, four or five hydrogen atoms, are replaced by deuterium.

By the term "$C_{1-2}$-alkyl" (including those which are part of other groups) are meant alkyl groups with 1 or 2 carbon atoms, by the term "$C_{1-3}$-alkyl" are meant branched and unbranched alkyl groups with 1 to 3 carbon atoms, and by the term "$C_{1-6}$-alkyl" are meant branched and unbranched alkyl groups with 1 to 6 carbon atoms. Examples include: methyl, ethyl, n-propyl, iso-propyl, n-butyl, iso-butyl, sec-butyl, tert-butyl, n-pentyl, iso-pentyl, neo-pentyl or hexyl. The following abbreviations may optionally also be used for the above-mentioned groups: Me, Et, n-Pr, i-Pr, n-Bu, i-Bu, t-Bu, etc. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-3}$-alkylene" (including those which are part of other groups) are meant branched and unbranched alkylene groups with 1 to 3 carbon atoms and by the term "$C_{2-4}$-alkylene" are meant branched and unbranched alkylene groups with 2 to 4 carbon atoms, by the term "$C_{1-6}$-alkylene" are meant branched and unbranched alkylene groups with 1 to 6 carbon atoms, by the term "$C_{2-6}$-alkylene" are meant branched and unbranched alkylene groups with 2 to 6 carbon atoms, and by the term "$C_{1-8}$-alkylene" are meant branched and unbranched alkylene groups with 1 to 8 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene, heptylene or octylene. Unless stated otherwise, the definitions propylene, butylene, pentylene, hexylene, heptylene and octylene include all the possible isomeric forms with the same number of carbons. Thus, for example, propylene also includes 1-methylethylene and butylene includes 1-methylpropylene, 1,1-dimethylethylene, 1,2-dimethylethylene.

It should also be mentioned that within the scope of the present invention the terms "alkylene" and "alkylenyl" are used synonymously.

By the term "$C_{3-6}$-cycloalkyl" (including those which are part of other groups) are meant cyclic alkyl groups with 3 to 6 carbon atoms and by the term "$C_{3-7}$-cycloalkyl" are meant cyclic alkyl groups with 3 to 7 carbon atoms. Examples of these include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

Compounds of general formula I may have acid groups, mainly carboxyl groups, and/or basic groups such as e.g. amino functions. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

The compounds according to the invention may be present as racemates, provided that they have only one chiral element, but may also be obtained as pure enantiomers, i.e. in the (R) or (S) form. Compounds which are present as racemates or in the (R) form are preferred.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

Methods of Preparation

The compounds of general formula I are prepared by methods known in principle. The following methods have proved particularly useful for preparing the compounds of general formula I according to the invention:

(a) For preparing compounds of general formula I wherein all the groups are as hereinbefore defined:

coupling a carboxylic acid of general formula V

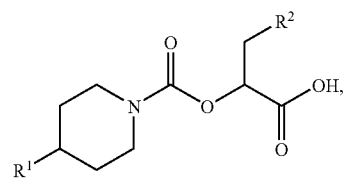

wherein $R^1$ and $R^2$ are as hereinbefore defined, with an amine of general formula VI

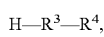

wherein $R^3$ and $R^4$ are as hereinbefore defined, the linking taking place via the nitrogen atom of $R^3$.

Before the reaction is carried out any carboxylic acid functions, primary or secondary amino functions or hydroxy functions present in the groups of the amine of formula H—R³—R⁴ may be protected by conventional protective groups and after the reaction has taken place any protective groups used may be cleaved again using methods familiar to those skilled in the art.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOOBt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30° C. and +30° C., preferably −20° C. and +25° C. If necessary, N-ethyl-diisopropylamine (Hünig base) is preferably used as an additional auxiliary base.

The so-called "anhydride process" is used as a further coupling method for synthesising compounds of general formula I (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the "mixed anhydride process" is preferred (J. R. Vaughan Jr., J. Amer. Chem. Soc. 73, 3547 (1951)), in which the mixed anhydride of the carboxylic acid of general formula V which is to be coupled and monoisobutyl carbonate is obtained, using isobutyl chlorocarbonate in the presence of bases such as 4-methylmorpholine or 4-ethylmorpholine. The preparation of this mixed anhydride and the coupling with the amines of general formula VI are carried out in a one-pot process, using the above-mentioned solvents and at temperatures between −20° C. and +25° C., preferably 0° C. and +25° C.

(b) For preparing compounds of general formula I wherein all the groups are as hereinbefore defined:

coupling a compound of general formula VII

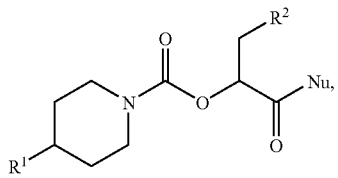

wherein $R^1$ and $R^2$ are as hereinbefore defined and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, wherein the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxo-pyrrolidin-1-yloxy, phthalimidyloxy, 1H-benzotriazol-1-yloxy or azide group, with an amine of general formula VI

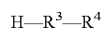

wherein all the groups are as hereinbefore defined and the link is effected via the nitrogen atom of the amine $R^3$.

Before the reaction is carried out any carboxylic acid functions, primary or secondary amino functions or hydroxy functions present in the groups of the amine of general formula VI may be protected by conventional protective groups and after the reaction has taken place any protective groups used may be cleaved again using methods familiar to those skilled in the art.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The new compounds of general formula I according to the invention contain one or more chiral centres. If for example there are two chiral centres present, the compounds may occur in the form of two diastereomeric pairs of antipodes. The invention includes the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+) or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula I is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The carboxylic acids of general formula V needed as starting compounds may be obtained by reacting piperidines of general formula VII

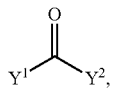

wherein $R^1$ is as hereinbefore defined, with carbonic acid derivatives of general formula IX

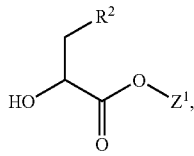

wherein $Y^1$ and $Y^2$ represent nucleofugic groups, which may be identical or different, preferably the chlorine atom, the p-nitrophenoxy or trichloromethoxy group, and with compounds of general formula X

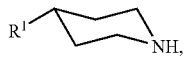

wherein $R^2$ is as hereinbefore defined and $Z^1$ denotes a protective group for a carboxy group, for example a $C_{1-6}$-alkyl or an optionally substituted benzyl group, wherein the alkyl groups may be straight-chain or branched and the benzyl group may be substituted by one or two methoxy groups.

Preferably $Z^1$ denotes the methyl, ethyl, tert-butyl or benzyl group. Before the reaction is carried out any hydroxy functions present in the group $R^2$ of a compound of formula VI may be protected by conventional protective groups and after the reaction is complete any protective groups used may be cleaved again using methods familiar to the skilled man.

In a first step the compounds of general formula VIII are reacted with the carbonic acid derivatives of general formula IX in a solvent, for example in dichloromethane, THF, pyridine or mixtures thereof, at a temperature between −20° C. to 50° C. in the presence of a base, for example triethylamine, pyridine or ethyldiisopropylamine. The intermediate thus formed may be purified or reacted further without purification. The reaction of these intermediates with compounds of general formula X also takes place in one of the abovementioned solvents and at the temperatures specified above, in the presence of a base, such as triethylamine or pyridine, with or without the addition of an activating reagent, such as e.g. 4-dimethylaminopyridine. To activate them the compounds of general formula X may also be deprotonated using a metal hydride, such as e.g. NaH or KH, while in this case there is no need for the base or the activating reagent to be present.

The starting compounds of formula VIII and IX are either commercially obtainable, known from the literature or may be prepared using methods known from the literature.

One way of obtaining compounds of general formula X comprises reacting aldehydes of general formula XI

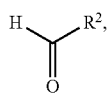

wherein $R^2$ is as hereinbefore defined, with N-acetylglycine in acetic anhydride as solvent in the presence of alkali metal acetate, preferably sodium or potassium acetate, at suitable temperatures, preferably at 80 to 130° C.

The azlactones obtained as primary product are hydrolysed without being isolated to form the compounds of general formula XII

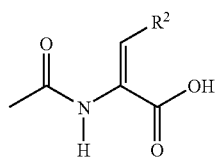

wherein $R^2$ is as hereinbefore defined.

Alternatively enamides of the general structure XIII

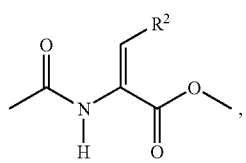

wherein $R^2$ is as hereinbefore defined, may be obtained by a coupling reaction of compounds of general formula XIV

wherein $R^2$ is as hereinbefore defined and Hal denotes the bromine or iodine atom, and methyl 2-acetylaminoacrylate.

The reaction is carried out in a suitable solvent such as tetrahydrofuran, dimethylformamide, 1,4-dioxane or acetonitrile, preferably acetonitrile, at temperatures between ambient temperature and 120° C., preferably between 50° C. and 80° C., in the presence of a suitable auxiliary base, such as triethylamine or ethyldiisopropylamine, preferably triethylamine, and a suitable catalyst system. Suitable catalyst systems constitute the combination of a palladium species, such as palladium(II) acetate or bis(acetonitrile)-palladium dichloride, preferably palladium(II) acetate, and a suitable phosphane ligand, such as triphenyl- or tris-o-tolyl-phosphane, preferably tris-o-tolyl-phosphane.

By further reaction of compounds of general formulae XII and XIII in the presence of aqueous inorganic acids, such as sulphuric, phosphoric or hydrochloric acid, but preferably hydrochloric acid, compounds of general formula XV are obtained

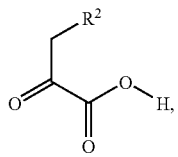

wherein $R^2$ is as hereinbefore defined.

These are then converted with suitable reducing agents into the compounds of general formula XVI

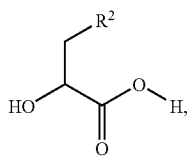

wherein $R^2$ is as hereinbefore defined.

Suitable reducing agents are alkali metal borohydrides, such as sodium or potassium borohydride. Other suitable reducing agents are chlorodialkylboranes, such as chlorodicyclohexylborane. If chiral chlorodialkylboranes, such as e.g. B-chlorodiisopinocampheylborane, are used, the compounds of general formula XIV may be isolated in enantiomerically pure form. The further reaction of compounds of general formula XIV to form compounds of general formula X is carried out in an alcoholic medium, preferably in methanol or ethanol, in the presence of a suitable acid, such as hydrochloric acid. Alternatively, the reaction may be carried out by reacting with thionyl chloride in alcoholic solvents, preferably methanol.

All the compounds of general formula I which contain primary or secondary amino, hydroxy or hydroxycarbonyl functions are preferably obtained from precursors with protective groups. Examples of protective groups for amino functions include a benzyloxycarbonyl, 2-nitrobenzyloxycarbonyl, 4-nitro-benzyloxycarbonyl, 4-methoxy-benzyloxycarbonyl, 2-chloro-benzyloxycarbonyl, 3-chloro-benzyloxycarbonyl, 4-chloro-benzyloxycarbonyl, 4-biphenylyl-α,α-dimethyl-benzyl-oxycarbonyl or 3,5-dimethoxy-α,α-dimethyl-benzyloxycarbonyl group, an alkoxycarbonyl group with a total of 1 to 5 carbon atoms in the alkyl moiety, for example the methoxycarbonyl, ethoxycarbonyl, n-propoxycarbonyl, iso-propoxycarbonyl, n-butoxycarbonyl, 1-methylpropoxycarbonyl, 2-methylpropoxy-carbonyl or tert-butyloxycarbonyl group, the allyloxycarbonyl, 2,2,2-trichloro-(1,1-dimethylethoxy)carbonyl or 9-fluorenylmethoxycarbonyl group or a formyl, acetyl or trifluoroacetyl group.

Examples of protective groups for hydroxy functions include a trimethylsilyl, triethylsilyl, triisopropyl, tert-butyldimethylsilyl or tert-butyldiphenylsilyl group, a tert-butyl, benzyl, 4-methoxybenzyl or 3,4-dimethoxybenzyl group.

Examples of protective groups for hydroxycarbonyl functions include an alkyl group with a total of 1 to 5 carbon atoms, for example the methyl, ethyl, n-propyl, isopropyl, n-butyl, tert-butyl, allyl, 2,2,2-trichloroethyl, benzyl or 4-methoxybenzyl group.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

Moreover, if they contain a carboxylic acid function, the new compounds of formula I may be converted into the addition salts thereof with inorganic or organic bases, particularly, for pharmaceutical use, into their physiologically acceptable addition salts. Suitable bases for this include for example sodium hydroxide, potassium hydroxide, ammonia, cyclohexylamine, dicyclohexylamine, ethanolamine, diethanolamine and triethanolamine.

The present invention relates to racemates if the compounds of general formula I have only one chiral element. However, the application also includes the individual diastereomeric pairs of antipodes or mixtures thereof which are obtained if there is more than one chiral element in the compounds of general formula I, as well as the individual optically active enantiomers of which the above-mentioned racemates are made up.

Also included in the subject matter of this invention are the compounds according to the invention, including the salts thereof, in which one or more hydrogen atoms, for example one, two, three, four or five hydrogen atoms, are replaced by deuterium.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM $MgCl_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity after the presence of 1 µM human CGRP-alpha during incubation.

The concentration binding curves are analysed using computer-aided non-linear curve fitting.

The compounds mentioned hereinbefore show $IC_{50}$ values ≦10000 nM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 µl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the $pA_2$ values of antagonistically acting substances are determined graphically.

The compounds according to the invention exhibit CGRP-antagonistic properties in the in vitro test model described, in a dosage range between $10^{-12}$ and $10^{-5}$ M.

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

Preferably, the compounds according to the invention are suitable for the acute and prophylactic treatment of migraine and cluster headaches, for treating irritable bowel syndrome (IBS) and for the preventive and acute-therapeutic treatment of hot flushes in oestrogen-deficient women.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, one to three times a day in each case.

If the treatment with CGRP antagonists and/or CGRP release inhibitors is given as a supplement to conventional hormone replacement, it is advisable to reduce the doses specified above, in which case the dosage may be from ⅕ of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiphlogistic, corticosteroids, calcium antagonists, $5-HT_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other $5\text{-HT}_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. mGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. iNOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. sst2 receptor agonists may be added.

The dosage of these active substances is expediently ⅕ of the lowest usually recommended dose to 1/1 of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the compounds of formula I are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain I dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula I are preferably used according to the invention to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as, for example, sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

EXPERIMENTAL SECTION

As a rule IR, $^1$H-NMR and mass spectra have been obtained for the compounds prepared. Unless stated otherwise, $R_f$ values are determined using ready-made TLC silica gel plates 60 F254 (E. Merck, Darmstadt, Item no. 1.05714) without chamber saturation.

The $R_f$ values determined under the heading Polygram-Alox are obtained using ready-made Polygram Alox N/UV$_{254}$ TLC films (coated with 0.2 mm aluminium oxide) made by Macherey-Nagel (Duren, Item no. 802 021).

The ratios given for the eluants relate to units by volume of the particular solvents. The units by volume given for NH$_3$ relate to a concentrated solution of NH$_3$ in water.

Unless stated otherwise, the acid, base and salt solutions used in working up the reaction solutions are aqueous systems of the specified concentrations. Silica gel made by Millipore (MATREX™, 35-70 μm) is used for chromatographic purifications.

Aluminium oxide (Alox) made by ICN Biomedicals (Eschwege, Item no. 02090) is used for chromatographic purifications. The required activity stage is obtained before use in accordance with the manufacturer's instructions.

The HPLC data provided are measured under the parameters listed below:

Method A:

| time (min) | percent by volume of water (with 0.1% formic acid) | percent by volume of acetonitrile (with 0.1% formic acid) |
| --- | --- | --- |
| 0 | 95 | 5 |
| 9 | 10 | 90 |
| 10 | 10 | 90 |
| 11 | 95 | 5 |

Analytical column: Zorbax column (Agilent Technologies), SB (Stable Bond) C18; 3.5 µm; 4.6×75 mm; column temperature: 30° C.; flow: 0.8 mL/min; injection volume: 5 µL; detection at 254 nm Method B:

| time (min) | percent by volume of water (with 0.1% formic acid) | percent by volume of acetonitrile (with 0.1% formic acid) |
|---|---|---|
| 0 | 95 | 5 |
| 4.5 | 10 | 90 |
| 5 | 10 | 90 |
| 5.5 | 90 | 10 |

Analytical column: Zorbax column (Agilent Technologies), SB (Stable Bond) C18; 3.5 µm; 4.6×75 mm; column temperature: 30° C.; flow: 1.6 mL/min; injection volume: 5 µL; detection at 254 nm Method C:

| time (min) | percent by volume of water (with 0.1% formic acid) | percent by volume of acetonitrile (with 0.1% formic acid) |
|---|---|---|
| 0 | 95 | 5 |
| 4 | 50 | 50 |
| 4.5 | 10 | 90 |
| 5 | 10 | 90 |
| 5.5 | 90 | 10 |

Analytical column: Zorbax column (Agilent Technologies), SB (Stable Bond) C18; 3.5 µm; 4.6×75 mm; column temperature: 30° C.; flow: 1.6 mL/min; injection volume: 5 µL; detection at 254 nm Method D:

| time (min) | percent by volume of water (with 0.04% TFA) | percent by volume of acetonitrile (with 0.04% TFA) |
|---|---|---|
| 0 | 80 | 20 |
| 15 | 20 | 80 |
| 17 | 20 | 80 |

Analytical column: Symmetry C8 Waters—4.6×150 mm; 5 micron, flow: 1.3 ml/min, column temperature: 25° C., detection at 254 nm.

In preparative HPLC purifications as a rule the same gradients are used as were used to obtain the analytical HPLC data.

The products are collected under mass control, the fractions containing product are combined and freeze-dried.

In the absence of any more information regarding the configuration, it is unclear whether there are pure enantiomers involved or whether partial or even total racemisation has taken place.

The following abbreviations are used in the test descriptions:

Cyc cyclohexane
DCM dichloromethane
DIPE diisopropylether
DMF N,N-dimethylformamide
EtOAc ethyl acetate
EtOH ethanol
HATU O-(7-azabenzotriazol-1-yl)-N,N,N',N'-tetramethyluronium hexafluoro-phosphate
AcOH acetic acid
i.vac. in vacuo (under vacuum)
MCPBA m-chloroperbenzoic acid
MeOH methanol
NaOAc sodium acetate
PE petroleum ether
RT room temperature
TBME tert-butylmethylether
TBTU O-(benzotriazol-1-yl)-N,N,N',N'-tetramethyluronium-tetrafluoroborate
TFA trifluoroacetic acid
THF tetrahydrofuran Amine A1

[1,4']bipiperidinyl-4-carbonitrile

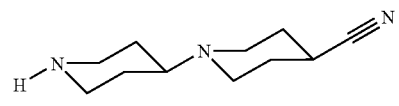

A1a) tert.butyl 4-cyano-[1,4']bipiperidinyl-1'-carboxylate 6.09 g (27.3 mmol) of NaBH(OAc)$_3$ were added batchwise to a suspension, cooled to 0° C., of 5.44 g (27.3 mmol) tert.butyl 4-oxo-piperidin-1-carboxylate, 3.00 g (27.2 mmol) 4-cyanopiperidine and 1.6 mL (28.0 mmol) AcOH in 400 mL DCM and the reaction mixture was stirred overnight, while warming up to RT. 400 mL water were added and the mixture was acidified with citric acid. The organic phase was separated off, the aqueous phase was made alkaline with saturated NaHCO$_3$ solution and extracted exhaustively with DCM. The combined organic phases were concentrated by evaporation i. vac. and the residue was crystallised with a little DIPE.

Yield: 7.1 g (89% of theory)
ESI-MS: (M+H)$^+$=294

A1b) [1,4']bipiperidinyl-4-carbonitrile 10 mL TFA were added to a suspension of 7.1 g (24.2 mmol) tert.butyl 4-cyano-[1,4']bipiperidinyl-1'-carboxylate in 100 mL DCM and the reaction mixture was stirred overnight at RT. The mixture was evaporated down i.vac., the residue was taken up in a little EtOH and combined with ethereal HCl. The precipitated salt was filtered off and dried. The product was obtained as the bis-hydrochloride salt.

Yield: 3.6 g (56% of theory)
ESI-MS: (M+H)$^+$=194

Amine A2

[1,4']bipiperidinyl-4-yl acetate

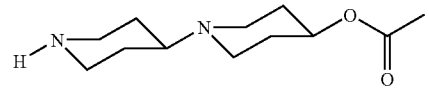

A2a) 1'-benzyl-[1,4']bipiperidinyl-4-ol 25.7 mL (87.4 mmol) titanium(IV)-isopropoxide were added dropwise to a mixture of 15.0 mL (79.3 mmol) 1-benzyl-piperidin-4-one and 8.0 g (79.3 mmol) 4-hydroxy-piperidine and the reaction mixture was stirred for 2 h at RT. It was diluted with 150 mL EtOH and NaBH$_3$CN was added batchwise. After the addition had ended the reaction mixture was stirred for 70 h at RT. 60 mL water were added, insoluble constituents were filtered off through Celite and the filtrate was evaporated down i.vac. Further purification was carried out by chromatography (silica gel, DCM/MeOH/NH$_3$ 80:20:1).

Yield: 17.1 g (79% of theory)
ESI-MS: (M+H)$^+$=275
R$_f$=0.51 (silica gel, DCM/MeOH/NH$_3$ 80:20:1)

A2b) 1'-benzyl-[1,4']bipiperidinyl-4-yl acetate

A solution of 1.5 g (5.47 mmol) 1'-benzyl-[1,4']bipiperidinyl-4-ol in 30 mL acetic anhydride was heated to 50° C. (bath temperature) for 1 h. The mixture was evaporated down i.vac. and the residue was purified by chromatography (silica gel, EtOAc/MeOH/NH$_3$ 95:5:0.5).

Yield: 1.46 g (84% of theory)
ESI-MS: (M+H)$^+$=317
R$_f$=0.43 (silica gel, EtOAc/MeOH/NH$_3$ 90:10:1)

A2c) [1,4']bipiperidinyl-4-yl acetate

A suspension of 1.4 g (4.42 mmol) 1'-benzyl-[1,4']bipiperidinyl-4-yl-acetate and 200 mg 10% Pd/C in 20 mL MeOH was hydrogenated at 3 bar hydrogen pressure for 8 h at RT and for 3 h at 40° C. Then another 200 mg of 10% Pd/C were added and the reaction mixture was hydrogenated for a further 6 h. To complete the reaction 200 mg Pd(OH)$_2$ was added and the mixture was hydrogenated for another 12 h. The catalyst was removed by suction filtering and the filtrate was evaporated down. The product was obtained as a viscous oil.

Yield: 1.00 g (100% of theory)
ESI-MS: (M+H)$^+$=227
Retention time (HPLC-MS): 0.5 min (method B)

Amine A3

4-methoxy-[1,4']bipiperidinyl

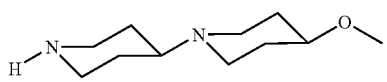

A3a) 1'-benzyl-4-methoxy-[1,4']bipiperidinyl

Under a nitrogen atmosphere 2.4 mL (43.4 mmol) AcOH was added to a solution, cooled to 0° C., of 5.00 g (43.4 mmol) 4-methoxy-piperidine and 9.30 mL (52.1 mmol) 1-benzyl-piperidin-4-one in 200 mL DCM, the reaction mixture was stirred for 2 h at this temperature and then combined batchwise with 19.3 g (91.2 mmol) NaBH(OAc)$_3$. After the addition had ended the mixture was stirred overnight at RT, the reaction solution was made alkaline with 30% K$_2$CO$_3$ solution and combined with 200 mL DCM. The organic phase was separated off, washed with 15% K$_2$CO$_3$ solution and evaporated down i.vac. The oily residue was acidified with methanolic HCl (1.25 M), concentrated by evaporation i.vac., the residue was taken up in EtOH, the precipitated product was suction filtered, triturated with PE, filtered and dried. The product was obtained as the bis-hydrochloride salt.

Yield: 2.1 g (13% of theory)

A3b) 4-methoxy-[1,4']bipiperidinyl

A suspension of 2.1 (5.87 mmol) 1'-benzyl-4-methoxy-[1,4']bipiperidinyl and 1.0 g 10% Pd/C in 50 mL MeOH and 20 mL water was hydrogenated for 8 h at RT and 3 bar hydrogen pressure. The catalyst was removed by suction filtering, the filtrate was concentrated by evaporation i.vac., the residue was triturated with diethyl ether, suction filtered and dried.

Yield: 1.50 g (94% of theory)
ESI-MS: (M+H)$^+$=199

Amine A4

1-(1,1-dioxo-hexahydro-1$\lambda^6$-thiopyran-4-yl)-piperazine

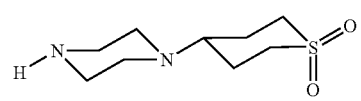

A4a) 1,1-dioxo-tetrahydro-1$\lambda^6$-thiopyran-4-one

A solution of 5.3 g (45.6 mmol) tetrahydrothiopyran-4-one in 50 mL EtOAc was heated to 50° C. At this temperature, 18.6 mL (110 mmol) peracetic acid solution (39% in AcOH) were slowly added dropwise, while the temperature was kept between 50-55° C. using an ice bath. After the addition had ended the reaction mixture was cooled to RT, during which time a precipitate was formed. This was suction filtered and dried. The product was reacted further without purification.

Yield: 6.70 g (99% of theory, purity 80%)
EI-MS: (M)$^+$=148
R$_f$=0.50 (silica gel, EtOAc)

A4b) 1-benzyl-4-(1,1-dioxo-hexahydro-1$\lambda^6$-thiopyran-4-yl)-piperazine A suspension of 5.1 g (27.5 mmol, purity 80%) 1,1-dioxo-tetrahydro-1$\lambda^6$-thiopyran-4-one, 7.0 mL (40.3 mmol) 1-benzyl-piperazine and 30 g molecular sieve A3 in 140 mL isopropanol was combined with a spatula tip of p-toluenesulphonic acid and refluxed for 7 h. The molecular sieve was filtered off, the reaction solution was combined with 8.0 g (37.7 mmol) NaBH(OAc)$_3$ and stirred overnight at RT. 1 g NaBH$_4$ was added to the reaction solution, the mixture was heated to 60° C. for 2 h, mixed with water and then filtered. The filtrate was acidified with 4 M HCl, freed from the isopropanol i.vac., made alkaline with saturated NaHCO$_3$ solution and extracted exhaustively with EtOAc. The combined organic phases were dried on Na$_2$SO$_4$, filtered and concentrated by evaporation i.vac. The residue was purified by chromatography (Alox, activity stage II-III, EtOAc).

Yield: 0.64 g (7% of theory)
ESI-MS: (M+H)$^+$=309
R$_f$=0.50 (Polygram-Alox, EtOAc)

A4c) 1-(1,1-dioxo-hexahydro-1λ⁶-thiopyran-4-yl)-piperazine

A suspension of 0.57 g (1.85 mmol) 1-benzyl-4-(1,1-di-oxo-hexahydro-1λ⁶-thiopyran-4-yl)-piperazine and 300 mg 10% Pd/C in 30 mL MeOH was hydrogenated at 50° C. and 50 psi hydrogen pressure for 10 h. The catalyst was removed by suction filtering and the filtrate was concentrated by evaporation i. vac. The product was reacted further without purification.

Yield: 0.38 g (94% of theory)
ESI-MS: (M+H)⁺=219

Amine A5

1-methyl-4-(4-methyl-piperidin-4-yl)-piperazine

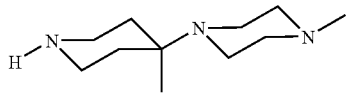

A5a) 1-benzyl-4-(4-methyl-piperazin-1-yl)-piperidine-4-carbonitrile

A solution of 10.0 g (45.3 mmol) 1-benzyl-4-hydroxy-piperidin-4-carbonitrile and 6.0 mL (53.6 mmol) N-methyl-piperazine in 50 mL MeOH was refluxed for 6 h. The mixture was evaporated down i.vac. to about 25 mL, during which time a precipitate was formed. 50 mL of ice water was added, the precipitate was filtered off and dried at 40° C.

Yield: 11.5 g (85% of theory)
ESI-MS: (M+H)⁺=299
$R_f$=0.58 (Polygram-Alox, PE/EtOAc 1:1)

A5b) 1-(1-benzyl-4-methyl-piperidin-4-yl)-4-methyl-piperazine 10 mL methylmagnesium chloride solution (30 mmol, 3 M in THF) were added at RT to a solution of 3.0 g (10.1 mmol) 1-benzyl-4-(4-methyl-piperazin-1-yl)-piperidin-4-carbonitrile in 50 mL dry THF and the reaction mixture was stirred for 2 h. It was combined with saturated NH₄Cl solution, stirred for 10 min, extracted exhaustively with diethyl ether and the combined organic phases were dried on Na₂SO₄. After the elimination of the desiccant and solvent the residue was purified by chromatography (Alox, activity stage II-III, gradient DCM/MeOH 100:1 to 50:1).

Yield: 1.01 g (33% of theory)
ESI-MS: (M+H)⁺=288

A5c) 1-methyl-4-(4-methyl-piperidin-4-yl)-piperazine

A suspension of 0.99 g (3.27 mmol) 1-(1-benzyl-4-methyl-piperidin-4-yl)-4-methyl-piperazine and 200 mg 10% Pd/C in 25 mL MeOH was hydrogenated at 50° C. and 50 psi hydrogen pressure for 2 h. To complete the reaction a further 200 mg catalyst were added and the reaction mixture was hydrogenated for a further 22 h at 60° C. and 50 psi hydrogen pressure. The catalyst was filtered off and the filtrate evaporated to dryness. The product was reacted further without purification.

Yield: 0.56 g (87% of theory)
ESI-MS: (M+H)⁺=198

Amine A6

4-(4-methyl-piperidin-4-yl)-morpholine

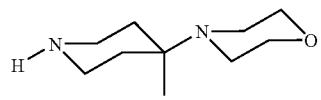

A6a) 1-benzyl-4-morpholin-4-yl-piperidin-4-carbonitrile

A solution of 5.25 g (23.8 mmol) 1-benzyl-4-hydroxy-piperidine-4-carbonitrile and 2.2 mL (25.2 mmol) morpholine in 30 mL MeOH was refluxed for 6 h. The mixture was evaporated to dryness i.vac., while the product was obtained in the form of crystals.

Yield: 6.9 g (100% of theory)
ESI-MS: (M+H)⁺=286

A6b) 4-(1-benzyl-4-methyl-piperidin-4-yl)-morpholine

Prepared analogously to Example A5b from 6.88 g (23.6 mmol) 1-benzyl-4-morpholin-4-yl-piperidin-4-carbonitrile and 25 mL methylmagnesium chloride solution (75 mmol, 3 M in THF).

Yield: 3.0 g (44% of theory)
ESI-MS: (M+H)⁺=275
$R_f$=0.6 (Polygram-Alox, DCM/MeOH 50:1)

A6c) 4-(4-methyl-piperidin-4-yl)-morpholine

A suspension of 3.0 g (10.4 mmol) 4-(1-benzyl-4-methyl-piperidin-4-yl)-morpholine and 150 mg 10% Pd/C in 50 mL MeOH was hydrogenated at 50° C. and 50 psi hydrogen pressure for 2 h. 1 mL concentrated HCl was added and the mixture was hydrogenated for a further 18 h at 50° C. and 50 psi hydrogen pressure. The catalyst was filtered off and the filtrate was evaporated to dryness. The product, which was obtained as the hydrochloride salt, was reacted further without purification.

Yield: 2.4 g (94% of theory)
ESI-MS: (M+H)⁺=185

Amine 7

Ethyl 3-[4,4']bipiperidinyl-1-yl-propionate

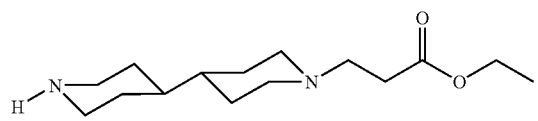

A7a) tert.butyl 1'-(2-ethoxycarbonyl-ethyl)-[4,4']bipiperidinyl-1-carboxylate 4.4 mL (40.6 mmol) ethyl acrylate were added to a solution of 10.0 g (37.3 mmol) tert.butyl [4,4']bipiperidinyl-1-carboxylate in 100 mL EtOH and the reaction mixture was refluxed for 2 h. To complete the reaction a further 1 mL (9.2 mmol) ethyl acrylate were added, the mixture was refluxed for 1 h and left overnight at RT. The solvent was eliminated i.vac. and the crude product was further reacted without any purification.

Yield: 14.0 g (100% of theory)
ESI-MS: (M+H)⁺=369

A7b) ethyl 3-[4,4']bipiperidinyl-1-yl-Propionate 28 mL TFA were added dropwise to a solution of 14.0 g of the crude product of Example A7a in 250 mL DCM and the reaction mixture was stirred for 4 h at RT. The mixture was evaporated down i.vac., the residue was taken up in 200 mL DCM and this solution was added batchwise to a solution of 20 g Na$_2$CO$_3$ in 120 mL water. The organic phase was separated off, the aqueous phase was extracted twice more with DCM and the combined organic phases were dried on Na$_2$SO$_4$. After the elimination of the desiccant and solvent the residue was dried and reacted without further purification.

Yield: 8.8 g (88% of theory)
ESI-MS: (M+H)⁺=269

Amine A8

Ethyl 3-[1,4']bipiperidinyl-4-yl-propionate

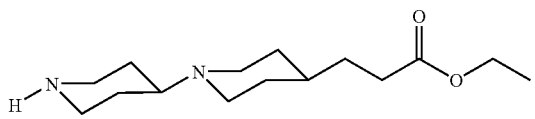

A8a) tert.butyl 4-(2-methoxycarbonyl-ethyl)-[1,4'] bipiperidinyl-1'-carboxylate

A solution of 4.00 g (19.3 mmol) methyl 3-piperidin-4-yl-propionate (used as the hydrochloride salt) and 3.85 g (19.3 mmol) tert.butyl 4-oxo-piperidine-1-carboxylate in 50 mL THF was adjusted to pH 5 with AcOH and the reaction mixture was stirred for 1 h at RT. 5.15 g (24.3 mmol) NaBH(OAc)$_3$ were added batchwise while being cooled and the reaction solution was stirred overnight at RT. 90 mL 30% K$_2$CO$_3$ solution were added dropwise, the mixture was extracted exhaustively with EtOAc and the combined organic phases were dried on Na$_2$SO$_4$. After the elimination of the desiccant and solvent the product was reacted further without any purification.

Yield: 5.4 g (79% of theory)
ESI-MS: (M+H)⁺=355
R$_f$=0.63 (silica gel, DCM/MeOH/NH$_3$ 80:20:2)

A8b) ethyl 3-[1,4']bipiperidinyl-4-yl-propionate

A solution of 5.4 g (15.2 mmol) tert.butyl 4-(2-methoxy-carbonyl-ethyl)-[1,4']bipiperidinyl-1'-carboxylate in 150 mL ethanolic HCl (1.25 M) was stirred overnight at RT. The solvent was largely eliminated i.vac., the precipitate formed was suction filtered and dried. The product, which was obtained as the bis-hydrochloride salt, was reacted further without purification.

Yield: 2.3 g (44% of theory)
ESI-MS: (M+H)⁺=269
Retention time (HPLC-MS): 1.2 min (method B)

Amine A9

Ethyl 4-(4-piperazin-1-yl-piperidin-1-yl)-butanoate

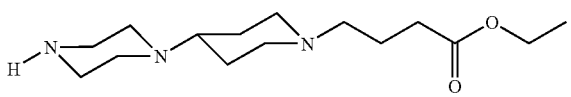

A9a) ethyl 4-[4-(4-benzyl-piperazin-1-yl)-piperidin-1-yl]-butanoate

A solution of 3.11 g (12.0 mmol) 1-benzyl-4-piperidin-4-yl-piperazine and 7.5 mL (12.0 mmol, 15% in water) 4-oxo-butanoic acid in 70 mL THF was adjusted to pH 5 with AcOH and stirred for 1 h at RT. While cooling with ice, 5.35 g (24.0 mmol) NaBH(OAc)$_3$ were added batchwise and the mixture was then stirred overnight at RT. 80 mL of 30% K$_2$CO$_3$ solution were added dropwise to the reaction mixture within 15 min and after the addition had ended this mixture was washed twice with EtOAc. The aqueous phase was evaporated down by half i.vac., neutralised with 1 M KHSO$_4$ solution, the precipitate formed was suction filtered, the filtrate was washed again with EtOAc and the aqueous phase was concentrated by evaporation i.vac. 150 mL of ethanolic HCl (1.25 M) was added and the mixture was stirred overnight at RT. The mixture was evaporated down i.vac., the residue was taken up in a little 15% K$_2$CO$_3$ solution, extracted exhaustively with EtOAc and the combined organic phases were dried on Na$_2$SO$_4$. After the elimination of the desiccant and solvent the residue was reacted further without any purification.

Yield: 2.9 g (65% of theory)
ESI-MS: (M+H)⁺=374

A9b) ethyl 4-(4-piperazin-1-yl-Piperidin-1-yl)-butanoate

A suspension of 2.9 g (7.76 mmol) ethyl 4-[4-(4-benzyl-piperazin-1-yl)-piperidin-1-yl]-butanoate and 300 mg 10% Pd/C in 60 mL MeOH was hydrogenated at RT and 50 psi hydrogen pressure for 24 h. The catalyst was filtered off, the mixture was evaporated down i.vac., the residue was taken up in a little DIPE and isopropanol and combined with 4 M HCl in 1,4-dioxane. The precipitated bis-hydrochloride salt was separated off and dried.

Yield: 2.5 g (90% of theory)
ESI-MS: (M+H)⁺=284
Retention time (HPLC-MS): 0.7 min (method B)

Amine A10

Ethyl 3-(4-piperazin-1-yl-piperidin-1-yl)-propionate

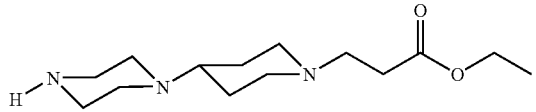

A10a) ethyl 3-[4-(4-benzyl-piperazin-1-yl)-piperidin-1-yl]-Propionate 5.5 mL (50.8 mmol) ethyl acrylate were added to a solution of 11.7 g (44.9 mmol) 1-benzyl-4-piperidin-4-yl-piperazine in 120 mL dry EtOH and the reaction mixture was refluxed for 1 h and then stirred overnight at RT. The solvent was eliminated i.vac. and the residue was dried for 1 h under an oil pump vacuum. The crude product was reacted further without purification.

Yield: 16.5 g (99% of theory)
ESI-MS: (M+H)$^+$=360

A10b) ethyl 3-(4-piperazin-1-yl-piperidin-1-yl)-propionate

A suspension of 16.5 g of the crude product from Example A10a and 1.6 g 10% Pd/C in 200 mL EtOH and was hydrogenated for 4 h at 50° C. and 50 psi hydrogen pressure. The catalyst was removed by suction filtering, the filtrate was evaporated down to about 120 mL and combined with 72 mL ethanolic HCl (1.3 M). The precipitate formed was suction filtered and dried i.vac. The product was obtained as the bis-hydrochloride salt.

Yield: 12.6 g (83% of theory)
ESI-MS: (M+H)$^+$=270

Amine A11

Ethyl 3-(4-piperidin-4-yl-piperazin-1-yl)-propionate

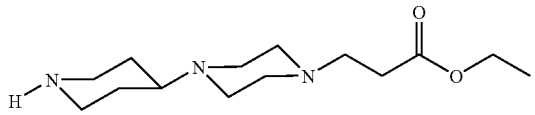

A11a) ethyl 3-[4-(1-benzyl-piperidin-4-yl)-piperazin-1-yl]-propionate 12.5 mL (73.0 mmol) ethyldiisopropylamine and 5.0 mL (46.1 mmol) ethyl acrylate were added to a solution of 11.0 g (33.2 mmol) 1-(1-benzyl-piperidin-4-yl)-piperazine (used as the bis-hydrochloride salt) in 40 mL EtOH and the reaction mixture was heated to 90° C. (bath temperature) for 3 h. After cooling the mixture was combined with water, extracted exhaustively with EtOAc and the combined organic phases were dried on Na$_2$SO$_4$. After the elimination of the desiccant and solvent the residue was purified by chromatography (silica gel, DCM/EtOH/NH$_3$ 100:10:1).

Yield: 6.8 g (56% of theory)
ESI-MS: (M+H)$^+$=360
R$_f$=0.64 (silica gel, DCM/MeOH/NH$_3$ 90:9:1)

A11b) ethyl 3-(4-piperidin-4-yl-piperazin-1-yl)-propionate

A suspension of 5.13 g (14.3 mmol) ethyl 3-[4-(1-benzyl-piperidin-4-yl)-piperazin-1-yl]-propionate and 1.0 g 10% Pd/C in 100 mL EtOH was hydrogenated for 2 h at 50° C. and 50 psi hydrogen pressure. The catalyst was filtered off and the filtrate was evaporated to dryness. The oily product was reacted further without purification.

Yield: 3.6 g (93% of theory)
ESI-MS: (M+H)$^+$=270

Amine A12

Ethyl([1,4']bipiperidinyl-4-yloxy)-acetate

A12a) benzyl 4-tert-butoxycarbonylmethoxy-[1,4']bipiperidinyl-1'-carboxylate 2.90 g (13.3 mmol) NaBH(OAc)$_3$ were added batchwise to a solution of 2.58 g (11.1 mmol)) tert.butyl 4-oxo-piperidine-1-carboxylate and 2.80 g (12.4 mmol) tert.butyl (piperidin-4-yloxy)-acetate in 30 mL THF and the reaction mixture was stirred overnight at RT. 50 mL of 1 M NaOH was added, the mixture was stirred for 1 h at RT, extracted exhaustively with EtOAc and the combined organic phases were dried on Na$_2$SO$_4$. After the elimination of the desiccant and solvent the residue was purified by chromatography (Alox, activity stage II-III, DCM/MeOH 100:1).

Yield: 3.1 g (65% of theory)
ESI-MS: (M+H)$^+$=433

A12b) tert.butyl ([1,4']bipiperidinyl-4-yloxy)-acetate

A suspension of 3.08 g (7.12 mmol) of benzyl 4-tert-butoxycarbonylmethoxy-[1,4']bipiperidinyl-1'-carboxylate and 300 mg of 10% Pd/C in 60 mL MeOH was hydrogenated at 50° C. and 50 psi hydrogen pressure for 2 h. The catalyst was removed by suction filtering and the filtrate was evaporated to dryness. The oil remaining was reacted further without purification.

Yield: 2.15 g (99% of theory)
ESI-MS: (M+H)$^+$=299

A12c) ethyl([1,4']bipiperidinyl-4-yloxy)-acetate

A solution of 100 mg (0.33 mmol) tert.butyl ([1,4']bipiperidinyl-4-yloxy)-acetate in 1 mL EtOH was combined with 2 mL ethanolic HCl with heating, the mixture was refluxed for a further 2 h and left overnight at RT. The precipitate formed was suction filtered and dried.

Yield: 71 mg (63% of theory)
ESI-MS: (M+H)$^+$=271

Example 1

(R)-1-heptylcarbamoyl-2-(4-hydroxy-3,5-dimethyl-phenyl)-ethyl 4-(2-oxo-1,2,4,5-tetrahydro-1,3-benzodiazepin-3-yl)-piperidine-1-carboxylate

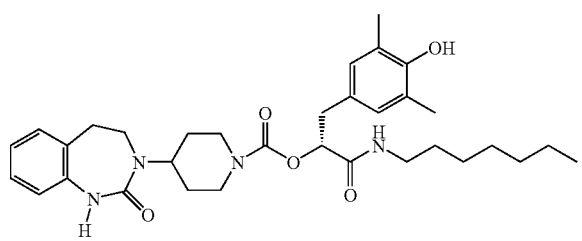

1a) 2-benzyloxy-5-bromo-1,3-dimethylbenzene 39.9 g (286 mmol) $K_2CO_3$ were added to a solution of 50.0 g (249 mmol) 2,6-dimethyl-4-bromophenol in 500 mL DMF and the mixture was stirred for 20 min. Then 34.0 mL (286 mmol) benzyl chloride were slowly added dropwise and the reaction mixture was stirred for 3 h at 100° C. bath temperature. After the reaction had ended the mixture was poured onto 500 mL water and extracted exhaustively with EtOAc. The organic phases were combined, dried on $Na_2SO_4$ and concentrated by evaporation i.vac.

Yield: quantitative
GC-MS: $(M^+)=290/292$ (Br)
$R_f=0.87$ (silica gel, Cyc/EtOAc 3:1)

1b) methyl 2-acetylamino-3-(4-benzyloxy-3,5-dimethyl-phenyl)-acrylate

Under a nitrogen atmosphere a mixture of 40.0 g (137 mmol) 2-benzyloxy-5-bromo-1,3-dimethylbenzene and 24.1 g (165 mmol) methyl 2-acetylamino-acrylate in 420 mL triethylamine and 200 mL acetonitrile was combined with 3.5 g (11.2 mmol) tri-o-tolyl-phosphane and 2.5 g (11.1 mmol) $Pd(OAc)_2$ and stirred for 18 h at 80° C. The precipitate was suction filtered, the filtrate concentrated by evaporation i.vac. and combined with 800 mL DCM and 800 mL water. The organic phase was separated off, suction filtered on $Na_2SO_4$, the solvent was eliminated i.vac., the residue was stirred with EtOAc, suction filtered and dried i.vac.

Yield: 31.1 g (64% of theory)
ESI-MS: $(M+H)^+=354$
Retention time (HPLC-MS): 8.6 min (method A)

1c) 3-(4-benzyloxy-3,5-dimethyl-phenyl)-2-oxo-propionic acid 31.1 g (88.1 mmol) methyl 2-acetylamino-3-(4-benzyloxy-3,5-dimethyl-phenyl)-acrylate in 150 mL 1,4-dioxane were combined with 125 mL 4 M HCl, refluxed for 7 h and stirred overnight at RT. The precipitate was suction filtered, washed with water and dried at 45° C. in the vacuum drying cupboard.

Yield: 14.3 g (54% of theory)
EI-MS: $(M)^+=298$
Retention time (HPLC-MS): 9.0 min (method A)

1d) (R)-3-(4-benzoyl-3,5-dimethyl-phenyl)-2-hydroxy-propionic acid

Under a nitrogen atmosphere a solution of 14.3 g (47.8 mmol) 3-(4-benzyloxy-3,5-dimethyl-phenyl)-2-oxo-propionic acid and 8.3 mL (59.8 mmol) triethylamine in 170 mL THF at −35° C. was combined with a solution of 22.1 (69.0 mmol) (1R)—B-chlorodiisopinocampheylborane in 70 mL THF within 30 min. After the addition had ended the cooling bath was removed and the reaction solution was stirred overnight at RT. The reaction mixture was made alkaline at 0° C. with 70 mL 1 M NaOH, combined with 100 mL TBME, stirred for 15 min and the phases were separated. The organic phase was washed with 50 mL water and three times with 50 mL of 1 M NaOH. The combined aqueous phases were acidified with semiconcentrated HCl, extracted exhaustively with EtOAc and the combined organic phases were dried on $Na_2SO_4$. After the elimination of the desiccant and solvent the residue was reacted further without any purification.

Yield: 14.0 g (98% of theory)
ESI-MS: $(M-H)^-=299$
Retention time (HPLC-MS): 7.9 min (method A)

1e) methyl (R)-3-(4-benzyloxy-3,5-dimethyl-phenyl)-2-hydroxy-propionate 2.0 mL (27.4 mmol) $SOCl_2$ were added dropwise to a solution, cooled to 0° C., of 14.0 g (23.3 mmol) (R)-3-(4-benzoyl-3,5-dimethyl-phenyl)-2-hydroxy-propionic acid in 150 mL MeOH and the reaction mixture was stirred for 1 h at RT. The reaction solution was concentrated by evaporation i.vac. and the residue was purified by chromatography (silica gel, Cyc/EtOAc 3:1).

Yield: 5.7 g (78% of theory)
ESI-MS: $(M+NH_4)^+=332$
Retention time (HPLC-MS): 9.1 min (method A)

1f) (R)-2-(4-benzyloxy-3,5-dimethyl-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere 1.93 g (9.58 mmol) 4-nitrophenyl chloroformate was added to a solution of 1.17 g (9.58 mmol) 4-dimethylaminopyridine in 50 mL pyridine, the mixture was stirred for 1.5 h at RT, combined with 3.0 g (9.58 mmol) methyl (R)-3-(4-benzyloxy-3,5-dimethyl-phenyl)-2-hydroxy-propionate and the mixture was stirred for 20 min at RT. Then 2.35 g (9.58 mmol) 3-piperidin-4-yl-1,3,4,5-tetrahydro-1,3-benzodiazepin-2-one were added and the mixture was stirred for 20 h at RT. The reaction mixture was concentrated by evaporation i. vac., the residue was taken up in EtOAc, the organic phase was washed with 10% $KHSO_4$ and saturated $NaHCO_3$ solution and dried on $Na_2SO_4$. After the elimination of the desiccant and solvent the residue was purified by chromatography (silica gel, gradient Cyc/EtOAc 1:1 to 1:2).

Yield: 3.21 g (57% of theory)
ESI-MS: $(M+H)^+=586$
Retention time (HPLC-MS): 10.4 min (method A)

1g) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate A solution of 3.21 g (5.48 mmol) (R)-2-(4-benzyloxy-3,5-dimethyl-phenyl)-1-methoxy-carbonyl-ethyl 4-(2-oxo-1,2,4,5-tetrahydro-1,3-benzodiazepin-3-yl)-piperidine-1-carboxylate in 80 mL THF was combined with a solution of 200 mg (8.35 mmol) LiOH in 40 mL water and the mixture was stirred for 1 h at RT. The reaction mixture was concentrated by evaporation i.vac., the residue was taken up in 100 mL water, acidified with 2 M HCl, the precipitate was suction filtered and dried in the vacuum drying cupboard at 40° C.

Yield: quantitative
ESI-MS: $(M+H)^+=572$
Retention time (HPLC-MS): 9.2 min (method A)

1h) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate 3.72 g (6.51 mmol) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate in 50 mL DCM were combined with 300 mg of 10% Pd/C and shaken at RT and 3 bar hydrogen until the reaction came to an end. The catalyst was removed by suction filtering and the solvent was concentrated by evaporation i.vac. The residue was triturated with DIPE and suction filtered.

Yield: 2.41 g (77% of theory)
ESI-MS: (M+H)$^+$=482
Retention time (HPLC-MS): 7.0 min (method A)

1i) (R)-1-heptylcarbamoyl-2-(4-hydroxy-3,5-dimethyl-phenyl)-ethyl 4-(2-oxo-1,2,4,5-tetrahydro-1,3-benzodiazepin-3-yl)-piperidine-1-carboxylate A solution of 100 mg (0.21 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate, 73 mg (0.23 mmol) TBTU and 36 µL (0.18 mmol) triethylamine in 1 mL DMF was stirred for 1 h at RT. Then 26 mg (0.23 mmol) n-heptylamine was added and the reaction mixture was stirred for 5 h at RT. The reaction solution was filtered through a syringe filter and purified directly by HPLC without any further working up. The fractions containing the product were combined and lyophilised.

Yield: 48 mg (40% of theory)
ESI-MS: (M−H)$^-$=577
Retention time (HPLC-MS): 4.6 min (method B)

The following compounds were prepared analogously from in each case 100 mg (Examples 1.1 to 1.5) or from in each case 80 mg (Example 1.6 to 1.8) of (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate and the corresponding amount of amine:

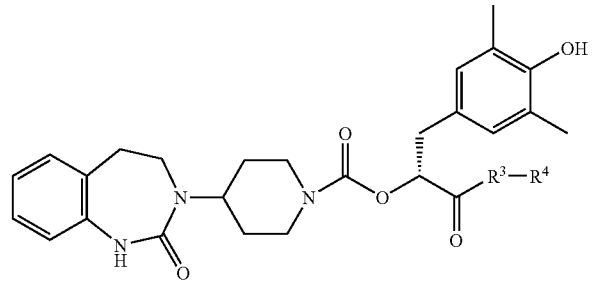

| Example | —R$^3$—R$^4$ | Yield (%) | Mass spectrum | Retention time HPLC (method) |
|---|---|---|---|---|
| 1.1 | | 27 | 648 [M + H]$^+$ | 3.1 min (B) |
| 1.2 | | 13 | 687 [M + H]$^+$ | 3.0 min (B) |
| 1.3 | | 52 | 631 [M + H]$^+$ | 3.6 min (B) |
| 1.4 | | 19 | 657 [M + H]$^+$ | 3.1 min (B) |

-continued
| Example | —R³—R⁴ | Yield (%) | Mass spectrum | Retention time HPLC (method) |
|---|---|---|---|---|
| 1.5 | *−NH−(CH₂)₅−N(CH₃)₂ | 46 | 608 [M + H]⁺ | 3.1 min (B) |
| 1.6 | *−(piperidine)−(piperazine)−cyclopropyl | 44 | 673 [M + H]⁺ | 2.6 min (B) |
| 1.7 | *−(piperidine)−(piperidine)−O−C(O)CH₃ | 42 | 690 [M + H]⁺ | 2.7 min (B) |
| 1.8 | *−NH−(CH₂)₆−NH−C(O)−O−C(CH₃)₃ | 59 | 680 [M + H]⁺ | 4.4 min (B) |
Example 1.9
(R)-1-(6-amino-hexylcarbamoyl)-2-(4-hydroxy-3,5-dimethyl-phenyl)-ethyl 4-(2-oxo-1,2,4,5-tetrahydro-1,3-benzodiazepin-3-yl)-piperidine-1-carboxylate
50
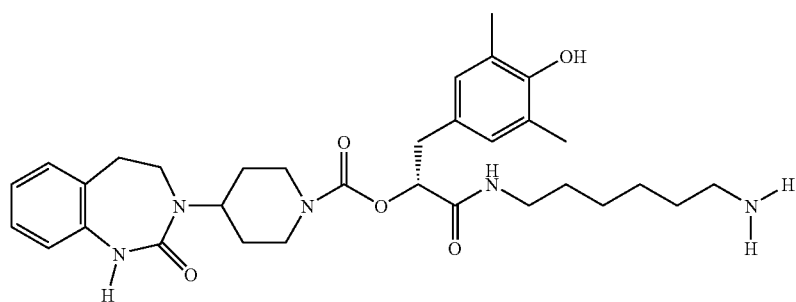

A solution of 55 mg (0.08 mmol) (R)-1-(6-tert-butoxycarbonylamino-hexylcarbamoyl)-2-(4-hydroxy-3,5-dimethyl-phenyl)-ethyl 4-(2-oxo-1,2,4,5-tetrahydro-1,3-benzodiazepin-3-yl)-piperidine-1-carboxylate (Example 1.8) in 1 mL of 1M HCl was stirred overnight at RT. The reaction solution was lyophilised and the residue was purified by HPLC. The fractions containing the product were combined and again lyophilised.

Yield: 4 mg (8% of theory)
ESI-MS: (M+H)$^+$=580
Retention time (HPLC-MS): 2.6 min (method B)

Example 1.10

(R)-1-(4-hydroxy-3,5-dimethyl-benzyl)-2-oxo-2-(3,4,5,6-tetrahydro-2H-4,4'-bipyridinyl-1-yl)-ethyl 4-(2-oxo-1,2,4,5-tetrahydro-1,3-benzodiazepin-3-yl)-piperidine-1-carboxylate

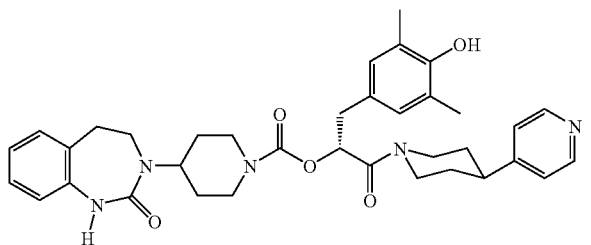

67 mg (0.42 mmol) 1,2,3,4,5,6-hexahydro-[4,4']bipyridinyl were added at RT to a solution of 182 mg (0.38 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate, 133 mg (0.42 mmol) TBTU and 66 µL (0.47 mmol) triethylamine in 10 mL THF and 2 mL DMF and the reaction mixture was stirred for 2 h. 20 mL EtOAc were added, the organic phase was washed with 20 mL semisaturated NaHCO$_3$ solution and dried on Na$_2$SO$_4$. After the elimination of the desiccant and solvent the residue was purified by HPLC. The fractions containing the product were combined, evaporated down, the residue was made alkaline with semisaturated NaHCO$_3$ solution, extracted with 50 mL EtOAc and the organic phase was dried on Na$_2$SO$_4$. After the elimination of the desiccant and solvent the residue was stirred with DIPE, suction filtered and dried.

Yield: 145 mg (61% of theory)
ESI-MS: (M+H)$^+$=626
Retention time (HPLC-MS): 3.1 min (method B)

Example 1.11

(R)-1-(4-hydroxy-3,5-dimethyl-benzyl)-2-oxo-2-piperazin-1-yl-ethyl 4-(2-oxo-1,2,4,5-tetrahydro-1,3-benzodiazepin-3-yl)-piperidine-1-carboxylate

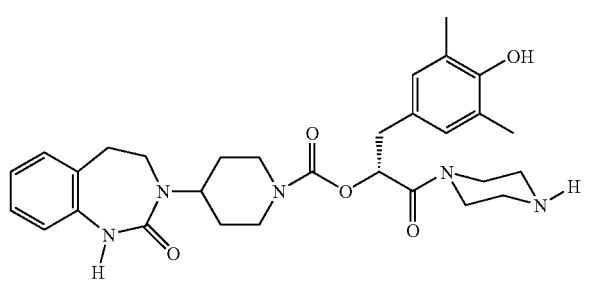

1.11a) (R)-1-(4-benzyloxy-3,5-dimethyl-benzyl)-2-(4-benzyl-piperazin-1-yl)-2-oxo-ethyl 4-(2-oxo-1,2,4,5-tetrahydro-1,3-benzodiazepin-3-yl)-piperidine-1-carboxylate A solution of 1.54 g (2.69 mmol) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1g), 952 mg (2.96 mmol) TBTU and 0.47 mL (3.37 mmol) triethylamine in 10 mL THF and 2 mL DMF the mixture was stirred for 1 h at RT. Then 0.52 mL (2.96 mmol) 1-benzyl-piperazine was added and the reaction mixture was stirred for another 14 h at RT. 30 mL EtOAc were added, the organic phase was washed with semisaturated NaHCO$_3$ solution and dried on Na$_2$SO$_4$. After the elimination of the desiccant and solvent the residue was purified by chromatography (silica gel, EtOAc/Cyc 95:5), the fractions containing the product were combined, evaporated down, the residue was triturated with DIPE, suction filtered and dried.

Yield: 1.62 g (82% of theory)
ESI-MS: (M+H)$^+$=730
Retention time (HPLC-MS): 4.3 min (method B)

1.11b) (R)-1-(4-hydroxy-3,5-dimethyl-benzyl)-2-oxo-2-piperazin-1-yl-ethyl 4-(2-oxo-1,2,4,5-tetrahydro-1,3-benzodiazepin-3-yl)-piperidine-1-carboxylate 1.62 g (2.22 mmol) (R)-1-(4-benzyloxy-3,5-dimethyl-benzyl)-2-(4-benzyl-piperazin-1-yl)-2-oxo-ethyl 4-(2-oxo-1,2,4,5-tetrahydro-1,3-benzodiazepin-3-yl)-piperidine-1-carboxylate in 40 mL MeOH were combined with 150 mg 10% Pd/C and hydrogenated at RT and 3 bar hydrogen until the reaction came to an end. The catalyst was removed by suction filtering and the solvent was concentrated by evaporation i.vac. The residue was purified by chromatography (silica gel, EtOAc/MeOH/NH$_3$ 85:13.5:1.5).

Yield: 1.03 g (85% of theory)
ESI-MS: (M+H)$^+$=550
Retention time (HPLC-MS): 2.7 min (method B)

Example 1.12

(R)-2-(4-cyclopropylmethyl-piperazin-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

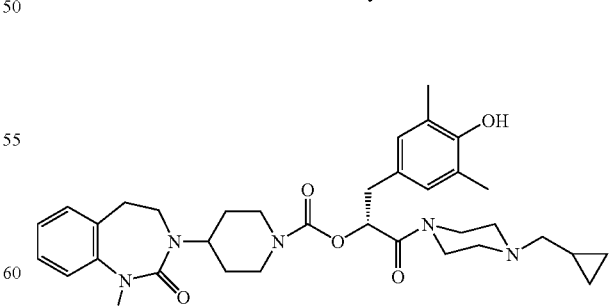

A solution of 100 mg (0.18 mmol) (R)-1-(4-hydroxy-3,5-dimethyl-benzyl)-2-oxo-2-piperazin-1-yl-ethyl 4-(2-oxo-1,2,4,5-tetrahydro-1,3-benzodiazepin-3-yl)-piperidine-1-carboxylate, 20 µL (0.37 mmol) AcOH and 41.6 µL (0.55 mmol)

cyclopropanecarbaldehyde in 2 mL THF/MeOH (2:1) was stirred overnight at RT.

After cooling to 0° C. the mixture was combined with 24 mg (0.36 mmol) NaBH₃CN, stirred for a further 4 h at this temperature and then overnight at RT. The solvents were eliminated, the residue was taken up in 1 mL DMF and purified by HPLC. The fractions containing the product were combined and lyophilised.

Yield: 45 mg (41% of theory)
ESI-MS: (M+H)⁺=604
Retention time (HPLC-MS): 3.1 min (method B)

The following compounds were prepared analogously from in each case 100 mg (R)-1-(4-hydroxy-3,5-dimethyl-benzyl)-2-oxo-2-piperazin-1-yl-ethyl 4-(2-oxo-1,2,4,5-tetrahydro-1,3-benzodiazepin-3-yl)-piperidine-1-carboxylate and the corresponding amount of aldehyde or ketone:

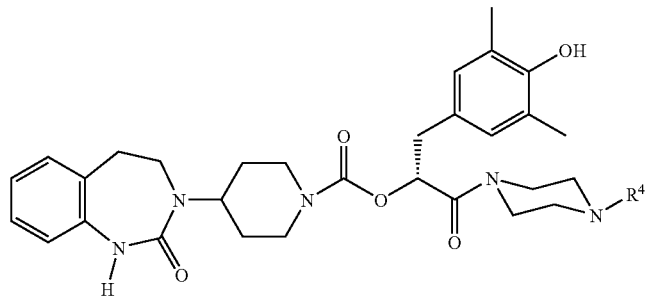

| Example | R⁴ | Yield (%) | Mass spectrum | Retention time HPLC (method) |
|---|---|---|---|---|
| 1.13 | *-cyclohexyl-S | 27 | 650 [M + H]⁺ | 3.2 min (B) |
| 1.14 | *-cyclohexyl-N(C(O)CH₃) | 58 | 675 [M + H]⁺ | 2.9 min (B) |
| 1.15 | *-CH₂CH(CH₃)₂ (isobutyl) | 17 | 620 [M + H]⁺ | 3.3 min (B) |
| 1.16 | *-CH₂-cyclopentyl | 57 | 632 [M + H]⁺ | 3.3 min (B) |
| 1.17 | *-cyclohexyl-C(CH₃)₂ | 46 | 660 [M + H]⁺ | 3.6 min (B) |

Example 1.18

(R)-1-(4-hydroxy-3,5-dimethyl-benzyl)-2-oxo-2-(1'-oxy-3,4,5,6-tetrahydro-2H-4,4'-bipyridinyl-1-yl)-ethyl 4-(2-oxo-1,2,4,5-tetrahydro-1,3-benzodiazepin-3-yl)-piperidine-1-carboxylate

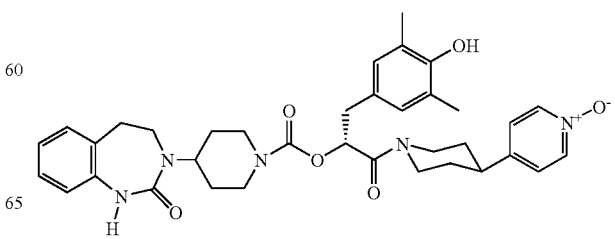

77 mg (0.46 mmol) MCPBA were added to a solution, cooled to 0° C., of 253 mg (0.40 mmol) (R)-1-(4-hydroxy-3,5-dimethyl-benzyl)-2-oxo-2-(3,4,5,6-tetrahydro-2H-4,4'-bipyridinyl-1-yl)-ethyl 4-(2-oxo-1,2,4,5-tetrahydro-1,3-benzodiazepin-3-yl)-piperidine-1-carboxylate (Example 1.10) in 10 mL chloroform and the reaction mixture was stirred for 2 h, during which time it heated up to RT. The mixture was evaporated down i.vac., the residue was taken up in a little DMF and purified by HPLC. The fractions containing the product were combined and lyophilised.
Yield: 107 mg (41% of theory)
ESI-MS: (M+H)$^+$=642
Retention time (HPLC-MS): 3.4 min (method B)

Example 1.19

(R)-1-(4-hydroxy-3,5-dimethyl-benzyl)-2-(1'-methyl-1'-oxy-4,4'-bipiperidinyl-1-yl)-2-oxo-ethyl 4-(2-oxo-1,2,4,5-tetrahydro-1,3-benzodiazepin-3-yl)-piperidine-1-carboxylate

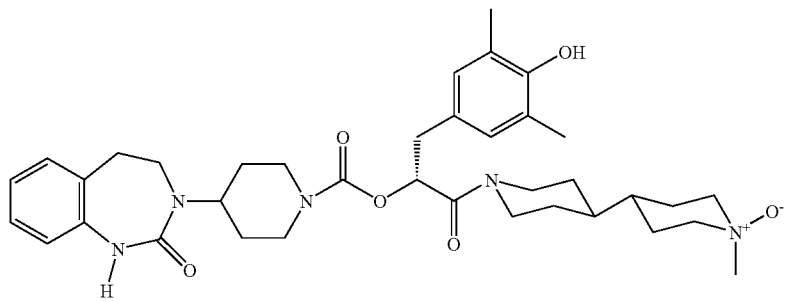

1.19a) (R)-1-(4-hydroxy-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate Prepared analogously to Example 1i from 150 mg (0.31 mmol) (R)-2-(4-hydroxy-3,5-dimethyl-phenyl)-1-carboxyethyl 4-(2-oxo-1,2,4,5-tetrahydro-1,3-benzodiazepin-3-yl)-piperidine-1-carboxylate and 62 mg (0.34 mmol) 1-methyl-[4,4']bipiperidinyl.
Yield: 42 mg (21% of theory)
ESI-MS: (M+H)$^+$=646
Retention time (HPLC-MS): 3.1 min (method B)

1.19b) (R)-1-(4-hydroxy-3,5-dimethyl-benzyl)-2-(1'-methyl-1'-oxy-4,4'-bipiperidinyl-1-yl)-2-oxo-ethyl 4-(2-oxo-1,2,4,5-tetrahydro-1,3-benzodiazepin-3-yl)-piperidine-1-carboxylate Prepared analogously to Example 1.18 from 40 mg (0.06 mmol) (R)-1-(4-hydroxy-3,5-dimethyl-benzyl)-2-(1'-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate and 17 mg (0.07 mmol) MCPBA.
Yield: 17 mg (41% of theory)
ESI-MS: (M+H)$^+$=662
Retention time (HPLC-MS): 3.2 min (method B)

Example 1.20

(R)-1-(4-hydroxy-3,5-dimethyl-benzyl)-2-oxo-2-[4-(4-oxy-morpholin-4-yl)-piperidin-1-yl]-ethyl 4-(2-oxo-1,2,4,5-tetrahydro-1,3-benzodiazepin-3-yl)-piperidine-1-carboxylate

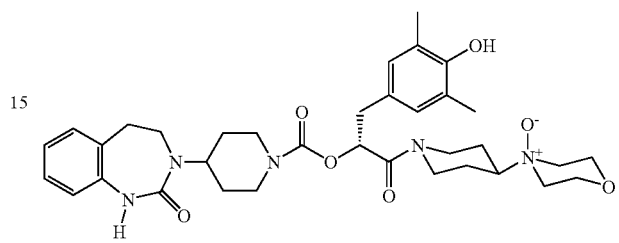

1.20a) (R)-1-(4-hydroxy-3,5-dimethyl-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate Prepared analogously to Example 1i from 70 mg (0.15 mmol) (R)-2-(4-hydroxy-3,5-dimethyl-phenyl)-1-carboxyethyl 4-(2-oxo-1,2,4,5-tetrahydro-1,3-benzodiazepin-3-yl)-piperidine-1-carboxylate and 25 mg (0.15 mmol) 4-piperidin-4-yl-morpholine.
Yield: 35 mg (38% of theory)
ESI-MS: (M+H)$^+$=634
Retention time (HPLC-MS): 5.6 min (method A)

1.20b) (R)-1-(4-hydroxy-3,5-dimethyl-benzyl)-2-oxo-2-[4-(4-oxy-morpholin-4-yl)-piperidin-1-yl]-ethyl 4-(2-oxo-1,2,4,5-tetrahydro-1,3-benzodiazepin-3-yl)-piperidine-1-carboxylate Prepared analogously to Example 1.18 from 80 mg (0.13 mmol) (R)-1-(4-hydroxy-3,5-dimethyl-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate and 24 mg (0.14 mmol) MCPBA.
Yield: 36 mg (44% of theory)
ESI-MS: (M+H)$^+$=650
Retention time (HPLC-MS): 4.1 min (method C)

Example 1.21

(R)-1-(4-hydroxy-3,5-dimethyl-benzyl)-2-(4-methoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate

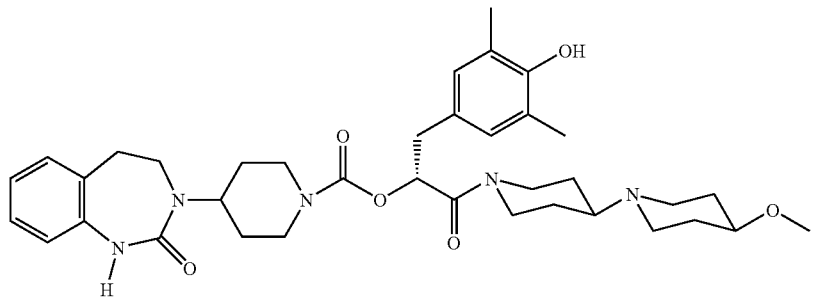

Prepared analogously to Example 1i from 80 mg (0.17 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate, 77 µL (0.55 mmol) triethylamine and 46 mg (0.17 mmol) 4-methoxy-[1,4']bipiperidinyl (used as the bis-hydrochloride salt).

Yield: 74 mg (67% of theory)

ESI-MS: $(M+H)^+=662$

Retention time (HPLC-MS): 6.1 min (method A)

Example 1.22

(R)-1-(4-hydroxy-3,5-dimethyl-benzyl)-2-oxo-2-[4-(1-oxo-1$\lambda^4$-thiomorpholin-4-yl)-piperidin-1-yl]-ethyl 4-(2-oxo-1,2,4,5-tetrahydro-1,3-benzodiazepin-3-yl)-piperidine-1-carboxylate

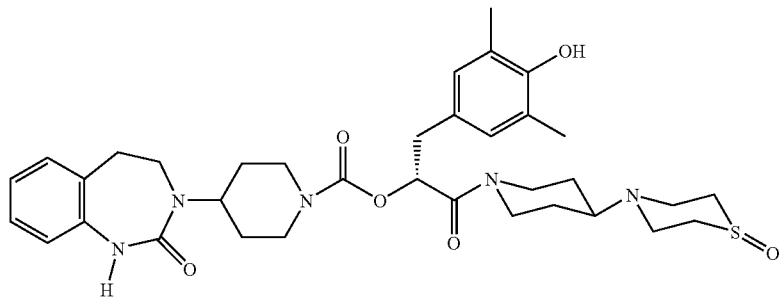

Prepared analogously to Example 1.21 from 80 mg (0.17 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate, 77 µL (0.55 mmol) triethylamine and 47 mg (0.17 mmol) 4-piperidin-4-yl-thiomorpholine-1-oxide (used as the bis-hydrochloride salt).

Yield: 45 mg (41% of theory)
ESI-MS: $(M+H)^+=666$
Retention time (HPLC-MS): 5.7 min (method A)

Example 1.23

(R)-2-[4-(1,1-dioxo-hexahydro-1λ$^6$-thiopyran-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

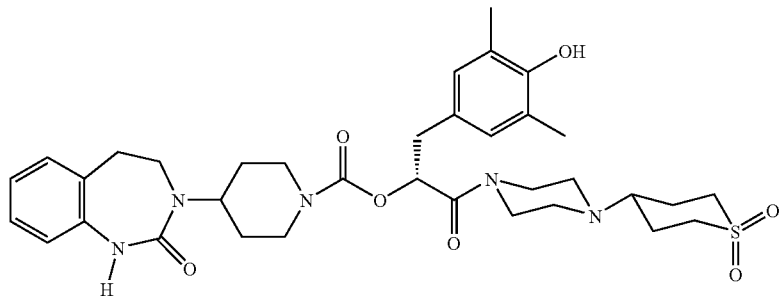

1.23a) (R)-1-(4-benzyloxy-3,5-dimethyl-benzyl)-2-[4-(1,1-dioxo-hexahydro-1λ$^6$ thiopyran-4-yl)-piperazin-1-yl]-2-oxo-ethyl 4-(2-oxo-1,2,4,5-tetrahydro-1,3-benzodiazepin-3-yl)-piperidine-1-carboxylate Prepared analogously to Example 1i from 150 mg (0.26 mmol) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1g) and 57 mg (0.26 mmol) 1-(1,1-dioxo-hexahydro-1λ$^6$-thiopyran-4-yl)-piperazine.

Yield: 49 mg (24% of theory)
ESI-MS: (M+H)$^+$=772
Retention time (HPLC-MS): 3.9 min (method B)

1.23b) (R)-2-[4-(1,1-dioxo-hexahydro-1λ$^6$-thiopyran-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate A solution of 45 mg (0.06 mmol) (R)-1-(4-benzyloxy-3,5-dimethyl-benzyl)-2-[4-(1,1-dioxo-hexahydro-1λ$^6$-thiopyran-4-yl)-piperazin-1-yl]-2-oxo-ethyl 4-(2-oxo-1,2,4,5-tetrahydro-1,3-benzodiazepin-3-yl)-piperidine-1-carboxylate in 10 mL MeOH was combined with 10 mg 10% Pd/C and hydrogenated at RT and 3 bar hydrogen pressure until the reaction came to an end. The catalyst was removed by suction filtering and the residue was purified by HPLC. The fractions containing the product were combined and lyophilised.

Yield: 23 mg (57% of theory)
ESI-MS: (M+H)$^+$=682
Retention time (HPLC-MS): 3.1 min (method B)

Example 1.24

(R)-1-(4-hydroxy-3,5-dimethyl-benzyl)-2-[4-methyl-4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

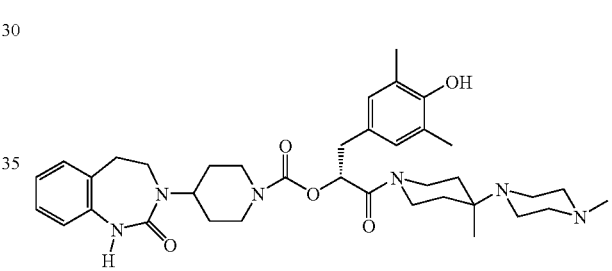

Prepared analogously to Example 1i from 80 mg (0.17 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1h) and 36 mg (0.18 mmol) 1-methyl-4-(4-methyl-piperidin-4-yl)-piperazine.
Yield: 36 mg (32% of theory)
ESI-MS: (M+H)$^+$=661
Retention time (HPLC-MS): 2.5 min (method B)

Example 1.25

(R)-1'-(4-hydroxy-3,5-dimethyl-benzyl)-2-(4-methyl-4-morpholin-4-yl-piperidin-1-yl)-2-oxo-ethyl 4-(2-oxo-1,2,4,5-tetrahydro-1,3-benzodiazepin-3-yl)-piperidine-1-carboxylate

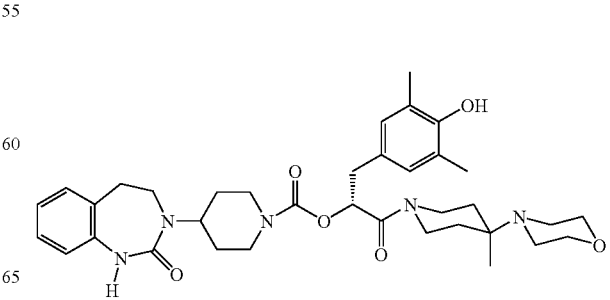

55 mg (0.22 mmol) 4-(4-methyl-piperidin-4-yl)-morpholine (used as the hydrochloride salt, purity 90%) were added at RT to a solution of 90 mg (0.19 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1h), 70 mg (0.22 mmol) TBTU and 70 µL (0.50 mmol) triethylamine in 1 mL DMF and the reaction mixture was stirred for 20 h. The reaction solution was poured onto saturated NaHCO₃ solution, the precipitate formed was filtered off and dried. Further purification was carried out by HPLC, the fractions containing the product were combined and lyophilised.

Yield: 32 mg (26% of theory)
ESI-MS: (M+H)⁺=648
Retention time (HPLC-MS): 3.0 min (method B)

Example 1.26

(R)-1-(4-formyloxy-3,5-dimethyl-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate

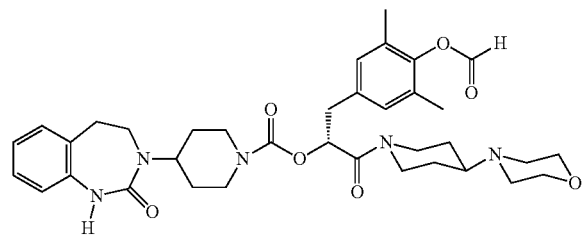

A solution of 100 µL acetic anhydride and 1 mL formic acid in 3 mL DCM was stirred for 2 h at RT (formation of the mixed anhydride). Then 100 mg (0.16 mmol) (R)-1-(4-hydroxy-3,5-dimethyl-benzyl)-2-(4-morpholin-4-yl-piperidin-1-yl)-2-oxo-ethyl 4-(2-oxo-1,2,4,5-tetrahydro-1,3-benzodiazepin-3-yl)-piperidine-1-carboxylate (Example 1.20a) were added and the reaction mixture was stirred for 2 h at RT. The reaction solution was evaporated down and the residue was again added to a solution of the mixed anhydride and stirred overnight at RT. The mixture was evaporated down i.vac. and the residue was purified by HPLC. The fractions containing the product were combined and lyophilised.

Yield: 77 mg (69% of theory)
ESI-MS: (M+H)⁺=662
Retention time (HPLC-MS): 3.1 min (method B)

Example 2

(R)-1-(4-hydroxy-3,5-dimethyl-benzyl)-2-[4-(4-methyl-piperazin-1-yl)-piperidin-1-yl]-2-oxo-ethyl 4-(5-oxo-3-phenyl-4,5-dihydro-1,2,4-triazol-1-yl)-piperidine-1-carboxylate

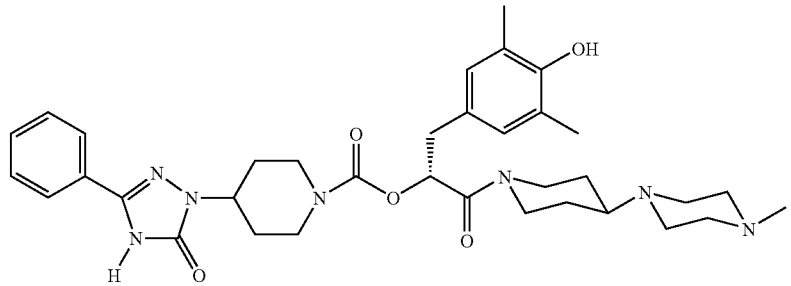

2a) (R)-2-(4-benzyloxy-3,5-dimethyl-phenyl)-1-methoxycarbonyl-ethyl 4-(5-oxo-3-phenyl-4,5-dihydro-1,2,4-triazol-1-yl)-piperidine-1-carboxylate Prepared analogously to Example 1f from 5.0 g (15.9 mmol) methyl (R)-3-(4-benzyloxy-3,5-dimethyl-phenyl)-2-hydroxy-propionate (Example 1e) and 5.98 g (15.9 mmol) 3-5-phenyl-2-piperidin-4-yl-2,4-dihydro-1,2,4-triazol-3-one (purity 65%).

Yield: 4.96 g (53% of theory)
ESI-MS: (M+H)⁺=585
Retention time (HPLC-MS): 5.0 min (method B)

2b) (R)-2-(4-benzyloxy-3,5-dimethyl-phenyl)-1-carboxy-ethyl 4-(5-oxo-3-phenyl-4,5-dihydro-1,2,4-triazol-1-yl)-piperidine-1-carboxylate A solution of 310 mg (12.93 mmol) LiOH in 30 mL water was added to a solution of 4.96 g (8.48 mmol) (R)-2-(4-benzyloxy-3,5-dimethyl-phenyl)-1-methoxy-carbonyl-ethyl 4-(5-oxo-3-phenyl-4,5-dihydro-1,2,4-triazol-1-yl)-piperidine-1-carboxylate in 50 mL THF and the reaction mixture was stirred for 7 h at RT. The solution was stored overnight at −18° C. and after heating to RT a further 310 mg LiOH were added to complete the reaction. After 1 h the reaction solution was concentrated by evaporation i.vac., the residue was taken up in 150 mL water and acidified with 1 M HCl. The precipitate was filtered off and dried at 40° C.

Yield: 4.75 g (98% of theory)
ESI-MS: (M+H)⁺=571
Retention time (HPLC-MS): 4.3 min (method B)

2c) (R)-1-carboxy-2-(4-hydroxy-3,5-dimethyl-phenyl)-ethyl 4-(5-oxo-3-phenyl-4,5-dihydro-1,2,4-triazol-1-yl)-piperidine-1-carboxylate A solution of 2.50 g (4.38 mmol) (R)-2-(4-benzyloxy-3,5-dimethyl-phenyl)-1-carboxy-ethyl 4-(5-oxo-3-phenyl-4,5-dihydro-1,2,4-triazol-1-yl)-piperidine-1-carboxylate in 50 mL DCM was combined with 250 mg 10% Pd/C and hydrogenated at RT and 3 bar hydrogen pressure for 4.5 h. To complete the reaction a further 250 mg of catalyst were added, the mixture was hydrogenated for 12 h at 40° C., combined with 25 mL THF and 250 mg catalyst and hydrogenated for a further 12 h at 40° C. The catalyst was removed by suction filtering and the filtrate was concentrated by evaporation i.vac. The residue was stirred with DIPE, suction filtered and dried.

Yield: 1.87 g (89% of theory)
ESI-MS: $(M-H)^- = 479$
Retention time (HPLC-MS): 3.5 min (method B)

2d) (R)-1-(4-hydroxy-3,5-dimethyl-benzyl)-2-[4-(4-methyl-piperazin-1-yl)-piperidin-1-yl]-2-oxo-ethyl 4-(5-oxo-3-phenyl-4,5-dihydro-1,24-triazol-1-yl)-piperidine-1-carboxylate A solution of 100 mg (0.21 mmol) (R)-1-carboxy-2-(4-hydroxy-3,5-dimethyl-phenyl)-ethyl 4-(5-oxo-3-phenyl-4,5-dihydro-1,2,4-triazol-1-yl)-piperidine-1-carboxylate, 74 mg (0.23 mmol) TBTU and 35 μL (0.26 mmol) triethylamine in 1 mL DMF was stirred for 1 h at RT. Then 39 mg (0.21 mmol) 1-methyl-4-piperidin-4-yl-piperazine was added and the reaction mixture was stirred for another 5 h at RT. The reaction solution was purified by HPLC without any further working up. The fractions containing the product were combined and lyophilised.

Yield: 40 mg (30% of theory)
ESI-MS: $(M+H)^+ = 646$
Retention time (HPLC-MS): 2.7 min (method B)

The following compounds were prepared analogously from in each case 100 mg (Examples 2.1 to 2.7) or 150 mg (Example 2.8) (R)-1-carboxy-2-(4-hydroxy-3,5-dimethyl-phenyl)-ethyl 4-(5-oxo-3-phenyl-4,5-dihydro-1,2,4-triazol-1-yl)-piperidine-1-carboxylate and the corresponding amount of amine:

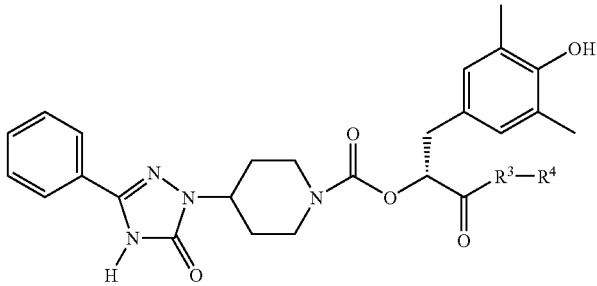

| Example | —R³—R⁴ | Yield (%) | Mass spectrum | Retention time HPLC (method) |
|---|---|---|---|---|
| 2.1 | | 22 | 646 [M + H]⁺ | 2.5 min (B) |
| 2.2 | | 28 | 645 [M + H]⁺ | 3.0 min (B) |
| 2.3 | | 29 | 631 [M + H]⁺ | 3.0 min (B) |
| 2.4 | | 25 | 591 [M + H]⁺ | 2.8 min (B) |
| 2.5 | | 28 | 633 [M + H]⁺ | 2.9 min (B) |
| 2.6 | | 24 | 631 [M + H]⁺ | 3.1 min (B) |
| 2.7 | | 23 | 721 [M + H]⁺ | 3.4 min (B) |

The following compounds were prepared analogously from in each case 250 mg (R)-2-(4-benzyloxy-3,5-dimethyl-phenyl)-1-carboxy-ethyl 4-(5-oxo-3-phenyl-4,5-dihydro-1,2,4-triazol-1-yl)-piperidine-1-carboxylate (Example 2b) and the corresponding amount of amine:

| Example | —R³—R⁴ | Yield (%) | Mass spectrum | Retention time HPLC (method) |
|---|---|---|---|---|
| 2.8 | *-N⟨piperidine⟩-⟨piperidine⟩-N-CH₂-C(O)-O-ethyl | 17 | 807 [M+H]⁺ | 3.2 min (B) |
| 2.9 | *-N⟨piperidine⟩-N⟨piperazine⟩-N-CH₂-C(O)-O-ethyl | 13 | 808 [M+H]⁺ | 3.1 min (B) |

Example 2.10

(R)-2-(4,4'-bipiperidinyl-1-yl)-1-(4-hydroxy-3,5-dimethyl-benzyl)-2-oxo-ethyl 4-(5-oxo-3-phenyl-4,5-dihydro-1,2,4-triazol-1-yl)-piperidine-1-carboxylate

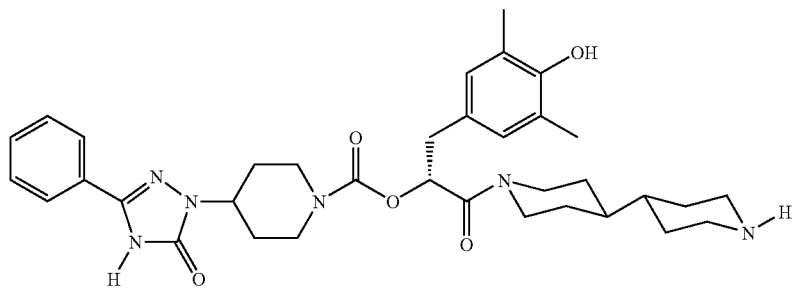

A solution of 51 mg (0.07 mmol) (R)-2-(1'-benzyl-4,4'-bipiperidinyl-1-yl)-1-(4-hydroxy-3,5-dimethyl-benzyl)-2-oxo-ethyl 4-(5-oxo-3-phenyl-4,5-dihydro-1,2,4-triazol-1-yl)-piperidine-1-carboxylate (Example 2.7) in 10 mL MeOH was combined with 5 mg 10% Pd/C and hydrogenated at RT and 3 bar hydrogen pressure until the reaction came to an end. The catalyst was removed by suction filtering and the residue was purified by HPLC. The fractions containing the product were combined and lyophilised.

Yield: 15 mg (45% of theory)
ESI-MS: (M−H)⁻=629
Retention time (HPLC-MS): 2.5 min (method B)

Example 2.11

(R)-2-(1'-ethoxycarbonylmethyl-4,4'-bipiperidinyl-1-yl)-1-(4-hydroxy-3,5-dimethyl-benzyl)-2-oxo-ethyl 4-(5-oxo-3-phenyl-4,5-dihydro-1,2,4-triazol-1-yl)-piperidine-1-carboxylate

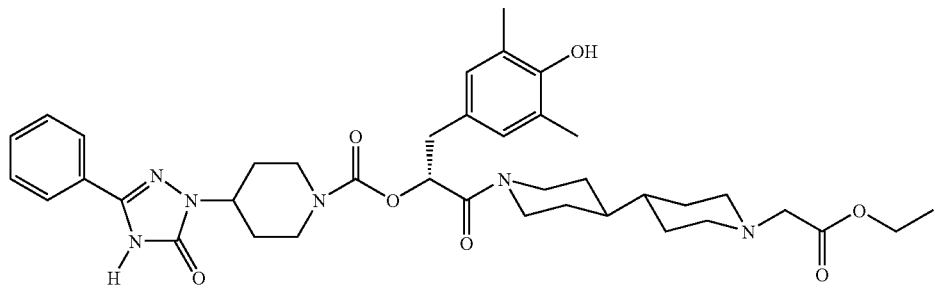

A solution of 58 mg (0.07 mmol) (R)-1-(4-benzyloxy-3,5-dimethyl-benzyl)-2-(1'-ethoxy-carbonyl methyl-4,4'-bipiperidinyl-1-yl)-2-oxo-ethyl 4-(5-oxo-3-phenyl-4,5-dihydro-1,2,4-triazol-1-yl)-piperidine-1-carboxylate (Example 2.8) in 5 mL EtOH was combined with 10 mg 10% Pd/C and hydrogenated at RT and 3 bar hydrogen pressure until the reaction came to an end. The catalyst was removed by suction filtering and the residue was purified by HPLC. The fractions containing the product were combined and lyophilised.

Yield: 23 mg (45% of theory)
ESI-MS: $(M+H)^+=717$
Retention time (HPLC-MS): 3.1 min (method B)

Example 2.12

(R)-2-(1'-carboxymethyl-4,4'-bipiperidinyl-1-yl)-1-(4-hydroxy-3,5-dimethyl-benzyl)-2-oxo-ethyl 4-(5-oxo-3-phenyl-4,5-dihydro-1,2,4-triazol-1-yl)-piperidine-1-carboxylate

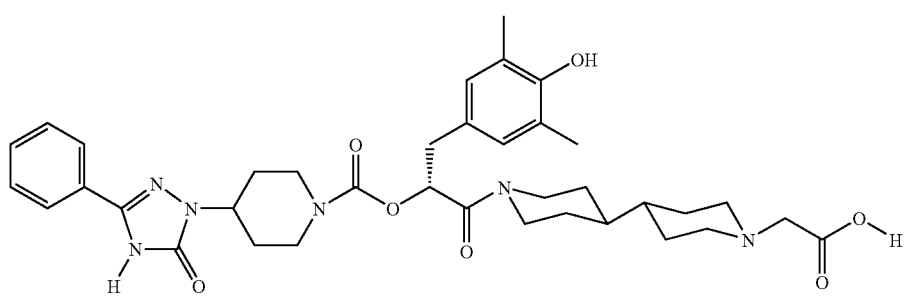

A solution of 1.2 mg (0.05 mmol) LiOH in 2 mL water was added to a solution of 21 mg (0.03 mmol) (R)-2-(1'-ethoxy-carbonylmethyl-4,4'-bipiperidinyl-1-yl)-1-(4-hydroxy-3,5-dimethyl-benzyl)-2-oxo-ethyl 4-(5-oxo-3-phenyl-4,5-dihydro-1,2,4-triazol-1-yl)-piperidine-1-carboxylate in 3 mL THF and the reaction mixture was stirred for 1 h at RT. The THF was evaporated down i.vac., the residue was acidified with 1 M HCl and again evaporated down i.vac. The residue was purified by HPLC, the fractions containing the product were combined and lyophilised.

Yield: 12 mg (58% of theory)
ESI-MS: $(M+H)^+=689$
Retention time (HPLC-MS): 2.9 min (method B)

Example 2.13

(R)-2-[4-(4-ethoxycarbonylmethyl-piperazin-1-yl)-piperidin-1-yl]-1-(4-hydroxy-3,5-dimethyl-benzyl)-2-oxo-ethyl 4-(5-oxo-3-phenyl-4,5-dihydro-1,2,4-triazol-1-yl)-piperidine-1-carboxylate

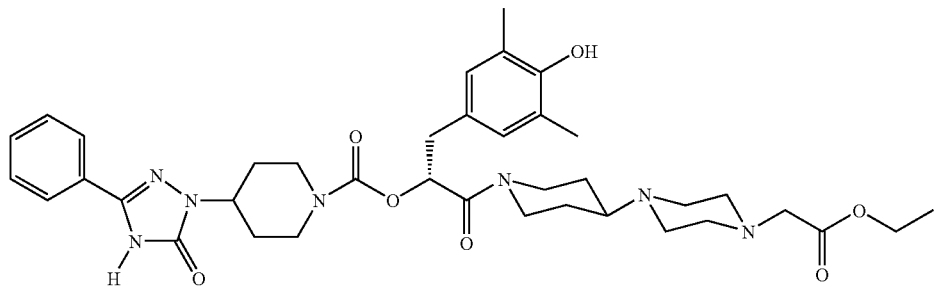

Prepared analogously to Example 2.11 from 47 mg (0.06 mmol) (R)-1-(4-benzyloxy-3,5-dimethyl-benzyl)-2-[4-(4-ethoxycarbonylmethyl-piperazin-1-yl)-piperidin-1-yl]-2-oxo-ethyl 4-(5-oxo-3-phenyl-4,5-dihydro-1,2,4-triazol-1-yl)-piperidine-1-carboxylate (Example 2.9).

Yield: 18 mg (43% of theory)
ESI-MS: $(M+H)^+=718$
Retention time (HPLC-MS): 3.0 min (method B)

Example 2.14

(R)-2-[4-(4-carboxymethyl-piperazin-1-yl)-piperidin-1-yl]-1-(4-hydroxy-3,5-dimethyl-benzyl)-2-oxo-ethyl 4-(5-oxo-3-phenyl-4,5-dihydro-1,2,4-triazol-1-yl)-piperidine-1-carboxylate

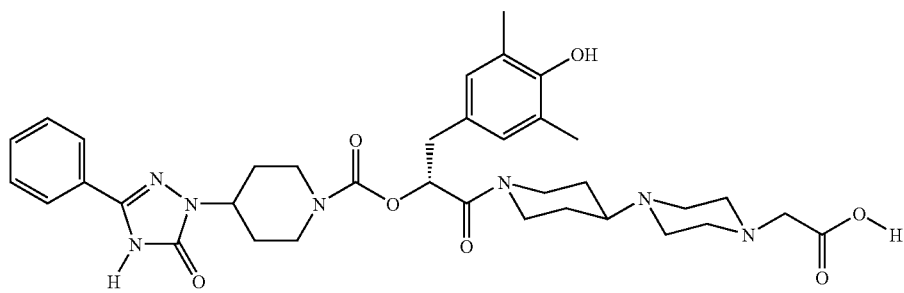

Prepared analogously to Example 2.12 from 38 mg (0.05 mmol) (R)-2-[4-(4-ethoxycarbonylmethyl-piperazin-1-yl)-piperidin-1-yl]-1-(4-hydroxy-3,5-dimethyl-benzyl)-2-oxo-ethyl 4-(5-oxo-3-phenyl-4,5-dihydro-1,2,4-triazol-1-yl)-piperidine-1-carboxylate and 2.1 mg (0.09 mmol) LiOH.

Yield: 20 mg (55% of theory)
ESI-MS: $(M+H)^+=690$
Retention time (HPLC-MS): 2.7 min (method B)

Example 3

(R)-1-(4-hydroxy-3,5-dimethyl-benzyl)-2-oxo-2-{1'-[2-(2-oxo-pyrrolidin-1-yl)-ethoxycarbonyl-methyl]-4,4'-bipiperidinyl-1-yl}-ethyl 4-(2-oxo-1,2,4,5-tetrahydro-1,3-benzodiazepin-3-yl)-piperidine-1-carboxylate

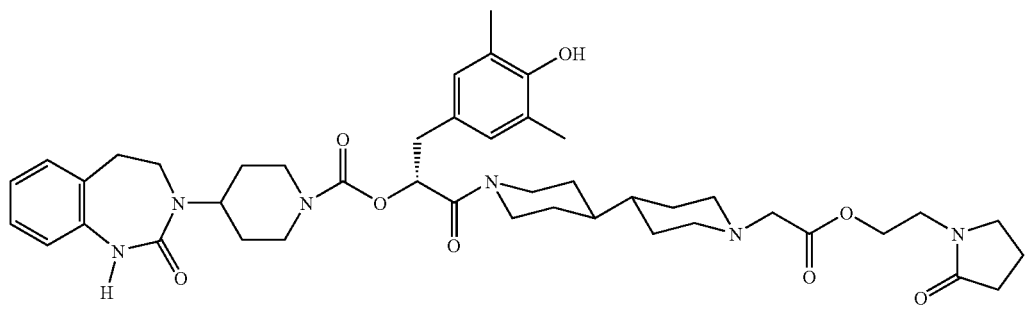

3a) (R)-1-(4-benzyloxy-3,5-dimethyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate 0.99 g (3.90 mmol) ethyl[4,4']bipiperidinyl-1-yl-acetate were added at RT to a solution of 2.00 g (3.50 mmol) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1g), 1.25 g (3.90 mmol) TBTU and 0.67 mL (3.90 mmol) ethyldiisopropylamine in 20 mL THF and 5 mL DMF and the reaction mixture was stirred overnight. 15% $K_2CO_3$ solution was added, the mixture was extracted exhaustively with EtOAc, the combined organic phases were washed with saturated NaCl solution and dried on $Na_2SO_4$. After the elimination of the desiccant and solvent the product was obtained, which was reacted further without purification.

Yield: 2.80 g (99% of theory)
ESI-MS: $(M+H)^+=809$
Retention time (HPLC-MS): 4.1 min (method B)

3b) (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate 2.80 g (3.47 mmol) (R)-1-(4-benzyloxy-3,5-dimethyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate in 30 mL MeOH were combined with 300 mg 10% Pd/C and hydrogenated at RT and 3 bar hydrogen until the reaction came to an end (24 h). The catalyst was removed by suction filtering and the solvent was concentrated by evaporation i.vac. The residue was dissolved in 30 mL THF, combined with a solution of 127 mg (5.33 mmol) LiOH in 10 mL water and the reaction mixture was stirred overnight at RT. The mixture was evaporated down i.vac. and the residue was purified by chromatography (silica gel, gradient DCM to $DCM/MeOH/NH_3$ 70:30:3). The fractions containing the product were combined, concentrated by evaporation i.vac., the residue was triturated with DIPE, suction filtered and dried.

Yield: 1.80 g (75% of theory)
ESI-MS: $(M+H)^+=690$
$R_f=0.16$ (silica gel, $DCM/MeOH/Cyc/NH_3$ 70:15:15:2)

3c) (R)-1-(4-hydroxy-3,5-dimethyl-benzyl)-2-oxo-2-{1'-[2-(2-oxo-pyrrolidin-1-yl)-ethoxycarbonyl-methyl]-4,4'-bipiperidinyl-1-yl}-ethyl 4-(2-oxo-1,2,4,5-tetrahydro-1,3-benzodiazepin-3-yl)-piperidine-1-carboxylate A solution of 80 mg (0.12 mmol) (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, 45 mg (0.14 mmol) TBTU and 32 μL (0.23 mmol) triethylamine in 1.2 mL DMF was stirred for 1 h at RT. Then 26 mg (0.23 mmol) 1-(2-hydroxy-ethyl)-pyrrolidin-2-one were added and the reaction mixture was stirred overnight at RT. The reaction solution was mixed with 5 drops of formic acid, filtered through a syringe filter and purified directly by HPLC without any further working up. The fractions containing the product were combined, extracted with 30 mL EtOAc, the organic phase was made alkaline with 5% $NaHCO_3$ solution, separated off and dried on $Na_2SO_4$. After the elimination of the desiccant and solvent the residue was triturated with DIPE, suction filtered and dried.

Yield: 26 mg (28% of theory)
ESI-MS: $(M+H)^+=801$
Retention time (HPLC-MS): 3.1 min (method B)

Example 3.1

(R)-1-(4-hydroxy-3,5-dimethyl-benzyl)-2-[1'-(2-methoxy-ethoxycarbonyl methyl)-4,4'-bipiperidinyl-1-yl]-2-oxo-ethyl 4-(2-oxo-1,2,4,5-tetrahydro-1,3-benzodiazepin-3-yl)-piperidine-1-carboxylate

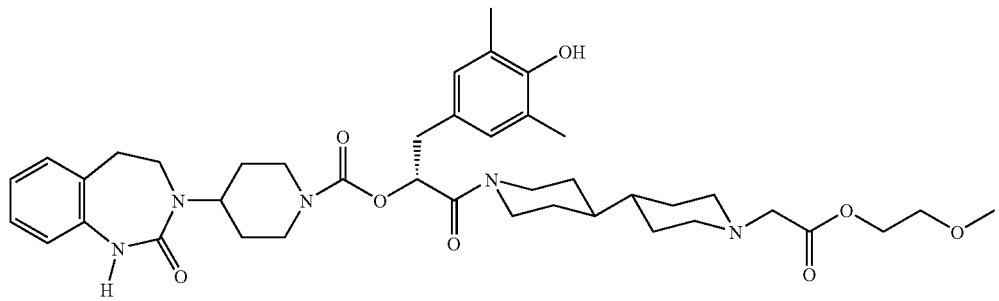

Prepared analogously to Example 3c from 80 mg (0.12 mmol) (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate and 18 µL (0.23 mmol) 2-methoxy-ethanol.

Yield: 33 mg (38% of theory)
ESI-MS: $(M+H)^+ = 748$
Retention time (HPLC-MS): 3.2 min (method B)

Example 3.2

(R)-2-(1'-hexyloxycarbonylmethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

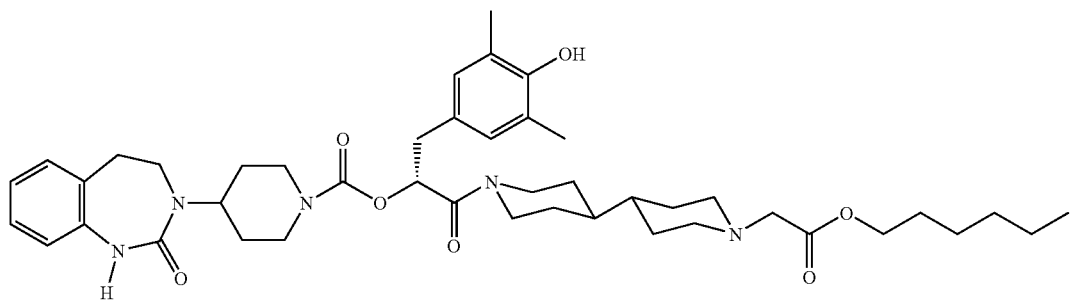

A solution of 80 mg (0.12 mmol) (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, 45 mg (0.14 mmol) TBTU and 32 µL (0.23 mmol) triethylamine in 1.2 mL DMF was stirred for 1 h at RT. Then 29 µL (0.23 mmol) 1-hexanol were added and the reaction mixture was stirred for 4 days at RT. The mixture was evaporated down i.vac., the residue was taken up in 30 mL EtOAc, the organic phase was washed with 20 mL 5% NaHCO₃ solution and dried on Na₂SO₄. After the elimination of the desiccant and solvent the residue was purified by chromatography (silica gel, gradient DCM/isopropanol 95:5 to DCM/isopropanol 90:10). The fractions containing the product were concentrated by evaporation i.vac., the residue was triturated with DIPE, suction filtered and dried.

Yield: 24 mg (27% of theory)
ESI-MS: $(M+H)^+ = 774$
Retention time (HPLC-MS): 4.0 min (method B)

Example 3.3

(R)-1-(4-hydroxy-3,5-dimethyl-benzyl)-2-oxo-2-{1'-[2-(2-oxo-piperidin-1-yl)-ethoxycarbonyl-methyl]-4,4'-bipiperidinyl-1-yl}-ethyl 4-(2-oxo-1,2,4,5-tetrahydro-1,3-benzodiazepin-3-yl)-piperidine-1-carboxylate

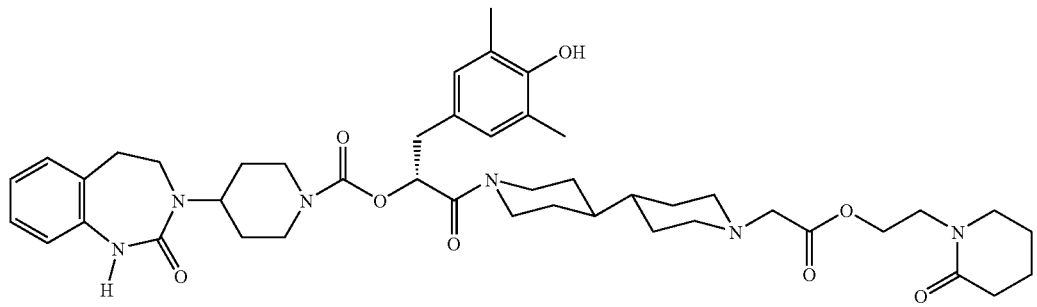

Prepared analogously to Example 3c from 80 mg (0.12 mmol) (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate and 33 mg (0.23 mmol) 1-(2-hydroxyethyl)-piperidin-2-one. After the elimination of the desiccant and solvent the residue was taken up in DCM and again purified by chromatography (silica gel, DCM/EtOH/NH$_3$ 95:5:0.5). The fractions containing the product were combined, concentrated by evaporation i.vac., triturated with DIPE, suction filtered and dried.

Yield: 23 mg (24% of theory)
ESI-MS: (M+H)$^+$=815
Retention time (HPLC-MS): 3.2 min (method B)

Example 3.4

(R)-1-(4-hydroxy-3,5-dimethyl-benzyl)-2-[1'-(2-morpholin-4-yl-ethoxycarbonylmethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate

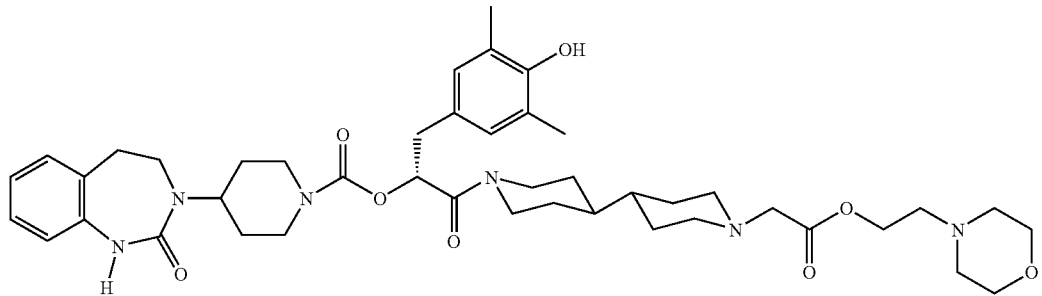

Prepared analogously to Example 3c from 80 mg (0.12 mmol) (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate and 17 μL (0.14 mmol) 2-morpholin-4-yl-ethanol. After purification by HPLC the product obtained was dissolved in 10 mL DCM and stirred with 5 mL of 5% NaHCO$_3$ solution. The organic phase was separated off and dried on Na$_2$SO$_4$. After the elimination of the desiccant and solvent the residue was triturated with diethyl ether, suction filtered and dried.

Yield: 32 mg (34% of theory)
ESI-MS: (M+H)$^+$=803
Retention time (HPLC-MS): 2.7 min (method B)

Example 3.5

(R)-2-(1'-dimethylcarbamoylmethoxycarbonylmethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

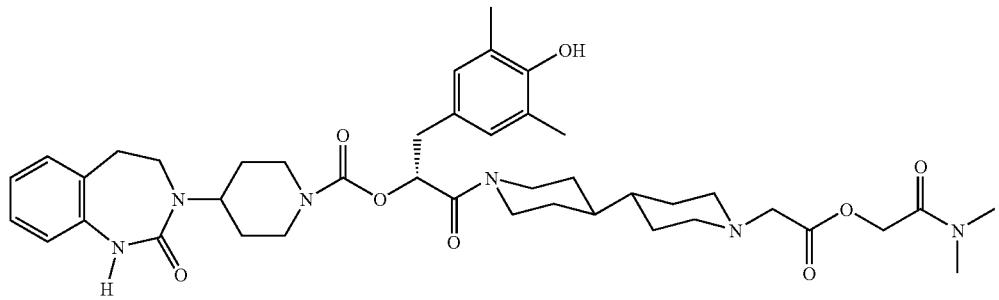

Prepared analogously to Example 3c from 100 mg (0.15 mmol) (R)-2-(1'-carboxymethyl-4,4'-bipiperidinyl-1-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate and 16 mg (0.16 mmol) 2-hydroxy-N,N-dimethyl-acetamide. After purification by HPLC the fractions containing the product were combined and lyophilised.

Yield: 45 mg (40% of theory)
ESI-MS: (M+H)$^+$=775
Retention time (HPLC-MS): 3.1 min (method B)

Example 4

(R)-1-(4-hydroxy-3,5-dimethyl-benzyl)-2-oxo-2-(4-{1-[2-(2-oxo-pyrrolidin-1-yl)-ethoxycarbonyl-methyl]-piperidin-4-yl}-piperazin-1-yl)-ethyl 4-(2-oxo-1,2,4,5-tetrahydro-1,3-benzodiazepin-3-yl)-piperidine-1-carboxylate 4a) (R)-1-(4-benzyloxy-3,5-dimethyl-benzyl)-2-[4-(1-ethoxycarbonylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate A solution of 2.80 g (4.90 mmol) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1g), 1.80 g (5.61 mmol) TBTU and 3.10 mL (22.08 mmol) triethylamine in 30 mL DMF was stirred for 1 h at RT. Then 2.00 g (5.48 mmol) ethyl (4-piperazin-1-yl-piperidin-1-yl)-acetate were added. The reaction mixture was stirred for 1 h at RT, poured onto 150 mL 15% K$_2$CO$_3$ solution and extracted with 200 mL EtOAc. The organic phase was extracted with 150 mL of 10% citric acid solution, the aqueous phase was made alkaline with 15% K$_2$CO$_3$ solution and extracted with 200 mL EtOAc. The organic phase was concentrated by evaporation i.vac. and the residue was purified by chromatography (silica gel, EtOH).

Yield: 2.00 g (51% of theory)
ESI-MS: (M+H)$^+$=809
Retention time (HPLC-MS): 3.9 min (method B)

4b) (R)-2-[4-(1-ethoxycarbonylmethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate 2.00 g (2.47 mmol) of (R)-1-(4-benzyloxy-3,5-dimethyl-benzyl)-2-[4-(1-ethoxycarbonylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate in 25 mL EtOH were combined with 200 mg 10% Pd/C and hydrogenated at RT and 3 bar hydrogen until the reaction came to an

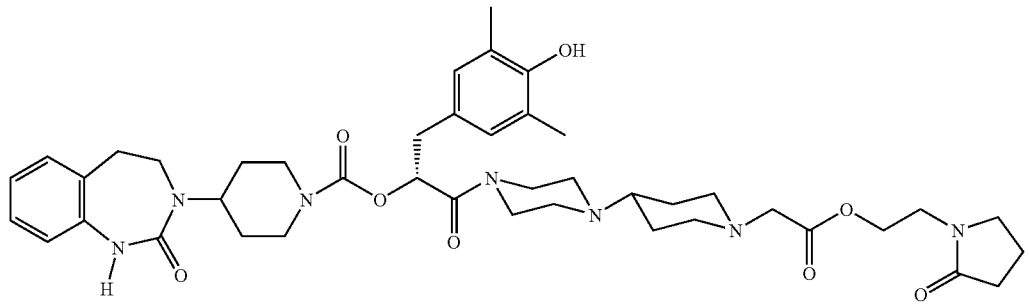

end. The catalyst was removed by suction filtering and the solvent was concentrated by evaporation i.vac. The residue was reacted further without any purification by chromatography.

Yield: 1.77 g (100% of theory)
ESI-MS: (M+H)$^+$=719
Retention time (HPLC-MS): 2.6 min (method B)

4c) (R)-2-[4-(1-carboxymethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate A solution of 96 mg (4.00 mmol) LiOH in 5 mL water was added at RT to a solution of 1.77 g (2.46 mmol) of (R)-2-[4-(1-ethoxycarbonylmethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate in 20 mL THF and the reaction solution was stirred overnight at RT. The mixture was evaporated down i.vac., the residue was taken up in 10 mL water and the aqueous phase was washed with 10 mL EtOAc. The aqueous phase was combined with 4 mL of 1 M HCl and this was again washed with 10 mL EtOAc. The aqueous phase was concentrated by evaporation i.vac. and dried. The product which contained LiCl was further reacted without purification.

Yield: 1.70 g (100% of theory)
ESI-MS: (M+H)$^+$=691
Retention time (HPLC-MS): 2.7 min (method B)

4d) (R)-1-(4-hydroxy-3,5-dimethyl-benzyl)-2-oxo-2-(4-{1-[2-(2-oxo-pyrrolidin-1-yl)-ethoxycarbonyl-methyl]-piperidin-4-yl}-piperazin-1-yl)-ethyl 4-(2-oxo-1,2,4,5-tetrahydro-1,3-benzodiazepin-3-yl)-piperidine-1-carboxylate 58 mg (0.18 mmol) TBTU were added at RT to a solution of 100 mg (0.15 mmol) (R)-2-[4-(1-carboxymethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate, 18 µL (0.16 mmol) 1-(2-hydroxy-ethyl)-pyrrolidin-2-one and 50 µL (0.36 mmol) triethylamine in 1.5 mL DMF and the reaction mixture was stirred for 2 h at RT. 10 mL of semisaturated NaHCO$_3$ solution were added, the precipitate formed was filtered off, dissolved in 1.5 mL DMF and purified by HPLC. The fractions containing the product were combined and lyophilised.

Yield: 13 mg (11% of theory)
ESI-MS: (M+H)$^+$=802
Retention time (HPLC-MS): 2.9 min (method B)

The following compounds were prepared analogously from in each case 100 mg (R)-2-[4-(1-carboxymethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate and the corresponding amount of the alcohol component:

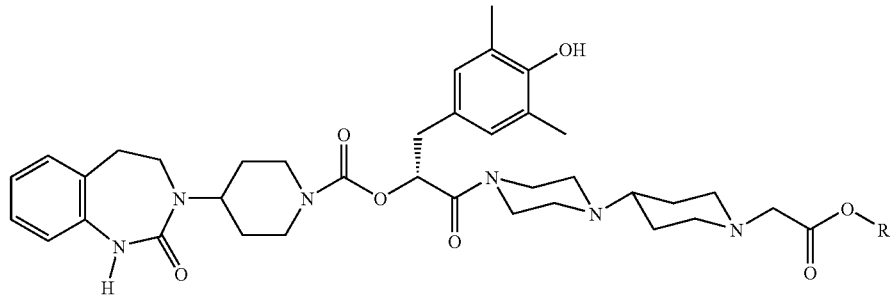

| Example | R | Yield (%) | Mass spectrum | Retention time HPLC (method) |
|---|---|---|---|---|
| 4.1 | * (propyl) | 17 | 733 [M + H]$^+$ | 3.0 min (B) |
| 4.2 | * (butyl) | 38 | 747 [M + H]$^+$ | 3.3 min (B) |
| 4.3 | *-CH$_2$-C(O)-N(CH$_3$)$_2$ | 11 | 776 [M + H]$^+$ | 2.9 min (B) |

Example 4.4

(R)-1-(4-hydroxy-3,5-dimethyl-benzyl)-2-(4-{1-[2-(2-methoxy-ethoxy)-ethoxycarbonylmethyl]-piperidin-4-yl}-piperazin-1-yl)-2-oxo-ethyl 4-(2-oxo-1,2,4,5-tetrahydro-1,3-benzodiazepin-3-yl)-piperidine-1-carboxylate

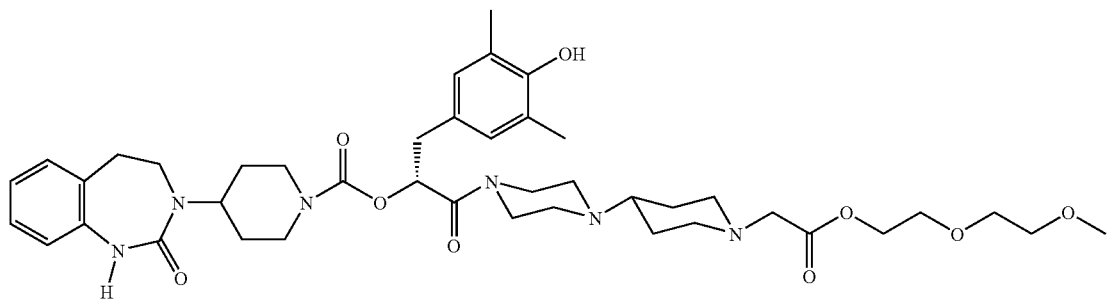

Prepared analogously to Example 4d from 70 mg (0.10 mmol) of (R)-2-[4-(1-carboxymethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate and 13 µL (0.11 mmol) 2-(2-methoxy-ethoxy)-ethanol. The reaction solution was purified by HPLC without any further working up; the fractions containing the product were combined and lyophilised.

Yield: 54 mg (68% of theory)
ESI-MS: $(M+H)^+=793$
Retention time (HPLC-MS): 2.8 min (method B)

Example 4.5

(R)-2-[4-(1-hexyloxycarbonylmethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

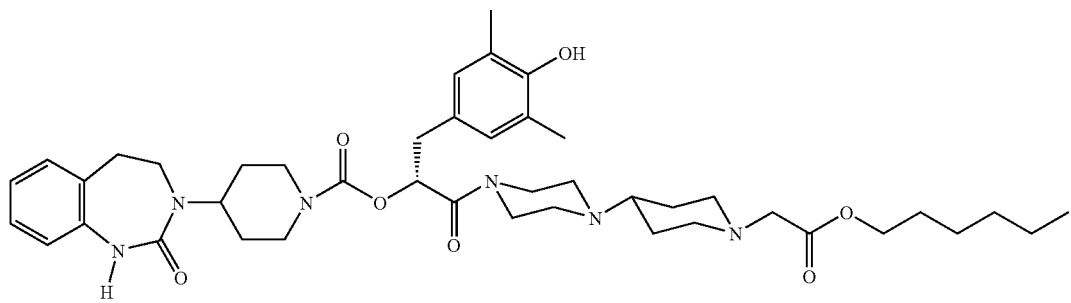

Prepared analogously to Example 4d from 934 mg (1.35 mmol) (R)-2-[4-(1-carboxymethyl-piperidin-4-yl)-piperazin-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate and 190 µL (0.11 mmol) 1-hexanol. The reaction solution was combined with 30 mL semisaturated NaHCO₃ solution, extracted with 50 mL EtOAc and the organic phase was dried on $Na_2SO_4$. After the elimination of the desiccant and solvent the residue was purified by chromatography (silica gel, EtOAc/MeOH/NH₃ 90:10:1).

Yield: 199 mg (19% of theory)
ESI-MS: $(M+H)^+=775$
Retention time (HPLC-MS): 3.6 min (method B)

Example 5

(R)-2-[1'-(2-dimethylcarbamoylmethoxycarbonyl-
ethyl)-4,4'-bipiperidinyl-1-yl]-1-(4-hydroxy-3,5-
dimethyl-benzyl)-2-oxo-ethyl 4-(2-oxo-1,2,4,5-tet-
rahydro-1,3-benzodiazepin-3-yl)-piperidine-1-
carboxylate

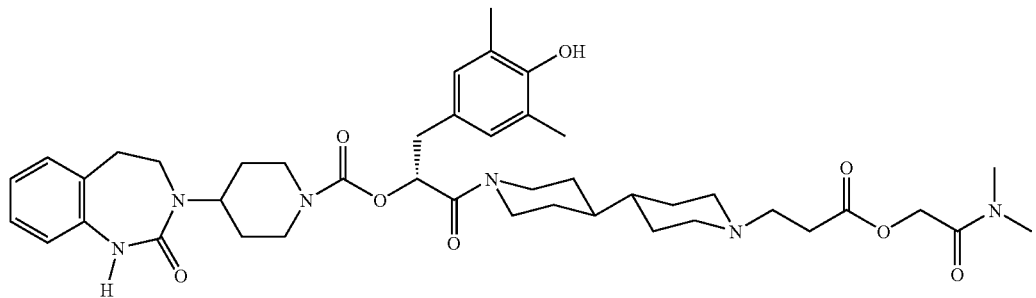

5a) (R)-1-(4-benzyloxy-3,5-dimethyl-benzyl)-2-[1'-
(2-ethoxycarbonyl-ethyl)-4,4'-bipiperidinyl-1-yl]-2-
oxo-ethyl 4-(2-oxo-1,2,4,5-tetrahydro-1,3-benzodi-
azepin-3-yl)-piperidine-1-carboxylate Prepared analogously to Example 3a from 2.00 g (3.50 mmol) (R)-2-(4-benzyloxy-3,5-dimethyl-phenyl)-1-car-boxy-ethyl (Example 1g) and 1.05 g (3.90 mmol) 3-[4,4']bipiperidinyl-1-yl-propionate ethyl 4-(2-oxo-1,2,4,5-tetrahydro-1,3-benzodiazepin-3-yl)-piperidine-1-carboxylate.

Yield: 2.90 g (100% of theory)
ESI-MS: (M+H)$^+$=823
Retention time (HPLC-MS): 4.0 min (method B)

5b) (R)-2-[1'-(2-carboxy-ethyl)-4,4'-bipiperidinyl-1-
yl]-1-(4-hydroxy-3,5-dimethyl-benzyl)-2-oxo-ethyl
4-(2-oxo-1,2,4,5-tetrahydro-1,3-benzodiazepin-3-yl)-
piperidine-1-carboxylate Prepared analogously to Example 3b from 2.90 g (3.35 mmol) (R)-1-(4-benzyloxy-3,5-dimethyl-benzyl)-2-[1'-(2-ethoxycarbonyl-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate, 300 mg 10% Pd/C (hydrogenation) and 128 mg LiOH (ester hydrolysis).

Yield: 1.70 g (71% of theory)
ESI-MS: (M+H)$^+$=704
R$_f$=0.20 (silica gel, DCM/MeOH/Cyc/NH$_3$ 70:15:15:2)

5c) (R)-2-[1'-(2-dimethylcarbamoylmethoxycar-
bonyl-ethyl)-4,4'-bipiperidinyl-1-yl]-1-(4-hydroxy-3,
5-dimethyl-benzyl)-2-oxo-ethyl 4-(2-oxo-1,2,4,5-
tetrahydro-1,3-benzodiazepin-3-yl)-piperidine-1-
carboxylate Prepared analogously to Example 1i from 100 mg (0.14 mmol) (R)-2-[1'-(2-carboxy-ethyl)-4,4'-bipiperidinyl-1-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate and 16 mg (0.16 mmol) 2-hydroxy-N,N-dimethyl-acetamide.

Yield: 35 mg (31% of theory)
ESI-MS: (M+H)$^+$=789
Retention time (HPLC-MS): 3.6 min (method B)

Example 6

Ethyl 1'-{(R)-3-(4-hydroxy-3,5-dimethyl-phenyl)-2-
[4-(2-oxo-1,2,4,5-tetrahydro-1,3-benzodiazepin-3-
yl)-piperidine-1-carbonyloxy]-propionyl}-1,4'-bipip-
eridinyl-4-carboxylate

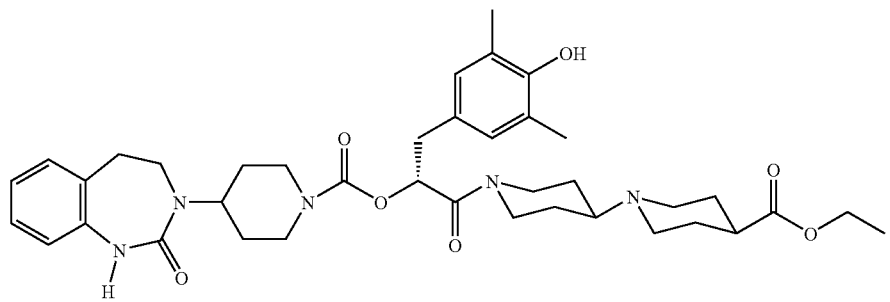

6a) ethyl 1'-{(R)-3-(4-benzyloxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate A solution of 400 mg (0.70 mmol) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1g), 250 mg (0.78 mmol) TBTU and 0.12 mL (3.73 mmol) triethylamine in 20 mL THF were stirred for 1 h at RT. Then 0.4 mL (2.87 mmol) triethylamine and 270 mg (0.86 mmol) ethyl[1,4']bipiperidinyl-4-carboxylate (used as the bis-hydrochloride salt) were added. The reaction mixture was stirred for 24 h at RT, diluted with EtOAc, washed with saturated NaHCO₃ solution and the organic phase was dried on Na₂SO₄. After the elimination of the desiccant and solvent the residue was purified by chromatography (Alox activity stage II-III, gradient DCM/EtOH 40:1 to DCM/EtOH 30:1).

Yield: 440 mg (79% of theory)
ESI-MS: (M+H)⁺=794
Retention time (HPLC-MS): 4.1 min (method B)

6b) ethyl 1'-[(R)-3-(4-hydroxy-3,5-dimethyl-phenyl)-2-[4-(2-oxo-1,2,4,5-tetrahydro-1,3-benzodiazepin-3-yl)-piperidine-1-carbonyloxy]-propionyl]-1,4'-bipiperidinyl-4-carboxylate 80 mg (0.10 mmol) ethyl 1'-{(R)-3-(4-benzyloxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate in 10 mL EtOH were combined with 30 mg 10% Pd/C and hydrogenated at 50° C. and 50 psi hydrogen for 1 h. The catalyst was removed by suction filtering and the solvent was concentrated by evaporation i. vac. The residue was triturated with diethyl ether, suction filtered and dried.

Yield: 37 mg (52% of theory)
ESI-MS: (M+H)⁺=704
Retention time (HPLC-MS): 3.2 min (method B)

Example 6.1

1'-{(R)-3-(4-hydroxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylic acid

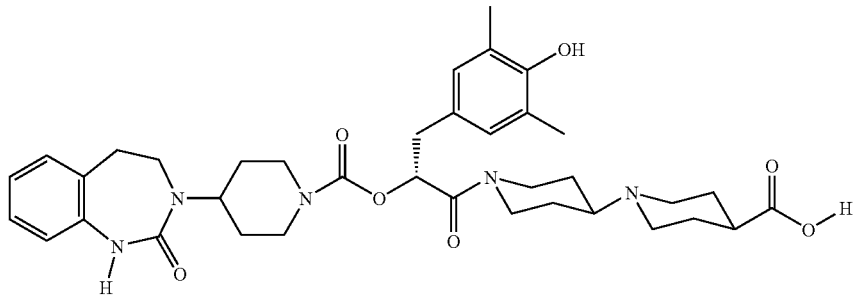

6.1a) 1'-{(R)-3-(4-benzyloxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylic acid A solution of 20 mg (0.84 mmol) LiOH in 3 mL water was added to a solution of 350 mg (0.44 mmol) ethyl 1'-{(R)-3-(4-benzyloxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate (Example 6a) in 15 mL THF and the reaction mixture was stirred for 3 h at RT. It was diluted with a little water, the THF was eliminated i.vac. and 4 M HCl was added to the aqueous solution while cooling with ice until an acidic reaction was obtained. The mixture was extracted exhaustively with DCM and dried on Na₂SO₄. After the elimination of the desiccant and solvent the residue was triturated with diethyl ether, suction filtered and dried, while the product was obtained as the hydrochloride salt.

Yield: 310 mg (88% of theory)
ESI-MS: (M+H)⁺=766

6.1 b) 1'-{(R)-3-(4-hydroxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylic acid 100 mg (0.13 mmol) 1'-{(R)-3-(4-benzyloxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bi-piperidinyl-4-carboxylic acid in 10 mL MeOH were combined with 30 mg 10% Pd/C and hydrogenated at 50° C. and 3 bar hydrogen for 2 h. The catalyst was removed by suction filtering and the solvent was concentrated by evaporation i. vac. The residue was triturated with diethyl ether, suction filtered and dried.

Yield: 64 mg (72% of theory)
ESI-MS: (M+H)$^+$=676
Retention time (HPLC-MS): 3.0 min (method B)

Example 6.2

Dimethylcarbamoyl methyl 1'-{(R)-3-(4-hydroxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate

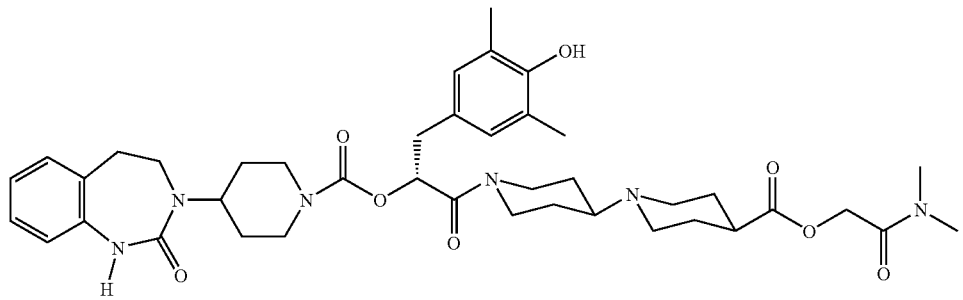

6.2a) dimethylcarbamoylmethyl 1'-{(R)-3-(4-benzyloxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate 30 mg (0.29 mmol) 2-hydroxy-N,N-dimethyl-acetamide were added at RT to a solution of 200 mg (0.25 mmol) 1'-{(R)-3-(4-benzyloxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylic acid (Example 6.1a), 90 mg (0.28 mmol) TBTU and 80 μL (3.73 mmol) triethylamine in 1.8 mL DMF and this was stirred for 20 h at RT. The reaction mixture was poured onto saturated NaHCO$_3$ solution, the precipitate formed was suction filtered and dried. Further purification was carried out by HPLC, the fractions containing the product were combined and lyophilised.

Yield: 100 mg (47% of theory)
ESI-MS: (M+H)$^+$=851
Retention time (HPLC-MS): 3.9 min (method B)

6.2b) dimethylcarbamoylmethyl 1'-{(R)-3-(4-hydroxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate 95 mg (0.11 mmol) dimethylcarbamoylmethyl 1'-{(R)-3-(4-benzyloxy-3,5-dimethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate in 10 mL THF were combined with 50 mg 10% Pd/C and hydrogenated at 50° C. and 50 psi hydrogen for 6 h. The catalyst was removed by suction filtering and the solvent was concentrated by evaporation i.vac. The residue was triturated with diethyl ether, suction filtered and dried.

Yield: 52 mg (61% of theory)
ESI-MS: (M+H)$^+$=761
Retention time (HPLC-MS): 3.1 min (method B)

Example 7

(R)-2-(4-ethoxycarbonylmethoxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

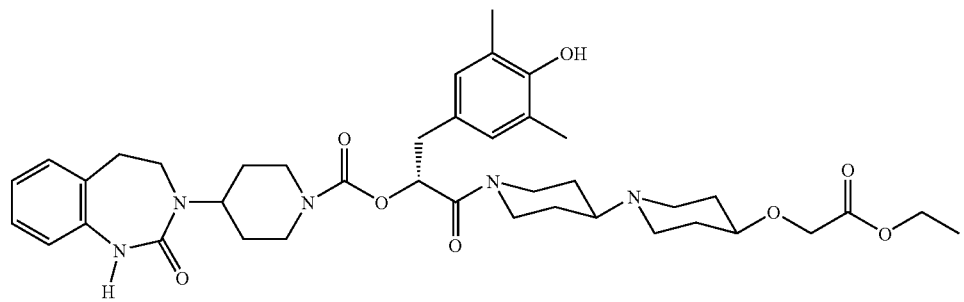

7a) (R)-1-(4-benzyloxy-3,5-dimethyl-benzyl)-2-(4-ethoxycarbonylmethoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate 220 mg (0.64 mmol) ethyl([1,4']bipiperidinyl-4-yloxy)-acetate (used as the bis-hydrochloride salt) were added at RT to a solution of 330 mg (0.58 mmol) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1g), 200 mg (0.62 mmol) TBTU and 0.30 mL (2.16 mmol) triethylamine in 3 mL DMF and the mixture was stirred for 4 h. The reaction mixture was combined with saturated NaHCO$_3$ solution while cooling with ice and the precipitate was suction filtered. This was dissolved in a little DCM and EtOH and purified by HPLC; the fractions containing the product were combined and lyophilised.

Yield: 340 mg (72% of theory)
ESI-MS: (M+H)$^+$=824
Retention time (HPLC-MS): 4.2 min (method B)

7b) (R)-2-(4-ethoxycarbonylmethoxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate 340 mg (0.41 mmol) (R)-1-(4-benzyloxy-3,5-dimethyl-benzyl)-2-(4-ethoxycarbonyl methoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate in 20 mL EtOH were combined with 100 mg 10% Pd/C and hydrogenated at 50° C. and 50 psi hydrogen for 2 h. The catalyst was removed by suction filtering and the solvent was concentrated by evaporation i.vac.

Yield: 270 mg (89% of theory)
ESI-MS: (M+H)$^+$=734
Retention time (HPLC-MS): 3.3 min (method B)

Example 7.1

(R)-2-(4-carboxymethoxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

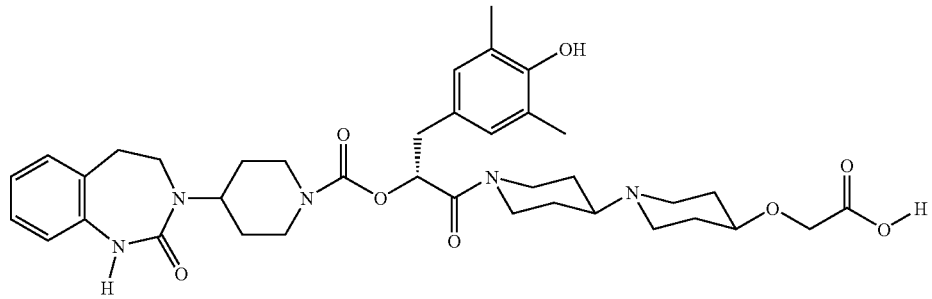

A solution of 15 mg (0.63 mmol) LiOH in 5 mL water was added to a solution of 180 mg (0.25 mmol) (R)-2-(4-ethoxycarbonylmethoxy-1,4'-bipiperidinyl-1'-yl)-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate in 15 mL THF and the reaction mixture was stirred for 4 h at RT. 0.66 mL of 1 M HCl were added and the mixture was concentrated by evaporation i.vac. The residue was taken up in a little DCM/MeOH (7:3) and filtered through silica gel. The filtrate was concentrated by evaporation i.vac., the residue was triturated with diethyl ether, suction filtered and dried.

Yield: 173 mg (100% of theory)
ESI-MS: (M+H)$^+$=706
Retention time (HPLC-MS): 2.9 min (method B)

Example 8

(R)-2-[4-(2-ethoxycarbonyl-ethyl)-1,4'-bipiperidinyl-1'-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

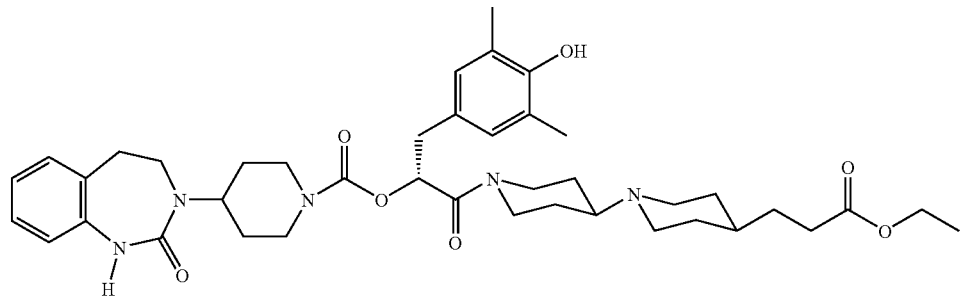

410 mg (1.20 mmol) ethyl 3-[1,4']bipiperidinyl-4-yl-propionate (used as the bis-hydrochloride salt) were added at RT to a solution of 500 mg (1.04 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1h), 385 mg (1.20 mmol) TBTU and 0.48 mL (3.40 mmol) triethylamine in 10 mL DMF and the mixture was stirred for 2 h. The reaction mixture was purified by HPLC without any further working up. The fractions containing the product were combined, concentrated by evaporation i.vac. and the residue was stirred with saturated NaHCO$_3$ solution. The precipitate formed was filtered off and dried.

Yield: 310 mg (41% of theory)
ESI-MS: (M+H)$^+$=732
Retention time (HPLC-MS): 2.4 min (method B)

Example 8.1

(R)-2-[4-(2-carboxy-ethyl)-1,4'-bipiperidinyl-1'-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

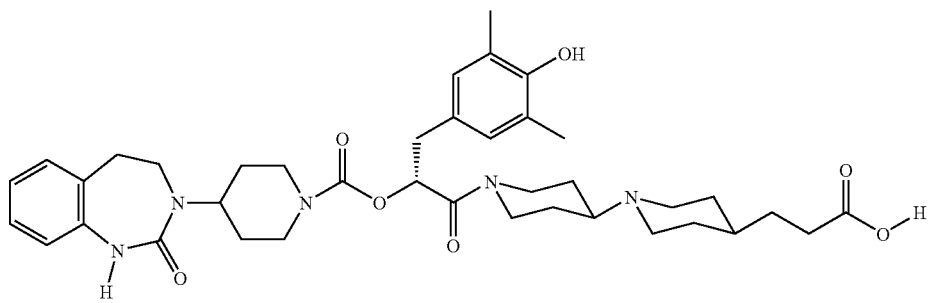

A solution of 2.6 mg (0.11 mmol) LiOH in 1 mL water was added to a solution of 50 mg (0.07 mmol) (R)-2-[4-(2-ethoxycarbonyl-ethyl)-1,4'-bipiperidinyl-1'-yl]-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate in 3 mL THF and the reaction mixture was stirred for 4 h at RT. The THF was eliminated in a nitrogen current and the crude product was purified by HPLC. The fractions containing the product were combined and lyophilised.

Yield: 32 mg (67% of theory)
ESI-MS: (M+H)$^+$=704
Retention time (HPLC-MS): 3.1 min (method B)

Example 9

(R)-2-{4-[1-(3-ethoxycarbonyl-propyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

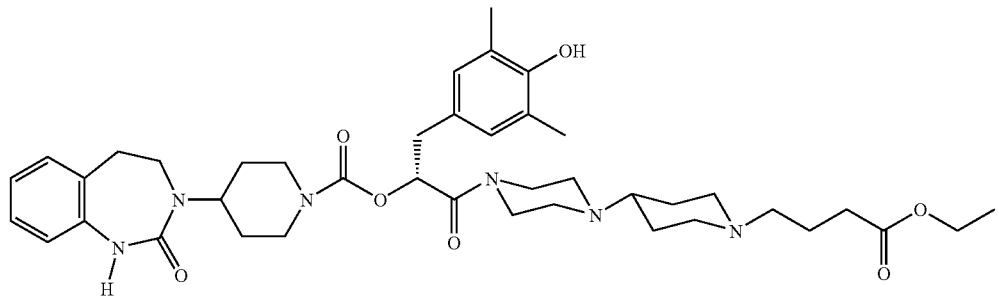

Prepared analogously to Example 8 from 500 mg (1.04 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate (Example 1h) and 385 mg (1.20 mmol) ethyl 4-(4-piperazin-1-yl-piperidin-1-yl)-butanoate.

Yield: 85 mg (11% of theory)
ESI-MS: $(M+H)^+=747$
Retention time (HPLC-MS): 2.8 min (method B)

Example 9.1

(R)-2-{4-[1-(3-carboxy-propyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate

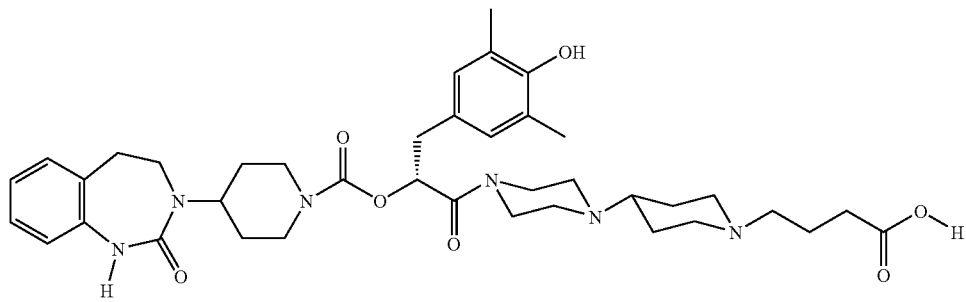

Prepared analogously to Example 8.1 from 50 mg (0.07 mmol) (R)-2-{4-[1-(3-ethoxycarbonyl-propyl)-piperidin-4-yl]-piperazin-1-yl}-1-(4-hydroxy-3,5-dimethyl-benzyl)-2-oxo-ethyl 4-(2-oxo-1,2,4,5-tetrahydro-1,3-benzodiazepin-3-yl)-piperidine-1-carboxylate and 2.6 mg (0.11 mmol) LiOH.

Yield: 24 mg (50% of theory)
ESI-MS: $(M+H)^+=719$
Retention time (HPLC-MS): 2.7 min (method B)

Example 10

(R)-1-(4-hydroxy-3-methoxy-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

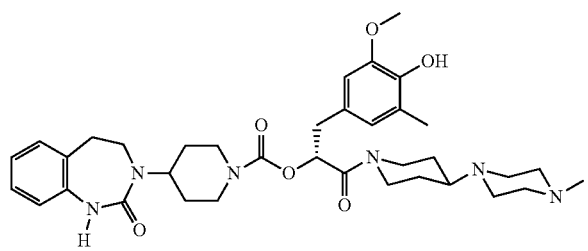

10a) 4-bromo-2-methoxy-6-methyl-phenol

A solution of 56.2 g (0.32 mol) N-bromosuccinimide in 1700 mL AcOH was added dropwise within 5.5 h to a solution of 42.3 g (0.31 mol) 2-methoxy-6-methyl-phenol in 450 mL AcOH and the mixture was stirred for 16 h at RT. The reaction mixture was concentrated by evaporation i.vac. and the residue was taken up in DCM. The organic phase was washed with 5% $NaHCO_3$ and saturated NaCl solution, dried on $Na_2SO_4$ and concentrated by evaporation i.vac. The red oil was used in the next reaction step without any further purification.

Yield: 65.9 g (66% of theory)
$R_f$=0.32 (silica gel, hexane/EtOAc 4:1)
Retention time (HPLC-MS): 11.1 min (method D)

10b)
2-benzyloxy-5-bromo-1-methoxy-3-methyl-benzene 45.7 g (0.33 mol) $K_2CO_3$ and a solution of 40.3 mL (0.33 mol) benzylbromide were added at RT to a solution of 65.9 g (0.26 mol) 4-bromo-2-methoxy-6-methyl-phenol in 330 mL DMF and the mixture was stirred for 18 h at RT. The mixture was filtered, concentrated by evaporation i.vac. and the residue was taken up in diethyl ether. The organic phase was washed with water, 5% $Na_2CO_3$ and NaCl solution, dried on $Na_2SO_4$ and concentrated by evaporation i.vac. The crude product was used in the next reaction step without any further purification.

Yield: 92.2 g (81% of theory)
$R_f$=0.56 (silica gel, hexane/EtOAc 4:1)
Retention time (HPLC-MS): 16.3 min (method D)

10c)
4-benzyloxy-3-methoxy-5-methyl-benzaldehyde 96 mL (240 mmol) n-butyllithium (2.5 M in hexane) were added dropwise at −75° C. to a solution of 61.2 g (119.5 mmol) 2-benzyloxy-5-bromo-1-methoxy-3-methyl-benzene in 240 mL THF and the mixture was stirred for 15 min at −75° C. A solution of 31 mL (402 mmol) DMF in 30 mL THF was added dropwise, the mixture was heated to 0° C. and stirred for another 2 h. The reaction was combined with saturated $NH_4Cl$ solution, diluted with 150 mL water and the phases were separated. The aqueous phase was extracted exhaustively with diethyl ether. The combined organic phases were washed with saturated NaCl solution, dried on $Na_2SO_4$ and concentrated by evaporation i.vac. Column chromatography (silica gel, hexane/EtOAc 85:15) yielded the product in the form of a yellow oil.

Yield: 27.1 g (88% of theory)
$R_f$=0.32 (silica gel, hexane/EtOAc 4:1)
Retention time (HPLC-MS): 13.3 min (method D)

10d) 2-acetylamino-3-(4-benzyloxy-3-methoxy-5-methyl-phenyl)-acrylic acid

A suspension of 27.0 g (105.4 mmol) 4-benzyloxy-3-methoxy-5-methyl-benzaldehyde, 18.5 g (158.0 mmol) N-acetylglycine and 12.96 g (158.0 mmol) NaOAc in 120 mL acetic anhydride was heated to 115° C. under nitrogen for 3.5 h. At 100° C. 60 mL water were slowly added dropwise and the mixture was stirred for 1 h. The reaction mixture was cooled to RT, poured into water and the aqueous phase was exhaustively extracted with EtOAc. The combined organic phases were washed with saturated NaCl solution, dried on Na$_2$SO$_4$ and concentrated by evaporation i.vac. The residue was triturated with isopropanol, the solid obtained was washed with isopropanol, diethyl ether and a little acetone and dried i.vac. at 45° C.

Yield: 21.2 (57% of theory)
R$_f$=0.24 (silica gel, hexane/EtOAc 4:1)
Retention time (HPLC-MS): 9.4 min (method D)

10e) 3-(4-benzyloxy-3-methoxy-5-methyl-phenyl)-2-oxo-propionic acid

The product was obtained analogously to Example 1c starting from 20.0 g (56.3 mmol) 2-acetylamino-3-(4-benzyloxy-3-methoxy-5-methyl-phenyl)-acrylic acid. The crude product was used in the next reaction step without any further purification.

Yield: 15.6 g (53% of theory)
Retention time (HPLC-MS): 11.9 min (method D)

10f) (R)-3-(4-benzyloxy-3-methoxy-5-methyl-phenyl)-2-hydroxy-propionic acid

The product was prepared analogously to Example 1d starting from 16.0 g (50.90 mmol) 3-(4-benzyloxy-3-methoxy-5-methyl-phenyl)-2-oxo-propionic acid.

Yield: 7.63 g (47% of theory)
Retention time (HPLC-MS): 9.8 min (method D)

10g) methyl (R)-3-(4-benzyloxy-3-methoxy-5-methyl-Phenyl)-2-hydroxy-propionate The product was prepared analogously to Example 1e starting from 7.6 g (24.02 mmol) (R)-3-(4-benzyloxy-3-methoxy-5-methyl-phenyl)-2-hydroxy-propionic acid.

Yield: 6.84 g (86% of theory)
Retention time (HPLC-MS): 11.7 min (method D)

10h) (R)-2-(4-benzyloxy-3-methoxy-5-methyl-Phenyl)-1-methoxycarbonyl-ethyl 4-(2-oxo-1,2,4,5-tetrahydro-1,3-benzodiazepin-3-yl)-piperidine-1-carboxylate The product was prepared analogously to Example 1f starting from 6.8 g (20.6 mmol) methyl (R)-3-(4-benzyloxy-3-methoxy-5-methyl-phenyl)-2-hydroxy-propionate in acetonitrile.

Yield: 8.16 g (66% of theory)
ESI-MS: (M+H)$^+$=602
Retention time (HPLC-MS): 14.1 min (method D)

10i) (R)-2-(4-benzyloxy-3-methoxy-5-methyl-phenyl)-1-carboxy-ethyl 4-(2-oxo-1,2,4,5-tetrahydro-1,3-benzodiazepin-3-yl)-piperidine-1-carboxylate The product was prepared analogously to Example 1g starting from 8.16 g (13.65 mmol) (R)-2-(4-benzyloxy-3-methoxy-5-methyl-phenyl)-1-methoxycarbonyl-ethyl 4-(2-oxo-1,2,4,5-tetrahydro-1,3-benzodiazepin-3-yl)-piperidine-1-carboxylate.

Yield: 7.83 g (98% of theory)
ESI-MS: (M+H)$^+$=588
Retention time (HPLC-MS): 12.2 min (method D)

10j) (R)-1-carboxy-2-(4-hydroxy-3-methoxy-5-methyl-phenyl)-ethyl 4-(2-oxo-1,2,4,5-tetrahydro-1,3-benzodiazepin-3-yl)-piperidine-1-carboxylate The product was prepared analogously to Example 1h starting from 7.80 g (13.27 mmol) (R)-2-(4-benzyloxy-3-methoxy-5-methyl-phenyl)-1-carboxy-ethyl 4-(2-oxo-1,2,4,5-tetrahydro-1,3-benzodiazepin-3-yl)-piperidine-1-carboxylate.

Yield: 5.33 g (80% of theory)
ESI-MS: (M+H)$^+$=498
Retention time (HPLC-MS): 8.4 min (method D)

10k) (R)-1-(4-hydroxy-3-methoxy-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate 84 mg (0.22 mmol) HATU was added at RT under nitrogen to a solution of 100 mg (0.20 mmol) (R)-1-carboxy-2-(4-hydroxy-3-methoxy-5-methyl-phenyl)-ethyl 4-(2-oxo-1,2,4,5-tetrahydro-1,3-benzodiazepin-3-yl)-piperidine-1-carboxylate, 37.8 µL (0.22 mmol) ethyldiisopropylamine and 44 mg (0.24 mmol) 1-methyl-4-(piperidin-4-yl)-piperazine in 5 mL DMF and the mixture was stirred for 3 h. The reaction mixture was concentrated by evaporation i.vac. at 50° C. and the crude product was purified by preparative HPLC-MS.

Yield: 89 mg (57% of theory)
ESI-MS: (M+H)$^+$=663
Retention time (HPLC-MS): 5.6 min (method D)

The following compounds were prepared analogously from in each case 100 mg (Examples 10.1 and 10.2) or 150 mg (Examples 10.3 to 10.5) of (R)-1-carboxy-2-(4-hydroxy-3-methoxy-5-methyl-phenyl)-ethyl 4-(2-oxo-1,2,4,5-tetrahydro-1,3-benzodiazepin-3-yl)-piperidine-1-carboxylate and the corresponding amount of amine:

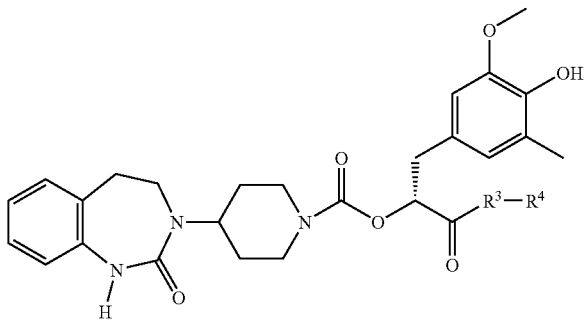

| Example | —R³—R⁴ | Yield (%) | Mass spectrum | Retention time HPLC (method) |
|---|---|---|---|---|
| 10.1 | ![structure] | 60 | 663 [M + H]⁺ | 3.1 min (D) |
| 10.2 | ![structure] | 71 | 662 [M + H]⁺ | 3.6 min (D) |
| 10.3 | ![structure] | quant. | 739 [M + H]⁺ | 3.8 min (D) |
| 10.4 | ![structure] | quant. | 749 [M + H]⁺ | 4.0 min (D) |
| 10.5 | ![structure] | quant. | 748 [M + H]⁺ | 6.3 min (D) |

Example 10.6

(R)-1-(4-hydroxy-3-methoxy-5-methyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate

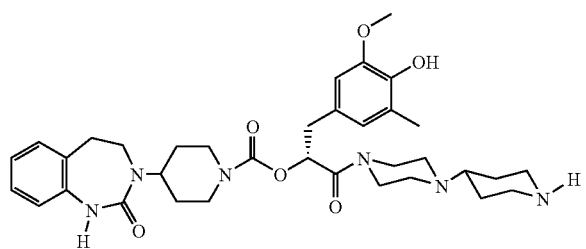

A solution of 220 mg (0.29 mmol) (R)-2-[4-(1-tert-butoxycarbonyl-piperidin-4-yl)-piperazin-1-yl]-1-(4-hydroxy-3-methoxy-5-methyl-benzyl)-2-oxo-ethyl 4-(2-oxo-1,2,4,5-tetrahydro-1,3-benzodiazepin-3-yl)-piperidine-1-carboxylate (Example 10.4) in 3 mL formic acid was stirred for 4 h at RT and then concentrated by evaporation i.vac. at 40° C. The crude product was purified by preparative HPLC-MS.

Yield: 13 mg (6% of theory)
ESI-MS: (M+H)⁺=649
Retention time (HPLC-MS): 3.8 min (method D)

Example 10.7

(R)-2-4,4'-bipiperidinyl-1-yl-1-(4-hydroxy-3-methoxy-5-methyl-benzyl)-2-oxo-ethyl 4-(2-oxo-1,2,4,5-tetrahydro-1,3-benzodiazepin-3-yl)-piperidine-1-carboxylate

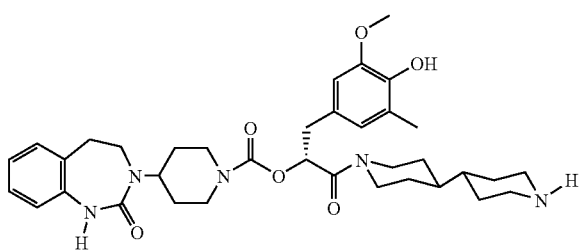

The product was prepared analogously to Example 10.6 starting from 210 mg (0.28 mmol) tert.butyl 1'-{(R)-3-(4-hydroxy-3-methoxy-5-methyl-phenyl)-2-[4-(2-oxo-1,2,4,5-tetrahydro-1,3-benzodiazepin-3-yl)-piperidine-1-carbonyloxy]-propionyl}-4,4'-bipiperidinyl-1-carboxylate (Example 10.5).

Yield: 164 mg (77% of theory)
ESI-MS: (M+H)$^+$=648
Retention time (HPLC-MS): 3.6 min (method D)

Example 10.8

(R)-1-(4-hydroxy-3-methoxy-5-methyl-benzyl)-2-oxo-2-(4-piperazin-1-yl-piperidin-1-yl)-ethyl 4-(2-oxo-1,2,4,5-tetrahydro-1,3-benzodiazepin-3-yl)-piperidine-1-carboxylate

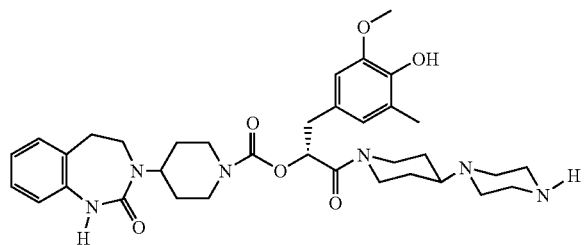

A suspension of 222 mg (0.30 mmol) (R)-2-[4-(4-benzyl-piperazin-1-yl)-piperidin-1-yl]-1-(4-hydroxy-3-methoxy-5-methyl-benzyl)-2-oxo-ethyl 4-(2-oxo-1,2,4,5-tetrahydro-1,3-benzodiazepin-3-yl)-piperidine-1-carboxylate (Example 10.3) and 60 mg 10% Pd/C in 10 mL EtOH and 6 mL MeOH was hydrogenated at 60 psi and RT for 72 h. The catalyst was filtered off and the crude product was purified by HPLC-MS.
Yield: 64 mg (28% of theory)
ESI-MS: (M+H)$^+$=649
Retention time (HPLC-MS): 3.2 min (method D)

Example 11

(R)-1-(3-ethyl-4-hydroxy-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate

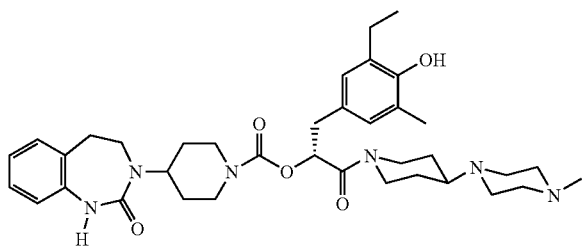

11a) 2-ethyl-6-methyl-phenol 19.4 mL (0.23 mmol) concentrated HCl and a solution of 16.1 g (0.23 mmol) sodium nitrite in water (approx. 70 mL) were added at 0° C. to a solution of 30 g (222 mmol) 2-ethyl-6-methyl-aniline in 135 mL EtOH and stirred for 15 min. This mixture was added at 45° C. to a solution of 10.5 mL of concentrated H$_2$SO$_4$ in 300 mL water and at the end of the addition heated to 70° C. The aqueous phase was cooled to RT and exhaustively extracted with EtOAc. The combined organic phases were extracted with 1 M NaOH solution. The aqueous phase was washed with DCM, acidified to pH 1 with 4 N HCl solution and extracted with DCM. The organic phase was washed with saturated NaCl solution, dried on Na$_2$SO$_4$ and concentrated by evaporation i.vac. The crude product was used in the subsequent reaction step without any further purification.
Yield: 12.0 g (40% of theory)

11b) 4-bromo-2-ethyl-6-methyl-phenol

A solution of 12.7 mL (247 mmol) bromine in 10 mL chloroform was added dropwise at RT to a solution of 33.6 g (247 mmol) 2-ethyl-6-methyl-phenol in 350 mL chloroform and the mixture was stirred for 2 h. The reaction mixture was combined with an aqueous NaHSO$_3$ solution and stirred for 20 min. The phases were separated and the organic phase was washed with saturated NaCl solution, dried on Na$_2$SO$_4$ and concentrated by evaporation i.vac. Column chromatography (silica gel, Cyc/EtOAc 9:1) yielded the product.
Yield: 39.8 g (75% of theory)
ESI-MS: (M+H)$^+$=214/216 (Br)
Retention time (HPLC-MS): 6.3 min (method D)

11c) 2-benzyloxy-5-bromo-1-ethyl-3-methyl-benzene

A suspension of 39.8 g (185 mmol) 4-bromo-2-ethyl-6-methyl-phenol, 63.9 g (0.46 mmol) K$_2$CO$_3$ and 22.0 mL (185 mmol) benzyl bromide in 450 mL acetonitrile was refluxed for 3 h, cooled to RT and concentrated by evaporation i.vac. The residue was combined with EtOAc, the organic phase was washed with water and saturated NaCl solution, dried on Na$_2$SO$_4$ and concentrated by evaporation i.vac.
Yield: 54.5 g (96% of theory)
ESI-MS: (M+H)$^+$=304/306 (Br)
Retention time (HPLC-MS): 9.4 min (method D)

11d) methyl (Z,E)-2-acetylamino-3-(4-benzyloxy-3-ethyl-5-methyl-phenyl)-acrylate Prepared analogously to Example 1b from 50.4 g (165.1 mmol) 2-benzyloxy-5-bromo-1-ethyl-3-methyl-benzene and 28.9 g (198.2 mmol) methyl 2-acetylamino-acrylate.
Yield: 41.0 g (68% of theory)
ESI-MS: (M+H)$^+$=368
Retention time (HPLC-MS): 4.5 min (method B)

11e) 3-(4-benzyloxy-3-ethyl-5-methyl-phenyl)-2-oxo-propionic acid 200 mL of 4 M HCl were added to a solution of 41.0 g (112 mmol) methyl (Z,E)-2-acetylamino-3-(4-benzyloxy-3-ethyl-5-methyl-phenyl)-acrylate in 300 mL 1,4-dioxane and the reaction solution was heated to 130° C. (bath temperature) for 7 h. The organic phase was separated off while hot, concentrated by evaporation i. vac. and the residue obtained was recrystallised from toluene.
Yield: 9.6 g (28% of theory)
ESI-MS: (M+H)$^+$=312
Retention time (HPLC-MS): 4.1 min (method B)

11f) (R)-3-(4-benzyloxy-3-ethyl-5-methyl-phenyl)-2-hydroxy-propionic acid

Under an argon atmosphere a solution of 9.59 g (30.7 mmol) 3-(4-benzyloxy-3-ethyl-5-methyl-phenyl)-2-oxo-propionic acid in 25 mL THF was combined with 4.26 mL (31.0 mmol) triethylamine, stirred for 5 min and cooled to −30° C. (internal temperature). A solution of 19.7 g (61.0 mmol) (1R)—B-chlorodiisopinocampheylborane in 35 mL was added dropwise and after the addition had ended the reaction solution was stirred for 30 min without cooling. 15 mL of 4 N NaOH were added (temperature increase to 20° C.), the mixture was stirred for another 5 min, cooled to 0° C., combined with 50 mL MTBE and stirred for 20 min. The organic phase was separated off and dried on Na$_2$SO$_4$. After the elimination of the desiccant and solvent the residue was reacted further without any purification.
Yield: 10.3 g (100% of theory)
ESI-MS: (M−H)$^-$=313
Retention time (HPLC-MS): 4.2 min (method B)

11g) methyl (R)-3-(4-benzyloxy-3-ethyl-5-methyl-phenyl)-2-hydroxy-propionate Prepared analogously to Example 1e from 10.3 g (30.7 mmol) (R)-3-(4-benzyloxy-3-ethyl-5-methyl-phenyl)-2-hydroxy-propionic acid and 4.71 mL (64.5 mmol) thionyl chloride. The crude product obtained was reacted further without purification.

11h) (R)-2-(4-benzyloxy-3-ethyl-5-methyl-phenyl)-1-methoxycarbonyl-ethyl 4-(2-oxo-1,2,4,5-tetrahydro-1,3-benzodiazepin-3-yl)-piperidine-1-carboxylate A solution of 7.12 g (34.3 mmol) 4-nitrophenyl-chloroformate in 30 mL THF was added within 10 min to a solution of 75 mL pyridine heated to 60° C. (bath temperature), the mixture was stirred for 10 min and then a solution of 10.0 g of the crude product from Example 11g in 50 mL pyridine was added dropwise. The mixture was stirred for another 1 h, combined with 6.72 g (27.4 mmol) 3-piperidin-4-yl-1,3,4,5-tetrahydro-1,3-benzodiazepin-2-one and the bath temperature was raised to 100° C. (2 h). The precipitate formed was filtered, the filtrate was concentrated by evaporation i.vac., the residue was combined with 150 mL EtOAc, the organic phase was washed twice with 50 mL of 1 M KHSO$_4$ solution and ten times with 50 mL of 15% K$_2$CO$_3$ solution and dried on Na$_2$SO$_4$. After the elimination of the desiccant and solvent the residue was purified by chromatography (silica gel, EtOAc/Cyc 2:1).

Yield: 2.28 g (14% of theory)
ESI-MS: (M+H)$^+$=600
Retention time (HPLC-MS): 5.4 min (method B)

11i) (R)-2-(4-benzyloxy-3-ethyl-5-methyl-phenyl)-1-carboxy-ethyl 4-(2-oxo-1,2,4,5-tetrahydro-1,3-benzodiazepin-3-yl)-piperidine-1-carboxylate A solution of 50 mg (2.09 mmol) LiOH in 5 mL water was added to a solution of 800 mg (1.33 mmol) (R)-2-(4-benzyloxy-3-ethyl-5-methyl-phenyl)-1-methoxy-carbonyl-ethyl 4-(2-oxo-1,2,4,5-tetrahydro-1,3-benzodiazepin-3-yl)-piperidine-1-carboxylate in 15 mL THF and the reaction mixture was stirred for 1 h at RT. The mixture was evaporated down i.vac., the residue was taken up in 50 mL water, and 2 M HCl was added until an acidic reaction was obtained. The precipitate formed was filtered off, washed with water and dried. Further purification was carried out by decocting with 150 mL water, filtration and drying again.

Yield: quantitative
ESI-MS: (M+H)$^+$=586
Retention time (HPLC-MS): 4.8 min (method B)

11k) (R)-1-carboxy-2-(3-ethyl-4-hydroxy-5-methyl-phenyl)-ethyl 4-(2-oxo-1,2,4,5-tetrahydro-1,3-benzodiazepin-3-yl)-piperidine-1-carboxylate 810 mg (1.38 mmol) (R)-2-(4-benzyloxy-3-ethyl-5-methyl-phenyl)-1-carboxy-ethyl 4-(2-oxo-1,2,4,5-tetrahydro-1,3-benzodiazepin-3-yl)-piperidine-1-carboxylate in 25 mL MeOH were combined with 80 mg of 10% Pd/C and hydrogenated at RT and 3 bar hydrogen until the reaction came to an end. The catalyst was removed by suction filtering and the solvent was concentrated by evaporation i.vac. The residue was triturated with DIPE, suction filtered and dried.

Yield: 639 mg (93% of theory)
ESI-MS: (M+H)$^+$=496
Retention time (HPLC-MS): 3.7 min (method B)

11l) (R)-1-(3-ethyl-4-hydroxy-5-methyl-benzyl)-2-[4-(4-methyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate 33 mg (0.18 mmol) 1-methyl-4-piperidin-4-yl-piperazine were added at RT to a solution of 80 mg (0.16 mmol) (R)-1-carboxy-2-(3-ethyl-4-hydroxy-5-methyl-phenyl)-ethyl 4-(2-oxo-1,2,4,5-tetrahydro-1,3-benzodiazepin-3-yl)-piperidine-1-carboxylate, 57 mg (0.18 mmol) TBTU and 28 μL (0.20 mmol) triethylamine in 1 mL DMF and the reaction mixture was stirred for 2 h. The reaction solution was purified by HPLC without any further working up, the fractions containing the product were combined and lyophilised.

Yield: 68 mg (64% of theory)
ESI-MS: (M+H)$^+$=661
Retention time (HPLC-MS): 3.0 min (method B)

The following compounds were prepared analogously from 80 mg (Example 11.1) or 150 mg (Example 11.2) of (R)-1-carboxy-2-(3-ethyl-4-hydroxy-5-methyl-phenyl)-ethyl 4-(2-oxo-1,2,4,5-tetrahydro-1,3-benzodiazepin-3-yl)-piperidine-1-carboxylate and the corresponding amount of amine:

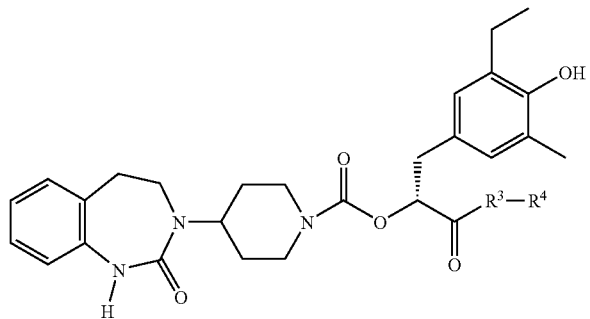

| Example | —R$^3$—R$^4$ | Yield (%) | Mass spectrum | Retention time HPLC (method) |
|---|---|---|---|---|
| 11.1 | 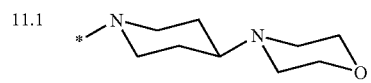 | 73 | 648 [M + H]$^+$ | 3.2 min (B) |

-continued

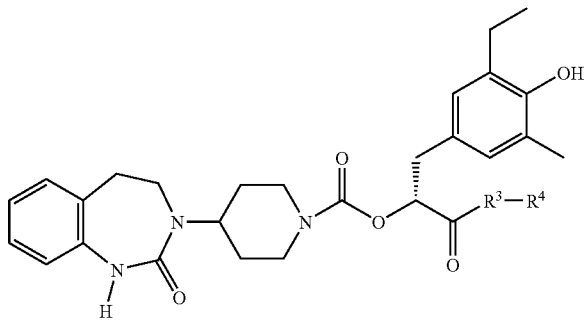

| Example | —R³—R⁴ | Yield (%) | Mass spectrum | Retention time HPLC (method) |
|---|---|---|---|---|
| 11.2 | 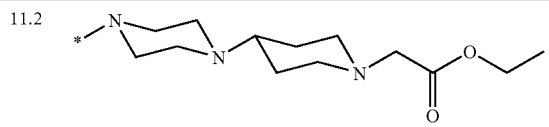 | 48 | 733 [M + H]⁺ | 3.0 min (B) |

Example 11.3

(R)-2-[4-(1-carboxymethyl-piperidin-4-yl)-piperazin-1-yl]-1-(3-ethyl-4-hydroxy-5-methyl-benzyl)-2-oxo-ethyl 4-(2-oxo-1,2,4,5-tetrahydro-1,3-benzodiazepin-3-yl)-piperidine-1-carboxylate

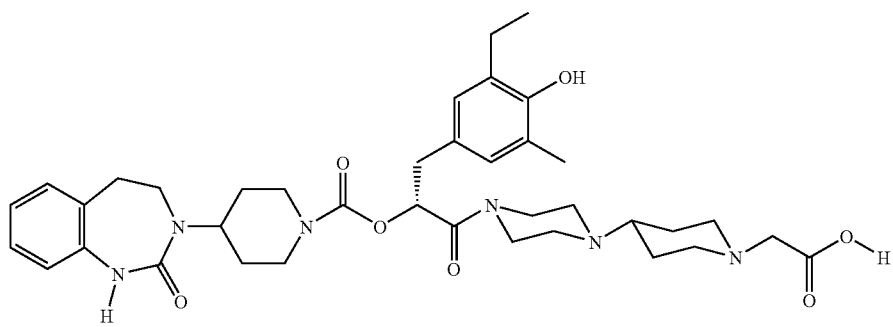

A solution of 3.7 mg (0.15 mmol) LiOH in 3 mL water was added to a solution of 73 mg (0.10 mmol) (R)-2-[4-(1-ethoxy-carbonylmethyl-piperidin-4-yl)-piperazin-1-yl]-1-(3-ethyl-4-hydroxy-5-methyl-benzyl)-2-oxo-ethyl 4-(2-oxo-1,2,4,5-tetrahydro-1,3-benzodiazepin-3-yl)-piperidine-1-carboxylate (Example 11.2) in 5 mL THF and the reaction mixture was stirred for 2 h at RT. The THF was eliminated i.vac., 1 M HCl was added until an acidic reaction was obtained and the mixture was evaporated down again i.vac. The residue was taken up in DMF and purified by HPLC; the fractions containing the product were combined and lyophilised.

Yield: 39 mg (56% of theory)

ESI-MS: (M+H)⁺=705

Retention time (HPLC-MS): 2.9 min (method B)

The Examples that follow describe the preparation of pharmaceutical formulations which contain as active substance any desired compound of general formula I:

Example I

Capsules for Powder Inhalation Containing 1 mg of Active Ingredient

Composition:

1 capsule for powder inhalation contains:

| | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient

Composition:

1 puff contains:

| | |
|---|---|
| active ingredient | 1.0 mg |
| benzalkonium chloride | 0.002 mg |
| disodium edetate | 0.0075 mg |
| purified water ad | 15.0 μl |

Method of Preparation:

The active ingredient and benzalkonium chloride are dissolved in water and transferred into Respimat® cartridges.

Example III

Inhalable Solution for Nebulisers Containing 1 mg of Active Ingredient

Composition:

1 vial contains:

| | |
|---|---|
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellant Gas-Operated Metered Dose Aerosol Containing 1 mg of Active Ingredient Composition:

1 puff contains:

| | |
|---|---|
| active ingredient | 1.0 mg |
| lecithin | 0.1% |
| propellant gas ad | 50.0 μl |

Method of Preparation:

The micronised active ingredient is homogeneously suspended in the mixture of lecithin and propellant gas. The suspension is transferred into a pressurised container with a metering valve.

Example V

Nasal Spray Containing 1 mg of Active Ingredient

Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

Example VI

Injectable Solution Containing 5 mg of Active Substance Per 5 ml

Composition:

| | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with WfI; transferred into ampoules under nitrogen gas.

Example VII

Injectable Solution Containing 100 mg of Active Substance per 20 ml

Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

Example VIII

Lyophilisate Containing 10 mg of Active Substance

Composition:

| | |
|---|---|
| Active substance | 10 mg |
| Mannitol | 300 mg |
| human serum albumin | 20 mg |
| water for injections ad | 2 ml |

Preparation:
Mannitol is dissolved in water for injections (WfI); human serum albumin is added; active ingredient is dissolved with heating; made up to specified volume with WfI; transferred into vials; freeze-dried.

Solvent for Lyophilisate:

| | |
|---|---|
| Polysorbate 80 = Tween 80 | 20 mg |
| mannitol | 200 mg |
| water for injections ad | 10 ml |

Preparation:
Polysorbate 80 and mannitol are dissolved in water for injections (WfI); transferred into ampoules.

Example IX

Tablets Containing 20 mg of Active Substance

Composition:

| | |
|---|---|
| active substance | 20 mg |
| lactose | 120 mg |
| corn starch | 40 mg |
| magnesium stearate | 2 mg |
| Povidone K 25 | 18 mg |

Preparation:
Active substance, lactose and corn starch are homogeneously mixed; granulated with an aqueous solution of Povidone; mixed with magnesium stearate; compressed in a tablet press; weight of tablet 200 mg.

Example X

Capsules Containing 20 mg Active Substance

Composition:

| | |
|---|---|
| active substance | 20 mg |
| corn starch | 80 mg |
| highly dispersed silica | 5 mg |
| magnesium stearate | 2.5 mg |

Preparation:
Active substance, corn starch and silica are homogeneously mixed; mixed with magnesium stearate; the mixture is packed into size for 3 hard gelatine capsules in a capsule filling machine.

Example XI

Suppositories Containing 50 mg of Active Substance

Composition:

| | |
|---|---|
| active substance | 50 mg |
| hard fat (Adeps solidus) q.s. ad | 1700 mg |

Preparation:
Hard fat is melted at about 38° C.; ground active substance is homogeneously dispersed in the molten hard fat; after cooling to about 35° C. it is poured into chilled moulds.

Example XII

Injectable Solution Containing 10 mg of Active Substance Per 1 ml

Composition:

| | |
|---|---|
| active substance | 10 mg |
| mannitol | 50 mg |
| human serum albumin | 10 mg |
| water for injections ad | 1 ml |

Preparation:
Mannitol is dissolved in water for injections (WfI); human serum albumin is added; active ingredient is dissolved with heating; made up to specified volume with WfI; transferred into ampoules under nitrogen gas.

What is claimed is:
1. A compound of the formula I wherein
$R^1$ denotes a group wherein
R$^{1.1}$ denotes H or H$_3$C—O—,
R$^2$ denotes a group of general formula II

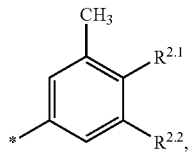

wherein
R$^{2.1}$ denotes HO, H$_3$CO, H—C(O)—O or H$_3$C—C(O)—O— and
R$^{2.2}$ denotes C$_{1-2}$-alkyl or H$_3$CO—,
R$^3$ denotes R$^4$—C$_{2-8}$-alkylene-NH— and
R$^4$ denotes H, H$_2$N, C$_{1-3}$-alkyl-NH, (C$_{1-3}$-alkyl)$_2$-N or C$_{1-6}$-alkyl-O—C(O)—NH— or
R$^3$ denotes a group of general formulae III

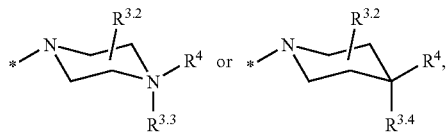

wherein
R$^{3.2}$ denotes H or C$_{1-3}$-alkyl,
R$^{3.3}$ denotes a free electron pair or an oxygen atom,
R$^{3.4}$ denotes H or C$_{1-3}$-alkyl and
R$^4$ denotes H, C$_{1-6}$-alkyl, H$_2$N—C$_{2-6}$-alkylene, C$_{1-3}$-alkyl-NH—C$_{2-6}$-alkylene, (C$_{1-3}$-alkyl)$_2$-N—C$_{1-6}$-alkylene, C$_{3-6}$-cycloalkyl-C$_{1-3}$-alkylene, NH$_2$, C$_{1-3}$-alkyl-NH or (C$_{1-3}$-alkyl)$_2$-N, or
R$^4$ denotes a group selected from

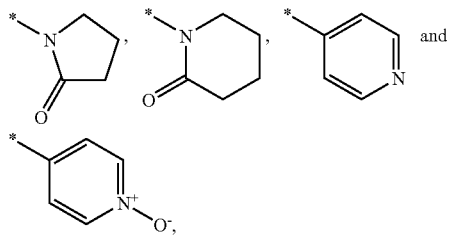

or
R$^4$ denotes a group of general formulae IV

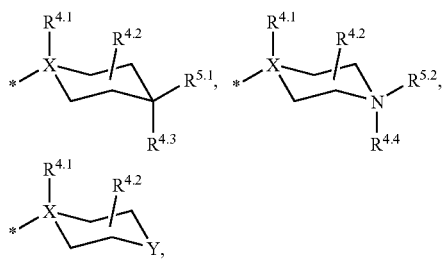

wherein
X denotes C and
R$^{4.1}$ denotes H, OH or C$_{1-3}$-alkyl or
X denotes N and
R$^{4.1}$ denotes a free electron pair or an oxygen atom, Y denotes O, S, S(O), S(O)$_2$, if X=N, or
Y denotes S, S(O), S(O)$_2$, if X=C,
R$^{4.2}$ denotes H or C$_{1-3}$-alkyl,
R$^{4.3}$ denotes H or C$_{1-3}$-alkyl,
R$^{4.4}$ denotes a free electron pair or, if R$^{5.2}$ is not H or C$_{1-3}$-alkyl-C(O)—, an oxygen atom,
R$^{5.1}$ denotes H, CN, OH, C$_{1-3}$-alkyl, C$_{1-3}$-alkyl-C(O)—O, C$_{1-3}$-alkyl-O, R$^{5.1,1}$—O—C(O), R$^{5.1,1}$—O—C(O)—C$_{2-4}$-alkylene or R$^{5.1,1}$—O—C(O)—C$_{1-3}$-alkylene-O,
R$^{5.1.1}$ denotes H, C$_{1-6}$-alkyl, H$_2$N—C(O)—C$_{1-3}$-alkylene, C$_{1-3}$-alkyl-NH—C(O)—C$_{1-3}$-alkylene, (C$_{1-3}$-alkyl)$_2$-N—C(O)—C$_{1-3}$-alkylene or C$_{1-3}$-alkyl-O—C(O)—O—C$_{1-3}$-alkylene,
R$^{5.2}$ denotes H, C$_{1-3}$-alkyl, C$_{3-6}$-cycloalkyl, C$_{3-6}$-cycloalkyl-C$_{1-3}$-alkylene, C$_{1-3}$-alkyl-C(O), R$^{5.2.1}$—O—C(O)—C$_{1-3}$-alkylene or R$^{5.2.2}$—C$_{2-4}$-alkylene-O—C(O)—C$_{1-3}$-alkylene,
R$^{5.2.1}$ denotes H, C$_{1-6}$-alkyl, C$_{1-6}$-alkyl-C(O)—O—C$_{1-3}$-alkylene, C$_{1-3}$-alkyl-O—C(O)—O—C$_{1-3}$-alkylene, C$_{3-7}$-cycloalkyl-O—C(O)—O—C$_{1-3}$-alkylene, H$_2$N—C(O)—C$_{1-3}$-alkylene, C$_{1-3}$-alkyl-NH—C(O)—C$_{1-3}$-alkylene, (C$_{1-3}$-alkyl)$_2$-N—C(O)—C$_{1-3}$-alkylene or R$^{5.2.1,1}$-C(O)—C$_{1-3}$-alkylene and
R$^{5.2.1.1}$ denotes a group selected from

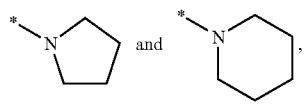

or
R$^{5.2.1}$ denotes a group selected from

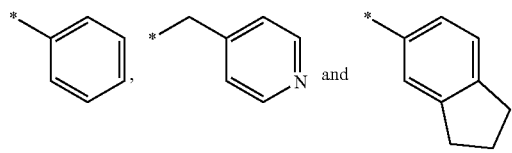

R$^{5.2.2}$ denotes H$_2$N, C$_{1-3}$-alkyl-NH, (C$_{1-3}$-alkyl)$_2$-N, C$_{1-3}$-alkyl-O or C$_{1-3}$-alkyl-O—C$_{2-4}$-alkylene-O, or
R$^{5.2.2}$ denotes a group selected from

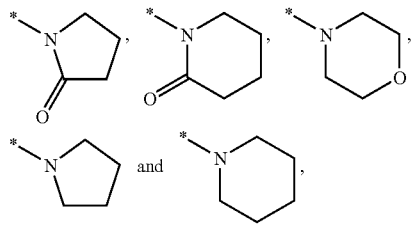

with the proviso that R$^3$ and R$^4$ are not bound to one another simultaneously via an N atom, or a tautomer or salt thereof.

2. A compound of the formula I according to claim 1, wherein $R^1$ denotes a group

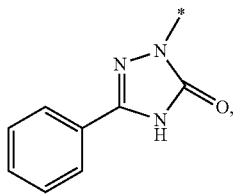

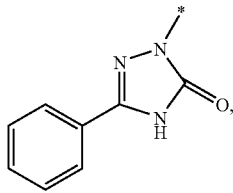

wherein
$R^{1.1}$ denotes H or $H_3C$—O—,
$R^2$ denotes a group of general formula II

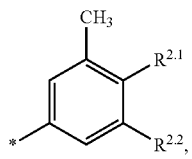

wherein
$R^{2.1}$ denotes HO, $H_3CO$, H—C(O)—O or $H_3C$—C(O)—O— and
$R^{2.2}$ denotes $C_{1-2}$-alkyl or $H_3CO$—,
$R^3$ denotes $R^4$—$C_{2-8}$-alkylene-NH— and
$R^4$ denotes $H_2N$, $C_{1-3}$-alkyl-NH, $(C_{1-3}$-alkyl$)_2$-N or $C_{1-6}$-alkyl-O—C(O)—NH, or
$R^3$ denotes a group of general formulae III

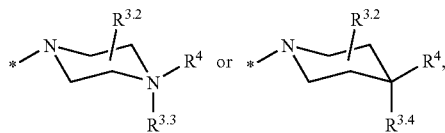

wherein
$R^{3.2}$ denotes H,
$R^{3.3}$ denotes a free electron pair or an oxygen atom,
$R^{3.4}$ denotes H or $C_{1-3}$-alkyl,
$R^4$ denotes H, $C_{1-6}$-alkyl, $H_2N$—$C_{2-6}$-alkylene, $C_{1-3}$-alkyl-NH—$C_{2-6}$-alkylene, $(C_{1-3}$-alkyl$)_2$-N—$C_{1-6}$-alkylene, $C_{3-6}$-cycloalkyl-$C_{1-3}$-alkylene, $H_2N$, $C_{1-3}$-alkyl-NH or $(C_{1-3}$-alkyl$)_2$-N, or
$R^4$ denotes a group selected from

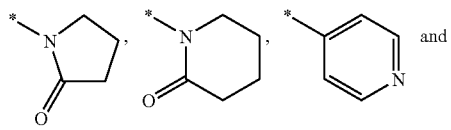

-continued

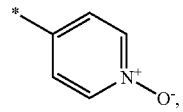

or
$R^4$ denotes a group of general formulae IV

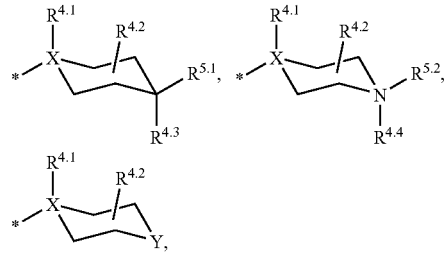

wherein
X denotes C and
$R^{4.1}$ denotes H, OH, $C_{1-3}$-alkyl or
X denotes N and
$R^{4.1}$ denotes a free electron pair or an oxygen atom,
Y denotes O, S, S(O), S(O)$_2$, if X=N, or
Y denotes S, S(O), S(O)$_2$, if X=C,
$R^{4.2}$ denotes H,
$R^{4.3}$ denotes H or $C_{1-3}$-alkyl,
$R^{4.4}$ denotes a free electron pair or, if $R^{5.2}$ is not H or $C_{1-3}$-alkyl-C(O)—, an oxygen atom,
$R^{5.1}$ denotes H, CN, OH, $C_{1-3}$-alkyl, $C_{1-3}$-alkyl-C(O)—O, $C_{1-3}$-alkyl-O, $R^{5.1,1}$—O—C(O), $R^{5.1,1}$—O—C(O)—$C_{2-4}$-alkylene or $R^{5.1,1}$—O—C(O)—$C_{1-3}$-alkylene-O,
$R^{5.1.1}$ denotes H, $C_{1-6}$-alkyl, $H_2N$—C(O)—$C_{1-3}$-alkylene, $C_{1-3}$-alkyl-NH—C(O)—$C_{1-3}$-alkylene, $(C_{1-3}$-alkyl$)_2$-N—C(O)—$C_{1-3}$-alkylene or $C_{1-3}$-alkyl-O—C(O)—O—$C_{1-3}$-alkylene,
$R^{5.2}$ denotes H, $C_{1-3}$-alkyl, $C_{3-6}$-cycloalkyl, $C_{3-6}$-cycloalkyl-$C_{1-3}$-alkylene, $C_{1-3}$-alkyl-C(O), $R^{5.2.1}$—O—C(O)—$C_{1-3}$-alkylene or $R^{5.2.2}$—$C_{2-4}$-alkylene-O—C(O)—$C_{1-3}$-alkylene,
$R^{5.2.1}$ denotes H, $C_{1-6}$-alkyl, $C_{1-6}$-alkyl-C(O)—O—$C_{1-3}$-alkylene, $C_{1-3}$-alkyl-O—C(O)—O—$C_{1-3}$-alkylene, $C_{3-7}$-cycloalkyl-O—C(O)—O—$C_{1-3}$-alkylene, $H_2N$—C(O)—$C_{1-3}$-alkylene, $C_{1-3}$-alkyl-NH—C(O)—$C_{1-3}$-alkylene, $(C_{1-3}$-alkyl$)_2$-N—C(O)—$C_{1-3}$-alkylene or $R^{5.2.1,1}$—C(O)—$C_{1-3}$-alkylene and
$R^{5.2.1.1}$ denotes a group selected from

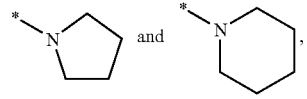

or
$R^{5.2.1}$ denotes a group selected from

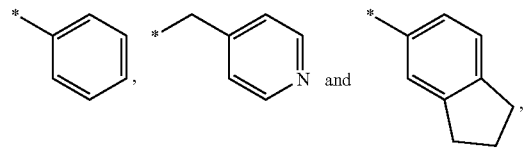

$R^{5.2.2}$ denotes $H_2N$, $C_{1-3}$-alkyl-NH, $(C_{1-3}$-alkyl$)_2$-N, $C_{1-3}$-alkyl-O or $C_{1-3}$-alkyl-O—$C_{2-4}$-alkylene-O, or $R^{5.2.2}$ denotes a group selected from

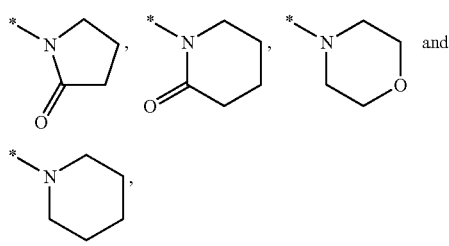

with the proviso that $R^3$ and $R^4$ are not bound to one another simultaneously via an N atom, or a tautomer or salt thereof.

3. A compound of the formula I according to claim 1, wherein $R^1$ denotes a group

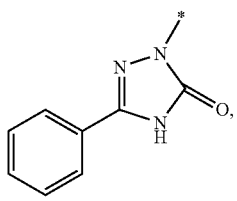

$R^2$ denotes a group selected from

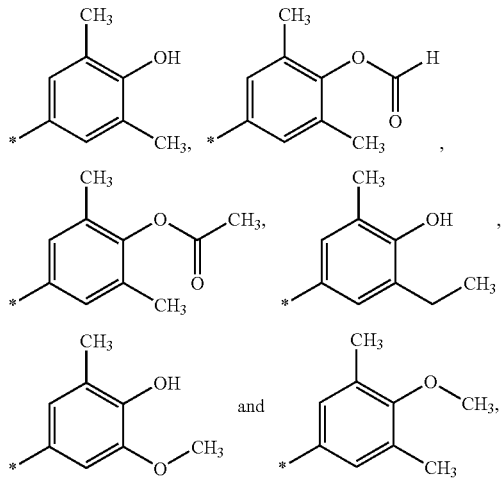

$R^3$ denotes $R^4$—$C_{2-8}$-alkylene-NH— and
$R^4$ denotes H, $H_2N$, $(C_{1-3}$-alkyl$)_2$-N or $C_{1-4}$-alkyl-O—C(O)—NH—, or
$R^3$ denotes a group selected from

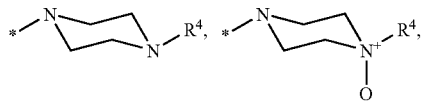

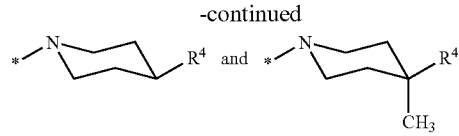

and
$R^4$ denotes H, $C_{1-6}$-alkyl, $(C_{1-3}$-alkyl$)_2$-N—$C_{1-6}$-alkylene, $C_{3-6}$-cycloalkyl-$C_{1-3}$-alkylene or $(C_{1-3}$-alkyl$)_2$-N, or
$R^4$ denotes a group selected from

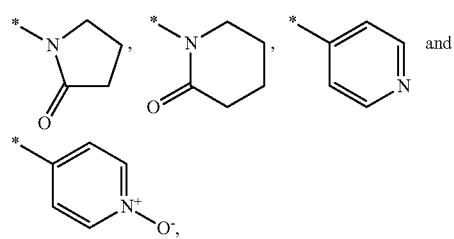

or
$R^4$ denotes a group selected from

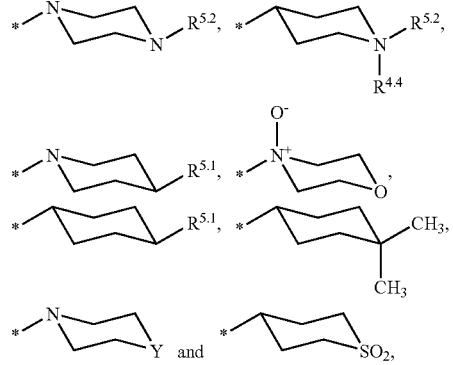

wherein
Y denotes O, S, S(O), S(O)$_2$,
$R^{4.4}$ denotes a free electron pair or, if $R^{5.2}$ is not H or $C_{1-3}$-alkyl-C(O)—, an oxygen atom,
$R^{5.1}$ denotes H, CN, OH, $C_{1-3}$-alkyl, $C_{1-3}$-alkyl-C(O)—O, $C_{1-3}$-alkyl-O, $R^{5.1,1}$—O—C(O), $R^{5.1,1}$—O—C(O)—$C_{2-4}$-alkylene or $R^{5.1,1}$—O—C(O)—$C_{1-3}$-alkylene-O,
$R^{5.1.1}$ denotes H, $H_2N$—C(O)—$C_{1-3}$-alkylene, $C_{1-3}$-alkyl-NH—C(O)—$C_{1-3}$-alkylene, $(C_{1-3}$-alkyl$)_2$-N—C(O)—$C_{1-3}$-alkylene or $C_{1-3}$-alkyl-O—C(O)—O—$C_{1-3}$-alkylene,
$R^{5.2}$ denotes H, cyclopropyl, cyclopropyl-methylene, $C_{1-3}$-alkyl-C(O), $R^{5.2.1}$—(O)—$C_{1-3}$-alkylene or $R^{5.2.2}$—$C_{2-4}$-alkylene-O—C(O)—$C_{1-3}$-alkylene,
$R^{5.2.1}$ denotes H, $C_{1-6}$-alkyl-C(O)—O—$C_{1-3}$-alkylene, $C_{1-3}$-alkyl-O—C(O)—O—$C_{1-3}$-alkylene, $(C_{1-3}$-alkyl$)_2$-N—C(O)—$C_{1-3}$-alkylene or $R^{5.2.1,1}$—C(O)—$C_{1-3}$-alkylene and $R^{5.2.1.1}$ denotes a group selected from

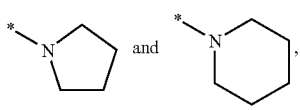
and or
$R^{5.2.1}$ denotes a group selected from

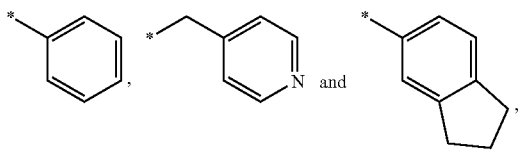

$R^{5.2.2}$ denotes $(C_{1-3}\text{-alkyl})_2\text{-N}$, $C_{1-3}\text{-alkyl-O}$ or $C_{1-3}\text{-alkyl-O}-C_{2-4}\text{-alkylene-O}$, or
$R^{5.2.2}$ denotes a group selected from

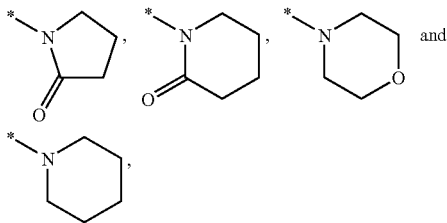

with the proviso that $R^3$ and $R^4$ are not bound to one another simultaneously via an N atom, or a tautomer or salt thereof.

4. A compound of the formula I according to claim 1, wherein
$R^1$ denotes a group

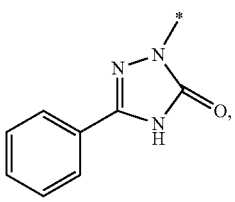

$R^2$ denotes a group selected from

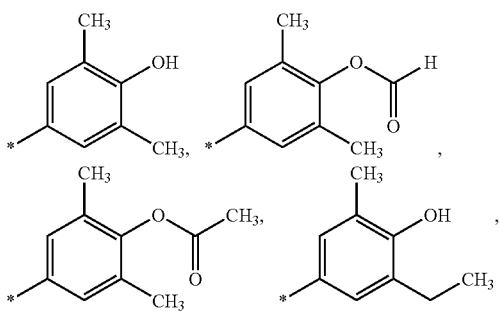

-continued

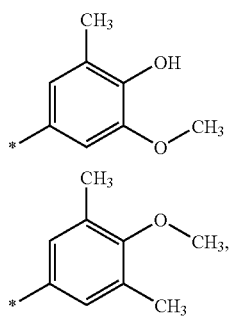

$R^3$—$R^4$ together denote a group selected from

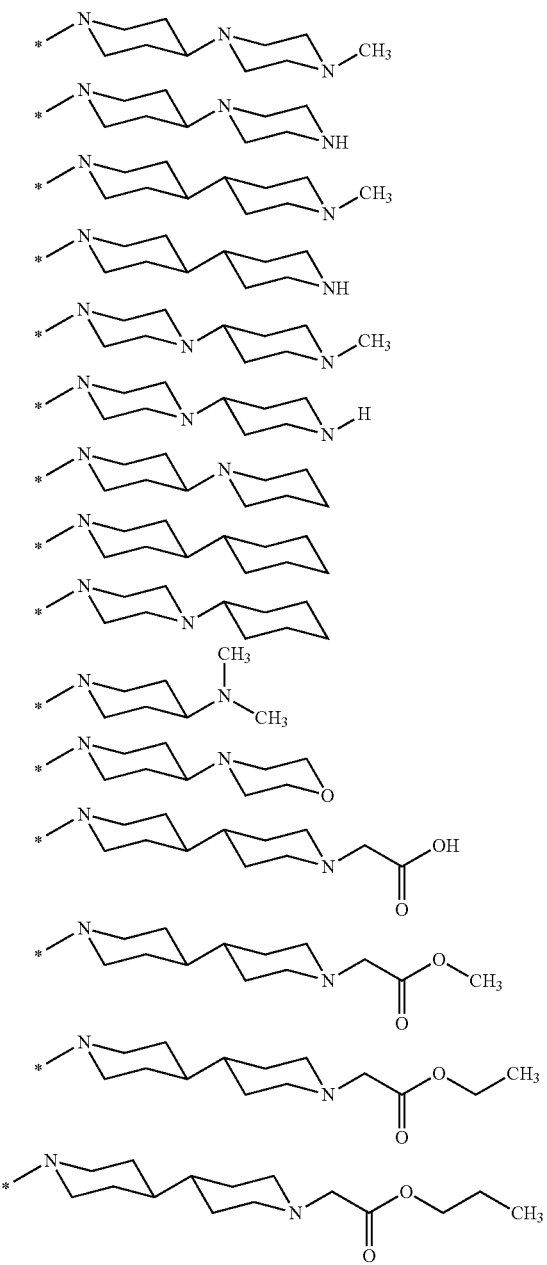

217
-continued
218
-continued
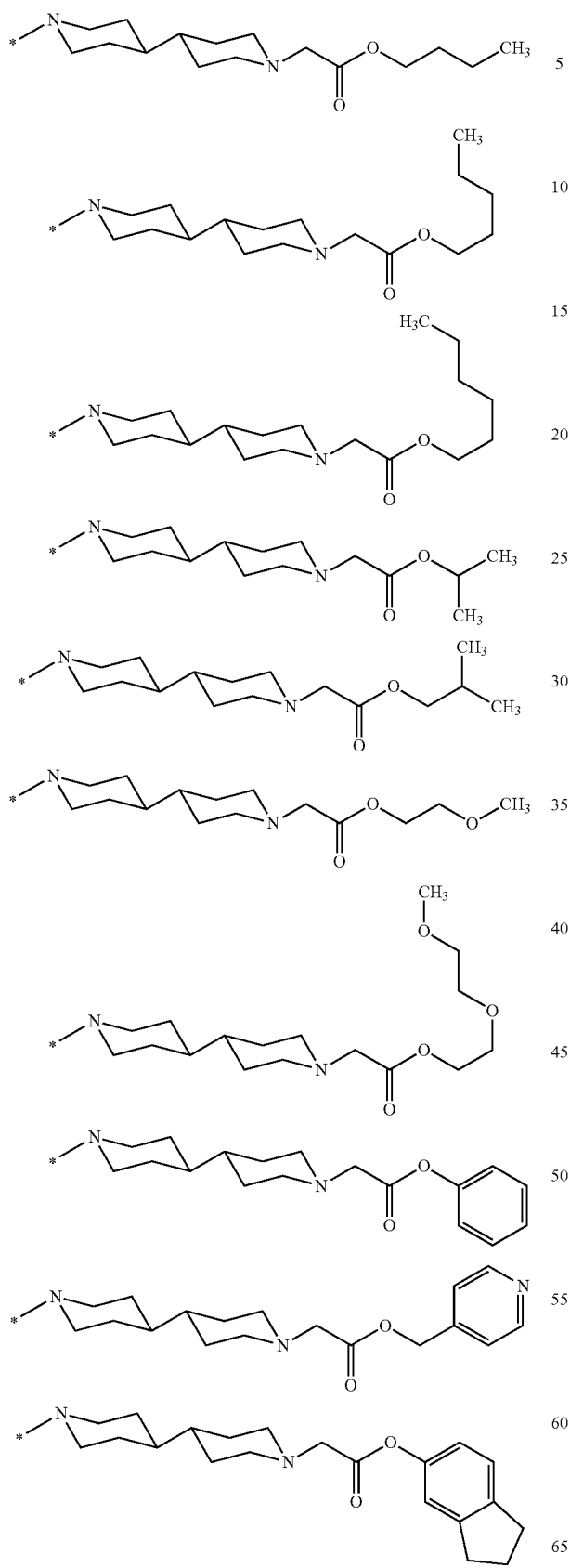
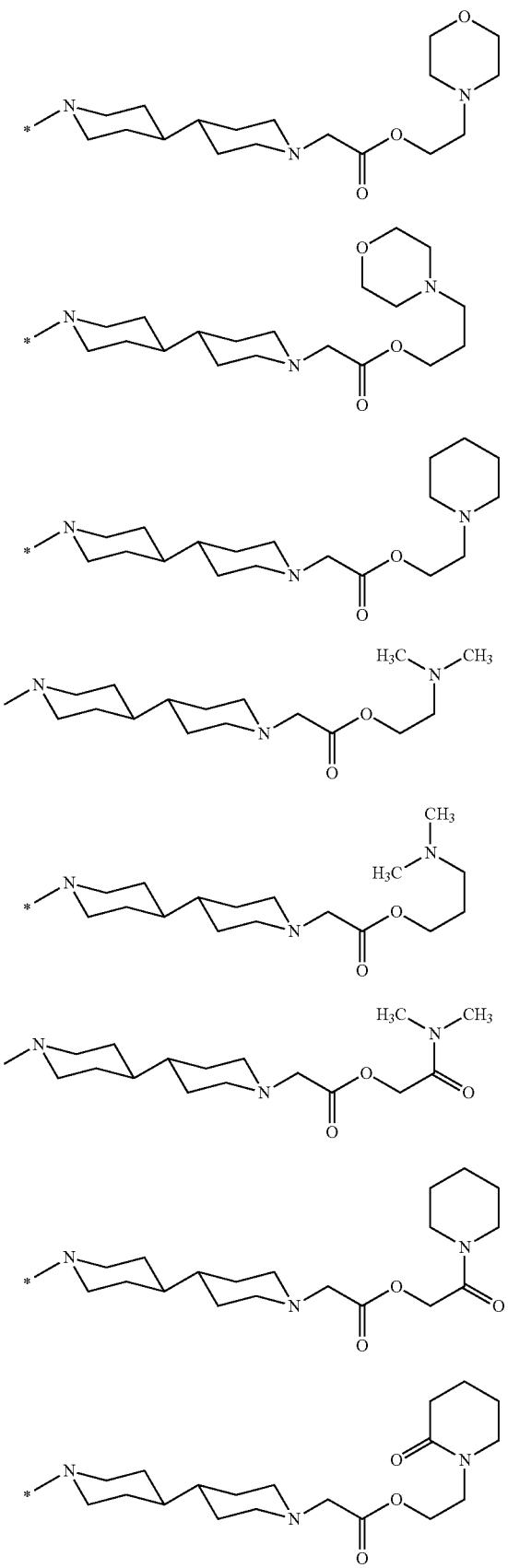

-continued
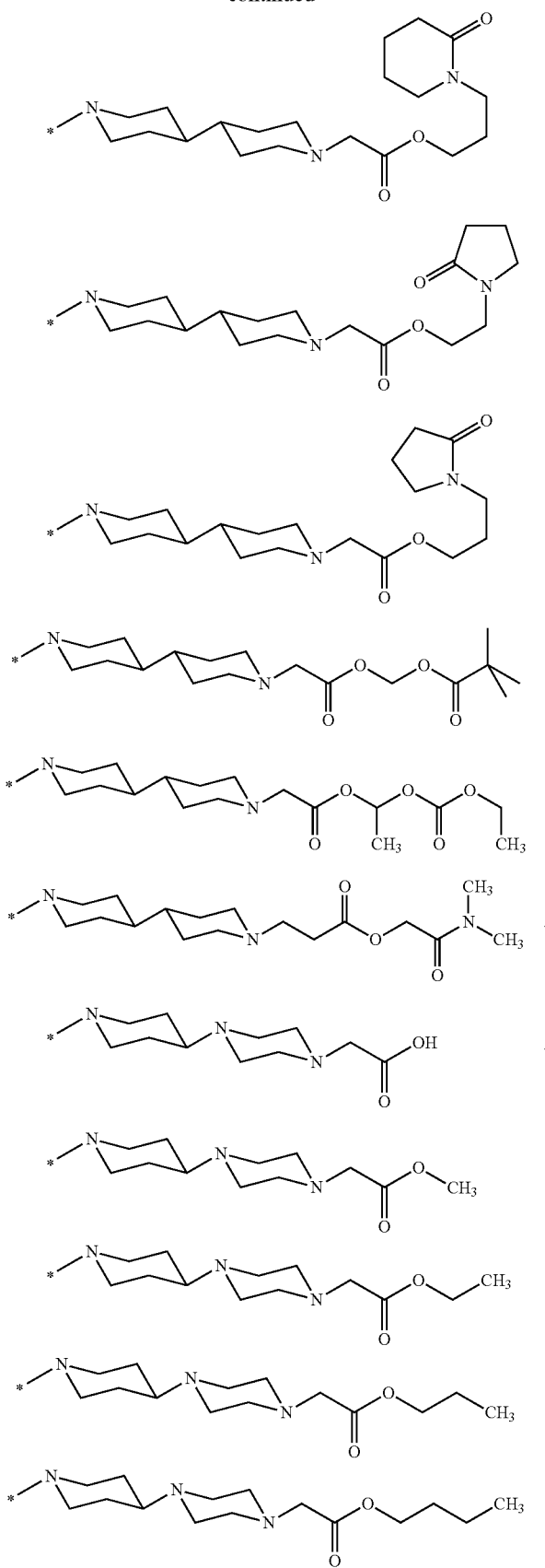
-continued
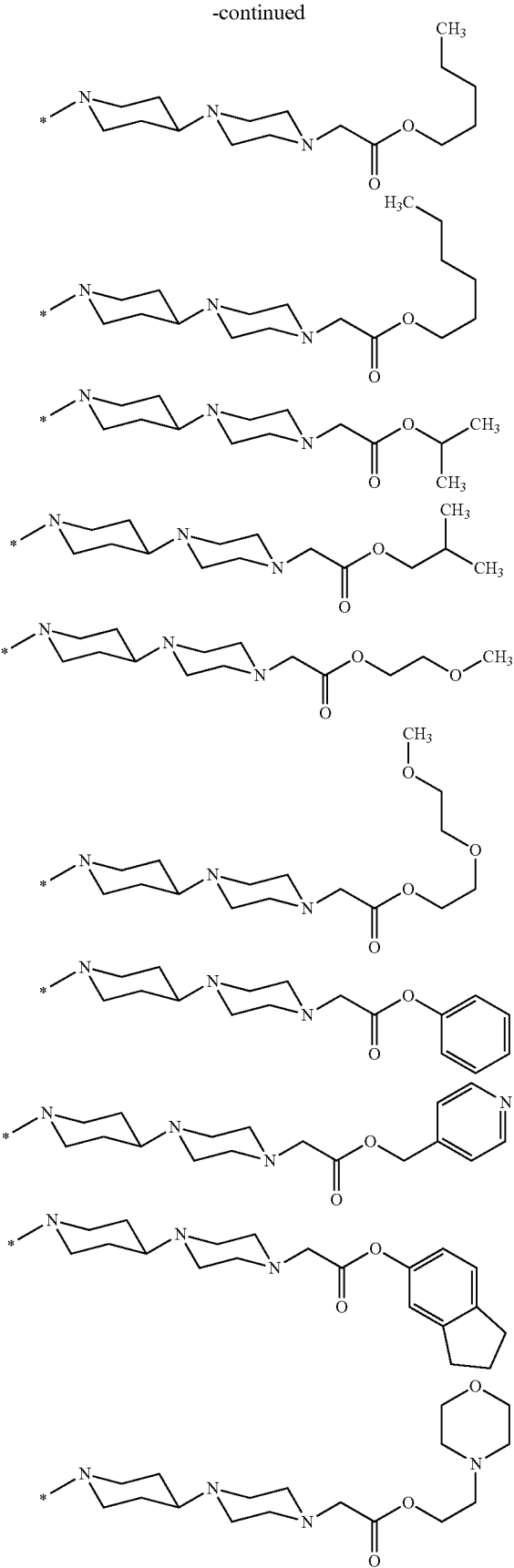

221
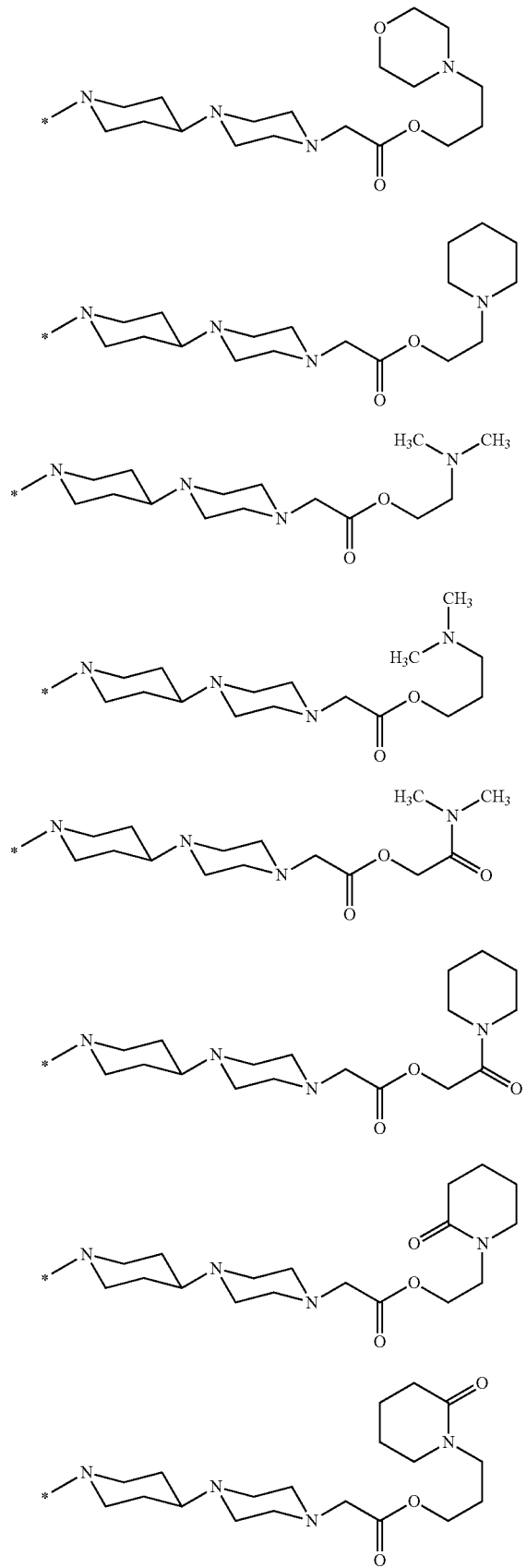
222
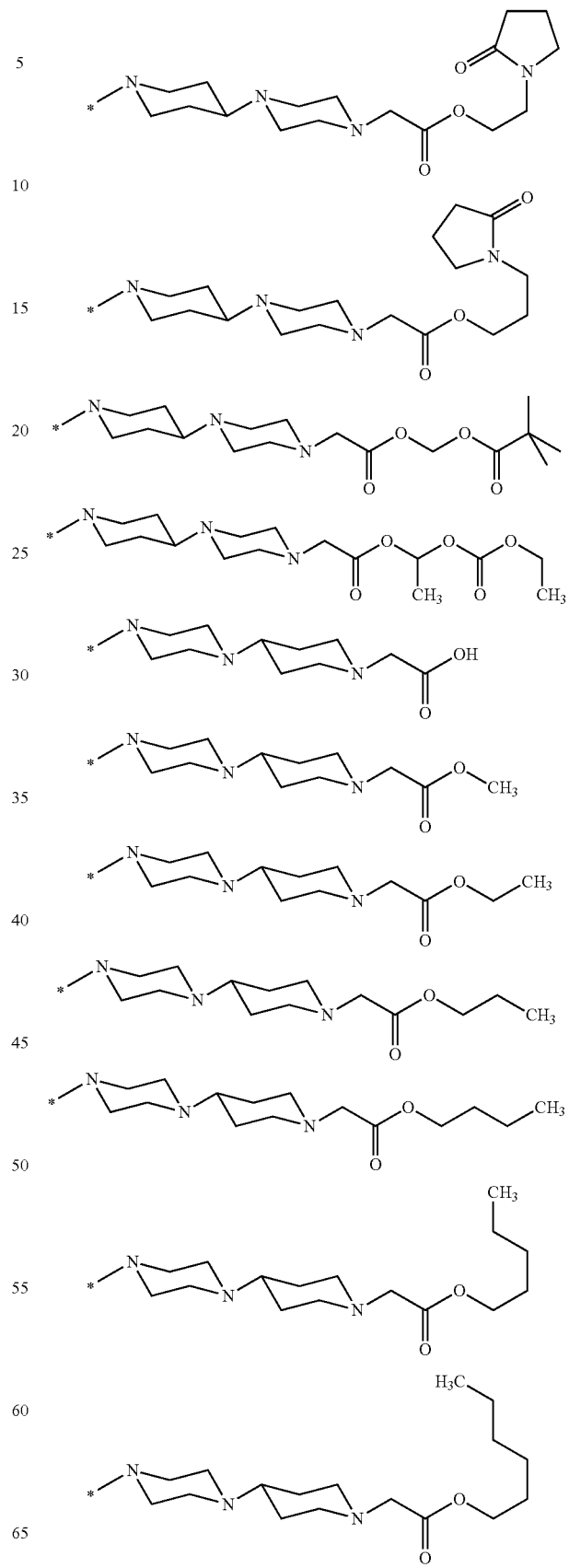

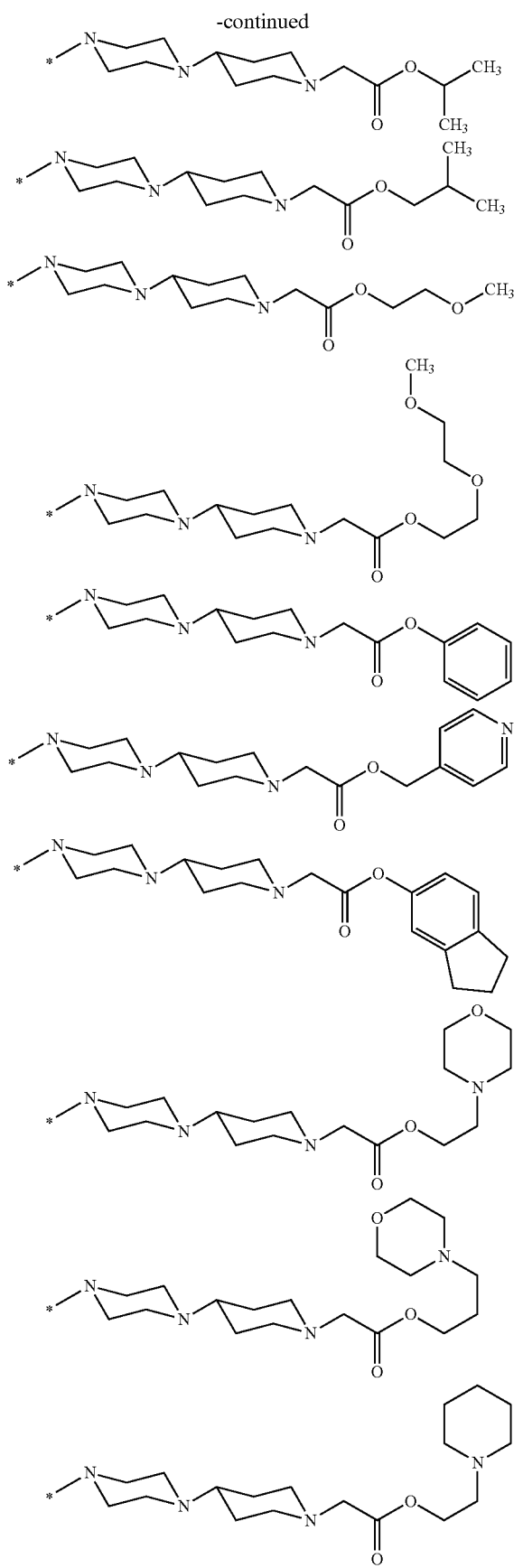
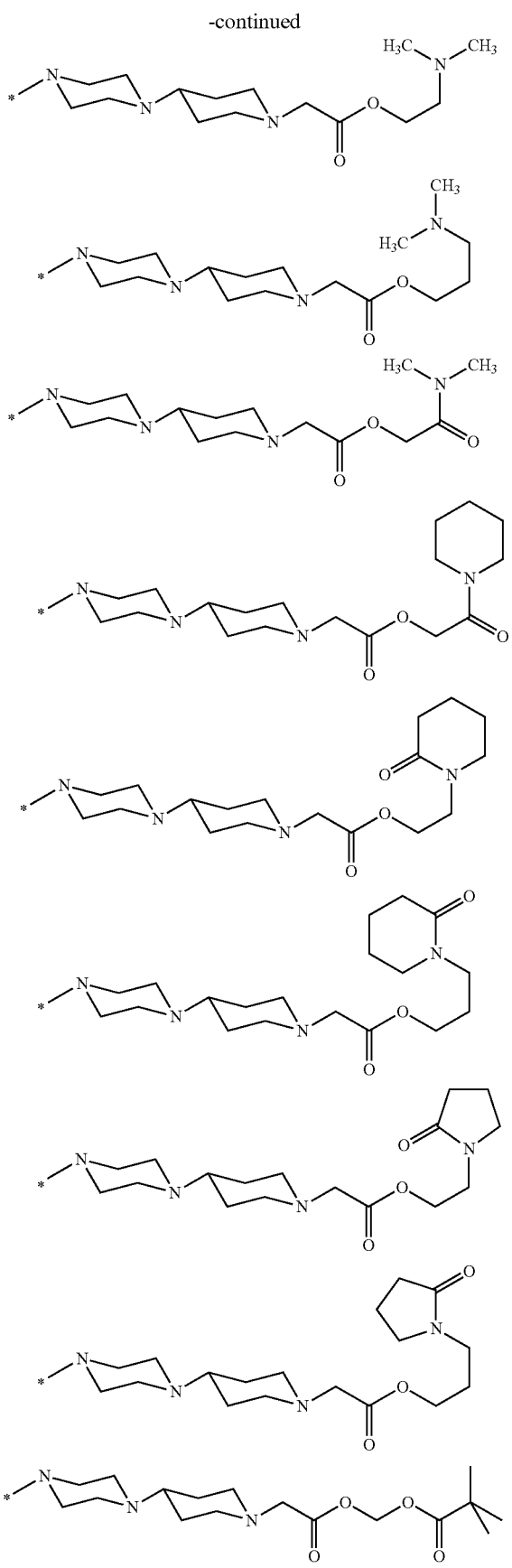

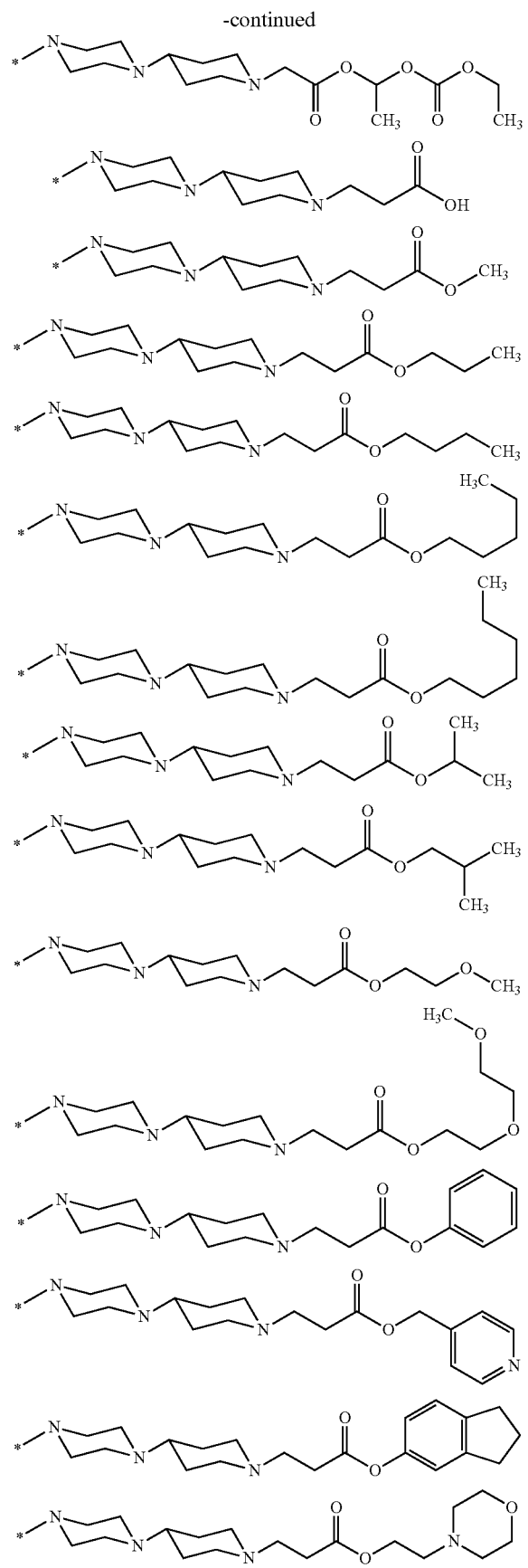
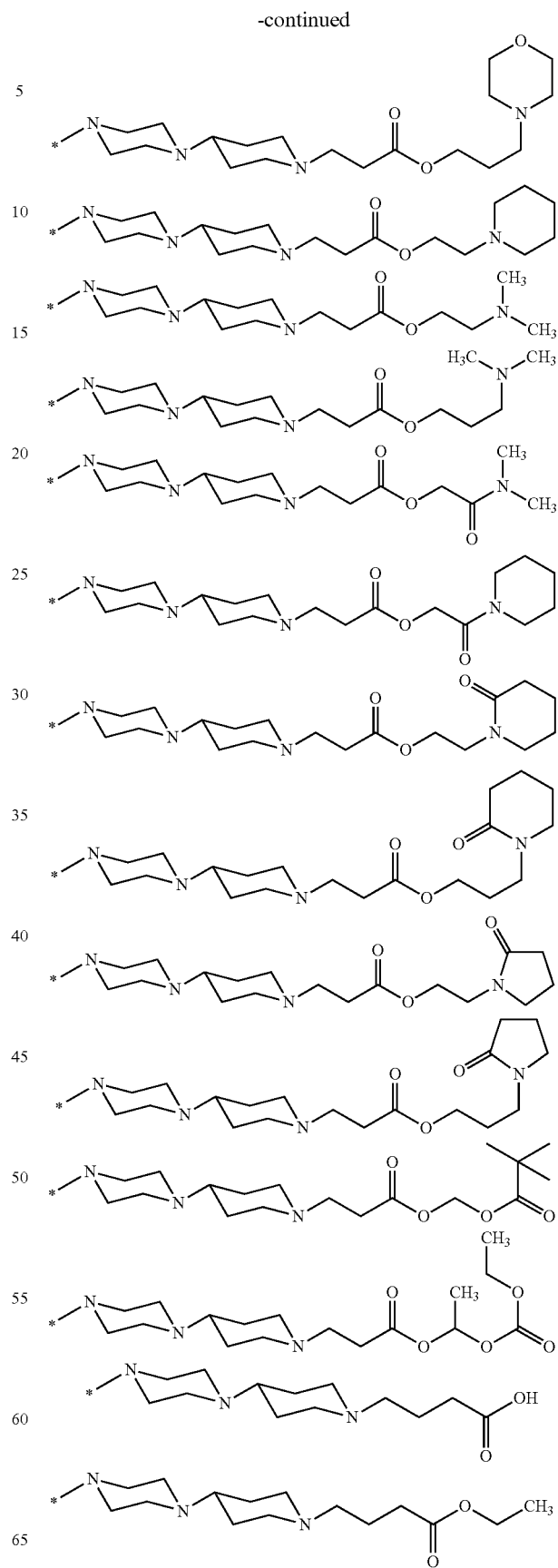

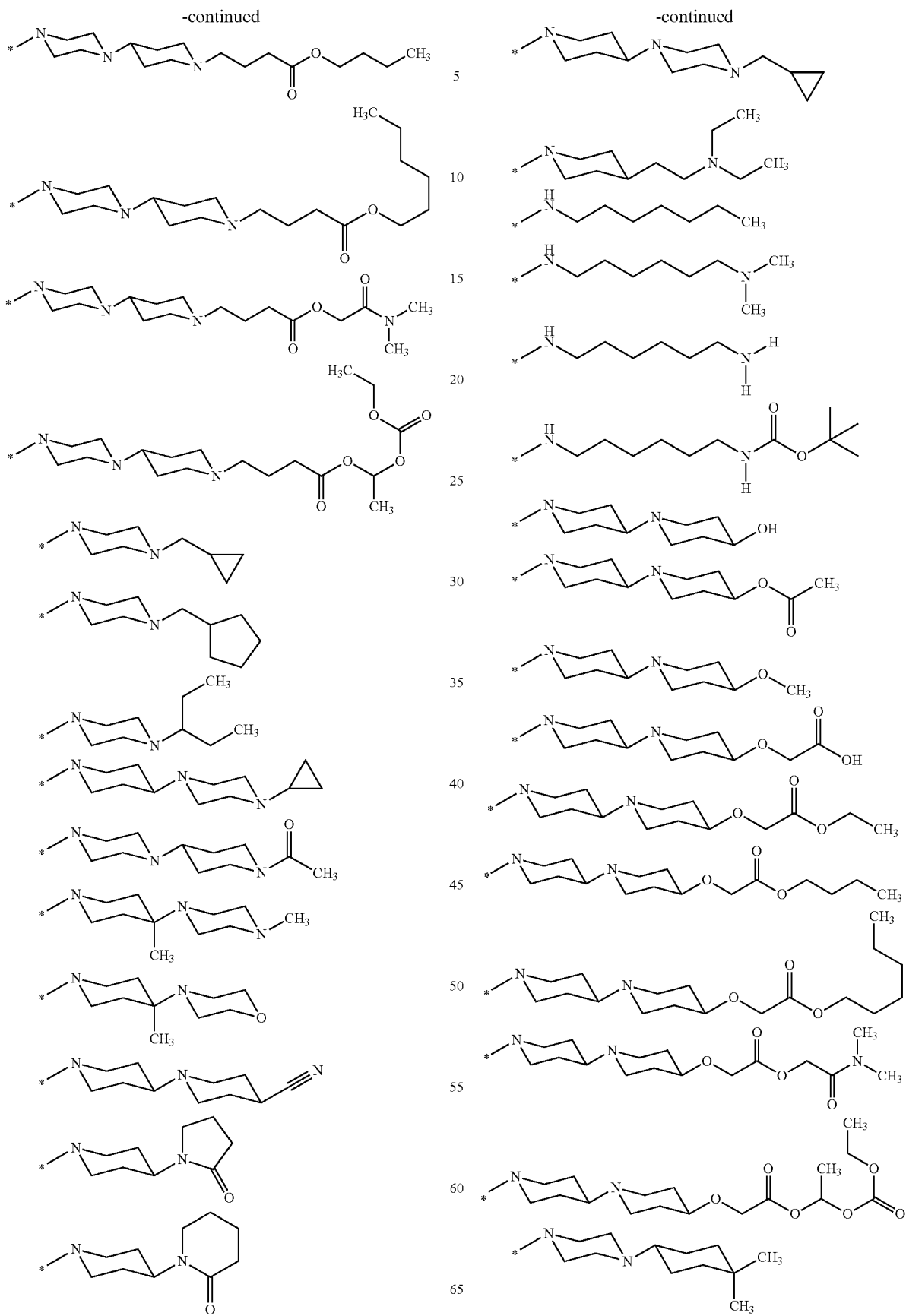

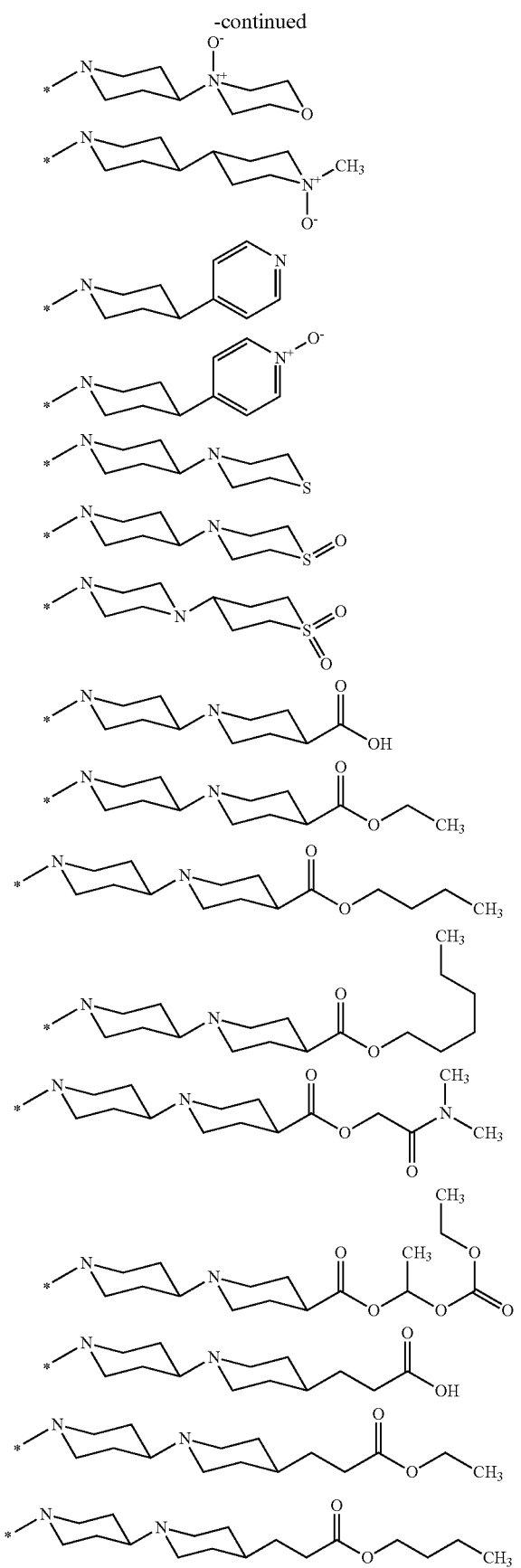
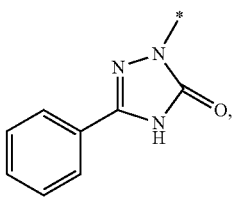
or a tautomer or salt thereof.
5. A compound of the formula I according to claim 1, wherein
$R^1$ denotes a group
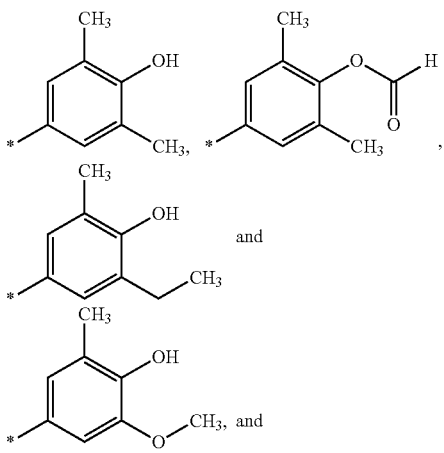
$R^2$ denotes a group selected from
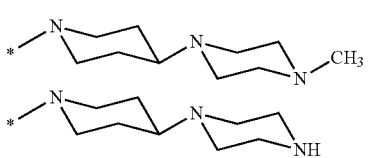
$R^3$—$R^4$ together denote a group selected from 231
-continued
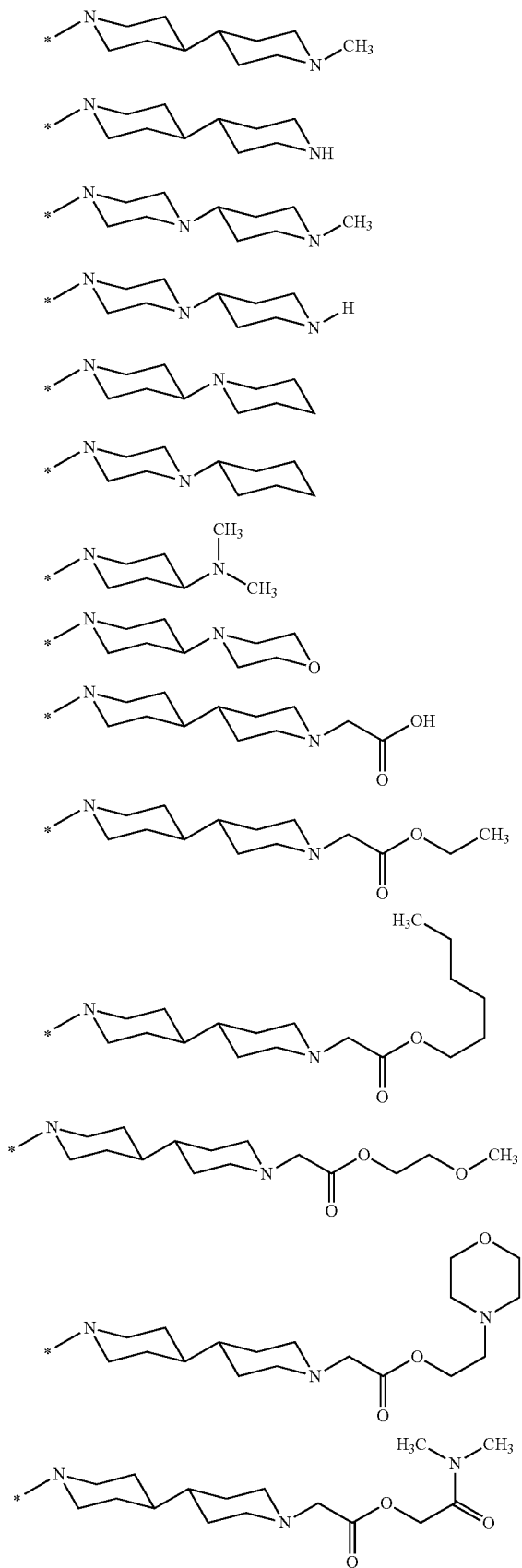
232
-continued
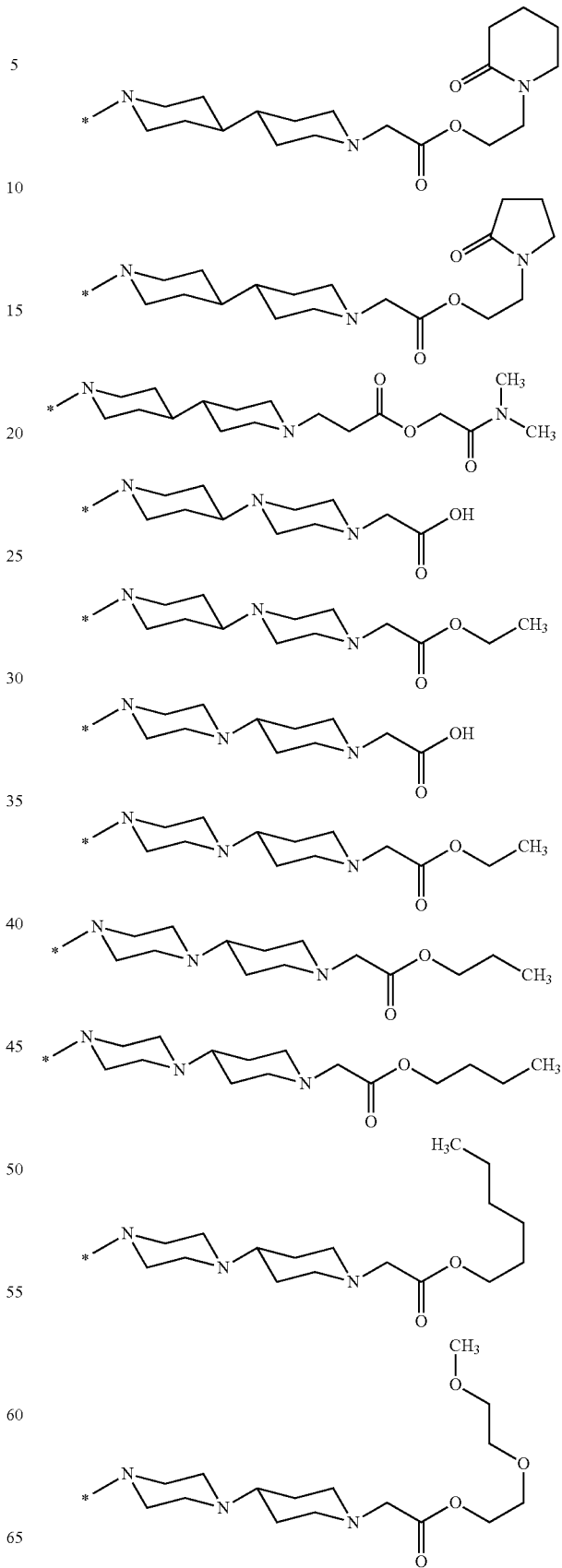

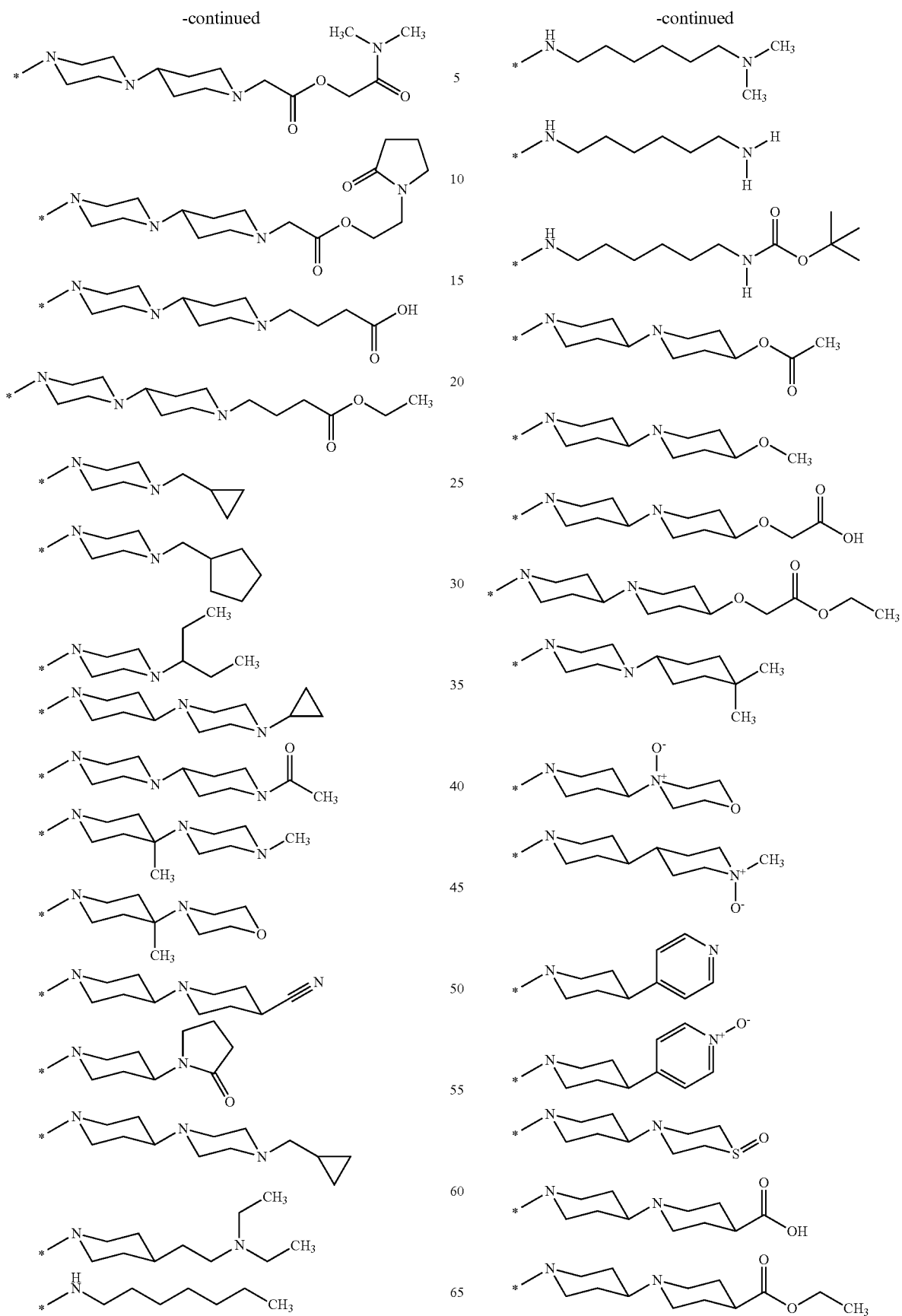

-continued
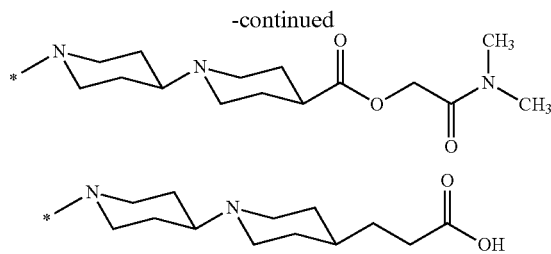
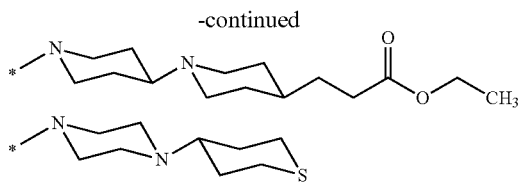
or a tautomer or salt thereof.
6. A compound of the formula I according to claim 1, selected from the group consisting of:
| No. | Structure |
|---|---|
| (1) | 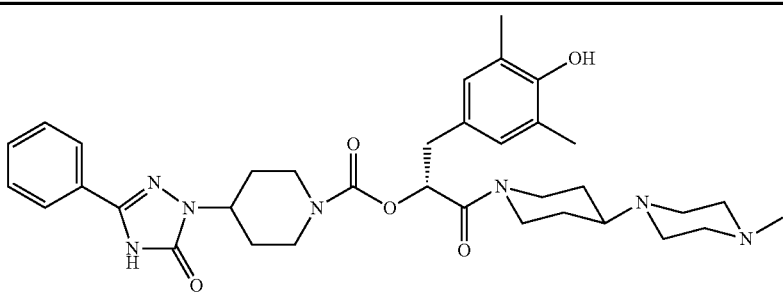 |
| (2) | 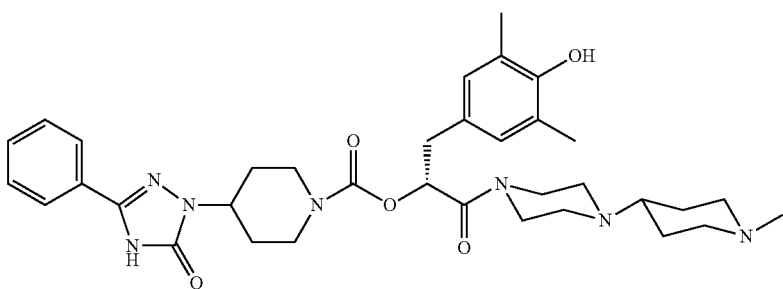 |
| (3) | 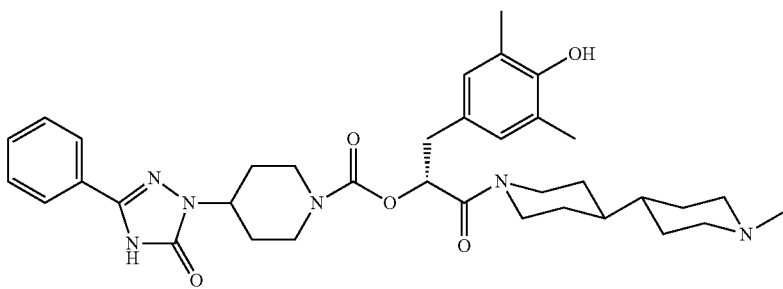 |
| (4) | 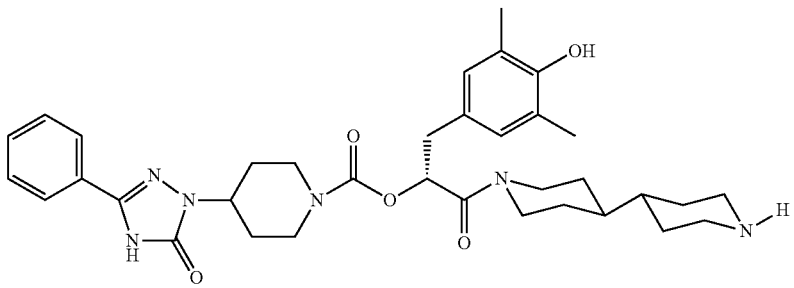 |

-continued
| No. | Structure |
|---|---|
| (5) | 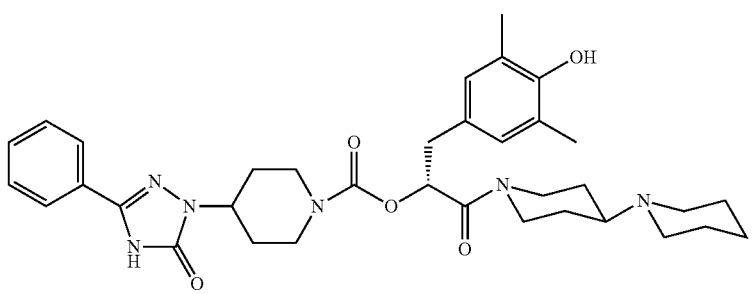 |
| (6) | 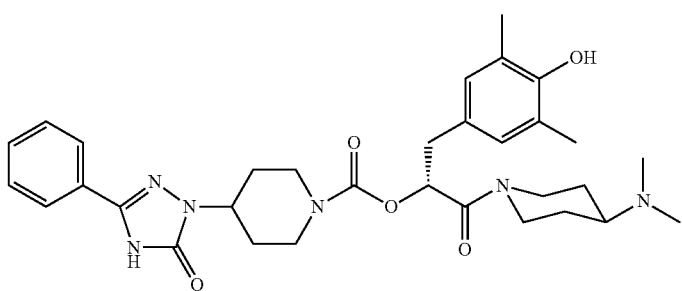 |
| (7) | 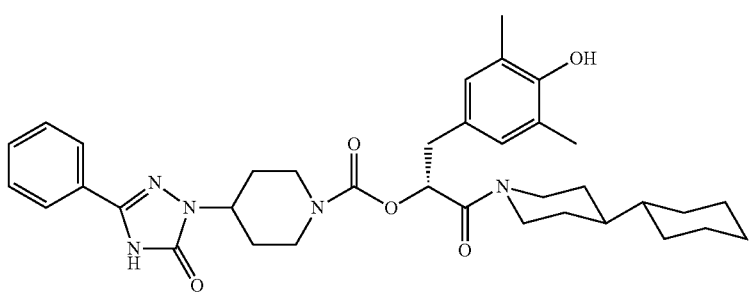 |
| (8) | 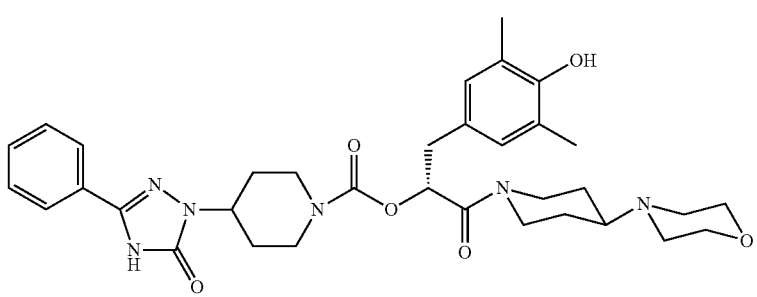 |
| (9) | 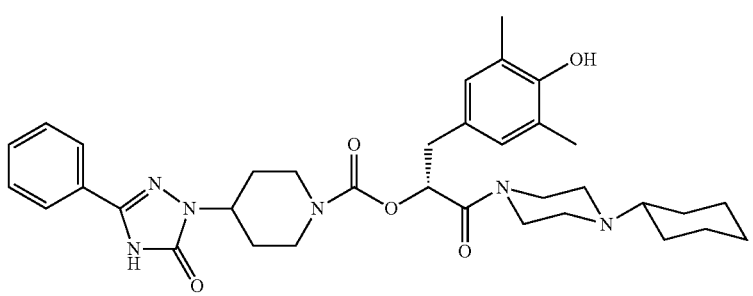 |

-continued
| No. | Structure |
|---|---|
| (10) | 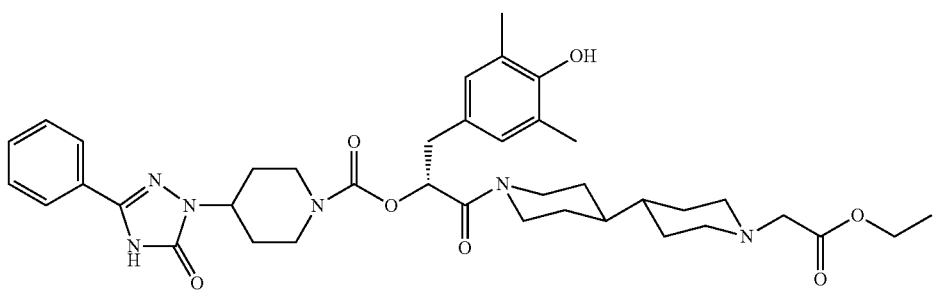 |
| (11) | 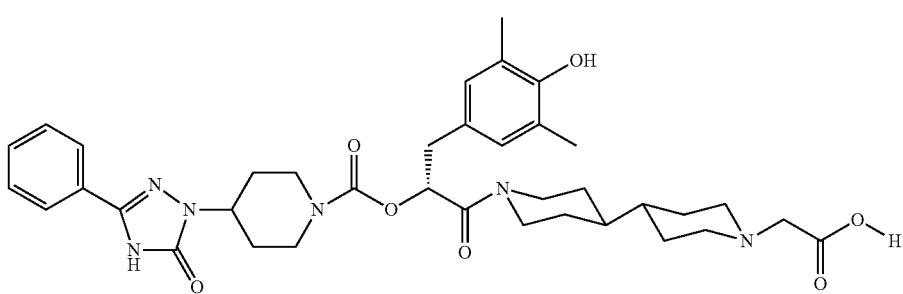 |
| (12) | 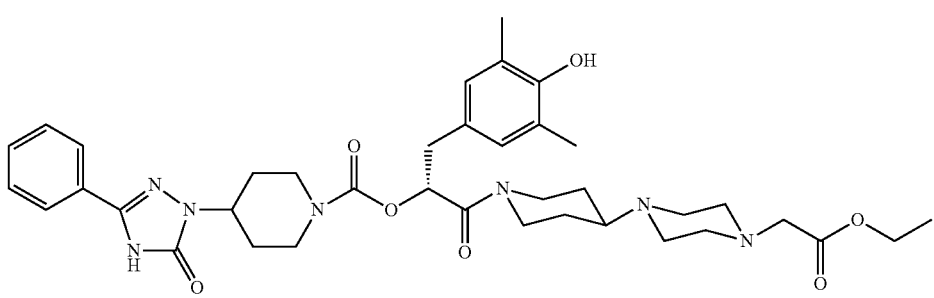 |
| (13) | 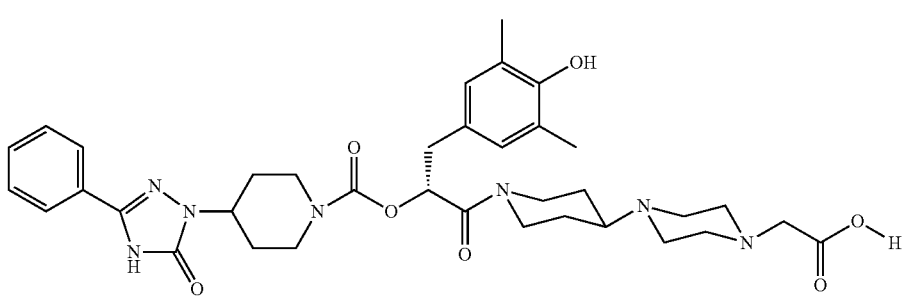 |
| (14) | 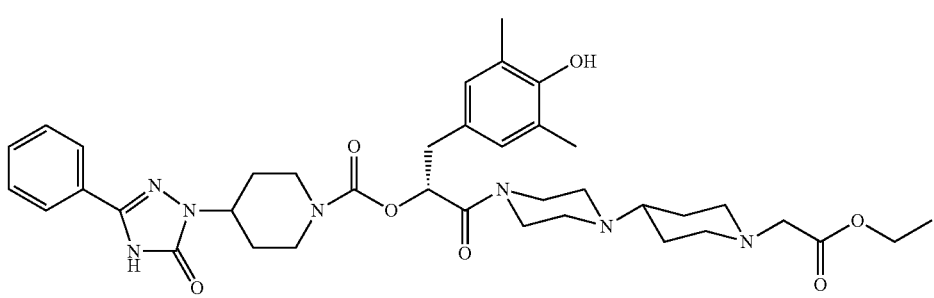 |

| No. | Structure |
|---|---|
| (15) | 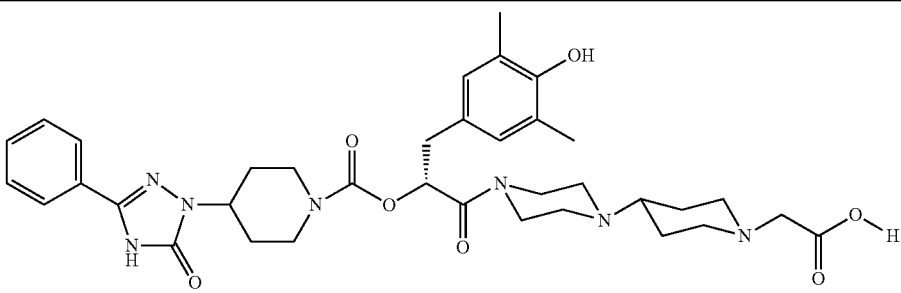 | or a tautomer or salt thereof.

7. A physiologically acceptable salt of a compound according to claim 1, 2, 3, 4, 5 or 6.

8. A pharmaceutical composition comprising a compound of the formula I, according to claim 1, 2, 3, 4, 5 or 6, or a physiologically acceptable salt thereof, optionally together with one or more inert carriers and/or diluents.

9. A method for treating or reducing the incidence of headaches which method comprises the administration, to a person who is suffering from a headache or is prone to suffer from headaches, a therapeutically or prophylactically effective amount of a compound of the formula I, according to claim 1, 2, 3, 4, 5 or 6, or a pharmaceutically acceptable salt thereof.

10. A method for treating non-insulin-dependent diabetes mellitus (NIDDM) which method comprises the administration, to a person who is suffering from NIDDM, a therapeutically or prophylactically effective amount of a compound of the formula I, according to claim 1, 2, 3, 4, 5 or 6, or a pharmaceutically acceptable salt thereof.

* * * * *